United States Patent
Upasani et al.

(10) Patent No.: US 10,435,431 B2
(45) Date of Patent: Oct. 8, 2019

(54) 3,3 DISUBSTITUTED 19-NOR PREGNANE COMPOUNDS, COMPOSITIONS, AND USES THEREOF

(71) Applicant: Sage Therapeutics, Inc., Cambridge, MA (US)

(72) Inventors: Ravindra B. Upasani, San Jose, CA (US); Benny C. Askew, Marshfield, MA (US); Boyd L. Harrison, Princeton Junction, NJ (US); Francesco G. Salituro, Marlborough, MA (US); Albert J. Robichaud, Cambridge, MA (US)

(73) Assignee: Sage Therapeutics, Inc., Cambridge, MA (US)

( * ) Notice: Subject to any disclaimer, the term of this patent is extended or adjusted under 35 U.S.C. 154(b) by 0 days.

(21) Appl. No.: 15/681,983

(22) Filed: Aug. 21, 2017

(65) Prior Publication Data

US 2017/0342103 A1    Nov. 30, 2017

Related U.S. Application Data

(63) Continuation of application No. 14/351,449, filed as application No. PCT/US2012/060136 on Oct. 12, 2012, now abandoned.

(60) Provisional application No. 61/698,204, filed on Sep. 7, 2012, provisional application No. 61/547,291, filed on Oct. 14, 2011.

(51) Int. Cl.
| | |
|---|---|
| *C07J 5/00* | (2006.01) |
| *C07J 7/00* | (2006.01) |
| *C07J 43/00* | (2006.01) |
| *C07J 31/00* | (2006.01) |
| *C07J 9/00* | (2006.01) |

(52) U.S. Cl.
CPC ........... *C07J 43/003* (2013.01); *C07J 5/0015* (2013.01); *C07J 7/002* (2013.01); *C07J 7/008* (2013.01); *C07J 7/0085* (2013.01); *C07J 9/005* (2013.01); *C07J 31/006* (2013.01)

(58) Field of Classification Search
CPC . C07J 75/00; C07J 5/0015; C07J 7/008; C07J 7/0085
USPC ........................................................ 552/600
See application file for complete search history.

(56) References Cited

U.S. PATENT DOCUMENTS

| | | | |
|---|---|---|---|
| 2,856,415 A | 10/1958 | Mihina | |
| 3,169,134 A | 2/1965 | Klimstra et al. | |
| 3,206,459 A | 9/1965 | Cross | |
| 3,580,937 A | 5/1971 | Campbell et al. | |
| 3,943,124 A | 3/1976 | Phillipps et al. | |

(Continued)

FOREIGN PATENT DOCUMENTS

| | | |
|---|---|---|
| CN | 1190404 A | 8/1998 |
| CN | 101412742 A | 4/2009 |

(Continued)

OTHER PUBLICATIONS

Qian et al., "The efficient and enantiospecific total synthesis of cyclopenta[b]phenanthrenes structurally related to neurosteroids", Adv. Syn. & Cata., 2010, vol. 352, Nos. 11-12, pp. 2057-2061.

Rogawski et al., "Neuroactive steroids for the treatment of status epilepticus", Epilepsia, 54:(2013), pp. 93-98.

Runyon et al., "17b-Nitro-5a-androstan-3a-ol and its 3b-methyl derivative: Neurosteroid analogs with potent anticonvulsant and anxiolytic activities", European Journal of Pharmacology 617, (2009), pp. 68-73.

Ruzicka et al., "Steroids and sex hormones. CXXXIX. The relation between constitution and odor of steroids. Methylandrostane and allopregnane derivatives", Helvetica Chimica Acta, 1947, vol. 30, pp. 867-878.

(Continued)

*Primary Examiner* — Barbara P Badio
(74) *Attorney, Agent, or Firm* — Goodwin Procter LLP

(57) ABSTRACT

Provided herein are 3,3-disubstituted 19-nor-steroidal compounds according to Formula (I) and (III):

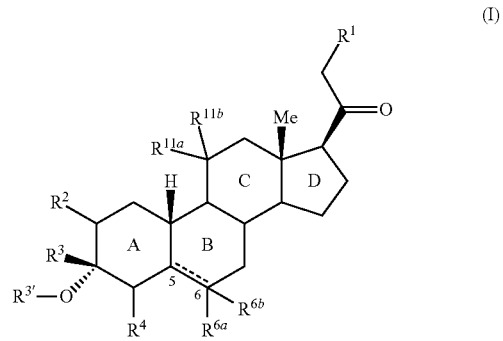

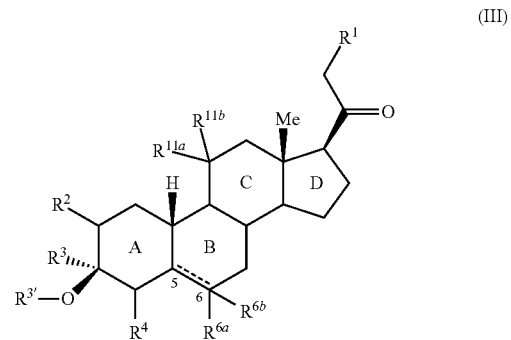

where $R^1$, $R^2$, $R^3$, $R^{3'}$, $R^4$, $R^{6a}$, $R^{6a}$, $R^{11a}$, and $R^{11b}$ are as defined herein. Compounds of the present invention are contemplated useful for the prevention and treatment of a variety of CNS-related conditions, for example, treatment of sleep disorders, mood disorders, insomnia, anxiety, depression, traumatic brain injury (TBI), stress, and epilepsy.

1 Claim, No Drawings

(56) References Cited

U.S. PATENT DOCUMENTS

| | | |
|---|---|---|
| 3,983,111 A | 9/1976 | Phillipps et al. |
| 3,998,829 A | 12/1976 | Phillips et al. |
| 4,071,625 A | 1/1978 | Grunwell et al. |
| 4,179,336 A | 12/1979 | Weber et al. |
| 4,192,871 A | 3/1980 | Phillipps et al. |
| 4,389,345 A | 6/1983 | Lenz |
| 5,593,983 A | 1/1997 | Campbell |
| 5,721,227 A | 2/1998 | Melloni et al. |
| 5,925,630 A | 7/1999 | Upasani et al. |
| 5,935,545 A | 8/1999 | Leary et al. |
| 5,939,545 A | 8/1999 | Upasani et al. |
| 6,133,280 A | 10/2000 | Brodie et al. |
| 6,143,736 A | 11/2000 | Upasani et al. |
| 6,277,838 B1 | 8/2001 | Upasani et al. |
| 6,717,002 B2 | 4/2004 | Yano et al. |
| 6,844,456 B2 | 1/2005 | Covey |
| 7,064,116 B2 | 6/2006 | Calogeropoulou et al. |
| 7,781,421 B2 | 8/2010 | Covey et al. |
| 8,759,330 B2 | 6/2014 | Covey et al. |
| 8,939,545 B2 | 1/2015 | Tunmore et al. |
| 9,156,876 B2 | 10/2015 | Covey |
| 9,365,611 B2 | 6/2016 | Martinez Botella et al. |
| 9,512,165 B2 | 12/2016 | Martinez Botella et al. |
| 9,630,986 B2 | 4/2017 | Covey et al. |
| 9,725,481 B2 | 8/2017 | Martinez Botella et al. |
| 9,765,110 B2 | 9/2017 | Covey |
| 10,246,482 B2 | 4/2019 | Harrison et al. |
| 2002/0091112 A1 | 7/2002 | Menzenbach et al. |
| 2005/0176976 A1 | 8/2005 | Calogeropoulou et al. |
| 2006/0094696 A1 | 5/2006 | Leese et al. |
| 2007/0014719 A1 | 1/2007 | Reading et al. |
| 2008/0269183 A1 | 10/2008 | Mellon et al. |
| 2009/0048218 A1 | 2/2009 | Kuhnke et al. |
| 2010/0152840 A1 | 6/2010 | Seguin et al. |
| 2010/0234335 A1 | 9/2010 | Gravanis et al. |
| 2010/0317638 A1 | 12/2010 | Covey et al. |
| 2011/0152840 A1 | 6/2011 | Lee et al. |
| 2011/0172242 A1 | 7/2011 | Helton et al. |
| 2014/0017675 A1 | 1/2014 | Ito |
| 2014/0050789 A1 | 2/2014 | Rogawski et al. |
| 2014/0094619 A1 | 4/2014 | Runyon et al. |
| 2014/0148412 A1 | 5/2014 | Hogenkamp |
| 2014/0235600 A1 | 8/2014 | Covey et al. |
| 2014/0275241 A1 | 9/2014 | Covey |
| 2015/0291654 A1 | 10/2015 | Upasani et al. |
| 2015/0315230 A1 | 11/2015 | Covey et al. |
| 2016/0068563 A1 | 3/2016 | Martinez Botella et al. |
| 2016/0083418 A1 | 3/2016 | Martinez Botella et al. |
| 2016/0108080 A1 | 4/2016 | Martinez Botella et al. |
| 2016/0229887 A1 | 8/2016 | Martinez Botella et al. |
| 2017/0233433 A1 | 8/2017 | Martinez Botella et al. |
| 2017/0246191 A1 | 8/2017 | Martinez Botella et al. |

FOREIGN PATENT DOCUMENTS

| | | |
|---|---|---|
| CN | 101624414 A | 1/2010 |
| CN | 104136452 A | 11/2014 |
| DE | 2526373 A1 | 12/1976 |
| DE | 2632677 A1 | 1/1978 |
| EP | 0104489 A1 | 4/1984 |
| EP | 0554436 A1 | 8/1993 |
| EP | 0656365 A1 | 6/1995 |
| EP | 0701444 A1 | 3/1996 |
| EP | 1038880 A2 | 9/2000 |
| FR | 1994 | 9/1963 |
| GB | 1380246 A | 1/1975 |
| GB | 1430942 A | 4/1976 |
| GB | 1570394 A | 7/1980 |
| GB | 1581234 A | 12/1980 |
| RU | 2194712 C2 | 12/2002 |
| RU | 2243232 C2 | 12/2004 |
| RU | 2010100334 A | 7/2011 |
| RU | 2675855 C2 | 12/2018 |
| WO | 1991016897 A1 | 11/1991 |
| WO | 9303732 A1 | 3/1993 |
| WO | 9305786 A1 | 4/1993 |
| WO | 9318053 A1 | 9/1993 |
| WO | 9427608 A1 | 12/1994 |
| WO | 1995021617 A1 | 8/1995 |
| WO | 1996003421 A1 | 2/1996 |
| WO | 1996016076 A1 | 5/1996 |
| WO | 9640043 A2 | 12/1996 |
| WO | 9805337 A1 | 2/1998 |
| WO | 0066614 A1 | 11/2000 |
| WO | 2005051972 A1 | 6/2005 |
| WO | 2005105822 A2 | 11/2005 |
| WO | 2006037016 A2 | 4/2006 |
| WO | 2006131392 A1 | 12/2006 |
| WO | 2008151745 A1 | 12/2008 |
| WO | 2008157460 A1 | 12/2008 |
| WO | 2010003391 A2 | 1/2010 |
| WO | 2010107815 A1 | 9/2010 |
| WO | 2012013816 A1 | 2/2012 |
| WO | 2012083090 A2 | 6/2012 |
| WO | 2012109752 A1 | 8/2012 |
| WO | 2012110010 A1 | 8/2012 |
| WO | 2012116290 A2 | 8/2012 |
| WO | 2013019711 A2 | 2/2013 |
| WO | 2013036835 A1 | 3/2013 |
| WO | 2013056181 A1 | 4/2013 |
| WO | 2013188792 A2 | 12/2013 |
| WO | 2014058736 A1 | 4/2014 |
| WO | 2014071449 A1 | 5/2014 |
| WO | 2014100228 A1 | 6/2014 |
| WO | 2014169831 A1 | 10/2014 |
| WO | 2014169832 A1 | 10/2014 |
| WO | 2014169833 A1 | 10/2014 |
| WO | 2014169836 A1 | 10/2014 |
| WO | 2015010054 A2 | 1/2015 |
| WO | 2015027227 A1 | 2/2015 |
| WO | 2015180679 A1 | 12/2015 |
| WO | 2015195962 A1 | 12/2015 |
| WO | 2016061527 A1 | 4/2016 |
| WO | 2016061537 A1 | 4/2016 |
| WO | 2016082789 A1 | 6/2016 |
| WO | 2016123056 A1 | 8/2016 |
| WO | 2016134301 A2 | 8/2016 |
| WO | 2016209847 A1 | 12/2016 |
| WO | 2017044659 A1 | 3/2017 |
| WO | 2017066626 A1 | 4/2017 |
| WO | 2017087864 A1 | 5/2017 |
| WO | 2017156103 A1 | 9/2017 |
| WO | 2017156418 A1 | 9/2017 |
| WO | 2018013613 A1 | 1/2018 |
| WO | 2018013615 A1 | 1/2018 |
| WO | 2018039378 A1 | 3/2018 |
| WO | 2019045121 A1 | 3/2019 |

OTHER PUBLICATIONS

Rychnovsky et al., "Synthesis of ent-cholesterol, the unnatural enantiomer", Journal of Organic Chemistry, 1992, vol. 57, No. 9, pp. 2732-2736.

Santaniello & Caspi, "Reduction of certain steroidal 19-sulfonic esters with metal hydrides", J. of Ster. Biochem, 1976, vol. 7, No. 3, pp. 223-227.

Sarett., "A new method for the preparation of 17(alpha)-hydroxy-20-ketopregnanes", J. Am. Chem. Soc., 1948, vol. 70, pp. 1454-1458.

Scaglione et al., "Neurosteroid Analogues. 14. Alternative Ring System Scaffolds: GABA Modulatory and Anesthetic Actions of Cyclopenta[b]phenanthrenes and Cyclopenta[b]anthracenes", 2008, Journal of Medicinal Chemistry, vol. 51, pp. 1309-1318.

Shen et al., "Microbial aromatization of 19-hydroxymethylepidehydroandrosterone acetate by Corynebacterium simplex", Huaxue Xuebao, 1983, vol. 41, No. 5, pp. 473-474, English Abstract Only.

Shu et al., "Characteristics of concatemeric GABM receptors containing alpha4/d subunits expressed in Xenopus oocytes" British Journal of Pharmacology (2012) 165, 2228-2243.

(56) References Cited

OTHER PUBLICATIONS

Slavíkováet al., "Allopregnanolone (3a-Hydroxy-5a-pregnan-20-one) Derivatives with a Polar Chain in Position 16a: Synthesis and Activity", Journal of Medicinal Chemistry, vol. 52, No. 7, (2009), 2119-2125.
Spiegel et al., "Use of Nonaqueous Solvents in Parenteral Products", Journal of Pharmaceutical Sciences, 1963, vol. 52, No. 10, pp. 917-927.
Starnes et al., "Thin-Layer Chromatography of 17-Kelosteroid 2,4-Dinitrophenylhydrazones", Journal of Clinical Endocrinology and Metabolism, 1966, vol. 26, No. 11, pp. 1245-1250.
Stastna et al., "Neurosteroid Analogues. 16. A New Explanation for the Lack of Anesthetic Effects in D16-Alphaxalone and Identification of a D17(20) Analogue with Potent Anesthetic Activity", Journal of Medicinal Chemistry, 2011, vol. 54, No. 11, pp. 3926-3934.
Stastna et al., "Stereoselectivity of sodium borohydride reduction of saturated steroidal ketones utilizing conditions of Luche reduction", Steroids, 2010, vol. 75, No. 10, pp. 721-725.
Stastna et al., "Synthesis of C3, C5, and C7 pregnane derivatives and their effect on NMDA receptor responses in cultured rat hippocampal neurons", Steroids, Elsevier Science Publishers, vol. 74, No. 2, (2008), pp. 256-263.
Stastna et al., "The use of symmetry in enantioselective synthesis: Four pairs of chrysene enantiomers prepared from 19-nortestosterone", Org. Biomol. Chem., 2011, vol. 9, pp. 4685-4694.
Supplemental European Search Report, European Patent Application No. 14826212.4, dated Feb. 16, 2017.
Tsai et al., "Synthesis and antiproliferative activity of 3a-hydroxyl-3b-methoxymethyl-5a-pregnan-20-one with a C-21 hydrophilic substituent", Heteroatom Chemistry, (2017), pp. 1-9.
Upasani et al., "3a-Hydroxy-3ß-(phenylethynyl)-5ß-pregnan-20-ones: Synthesis and Pharmacological Activity of Neuroactive Steroids with High Affinity for GABAA Receptors", J. Med. Chem. (1997) vol. 40, No. 1, pp. 73-84.
Vanover et al., "Behavioral characterization of Co 134444 (3a-hydroxy-21-(1'-imidazolyl)-3b-methoxymethyl-5a-pregnan-20-one), a novel sedative-hypnotic neuroactive steroid", Psychopharmacology (2001), vol. 155, pp. 285-291.
Vanover et al., "Characterization of the Anxiolytic Properties of a Novel Neuroactive Steroid, Co 2-6749 (GMA-839; WAY-141839; 3a, 21-Dihydroxy-3b-trifluoromethyl-19-nor-5b-pregnan-20-one), a Selective Modulator of y-Aminobutyric AcidA Receptors", The Journal of Pharmacology and Experimental Therapeutics, (2000), vol. 295, No. 1, pp. 337-345.
Vanover et al., "Response-Rate Suppression in Operant Paradigm as Predictor of Soporific Potency in Rats and Identification of Three Novel Sedative-Hypnotic Neuroactive Steroids", The Journal of Pharmacology and Experimental Therapeutics, (1999), vol. 291, No. 3, pp. 1317-1323.
Wicha et al., "Transformations of steroidal neopentyl systems. II. Migration of acetate from the 3beta—to the 19-hydroxyl in delta 5 and A/B-trans steroids", Canadian Journal of Chemistry, 1967, vol. 45, No. 7, pp. 707-711.
Wicha et al., "Transformations of steroidal neopentyl systems. IV. Stereochemistry of Products of Reaction of Methyllithium with Steroidal A5-19-aldehydes", Journal of the Chemical Society (Section) C: Organic, 1968, vol. 14, 1740-1746.
Wicha et al., "Transformations of steroidal neopentyl systems. V. Synthesis and proof of the configuration of 19amethyl-195-alcohols", Journal of the Chemical Society [Section] C: Organic, 1969, vol. 6, pp. 947-951.
Wicha et al., "Transformations of steroidal neopentyl systems. VI. Intramolecular Claisen condensation of 19R-acetoxy—19A-methyl-3-ones of the 5alpha series", Tetrahedron, 1969, vol. 25, No. 17, pp. 3961-3968.
Wicha et al., "Transformations of steroidal neopentyl systems. VII. Mechanism of the transformation of (19R)-(19)-hydroxy-19-methyl-3-oxo-5alpha-to 3alpha-hydroxy-19-methyl-19-oxo-5alpha-analogs", Journal of Organic Chemistry, 1973, vol. 38 No. 7, pp. 1280-1283.
Wu, "A New Classification of Prodrugs: Regulatory Perspectives", Pharmaceuticals, 2009, vol. 2, pp. 77-81.
Zeng et al., "Neurosteroid Analogues. 10. The Effect of Methyl Group Substitution at the C-6 and C-7 Positions on the GABA Modulatory and Anesthetic Actions of (3a,5a) -and (3a, 5b)-3-Hydroxypregnan-20-one", Journal of Medicinal Chemistry, (2005). vol. 48, pp. 3051-3059.
Zonana et al., "The Neurobiology of Postpartum Depression", CNS Spectrums, (2005), pp. 792-799, 805.
Zorumski et al., "Enantioselective Modulation of GABAergic Synaptic Transmission by Steroids and Benz[dindenes in Hippocampal Microcultures", Synapse, (1998), vol. 29, pp. 162-171.
International Search Report and Written Opinion for Corresponding International Application No. PCT/US15/36500 dated Sep. 11, 2015.
International Search Report and Written Opinion for Corresponding International Application No. PCT/US15/56054 dated Feb. 9, 2016.
International Search Report and Written Opinion for Corresponding International Application No. PCT/US2013/076214 dated Aug. 29, 2016.
International Search Report and Written Opinion for Corresponding International Application No. PCT/US2014/052417 dated Nov. 19, 2014.
International Search Report and Written Opinion for Corresponding International Application No. PCT/US2014/092369 dated Aug. 25, 2015.
International Search Report and Written Opinion for Corresponding International Application No. PCT/US2015/056066 dated Feb. 8, 2016.
International Search Report and Written Opinion for Corresponding International Application No. PCT/US2016/014835 dated Jun. 9, 2016.
International Search Report and Written Opinion for Corresponding International Application No. PCT/US2016/018748 dated Aug. 29, 2016.
International Search Report and Written Opinion for Corresponding International Application No. PCT/US2016/062874 dated Jan. 30, 2017.
International Search Report and Written Opinion for Corresponding International Application No. PCT/US2017/041600 dated Dec. 1, 2017.
International Search Report and Written Opinion for Corresponding International Application No. PCT/US2017/041605 dated Dec. 12, 2017.
International Search Report and Written Opinion for Corresponding International Application No. PCT/US2017/048267 dated Aug. 29, 2016.
International Search Report and Written Opinion for International Application No. PCT/CN2013/074312 dated Jan. 23, 2014.
International Search Report and Written Opinion for International Application No. PCT/CN2013/074319 dated Jan. 23, 2014.
International Search Report and Written Opinion for International Application No. PCT/CN2013/074323 dated Jan. 30, 2014.
International Search Report and Written Opinion for International Application No. PCT/CN2013/074325 dated Jan. 23, 2014.
International Search Report and Written Opinion for International Application No. PCT/CN2014/075585 dated Aug. 4, 2014.
International Search Report and Written Opinion for International Application No. PCT/CN2014/075593 dated Jul. 22, 2014.
International Search Report and Written Opinion for International Application No. PCT/CN2014/075594 dated Jul. 16, 2014.
International Search Report and Written Opinion for International Application No. PCT/CN2014/075600 dated Jul. 29, 2014.
International Search Report and Written Opinion for International Application No. PCT/US14/47246, dated Jan. 22, 2015.
International Search Report for International Application No. PCT/US2012/060136 dated Mar. 27, 2013.
Jiang et al., "Neurosteroid analogues. 9. Conformationally constrained pregnanes: structure-activity studies of 13,24-cyclo-18, 21-dinorcholane analogues of the GABA modulatory and anesthetic

(56) References Cited

OTHER PUBLICATIONS steroids (3a,5a)- and (3a,5a)-3-hydroxypregnan-20-one", Journal of Medicinal Chemistry, 2003, vol. 46, pp. 5334-5348.
Kaji et al., "Synthesis of 3-epi-6, 7-dideoxyxestobergsterol A", Chem. & Pharm. Bulletin, 2000, vol. 48, No. 10, pp. 1480-1483.
Katona et al., "Neurosteroid analogues. 12. Potent enhancement of GABA-mediated chloride currents at GABAA receptors by ent-androgens", European Journal of Medicinal Chemistry, 2008, vol. 43, pp. 107-113.
Knox et al., "Steroids. CCLXXVIII. Reductions of 19-substituted androst-4-en-3-ones and related compounds", Journal of Organic Chemistry, 1965, vol. 30, No. 7, pp. 2198-2205.
Krafft et al., "Synthesis of the C/D/E and A/B Rings of Xestobergsterol—(A)", Journal of Organic Chemistry, American Chemical Society, vol. 64, No. 7, (1999), pp. 2475-2485.
Krishnan et al., "Neurosteroid Analogues. Chapter 17. Inverted Binding Orientations of Androsterone Enantiomers at the Steroid Potentiation Site on y-Aminobutyric Acid Type A Receptors", Journal of Medicinal Chemistry, 2012, vol. 55, No. 3, pp. 1334-1345.
Lan et al., "Neurosteroid Analogues. 4. The Effect of Methyl Substitution at the C-5 and C-10 Positions of Neurosteroids on Electrophysiological Activity at GABAA Receptors", Journal of Medicinal Chemistry, (1996), vol. 39, pp. 4218-4232.
Lewbart et al., "Oxidation of Steroidal a-Ketols to Glyoxals with Cupric Acetate", Journal of Organic Chemistry, (1963), vol. 28, No. 8, pp. 2001-2006.
Li et al., "Neuroactive Steroids and Human Recombinant p1 GABAc Receptors", Journal of Pharmacology and Experimental Therapeutics, (2007), vol. 323, pp. 236-247.
Mangialasche et al., "Alzheimer's disease: clinical trials and drug development", Lance Neurology, vol. 9 (2010), pp. 702-716.
Matsui et al., "Comparative fate of testosterone and testosterone sulfate in female rats: C19O2 and C19O3 steroid metabolites in the bile", Journal of Steroid Biochemistry, 1977, 8(4), pp. 323-328.
Mok et al., "Evidence that 5a-pregnan-3a-ol-20-one is the metabolite responsible for progesterone anesthesia", Brain Research (1990), 533(1), pp. 42-45.
Morrow et al., "Characterization of Steroid Interactions with gamma-Aminobutyric Acid Receptor-Gated Chloride Ion Channels: Evidence for Multiple Steroid Recognition Sites", 1989, Molecular Pharmacology, 37, pp. 263-270.
Nilsson et al., "Neurosteroid analogues. 6. The synthesis and GABAA receptor pharmacology of enantiomers of dehydroepiandrosterone sulfate, pregnenolone sulfate, and (3a,5b)-3-hydroxypregnan-20-one sulfate", Journal of Medicinal Chemistry, 1998, vol. 41, pp. 2604-2613.
Notification of Transmittal of the International Search Report and the Written Opinion of the International Searching authority, or the Declaration, International Application No. PCT/US13/45933, dated Dec. 3, 2013, 5 Pages.
Paradiso et al., "Steroid Inhibition of Rat Neuronal Nicotinic a4B2 Receptors Expressed in HEK 293 Cells", Journal of Molecular Pharmacology, (2000), vol. 58, pp. 341-351.
Paul et al., "Neuroactive Steroids", The Journal of the Federation of American Societies for Experimental Biology, (1992), pp. 2311-2322.
Peart et al., "Hydroxylation of steroids by Fusarium oxysporum, Exophiala jeanselmei and Ceratocystis paradoxa", Steroids, vol. 76, No. 12, (2011), pp. 1317-1330.
Pechet et al., "Metabolism of 19-hydroxycorticosterone. Isolation and characterization of three metabolites", Journal of Biological Chemistry, Jan. 1, 1961, vol. 236, No. 10, pp. PC68-PC69.
Phillipps et al., "A New Series of Steroidal Antidysrhythmic Agents," J. Steroid Biochem. 19(1):759-765 (1983).
Phillipps et al., "Water-soluble Steroidal Anaesthetics", Journal of Steroid Biochemistry 11:79-86 (1979).
Phillipps, "Structure-Activity Relationships in Steroidal Anaesthetics", Journal of Steroid Biochemistry, (1975), vol. 6, pp. 607-613.
Phillipps, "Structure-Activity Relationships in Steroidal Anaesthetics", Nol. Mech. Gen. Anaesth. Glaxo Symposium, (1974), pp. 32-47.
PubChem-70249446 (2012), entire document.
Purdy et al., "Synthesis, Metabolism, and Pharmacological Activity of 3a-Hydroxy Steroids Which Potentiate GABA-Receptor-Mediated Chloride Ion Uptake in Rat Cerebral Cortical Synaptoneurosomes", Journal of Medicinal Chemistry, (1990), vol. 33, pp. 1572-1581.
Qian et al., "Neurosteroid Analogues, 18. Structure-Activity Studies of ent-Steroid Potentiators of y-Aminobutyric Acid Type A Receptors and Comparison of Their Activities with Those of Alphaxalone and Allopregnanolone", Journal of Medicinal Chemistry, 2014, vol. 57, No. 1, pp. 171-190.
Anderson et al., "Anesthetic Activity of Novel Water-Soluble 2b-Morpholinyl Steroids and Their Modulatory Effects at GABA-A Receptors", Journal of Medicinal Chemistry., 1997, vol. 40, pp. 1668-1681.
Anderson et al., "Conformationally Constrained Anesthetic Steroids That Modulate GABAA Receptors," Journal of Medicinal Chemistry, 2000, vol. 43, No. 22, pp. 4118-4125.
Atack, "Development of Subtype-Selective GABAA Receptor Compounds for the Treatment of Anxiety, Sleep Disorders and Epilepsy", GABA and Sleep. Molecular, Functional and Clinical Aspects. 2010, pp. 25-72.
Banday et al., "D-ring substituted 1,2,3-triazolyl 20-keto pregnenanes as potential anticancer agents: Synthesis and biological evaluation", Steroids, (2010), vol. 75, No. 12, pp. 801-804, Abstract.
Bandyopadhyaya et al., "Neurosteroid Analogs. 15. A Comparative Study of the Anesthetic and GABAergic Actions of Alphaxalone, D16-Alphaxalone and Their Corresponding 17-Carbonitrile Analogs, "Bioorganic & Medicinal Chemistry Letters 20:6680-6684 (2010).
Berge et al., J. Pharmaceutical Sciences, 1977, vol. 66, pp. 1-19.
Bernstein, "Rett Syndrome Medication", Medscape, (2017).
Bjorkhem et al., "Steroid hormone metabolism in developing rates", Eur. J.Biochem., 1972, vol. 27, No. 2, pp. 318-326.
Botella et al., "Neuroactive Steroids. 1. Positive Allosteric Modulators of the (g-Aminobutyric Acid)A Receptor: Structure-Activity Relationships of Heterocyclic Substitution at C-21", Journal of Medical Chemistry, 2015, pp. 3500-3511.
Botella et al., "Neuroactive Steroids. 2. 3a-Hydroxy-3b-methyl-21-(4-cyano-1H-pyrazol-1-yl)-19-nor-5b-pregnan-20-one (SAGE-217): A Clinical Next Generation Neuroactive Steroid Positive Allosteric Modulator of the (g-Aminobutyric Acid) A Receptor" Journal of Medical Chemistry, 2017, 10 pp A-J.
Caspi et al., "Stereochemistry of 19-hydroxy-19alpha-methyl steroids," Chemical Communications, 1966, vol. 7, pp. 209-210.
Cerny et al., "Syntheses of 19-[O-(carboxymethyl)oxime] haptens of epipregnanolone and pregnanolone", Steroids, 2006, vol. 71(2), pp. 120-128.
Cerny et al., "Synthetic approach to 5alpha-pregnanolone 19-[0-(carboxymethyl) oxime] derivatives", Collection of Czechoslovak Chemical Communications, 2004, vol. 69, No. 9, pp. 1805-1817.
Chodounska et al., "Epalons: Synthesis of 3a, 7a-Dihydroxy-5a-Pregnan-20-One", Collection Symposium Series, vol. 63, No. 10, (1998), pp. 1543-1548.
Database CAPLUS in STN, Acc. No. 1995:986323, UPASANI et al., WO 9521617 A1 (Aug. 17, 1995) (abstract). [Upasani, Ravindra B. "Androstanes and pregnanes for allosteric modulation of GABA receptor, and preparation and therapeutic uses of compounds".].
Database CAPLUS in STN, Acc. No. 1998:112239, Lan, WO 9805337 A1 (Feb. 12, 1998) (abstract). [Lan, Nancy C., "Use of GABA agonists and NMDA receptor antagonists for the treatment of migraine headache".].
Deluca et al., "Synthesis of 3b-Hydroxy[21-14C] -5b-pregn-8(14)-en-20-one from Chenodeoxycholic Acid", Helvetica Chemica Acta, vol. 69, (1986), pp. 1844-1850.
Deniau et al., "Synthesis of fluorinated analogues of the neurosteroid GABA receptor antagonist, 17-PA", Journal of Fluorine Chemistry, (2008), vol. 129, No. 9, pp. 881-887.
Dorwald, "Side Reactions in Organic Synthesis", 2005, Wiley-VCH, Preface, p. IX.

(56) References Cited

OTHER PUBLICATIONS

Edgar et al., "CCD-3693: An Orally Bioavailable Analog of the Endogenous Neuroactive Steroid, Pregnanolone, Demonstrates Potent Sedative Hypnotic Actions in the Rat" The Journal of Pharmacology and Experimental Therapeutics (1997) vol. 282, No. 1, pp. 420-429.

Evers et al., "A Synthetic 18-Norsleroid Distinguishes Between Two Neuroactive Steroid Binding Sites on GABAA Receptors", Journal of Pharmacology and Experimental Therapeutics, 2010, vol. 333, No. 2, pp. 404-413.

Extended European Search Report for application PCT/CN2014075593 dated Aug. 26, 2016.

Extended European Search Report for application PCT/CN2014075594 dated Aug. 26, 2016.

Fajkos et al., "Steroids. XXIII. Synthesis and configuration of the two stereoisomeric 3b-hydroxy-16-acetylandrostanes", Chemicke Listy pro Vedu a Prumysl, 1956, vol. 50, pp. 791-799, Abstract only.

Fesik et al., "Geometric Requirements for Membrance Perturbation and Anesthetic Activity", Molecular Pharmacology, 1985, vol. 27, pp. 624-629.

Gasior et al., "Neuroactive steroids: potential therapeutic use in neurological and psychiatric disorders", Trends in Pharmacological Science, (1999), vol. 20, No. 3, pp. 107-112.

Green et al., "The nonfeminizing enantiomer of 17b-estradiol exerts protective effects in neuronal cultures and a rat model of cerebral ischemia", Endocrinology, 2001, vol. 142, pp. 400-406.

Gustafsson et al., "Steroid excretion patterns in urine from ovariectomized and adrenalectomized rats", Biochmica ET Biophysica ACTA—Lipids and Lipid Metabolism, Elsevier Science BV, 1972, vol. 280, No. 1, pp. 182-186.

Gustafsson et al., "Steroids in Germfree and Conventional Rats. 7. Identification of C19 and C21 Steroids in faeces from Conventional Rats", European Journal of Biochemistry, 1968, vol. 6, No. 2, pp. 248-255.

Gyermek et al., "Steroids, CCCX. 1 Structure-Activity Relationship of Some Steroidal Hypnotic Agents", Journal of Medicinal Chemistry, 1968, vol. 11, No. 1, pp. 117-125.

Han et al., "Neurosteroid Analogs. 3. The Synthesis and Electrophysiological Evaluation of Benz[e]indene Congeners of Neuroactive Steroids Having the 5b-Configuration", Journal of of Medicinal Chemistry, 1995, vol. 38, No. 22, pp. 4548-4556.

Harrison et al., "Structure-Activity Relationships for Steroid Interaction with the y-Aminobutyric AcidA Receptor Complex" The Journal of Pharmacology and Experimental Therapeutics (1987) vol. 241, No. 1, pp. 346-353.

Hauser et al., "Steroids. CCV. Fragmentations and intramolecular abstractions of tertiary hydrogen atoms by primary oxy radicals with fixed reaction centers", Helv. Chim. Acta, 1964, vol. 47, pp. 1961-1979.

Hawkinson et al., "3a-Hydroxy-3b-trifluoromethyl-5a-pregnan-20-one (Co Feb. 1970): A Partial Agonist at the Neuroactive Steroid Site of the y-Aminobutyric acidA Receptor" Molecular Pharmacology (1996) vol. 49, pp. 897-906.

Hawkinson et al., "Correlation of Neuroactive Steroid Modulation of [35S]t-Butylbicyclophosphorothionate and [3H] Flunitrazepam Binding and y-Aminobutyric AcidA Receptor Function", Molecular Pharmacology (1994) vol. 46, pp. 977-985.

Hawkinson et al., "Substituted 3b-Phenylethynyl Derivatives of 3a-Hydroxy-5a-pregnan-20-one: Remarkably Potent Neuroactive Steroid Modulators of y-Aminobutyric AcidA Receptors", The Journal of Pharmacology and Experimental Therapeutics(1998), vol. 287, No. 1, pp. 198-207.

Heard et al., "Steroids. VII. Preparation of of androstan-3(b)-o1-7-one from from dehydroisoandrosterone", Journal of Biological Chemistry, 1946, vol. 165, pp. 677-685.

Hewett et al., "Amino steroids. Part III. 2- and 3-Amino-5a-androstanes", Journal of the Chemical Society, 1968, vol. 9, pp. 1134-1140.

Hill et al., "Pholochemische Reaktionen. 32 Milleilung. UV-Bestrahlung von gesattigten und bela,gamma—ngesalligten, nomoal-lylisch konjugierten steroidaldehyden", Helvetica Chimica Acta, 1946, vol. 49, No. 1, pp. 292-311, Abstract only.

Hogenkamp et al., "Pharmacological profile of a 17b-heteroaryl-substituted neuroactive steroid", Psychopharmacology, vol. 231, (2014), pp. 3517-3524.

Hogenkamp et al., "Synthesis and in Vitro Activity of 3b-Substituted-3a-hydroxypregnan-20-ones: Allosteric Modulators of the GABAA Receptor", Journal of Medicinal Chemistry, (1997), vol. 40, pp. 61-72.

Hu et al., "Neurosteroid analogues. Part 5. Enantiomers of neuroactive steroids and benz[e]indenes: total synthesis, 18 electrophysiological effects on GABAA receptor function and anesthetic actions in tadpoles", J. Chem. Soc. Perkin Trans 1, 1997, pp. 3665-3671.

Hu et al., "Neurosteroid Analogues: Structure-Activity Studies of Benz(e] indene Modulators of GABAA Receptor Function. 1. The Effect of 6-Melhyl Substitution on the Electrophysiological Activity of 7-Substituted Benz[e]indene-3-carbonitriles", Journal of Medicinal Chemistry, (1993), pp. 3956-3967.

Im et al., "Studies on the Mechanism of Interactions between Anesthetic Steroids and y-Aminobutyric AcidA Receptors", Molecular Pharmacology (1990), 37(3), pp. 429-434.

International Search Report and Written Opinion for Corresponding International Application No. PCT/CN2014/078820 dated Feb. 27, 2015.

International Search Report and Written Opinion for Corresponding International Application No. PCT/CN2015/080216 dated Aug. 3, 2015.

International Search Report and Written Opinion for Corresponding International Application No. PCT/CN2015/095765 dated Mar. 4, 2016.

Anonymous: "Archive History for NCT03000530", Aug. 4, 2017, Retrieved from the Internet: <URL:https://www.clinicaltrials.gov/ct2/his> tory/NCT03000530?V—_6=View#StudyPageTop; [retrieved on Nov. 20, 2018].

CAS Registry No. 1040410-23-8 [Database Registry in STN]; STN Entry Date: Aug. 12, 2008; Chemical Name: 1-((3S,8R,9S,10S,13S,14S,17S)-3-hydroxy-10,13-dimethyl-2,3,4,5,8,9,10,11,12,13,14,15,16,17-tetradecahydro-1H-cyclopenta[a]phenanthren-17-yl)ethan-1-one.

CAS Registry No. 162882-77-1 [Database Registry in STN]; STN Entry Date: May 11, 1995; Chemical Name: (3a,5b)-3-Hydroxy-3-methyl-19-norpregnan-20-one.

CAS Registry No. 162883-68-3 [Database Registry in STN]; STN Entry Date: May 11, 1995; Chemical Name: 19-Norpregnan-20-one, 3-hydroxy-3-methyl-, (3a,5a)-.

Chen et al., "The mechanism investigation in substitution of 21-bromo-3a-hydroxy-3b-methoxymethyl-5a-pregnan-20-one with nucleophiles", Steroids, vol. 71, (2006), pp. 942-948.

Database Medline, US National Library of Medicine, Bethesda, MD, 1984, Welling: "Intentions affecting drug absorption", Database accession No. NLM6388952, abstract.

Eimon et al., "Brain activity patterns in high-throughput electrophysiology screen predict both drug efficacies and side affects", Nature Communications, (2018) 9:219, pp. 1-14.

Gottesmann, "GABA Mechanisms and Sleep", Neuroscience, (2002), vol. 111, No. 2, pp. 231-239.

Gunduz-Bruce et al.,"Sage-217 in Subjects with Major Depressive Disorder: Efficacy and Safety Results from Open-Label Part A of a Phase 2a Study", Poster, (Presented on Sep. 2-5, 2017 at the 30th ECNP Congress, Paris, France.

Hawkins et al., "The synthetic neuroactive steroid SGE-516 reduces seizure burden and improves survival in a Dravet syndrome mouse model", Science Reports, (2017), pp. 1-8.

International Search Report and Written Opinion for Corresponding International Application No. PCT/US2018/050012 dated Dec. 7, 2018.

International Search Report and Written Opinion for Corresponding International Application No. PCT/US2018/051048 dated Jan. 11, 2019.

Kanes et al., "A multiple-ascending dose study of the neuroactive steroid Sage-217", Biological Psychiatry, vol. 81, No. 10, 2017, pp. S347.

(56) References Cited

OTHER PUBLICATIONS

Kanes et al., "A single-ascending dose study of the neuroactive steroid Sage-217", Biological Psychiatry, vol. 81, No. 10, 2017, pp. S31.
Möhler, "The GABA system in anxiety and depression and its therapeutic potential", Neuropharmacology, (2012) 62; pp. 42-53.
Sage Therapeutics: "Sage Therapeutics Advances SAGE-217 into Placebo-Controlled Phase 2 Clinical Trial in Major Depressive Disorder", Feb. 13, 2017, Retrieved from the Internet: <URL:https://investor.sagerx.com/static-fil> es/80fflf35-fc4c-4eb2-9456-3228ec891a59; [retrieved on Dec. 21, 2018].
Welling, "Interactions affecting drug absorption", Clinical Pharmacokinetics, vol. 9, No. 5, Sep. 1984 (Sep. 1984), pp. 404-434.

3,3 DISUBSTITUTED 19-NOR PREGNANE COMPOUNDS, COMPOSITIONS, AND USES THEREOF

RELATED APPLICATIONS

This application is a continuation of U.S. Ser. No. 14/351,449 filed Apr. 11, 2014, which is a national stage application under 35 U.S.C. § 371 of International Application No. PCT/US2012/060136 filed Oct. 12, 2012, published as International Publication No. WO2013/056181 on Apr. 18, 2013, which claims priority under 35 U.S.C. § 119(e) to U.S. provisional patent applications, U.S. Ser. No. 61/547,291, filed Oct. 14, 2011 and U.S. Ser. No. 61/698,204, filed Sep. 7, 2012, each of which is incorporated herein by reference.

BACKGROUND OF THE INVENTION

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately −70 mV, the cell interior being negative with respect to the cell exterior. The potential (voltage) is the result of ion ($K^+$, $Na^+$, $Cl^-$, organic anions) balance across the neuronal semipermeable membrane. Neurotransmitters are stored in presynaptic vesicles and are released under the influence of neuronal action potentials. When released into the synaptic cleft, an excitatory chemical transmitter such as acetylcholine will cause membrane depolarization (change of potential from −70 mV to −50 mV). This effect is mediated by postsynaptic nicotinic receptors which are stimulated by acetylcholine to increase membrane permeability to $Na^+$ ions. The reduced membrane potential stimulates neuronal excitability in the form of a postsynaptic action potential.

In the case of the GABA receptor complex (GRC), the effect on brain excitability is mediated by GABA, a neurotransmitter. GABA has a profound influence on overall brain excitability because up to 40% of the neurons in the brain utilize GABA as a neurotransmitter. GABA regulates the excitability of individual neurons by regulating the conductance of chloride ions across the neuronal membrane. GABA interacts with its recognition site on the GRC to facilitate the flow of chloride ions down an electrochemical gradient of the GRC into the cell. An intracellular increase in the levels of this anion causes hyperpolarization of the transmembrane potential, rendering the neuron less susceptible to excitatory inputs (i.e., reduced neuron excitability). In other words, the higher the chloride ion concentration in the neuron, the lower the brain excitability (the level of arousal).

It is well-documented that the GRC is responsible for the mediation of anxiety, seizure activity, and sedation. Thus, GABA and drugs that act like GABA or facilitate the effects of GABA (e.g., the therapeutically useful barbiturates and benzodiazepines (BZs), such as VALIUM® (Diazepam)) produce their therapeutically useful effects by interacting with specific regulatory sites on the GRC. Accumulated evidence has now indicated that in addition to the benzodiazepine and barbiturate binding site, the GRC contains a distinct site for neuroactive steroids (Lan, N. C. et al., *Neurochem. Res.* 16:347-356 (1991)).

Neuroactive steroids can occur endogenously. The most potent endogenous neuroactive steroids are 3α-hydroxy-5-reduced pregnan-20-one and 3α-21-dihydroxy-5-reduced pregnan-20-one, metabolites of hormonal steroids progesterone and deoxycorticosterone, respectively. The ability of these steroid metabolites to alter brain excitability was recognized in 1986 (Majewska, M. D. et al., *Science* 232:1004-1007 (1986); Harrison, N. L. et al., *J Pharmacol. Exp. Ther.* 241:346-353 (1987)).

The ovarian hormone progesterone and its metabolites have been demonstrated to have profound effects on brain excitability (Backstrom, T. et al., *Acta Obstet. Gynecol. Scand. Suppl.* 130:19-24 (1985); Pfaff, D. W and McEwen, B. S., *Science* 219:808-814 (1983); Gyermek et al., *J Med Chem.* 11: 117 (1968); Lambert, J. et al., *Trends Pharmacol. Sci.* 8:224-227 (1987)). The levels of progesterone and its metabolites vary with the phases of the menstrual cycle. It has been well documented that the levels of progesterone and its metabolites decrease prior to the onset of menses. The monthly recurrence of certain physical symptoms prior to the onset of menses has also been well documented. These symptoms, which have become associated with premenstrual syndrome (PMS), include stress, anxiety, and migraine headaches (Dalton, K., *Premenstrual Syndrome and Progesterone Therapy*, 2nd edition, Chicago Yearbook, Chicago (1984)). Subjects with PMS have a monthly recurrence of symptoms that are present in premenses and absent in postmenses.

In a similar fashion, a reduction in progesterone has also been temporally correlated with an increase in seizure frequency in female epileptics, i.e., catamenial epilepsy (Laidlaw, J., *Lancet*, 1235-1237 (1956)). A more direct correlation has been observed with a reduction in progesterone metabolites (Rosciszewska et al., *J. Neurol. Neurosurg. Psych.* 49:47-51 (1986)). In addition, for subjects with primary generalized petit mal epilepsy, the temporal incidence of seizures has been correlated with the incidence of the symptoms of premenstrual syndrome (Backstrom, T. et al., *J. Psychosom. Obstet. Gynaecol.* 2:8-20 (1983)). The steroid deoxycorticosterone has been found to be effective in treating subjects with epileptic spells correlated with their menstrual cycles (Aird, R. B. and Gordan, G., *J. Amer. Med. Soc.* 145:715-719 (1951)).

A syndrome also related to low progesterone levels is postnatal depression (PND). Immediately after birth, progesterone levels decrease dramatically leading to the onset of PND. The symptoms of PND range from mild depression to psychosis requiring hospitalization. PND is also associated with severe anxiety and irritability. PND-associated depression is not amenable to treatment by classic antidepressants, and women experiencing PND show an increased incidence of PMS (Dalton, K., *Premenstrual Syndrome and Progesterone Therapy*, 2nd edition, Chicago Yearbook, Chicago (1984)).

Collectively, these observations imply a crucial role for progesterone and deoxycorticosterone and more specifically their metabolites in the homeostatic regulation of brain excitability, which is manifested as an increase in seizure activity or symptoms associated with catamenial epilepsy, PMS, and PND. The correlation between reduced levels of progesterone and the symptoms associated with PMS, PND, and catamenial epilepsy (Backstrom, T. et al., *J Psychosom. Obstet. Gynaecol.* 2:8-20 (1983)); Dalton, K., Premenstrual Syndrome and Progesterone Therapy, 2nd edition, Chicago Yearbook, Chicago (1984)) has prompted the use of progesterone in their treatment (Mattson et al., "Medroxyprogesterone therapy of catamenial epilepsy," in *Advances in Epileptology: XVth Epilepsy International Symposium*, Raven Press, New York (1984), pp. 279-282, and Dalton, K.,

*Premenstrual Syndrome and Progesterone Therapy*, 2nd edition, Chicago Yearbook, Chicago (1984)). However, progesterone is not consistently effective in the treatment of the aforementioned syndromes. For example, no dose-response relationship exists for progesterone in the treatment of PMS (Maddocks et al., *Obstet. Gynecol.* 154:573-581 (1986); Dennerstein et al., *Brit. Med J* 290:16-17 (1986)).

New and improved neuroactive steroids are needed that act as modulating agents for brain excitability, as well as agents for the prevention and treatment of CNS-related diseases. The compounds, compositions, and methods described herein are directed toward this end.

SUMMARY OF THE INVENTION

The present invention is based, in part, on the desire to provide novel 19-nor compounds with good potency, pharmacokinetic (PK) properties, oral bioavailability, formulatability, stability, safety, clearance and/or metabolism. One key feature of the compounds as described herein is disubstitution at the C3 position. The inventors envision disubstitution at C-3 will eliminate the potential for oxidation to the ketone, prevent further metabolism, and reduce the potential for secondary elimination pathways, such as glucuronidation. The inventors further envision the overall effect of C3 disubstitution should be of improving the overall PK parameters and reducing potential toxicities and side effects, which may allow, in certain embodiments, administration orally and/or chronically. Another key feature of the compounds as described herein is the presence of a hydrogen at the C10 position ("19-nor") rather than a methyl group. The inventors envision 19-nor compounds, as compared to their C10-methyl counterparts, will have improved physical properties, such as improved solubility. The inventors envision further enhancement of solubility, for example, when the AB ring system is in the cis configuration.

Thus, in one aspect, provided herein are compounds according to Formula (I) or (III):

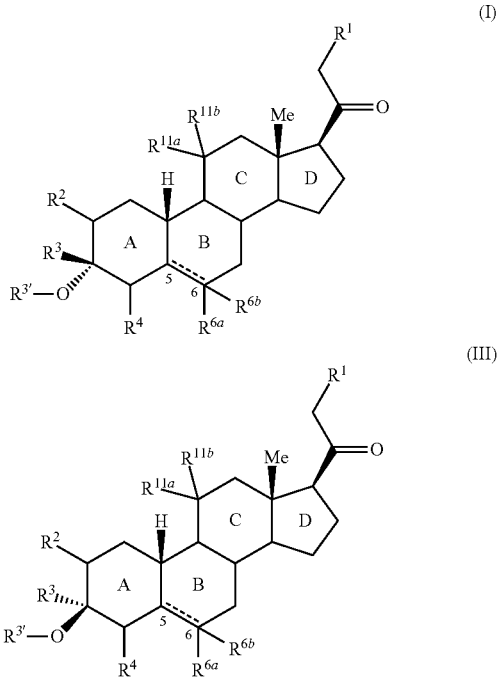

or a pharmaceutically acceptable salt, solvate, hydrate, prodrug, stereoisomer, tautomer, isotopic variant, or N-oxide thereof, or a combination thereof; wherein $R^2$, $R^4$, $R^{6a}$, $R^{6b}$, $R^{11a}$, $R^{11b}$, are as defined herein, $R^1$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{41}$, $-SR^{41}$, $-N(R^{41})_2$, $-OC(=O)R^{41}$, $-OC(=O)OR^{41}$, $-OC(=O)SR^{41}$, $-OC(=O)N(R^{41})_2$, $-SC(=O)R^{42}$, $-SC(=O)OR^{41}$, $-SC(=O)SR^{41}$, $-SC(=O)N(R^{41})_2$, $-NHC(=O)R^{41}$, $-NHC(=O)OR^{41}$, $-NHC(=O)SR^{41}$, $-NHC(=O)N(R^{41})_2$, $-OS(=O)_2R^{42}$, $-OS(=O)_2OR^{41}$, $-S-S(=O)_2R^{42}$, $-S-S(=O)_2OR^{41}$, $-S(=O)R^{42}$, $-SO_2R^{42}$, or $-S(=O)_2OR^{41}$, wherein each instance of $R^{41}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, a nitrogen protecting group when attached to a nitrogen atom, or two $R^{41}$ groups are joined to form an substituted or unsubstituted heterocyclic or heteroaryl ring; and $R^{42}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^3$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and $R^{3'}$ is hydrogen, $-C(=O)R^{C1}$, $-C(=O)OR^{C1}$, $-C(=O)SR^{C1}$, $-C(=O)N(R^{C1})_2$, $-S(=O)_2R^{C2}$, $-S(=O)_2OR^{C1}$, $-P(=O)_2R^{C2}$, $-P(=O)_2OR^{C1}$, $-P(=O)(OR^{C1})_2$, $-P(=O)(R^{C2})_2$, or $-P(=O)(R^{C2})(OR^{C1})$, wherein $R^{C1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group when attached to an oxygen atom, a sulfur protecting group when attached to a sulfur atom, a nitrogen protecting group when attached to a nitrogen atom, or two $R^{C1}$ groups are joined to form an substituted or unsubstituted heterocyclic ring; and $R^{C2}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

wherein ===== independently represents a single or double bond, provided if a double bond is present in Ring B, then one of $R^{6a}$ or $R^{6b}$ is absent, and provided if a single bond is present in Ring B, then the hydrogen at C5 is in the alpha or beta position.

In another aspect, provided is a pharmaceutical composition comprising a compound of Formula (I) or (III) and a pharmaceutically acceptable carrier. In certain embodiments, the compound of the present invention is provided in an effective amount in the pharmaceutical composition. In certain embodiments, the compound of the present invention is provided in a therapeutically effective amount. In certain embodiments, the compound of the present invention is provided in a prophylactically effective amount.

Compounds as described herein, act, in certain embodiments, as GABA modulators, e.g., effecting the $GABA_A$ receptor in either a positive or negative manner. As modulators of the excitability of the central nervous system (CNS), as mediated by their ability to modulate $GABA_A$ receptor, such compounds are expected to have CNS-activity.

Thus, in another aspect, provided are methods of treating a CNS-related condition in a subject in need thereof, comprising administering to the subject an effective amount of a compound of Formula (I) or (III) to the subject. In certain embodiments, the CNS-related condition is insomnia, depression, mood disorders, convulsive disorders, memory disorders, attention disorders, anxiety disorders, bipolar disorder, schizophrenia, depression, bipolar disorder, schizoaffective disorder, mood disorders, anxiety disorders, personality disorders, psychosis, compulsive disorders, post-traumatic stress disorder, Autism spectrum disorder, dysthymia, social anxiety disorder, obsessive compulsive disorder, pain, sleep disorders, memory disorders, dementia, Alzheimer's disease, a seizure disorder, traumatic brain injury, stroke, addictive disorders, autism, Huntington's disease, Parkinson's disease, Rett syndrome, withdrawal syndromes, or tinnitus.

Other objects and advantages will become apparent to those skilled in the art from a consideration of the ensuing detailed description, examples, and claims.

Definitions

Chemical Definitions

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Thomas Sorrell, Organic Chemistry, University Science Books, Sausalito, 1999; Smith and March, March's Advanced Organic Chemistry, 5th Edition, John Wiley & Sons, Inc., New York, 2001; Larock, Comprehensive Organic Transformations, VCH Publishers, Inc., New York, 1989; and Carruthers, Some Modern Methods of Organic Synthesis, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

As used herein and unless otherwise indicated, the term "enantiomerically pure R-compound" refers to at least about 80% by weight R-compound and at most about 20% by weight S-compound, at least about 90% by weight R-compound and at most about 10% by weight S-compound, at least about 95% by weight R-compound and at most about 5% by weight S-compound, at least about 99% by weight R-compound and at most about 1% by weight S-compound, at least about 99.9% by weight R-compound or at most about 0.1% by weight S-compound. In certain embodiments, the weights are based upon total weight of compound.

As used herein and unless otherwise indicated, the term "enantiomerically pure S-compound" or "S-compound" refers to at least about 80% by weight S-compound and at most about 20% by weight R-compound, at least about 90% by weight S-compound and at most about 10% by weight R-compound, at least about 95% by weight S-compound and at most about 5% by weight R-compound, at least about 99% by weight S-compound and at most about 1% by weight R-compound or at least about 99.9% by weight S-compound and at most about 0.1% by weight R-compound. In certain embodiments, the weights are based upon total weight of compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The articles "a" and "an" may be used herein to refer to one or to more than one (i.e. at least one) of the grammatical objects of the article. By way of example "an analogue" means one analogue or more than one analogue.

The following terms are intended to have the meanings presented therewith below and are useful in understanding the description and intended scope of the present invention.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl.

"Alkylene" refers to a substituted or unsubstituted alkyl group, as defined above, wherein two hydrogens are removed to provide a divalent radical. Exemplary divalent alkylene groups include, but are not limited to, methylene (—$CH_2$—), ethylene (—$CH_2CH_2$—), the propylene isomers (e.g., —$CH_2CH_2CH_2$— and —$CH(CH_3)CH_2$—) and the like.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkenylene" refers a substituted or unsubstituted alkenyl group, as defined above, wherein two hydrogens are removed to provide a divalent radical. Exemplary divalent alkenylene groups include, but are not limited to, ethenylene (—CH═CH—), propenylenes (e.g., —CH═CHCH$_2$— and —C(CH$_3$)═CH— and —CH═C(CH$_3$)—), and the like.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

"Alkynylene" refers a substituted or unsubstituted alkynyl group, as defined above, wherein two hydrogens are removed to provide a divalent radical. Exemplary divalent alkynylene groups include, but are not limited to, ethynylene, propynylene, and the like.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl. In certain embodiments, an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following:

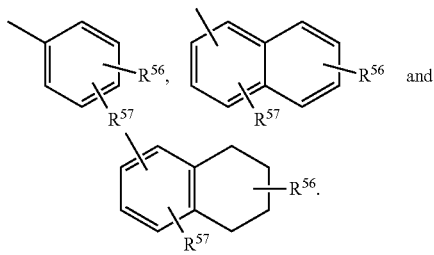

In these formulae one of $R^{56}$ and $R^{57}$ may be hydrogen, and at least one of $R^{56}$ and $R^{57}$ is each independently selected from $C_1$-$C_8$ alkyl, $C_1$-$C_8$ haloalkyl, 4-10 membered heterocyclyl, alkanoyl, $C_1$-$C_8$ alkoxy, heteroaryloxy, alkylamino, arylamino, heteroarylamino, —$NR^{58}COR^{59}$, —$NR^{58}SOR^{59}$, —$NR^{58}SO_2R^{59}$, —COOalkyl, —COOaryl, —$CONR^{58}R^{59}$, —$CONR^{58}OR^{59}$, —$NR^{58}R^{59}$, —$SO_2NR^{58}R^{59}$, —S-alkyl, —SOalkyl, —$SO_2$alkyl, —Saryl, —SOaryl, —$SO_2$aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, $C_1$-$C_8$ alkyl, $C_1$-$C_4$ haloalkyl, $C_3$-$C_{10}$ cycloalkyl, 4-10 membered heterocyclyl, $C_6$-$C_{10}$ aryl, substituted $C_6$-$C_{10}$ aryl, 5-10 membered heteroaryl, or substituted 5-10 membered heteroaryl.

"Fused aryl" refers to an aryl having two of its ring carbon in common with a second aryl ring or with an aliphatic ring.

"Aralkyl" is a subset of alkyl and aryl, as defined herein, and refers to an optionally substituted alkyl group substituted by an optionally substituted aryl group.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl.

Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

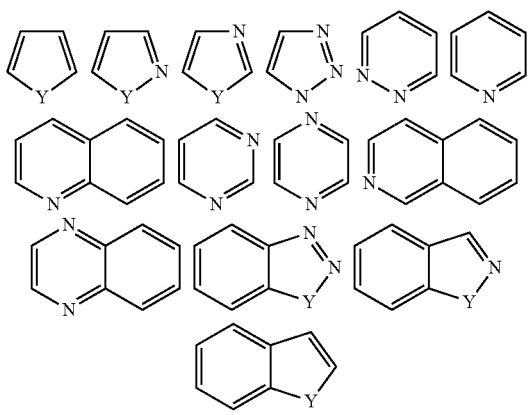

wherein each Y is selected from carbonyl, N, NR$^{65}$, O, and S; and R$^{65}$ is independently hydrogen, C$_1$-C$_8$ alkyl, C$_3$-C$_{10}$ cycloalkyl, 4-10 membered heterocyclyl, C$_6$-C$_{10}$ aryl, and 5-10 membered heteroaryl.

Examples of representative aryl having heteroatom-containing substitutions include the following:

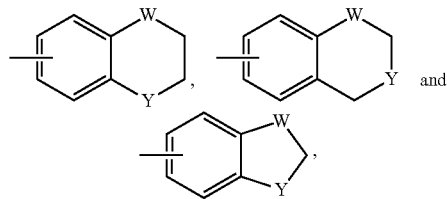

wherein each W is selected from C(R$^{66}$)$_2$, NR$^{66}$, O, and S; and each Y is selected from carbonyl, NR$^{66}$, O, and S; and R$^{66}$ is independently hydrogen, C$_1$-C$_8$ alkyl, C$_3$-C$_{10}$ cycloalkyl, 4-10-membered heterocyclyl, C$_6$-C$_{10}$ aryl, and 5-10-membered heteroaryl.

"Heteroaralkyl" is a subset of alkyl and heteroaryl, as defined herein, and refers to an optionally substituted alkyl group substituted by an optionally substituted heteroaryl group.

"Carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is a substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl.

Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

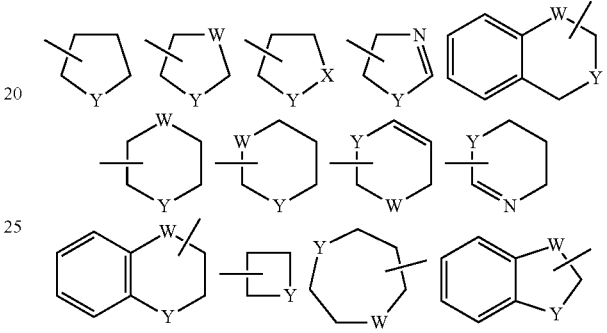

wherein each W is selected from $CR^{67}$, $C(R^{67})_2$, $NR^{67}$, O, and S; and each Y is selected from $NR^{67}$, O, and S; and $R^{67}$ is independently hydrogen, $C_1$-$C_8$ alkyl, $C_3$-$C_{10}$ cycloalkyl, 4-10 membered heterocyclyl, $C_6$-$C_{10}$ aryl, 5-10 membered heteroaryl. These heterocyclyl rings may be optionally substituted with one or more substituents selected from the group consisting of the group consisting of acyl, acylamino, acyloxy, alkoxy, alkoxycarbonyl, alkoxycarbonylamino, amino, substituted amino, aminocarbonyl (carbamoyl or amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

"Acyl" refers to a radical —C(O)R$^{20}$, where R$^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein R$^{20}$ is a group other than hydrogen. Representative acyl groups include, but are not limited to, formyl (—CHO), acetyl (—C(═O)CH$_3$), cyclohexylcarbonyl, cyclohexylmethylcarbonyl, benzoyl (—C(═O)Ph), benzylcarbonyl (—C(═O)CH$_2$Ph), —C(O)—C$_1$-C$_8$ alkyl, —C(O)—(CH$_2$)$_t$(C$_6$-C$_{10}$ aryl), —C(O)—(CH$_2$)$_t$(5-10 membered heteroaryl), —C(O)—

$(CH_2)_t(C_3\text{-}C_{10}$ cycloalkyl), and —C(O)—$(CH_2)_t$(4-10 membered heterocyclyl), wherein t is an integer from 0 to 4. In certain embodiments, $R^{21}$ is $C_1\text{-}C_8$ alkyl, substituted with halo or hydroxy; or $C_3\text{-}C_{10}$ cycloalkyl, 4-10 membered heterocyclyl, $C_6\text{-}C_{10}$ aryl, arylalkyl, 5-10 membered heteroaryl or heteroarylalkyl, each of which is substituted with unsubstituted $C_1\text{-}C_4$ alkyl, halo, unsubstituted $C_1\text{-}C_4$ alkoxy, unsubstituted $C_1\text{-}C_4$ haloalkyl, unsubstituted $C_1\text{-}C_4$ hydroxyalkyl, or unsubstituted $C_1\text{-}C_4$ haloalkoxy or hydroxy.

"Acylamino" refers to a radical —$NR^{22}C(O)R^{23}$, where each instance of $R^{22}$ and $R^{23}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein, or $R^{22}$ is an amino protecting group. Exemplary "acylamino" groups include, but are not limited to, formylamino, acetylamino, cyclohexylcarbonylamino, cyclohexylmethyl-carbonylamino, benzoylamino and benzylcarbonylamino. Particular exemplary "acylamino" groups are —$NR^{24}C(O)$—$C_1\text{-}C_8$ alkyl, —$NR^{24}C(O)$—$(CH_2)_t(C_6\text{-}C_{10}$ aryl), —$NR^{24}C(O)$—$(CH_2)_t$(5-10 membered heteroaryl), —$NR^{24}C(O)$—$(CH_2)_t(C_3\text{-}C_{10}$ cycloalkyl), and —$NR^{24}C(O)$—$(CH_2)_t$(4-10 membered heterocyclyl), wherein t is an integer from 0 to 4, and each $R^{24}$ independently represents H or $C_1\text{-}C_8$ alkyl. In certain embodiments, $R^{25}$ is H, $C_1\text{-}C_8$ alkyl, substituted with halo or hydroxy; $C_3\text{-}C_{10}$ cycloalkyl, 4-10 membered heterocyclyl, $C_6\text{-}C_{10}$ aryl, arylalkyl, 5-10 membered heteroaryl or heteroarylalkyl, each of which is substituted with unsubstituted $C_1\text{-}C_4$ alkyl, halo, unsubstituted $C_1\text{-}C_4$ alkoxy, unsubstituted $C_1\text{-}C_4$ haloalkyl, unsubstituted $C_1\text{-}C_4$ hydroxyalkyl, or unsubstituted $C_1\text{-}C_4$ haloalkoxy or hydroxy; and $R^{26}$ is H, $C_1\text{-}C_8$ alkyl, substituted with halo or hydroxy; $C_3\text{-}C_{10}$ cycloalkyl, 4-10 membered heterocyclyl, $C_6\text{-}C_{10}$ aryl, arylalkyl, 5-10 membered heteroaryl or heteroarylalkyl, each of which is substituted with unsubstituted $C_1\text{-}C_4$ alkyl, halo, unsubstituted $C_1\text{-}C_4$ alkoxy, unsubstituted $C_1\text{-}C_4$ haloalkyl, unsubstituted $C_1\text{-}C_4$ hydroxyalkyl, or unsubstituted $C_1\text{-}C_4$ haloalkoxy or hydroxyl; provided at least one of $R^{25}$ and $R^{26}$ is other than H.

"Acyloxy" refers to a radical —$OC(O)R^{27}$, where $R^{27}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. Representative examples include, but are not limited to, formyl, acetyl, cyclohexylcarbonyl, cyclohexylmethylcarbonyl, benzoyl and benzylcarbonyl. In certain embodiments, $R^{28}$ is $C_1\text{-}C_8$ alkyl, substituted with halo or hydroxy; $C_3\text{-}C_{10}$ cycloalkyl, 4-10 membered heterocyclyl, $C_6\text{-}C_{10}$ aryl, arylalkyl, 5-10 membered heteroaryl or heteroarylalkyl, each of which is substituted with unsubstituted $C_1\text{-}C_4$ alkyl, halo, unsubstituted $C_1\text{-}C_4$ alkoxy, unsubstituted $C_1\text{-}C_4$ haloalkyl, unsubstituted $C_1\text{-}C_4$ hydroxyalkyl, or unsubstituted $C_1\text{-}C_4$ haloalkoxy or hydroxy.

"Alkoxy" refers to the group —$OR^{29}$ where $R^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, $R^{29}$ is a group that has 1 or more substituents, for instance from 1 to 5 substituents, and particularly from 1 to 3 substituents, in particular 1 substituent, selected from the group consisting of amino, substituted amino, $C_6\text{-}C_{10}$ aryl, aryloxy, carboxyl, cyano, $C_3\text{-}C_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, —O—$(CH_2)_t(C_6\text{-}C_{10}$ aryl), —O—$(CH_2)_t$(5-10 membered heteroaryl), —O—$(CH_2)_t(C_3\text{-}C_{10}$ cycloalkyl), and —O—$(CH_2)_t$(4-10 membered heterocyclyl), wherein t is an integer from 0 to 4 and any aryl, heteroaryl, cycloalkyl or heterocyclyl groups present, may themselves be substituted by unsubstituted $C_1\text{-}C_4$ alkyl, halo, unsubstituted $C_1\text{-}C_4$ alkoxy, unsubstituted $C_1\text{-}C_4$ haloalkyl, unsubstituted $C_1\text{-}C_4$ hydroxyalkyl, or unsubstituted $C_1\text{-}C_4$ haloalkoxy or hydroxy. Particular exemplary 'substituted alkoxy' groups are —$OCF_3$, —$OCH_2CF_3$, —$OCH_2Ph$, —$OCH_2$-cyclopropyl, —$OCH_2CH_2OH$, and —$OCH_2CH_2NMe_2$.

"Amino" refers to the radical —$NH_2$.

"Substituted amino" refers to an amino group of Formula —$N(R^{38})_2$ wherein $R^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{38}$ is not a hydrogen. In certain embodiments, each $R^{38}$ is independently selected from: hydrogen, $C_1\text{-}C_8$ alkyl, $C_3\text{-}C_8$ alkenyl, $C_3\text{-}C_8$ alkynyl, $C_6\text{-}C_{10}$ aryl, 5-10 membered heteroaryl, 4-10 membered heterocyclyl, or $C_3\text{-}C_{10}$ cycloalkyl; or $C_1\text{-}C_8$ alkyl, substituted with halo or hydroxy; $C_3\text{-}C_8$ alkenyl, substituted with halo or hydroxy; $C_3\text{-}C_8$ alkynyl, substituted with halo or hydroxy, or —$(CH_2)_t(C_6\text{-}C_{10}$ aryl), —$(CH_2)_t$(5-10 membered heteroaryl), —$(CH_2)_t(C_3\text{-}C_{10}$ cycloalkyl), or —$(CH_2)_t$(4-10 membered heterocyclyl), wherein t is an integer between 0 and 8, each of which is substituted by unsubstituted $C_1\text{-}C_4$ alkyl, halo, unsubstituted $C_1\text{-}C_4$ alkoxy, unsubstituted $C_1\text{-}C_4$ haloalkyl, unsubstituted $C_1\text{-}C_4$ hydroxyalkyl, or unsubstituted $C_1\text{-}C_4$ haloalkoxy or hydroxy; or both $R^{38}$ groups are joined to form an alkylene group.

Exemplary 'substituted amino' groups are —$NR^{39}$—$C_1\text{-}C_8$ alkyl, —$NR^{39}$—$(CH_2)_t(C_6\text{-}C_{10}$ aryl), —$NR^{39}$—$(CH_2)_t$(5-10 membered heteroaryl), —$NR^{39}$—$(CH_2)_t(C_3\text{-}C_{10}$ cycloalkyl), and —$NR^{39}$—$(CH_2)_t$(4-10 membered heterocyclyl), wherein t is an integer from 0 to 4, for instance 1 or 2, each $R^{39}$ independently represents H or $C_1\text{-}C_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1\text{-}C_4$ alkyl, halo, unsubstituted $C_1\text{-}C_4$ alkoxy, unsubstituted $C_1\text{-}C_4$ haloalkyl, unsubstituted $C_1\text{-}C_4$ hydroxyalkyl, or unsubstituted $C_1\text{-}C_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both mono-substituted amino and disubstituted amino groups.

"Azido" refers to the radical —$N_3$.

"Carbamoyl" or "amido" refers to the radical —C(O)NH$_2$.

"Substituted carbamoyl" or "substituted amido" refers to the radical —C(O)N($R^{62}$)$_2$ wherein each $R^{62}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{62}$ is not a hydrogen. In certain embodiments, $R^{62}$ is selected from H, $C_1$-$C_8$ alkyl, $C_3$-$C_{10}$ cycloalkyl, 4-10 membered heterocyclyl, $C_6$-$C_{10}$ aryl, aralkyl, 5-10 membered heteroaryl, and heteroaralkyl; or $C_1$-$C_8$ alkyl substituted with halo or hydroxy; or $C_3$-$C_{10}$ cycloalkyl, 4-10 membered heterocyclyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; provided that at least one $R^{62}$ is other than H. Exemplary 'substituted carbamoyl' groups include, but are not limited to, —C(O)N$R^{64}$—$C_1$-$C_8$ alkyl, —C(O)N$R^{64}$—(CH$_2$)$_t$($C_6$-$C_{10}$ aryl), —C(O)N$R^{64}$—(CH$_2$)$_t$(5-10 membered heteroaryl), —C(O)N$R^{64}$—(CH$_2$)$_t$($C_3$-$C_{10}$ cycloalkyl), and —C(O)N$R^{64}$—(CH$_2$)$_t$(4-10 membered heterocyclyl), wherein t is an integer from 0 to 4, each $R^{64}$ independently represents H or $C_1$-$C_8$ alkyl and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Carboxy" refers to the radical —C(O)OH.

"Cyano" refers to the radical —CN.

"Halo" or "halogen" refers to fluoro (F), chloro (Cl), bromo (Br), and iodo (I). In certain embodiments, the halo group is either fluoro or chloro.

"Hydroxy" refers to the radical —OH.

"Nitro" refers to the radical —NO$_2$.

"Cycloalkylalkyl" refers to an alkyl radical in which the alkyl group is substituted with a cycloalkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocyclylalkyl" refers to an alkyl radical in which the alkyl group is substituted with a heterocyclyl group. Typical heterocyclylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Cycloalkenyl" refers to substituted or unsubstituted carbocyclyl group having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Fused cycloalkenyl" refers to a cycloalkenyl having two of its ring carbon atoms in common with a second aliphatic or aromatic ring and having its olefinic unsaturation located to impart aromaticity to the cycloalkenyl ring.

"Ethenyl" refers to substituted or unsubstituted —(CH=CH)—.

"Ethylene" refers to substituted or unsubstituted —(CH$_2$—CH$_2$)—.

"Ethynyl" refers to —(C≡C)—.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —O$R^{aa}$, —ON($R^{bb}$)$_2$, —N($R^{bb}$)$_2$, —N($R^{bb}$)$_3^+$X$^-$, —N(O$R^{cc}$)$R^{bb}$, —SH, —S$R^{aa}$, —SS$R^{cc}$, —C(=O)$R^{aa}$, —CO$_2$H, —CHO, —C(O$R^{cc}$)$_2$, —CO$_2$$R^{aa}$, —OC(=O)$R^{aa}$, —OCO$_2$$R^{aa}$, —C(=O)N($R^{bb}$)$_2$, —OC(=O)N($R^{bb}$)$_2$, —N$R^{bb}$C(=O)$R^{aa}$, —N$R^{bb}$CO$_2$$R^{aa}$, —N$R^{bb}$C(=O)N($R^{bb}$)$_2$, —C(=N$R^{bb}$)$R^{aa}$, —C(=N$R^{bb}$)O$R^{aa}$, —OC(=N$R^{bb}$)$R^{aa}$, —OC(=N$R^{bb}$)O$R^{aa}$, —C(=N$R^{bb}$)N($R^{bb}$)$_2$, —OC(=N$R^{bb}$)N($R^{bb}$)$_2$, —N$R^{bb}$C(=N$R^{bb}$)N($R^{bb}$)$_2$, —C(=O)N$R^{bb}$SO$_2$$R^{aa}$, —N$R^{bb}$SO$_2$$R^{aa}$, —SO$_2$N($R^{bb}$)$_2$, —SO$_2$$R^{aa}$, —SO$_2$O$R^{aa}$, —OSO$_2$$R^{aa}$, —S(=O)$R^{aa}$, —OS(=O)$R^{aa}$, —Si($R^{aa}$)$_3$, —OSi($R^{aa}$)$_3$—C(=S)N($R^{bb}$)$_2$, —C(=O)S$R^{aa}$, —C(=S)S$R^{aa}$, —SC(=S)S$R^{aa}$, —SC(=O)S$R^{aa}$, —OC(=O)S$R^{aa}$, —SC(=O)O$R^{aa}$, —SC(=O)$R^{aa}$, —P(=O)$_2$$R^{aa}$, —OP(=O)$_2$$R^{aa}$, —P(=O)($R^{aa}$)$_2$, —OP(=O)($R^{aa}$)$_2$, —OP(=O)(O$R^{cc}$)$_2$, —P(=O)$_2$N($R^{bb}$)$_2$, —OP(=O)$_2$N($R^{bb}$)$_2$, —P(=O)(N$R^{bb}$)$_2$, —OP(=O)(N$R^{bb}$)$_2$, —N$R^{bb}$P(=O)(O$R^{cc}$)$_2$, —N$R^{bb}$P(=O)(N$R^{bb}$)$_2$, —P($R^{cc}$)$_2$, —P($R^{cc}$)$_3$, —OP($R^{cc}$)$_2$, —OP($R^{cc}$)$_3$, —B($R^{aa}$)$_2$, —B(O$R^{cc}$)$_2$, —B$R^{aa}$(O$R^{cc}$), $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups; or two geminal hydrogens on a carbon atom are replaced with the group =O, =S, =NN($R^{bb}$)$_2$, =NN$R^{bb}$C(=O)$R^{aa}$, =NN$R^{bb}$C(=O)O$R^{aa}$, =NN$R^{bb}$S(=O)$_2$$R^{aa}$, =N$R^{bb}$, or =NO$R^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2$$R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3$$^+$X$^-$, —N(O$R^{ee}$)$R^{ff}$, —SH, —S$R^{ee}$, —SS$R^{ee}$, —C(=O)$R^{ee}$, —CO$_2$H, —CO$_2$$R^{ee}$, —OC(=O)$R^{ee}$, —OCO$_2$$R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2$$R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2$$R^{ee}$, —SO$_2$N($R^{ff}$)$_2$, —SO$_2$$R^{ee}$, —SO$_2$O$R^{ee}$, —OSO$_2$$R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)$_2$$R^{ee}$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2$$R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on a nitrogen atom is a nitrogen protecting group (also referred to as an amino protecting group). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2$$R^{aa}$, —SO$_2$$R^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'-and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —$R^{aa}$, —$N(R^{bb})_2$, —C(=O)$SR^{aa}$, —C(=O)$R^{aa}$, —$CO_2R^{aa}$, —C(=O)$N(R^{bb})_2$, —C(=$NR^{bb}$)$R^{aa}$, —C(=$NR^{bb}$)$OR^{aa}$, —C(=$NR^{bb}$)$N(R^{bb})_2$, —S(=O)$R^{aa}$, —$SO_2R^{aa}$, —Si$(R^{aa})_3$, —$P(R^{cc})_2$, —$P(R^{cc})_3$, —P(=O)$R^{aa}$, —P(=O)$(R^{aa})$, —P(=O)$(OR^{cc})$, —P(=O)$N(R^{bb})$, and P(=O)$(NR^{bb})$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Conditions for Forming Exemplary Oxygen Protecting Groups:

| Oxygen Protecting Group | Formation |
| --- | --- |
| Allylsulfonate (Als-OR): $CH_2$=CHCH$_2$SO$_2$R | 1. Allylsulfonyl chloride, Pyr, $CH_2Cl_2$, 55-71% yield |
| Methanesulfonate (Mesylate) (RO-Ms): MeSO$_3$R | 1. MsCl, Et$_3$N, $CH_2Cl_2$, 0° C., generally >90% yield |
| Benzylsulfonate: ROSO$_2$Bn | 1. BnSO$_2$Cl, 2,6-lutidine, $CH_2Cl_2$, >72% yield |
| Tosylate (TsOR): $CH_3C_6H_4SO_3R$ | 1. TsCl, Pyridine<br>2. 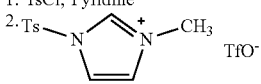<br>This reagent selectively protects a primary alcohol in the presence of a secondary alcohol<br>3. TsCl, DABCO, $CH_2Cl_2$, MTBE or AcOEt, 45-97% yield. In many cases, these conditions were found to be superior to the use of pyridine as a base. DABCO is also less toxic than pyridine, which may prove useful in a commercial setting. |
| Acetate Ester (ROAc): $CH_3CO_2R$ | 1. Ac$_2$O, Pyr, 20° C., 12 h, 100% yield. This is one of the most common methods for the introduction of acetate groups. By running the reaction at lower temperatures, good selectivity can be achieved for primary alcohols over secondary alcohols. Tertiary alcohols are generally not acylated under these conditions.<br>2. CH$_3$COCl, 25° C., 16 h, 67-79% yield.<br>3. CH$_3$COCl, $CH_2Cl_2$, collidine, 91% yield. A primary acetate was formed selectively in the presence of a secondary. These conditions are suitable for a variety of other esters.<br>4. 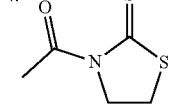<br>NaH, 93% yield. Primary alcohols are selectively acylated. |

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

"Compounds of the present invention", and equivalent expressions, are meant to embrace the compounds as described herein, in particular compounds according to any of Formulae recited and/or described herein, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits. These and other exemplary substituents are described in more detail in the Detailed Description, Examples, and claims. The invention is not intended to be limited in any manner by the above exemplary listing of substituents.

Other Definitions

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like.

The term "pharmaceutically acceptable cation" refers to an acceptable cationic counter-ion of an acidic functional group. Such cations are exemplified by sodium, potassium, calcium, magnesium, ammonium, tetraalkylammonium cations, and the like. See, e.g., Berge, et al., *J. Pharm. Sci.* (1977) 66(1): 1-79.

"Solvate" refers to forms of the compound that are associated with a solvent or water (also referred to as "hydrate"), usually by a solvolysis reaction. This physical association includes hydrogen bonding. Conventional solvents include water, ethanol, acetic acid, and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

"Condition," "disease," and "disorder" are used interchangeably herein.

An "effective amount" means the amount of a compound that, when administered to a subject for treating or preventing a disease, is sufficient to effect such treatment or prevention. The "effective amount" can vary depending on the compound, the disease and its severity, and the age, weight, etc., of the subject to be treated. A "therapeutically effective amount" refers to the effective amount for therapeutic treatment. A "prophylatically effective amount" refers to the effective amount for prophylactic treatment.

"Preventing" or "prevention" or "prophylactic treatment" refers to a reduction in risk of acquiring or developing a disease or disorder (i.e., causing at least one of the clinical symptoms of the disease not to develop in a subject not yet exposed to a disease-causing agent, or predisposed to the disease in advance of disease onset). The term "prophylaxis" is related to "prevention," and refers to a measure or procedure the purpose of which is to prevent, rather than to treat or cure a disease.

"Treating" or "treatment" or "therapeutic treatment" of any disease or disorder refers to ameliorating the disease or disorder (i.e., arresting the disease or reducing the manifestation, extent or severity of at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e., $^3$H, and carbon-14, i.e., $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O, and $^{13}$N, and would be useful in Positron Emission Topography (PET) studies for examining substrate receptor occupancy. All isotopic variants of the compounds provided herein, radioactive or not, are intended to be encompassed within the scope of the invention.

"Stereoisomers": It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

"Pharmaceutically acceptable metabolically cleavable group" refers to a group which is cleaved in vivo to yield the parent molecule of the structural Formula indicated herein. Examples of metabolically cleavable groups include —COR, —COOR, —CONRR and —CH$_2$OR radicals, where R is selected independently at each occurrence from alkyl, trialkylsilyl, carbocyclic aryl or carbocyclic aryl substituted with one or more of alkyl, halogen, hydroxy or alkoxy. Specific examples of representative metabolically cleavable groups include acetyl, methoxycarbonyl, benzoyl, methoxymethyl and trimethylsilyl groups.

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. Particularly the $C_1$ to $C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of the invention.

"Compounds of the present invention", and equivalent expressions, are meant to embrace the compounds as described herein, in particular compounds according to any of Formulae recited and/or described herein, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

DETAILED DESCRIPTION OF CERTAIN EMBODIMENTS OF THE INVENTION

As described herein, the present invention is based, in part, on the desire to provide novel 19-nor compounds with good potency, pharmacokinetic (PK) properties, oral bioavailability, formulatability, stability, safety, clearance and/or metabolism. One key feature of the compounds as described herein is disubstitution at the C3 position. The inventors envision disubstitution at C-3 will eliminate the potential for oxidation to the ketone, prevent further metabolism, and reduce the potential for secondary elimination pathways, such as glucuronidation. The inventors further envision the overall effect of C3 disubstitution should be of improving the overall PK parameters and reducing potential toxicities and side effects, which may allow, in certain embodiments, administration orally and/or chronically. Another key feature of the compounds as described herein is the presence of a hydrogen at the C10 position ("19-nor") rather than a methyl group. The inventors envision 19-nor compounds, as compared to their C10-methyl counterparts, will have improved physical properties, such as improved solubility. The inventors envision further enhancement of solubility, for example, when the AB ring system is in the cis configuration.

Thus, in one aspect, provided is a 3,3-disubstituted 19-nor pregnane compound of Formula (I):

(I)

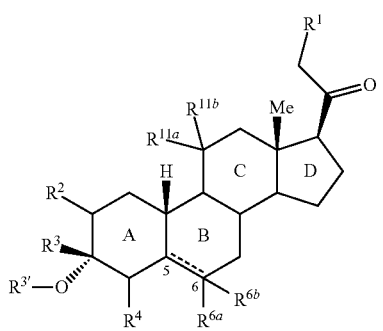

or a pharmaceutically acceptable salt, solvate, hydrate, prodrug, stereoisomer, tautomer, isotopic variant, or N-oxide thereof, or a combination thereof;
wherein:
$R^1$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{A1}$, $-SR^{A1}$, $-N(R^{A1})_2$, $-OC(=O)R^{A1}$, $-OC(=O)OR^{A1}$, $-OC(=O)SR^{A1}$, $-OC(=O)N(R^{A1})_2$, $-SC(=O)R^{A2}$, $-SC(=O)OR^{A1}$, $-SC(=O)SR^{A1}$, $-SC(=O)N(R^{A1})_2$, $-NHC(=O)R^{A1}$, $-NHC(=O)OR^{A1}$, $-NHC(=O)SR^{A1}$, $-NHC(=O)N(R^{A1})_2$, $-OS(=O)_2R^{A2}$, $-OS(=O)_2OR^{A1}$, $-S-S(=O)_2R^{A2}$, $-S-S(=O)_2OR^{A1}$, $-S(=O)R^{A2}$, $-SO_2R^{A2}$, or $-S(=O)_2OR^{A1}$, wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, a nitrogen protecting group when attached to a nitrogen atom, or two $R^{A1}$ groups are joined to form an substituted or unsubstituted heterocyclic or heteroaryl ring; and $R^{A2}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^2$ is hydrogen, halo, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OH$, $-OR^{B1}$, $-OC(=O)R^{B1}$, $-NH_2$, $-N(R^{B1})_2$, or $-NR^{B1}C(=O)R^{B1}$, wherein each instance of $R^{B1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group when attached to an oxygen atom, a nitrogen protecting group when attached to a nitrogen atom, or two $R^{B1}$ groups are joined to form an substituted or unsubstituted heterocyclic ring;

$R^3$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^{3'}$ is hydrogen, $-C(=O)R^{C1}$, $-C(=O)OR^{C1}$, $-C(=O)SR^{C1}$, $-C(=O)N(R^{C1})_2$, $-S(=O)_2R^{C2}$, $-S(=O)_2OR^{C1}$, $-P(=O)_2R^{C2}$, $-P(=O)_2OR^{C1}$, $-P(=O)(OR^{C1})_2$, $-P(=O)(R^{C2})_2$, or $-P(=O)(R^{C2})(OR^{C1})$, wherein $R^{C1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group when attached to an oxygen atom, a sulfur protecting group when attached to a sulfur atom, a nitrogen protecting group when attached to a nitrogen atom, or two $R^{C1}$ groups are joined to form an substituted or unsubstituted heterocyclic ring; and $R^{C2}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^4$ is selected from hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl;

each of $R^{6a}$ and $R^{6b}$ is independently hydrogen, halo, substituted or unsubstituted alkyl, substituted or unsubstituted alkenyl, or substituted or unsubstituted alkynyl, or $R^{6a}$ and $R^{6b}$ are joined to form an oxo (=O) group;

each of $R^{11a}$ and $R^{11b}$ is independently hydrogen, halo, substituted or unsubstituted alkyl, substituted or unsubstituted alkenyl, substituted or unsubstituted alkynyl, $-OH$, $-OR^{D1}$, $-OC(=O)R^{D1}$, $-NH_2$, $-N(R^{D1})_2$, or $-NR^{D1}C(=O)R^{D1}$, wherein each instance of $R^{D1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group when attached to an oxygen atom, a nitrogen protecting group when attached to a nitrogen atom, or two $R^{D1}$ groups are joined to form an substituted or unsubstituted heterocyclic ring; or $R^{11a}$ and $R^{11b}$ are joined to form an oxo (=O) group;

wherein ====== represents a single or double bond, provided if a double bond is present in Ring B, then one of $R^{6a}$ or $R^{6b}$ is absent, and provided if a single bond is present in Ring B, then the hydrogen at C5 is in the alpha or beta position;

provided that the following compounds, and pharmaceutically acceptable salts thereof, are specifically excluded:

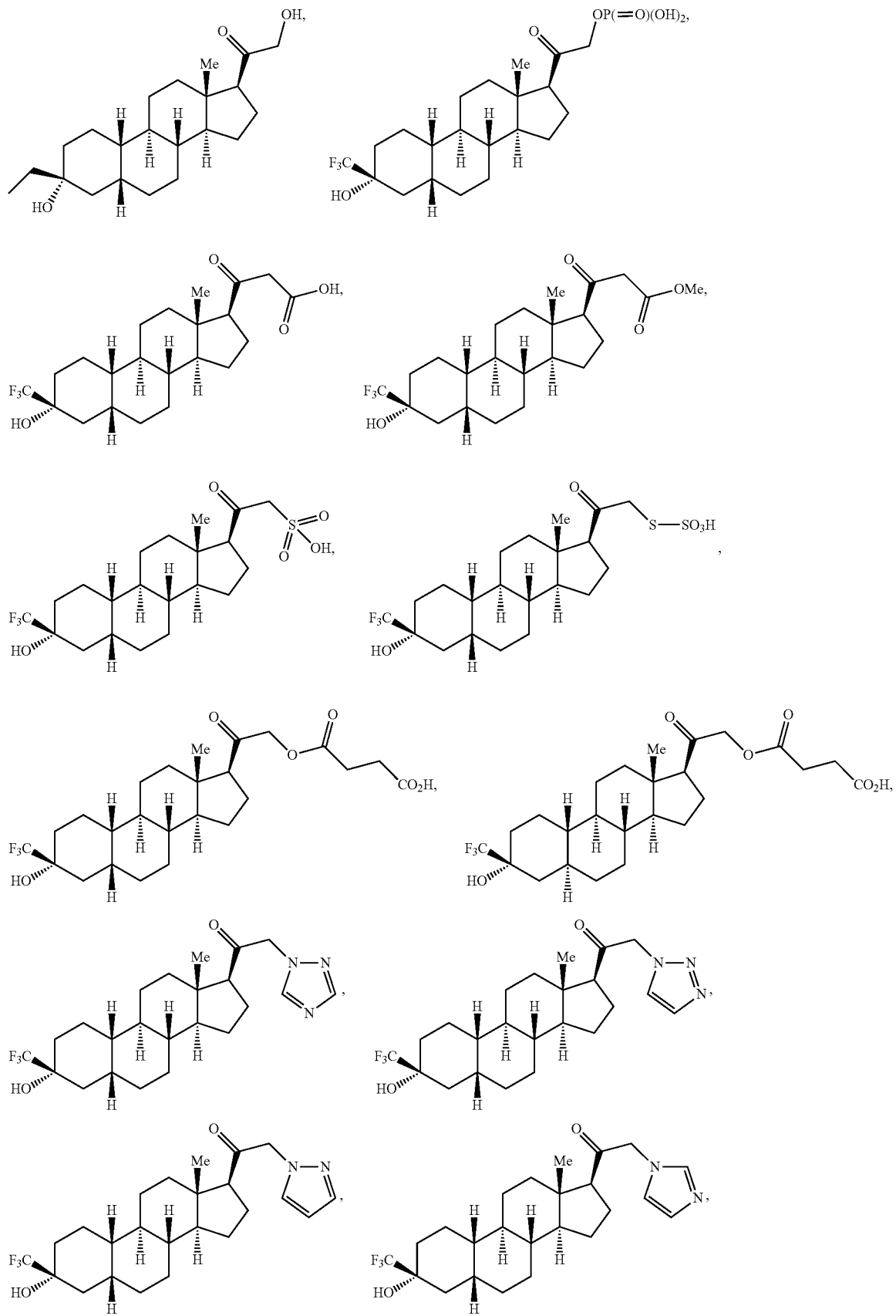

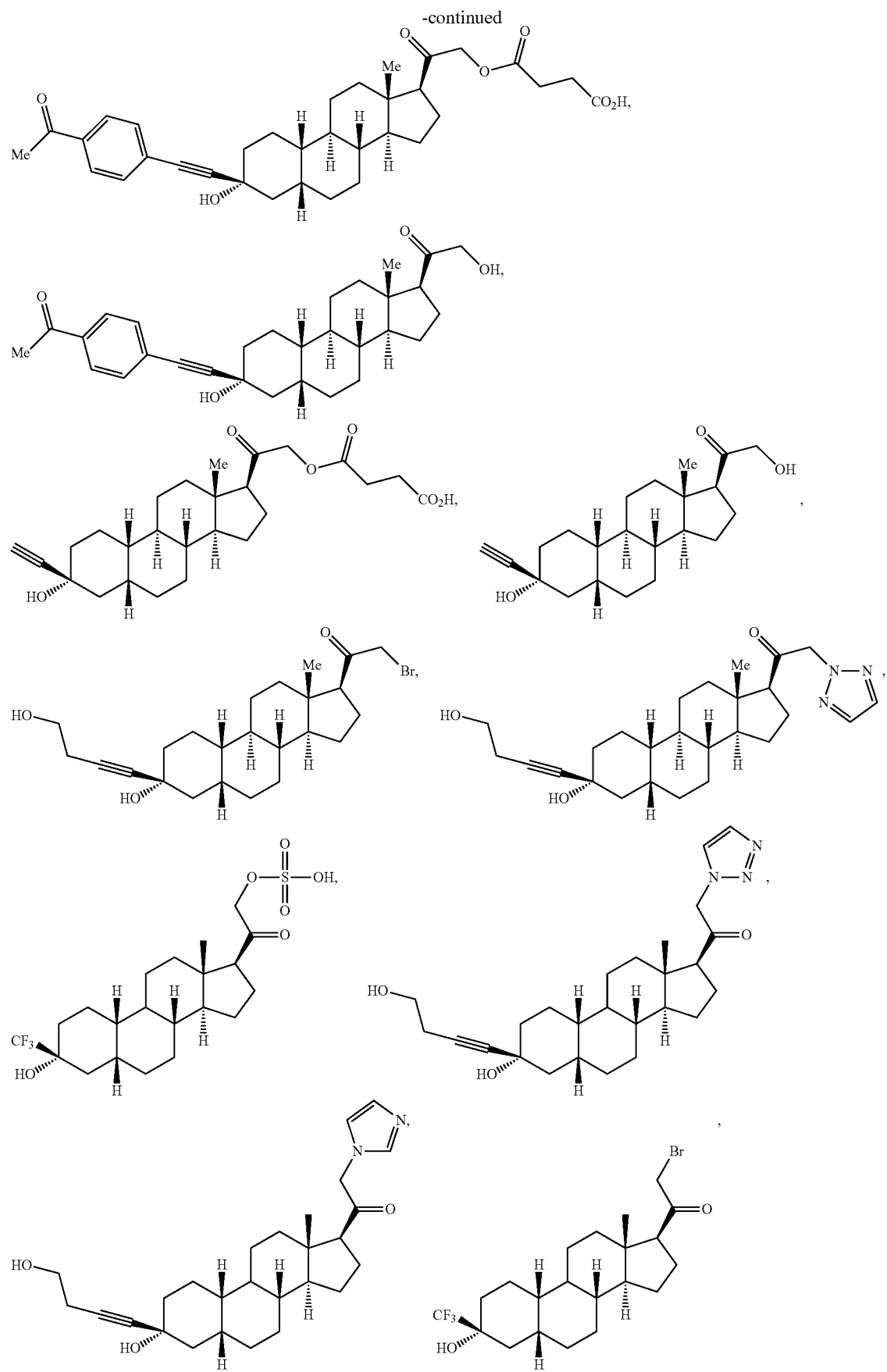

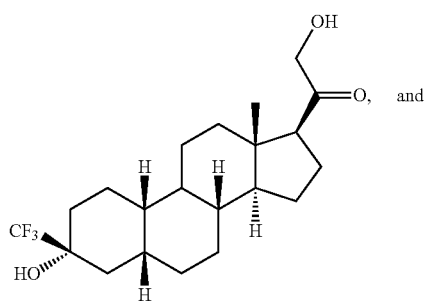 and 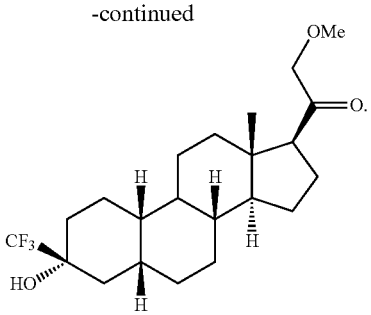

In another aspect, provided is a 3,3-disubstituted 19-nor pregnane compound of Formula (III):

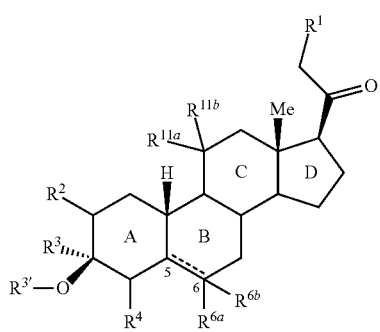

or a pharmaceutically acceptable salt, solvate, hydrate, prodrug, stereoisomer, tautomer, isotopic variant, or N-oxide thereof, or a combination thereof; wherein $R^1$, $R^2$, $R^3$, $R^{3'}$, $R^4$, $R^{6a}$, $R^{6b}$, $R^{11a}$, and $R^{11b}$ are as defined herein.

In certain embodiments, the compound is a pharmaceutically acceptable salt, e.g., a sodium, potassium, ammonium, or calcium salt. In certain embodiments, the compound is a sodium salt. In certain embodiments, the compound is an acid addition salt, e.g., hydrochloride, hydrobromide, benzoate, mesylate, orbesylate salt.

Compounds of Formula (I) and (III) are contemplated, in certain embodiments, to act as GABA modulators.

Group $R^1$

As generally described herein, $R^1$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A1}$, —$SR^{A1}$, —$N(R^{A1})_2$, —$OC(=O)R^{A1}$, —$OC(=O)OR^{A1}$, —$OC(=O)SR^{A1}$, —$OC(=O)N(R^{A1})_2$, —$SC(=O)R^{A2}$, —$SC(=O)OR^{A1}$, —$SC(=O)SR^{A1}$, —$SC(=O)N(R^{A1})_2$, —$NHC(=O)R^{A1}$, —$NHC(=O)OR^{A1}$, —$NHC(=O)SR^{A1}$, —$NHC(=O)N(R^{A1})_2$, —$OS(=O)_2R^{A2}$, —$OS(=O)_2OR^{A1}$, —$S-S(=O)_2R^{A2}$, —$S-S(=O)_2OR^{A1}$, —$S(=O)R^{A2}$, —$SO_2R^{A2}$, or —$S(=O)_2OR^{A1}$, wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, a nitrogen protecting group when attached to a nitrogen atom, or two $R^{A1}$ groups are joined to form an substituted or unsubstituted heterocyclic or heteroaryl ring; and $R^{A2}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl.

In certain embodiments, $R^1$ is hydrogen.

In certain embodiments, $R^1$ is halogen, e.g., fluoro, bromo, chloro, or iodo. In certain embodiments, $R^1$ is bromo.

In certain embodiments, $R^1$ is substituted or unsubstituted alkyl, e.g., substituted or unsubstituted $C_{1-6}$alkyl, $C_{2-6}$alkyl, $C_{3-6}$alkyl, $C_{4-6}$alkyl, $C_{5-6}$alkyl, $C_1$alkyl, $C_2$alkyl, $C_3$alkyl, $C_4$alkyl, $C_5$alkyl, or $C_6$alkyl. In certain embodiments, $R^1$ is a substituted alkyl (e.g., haloalkyl, alkyoxyalkyl).

In certain embodiments, $R^1$ is substituted or unsubstituted alkenyl, e.g., substituted or unsubstituted $C_{2-6}$alkenyl, substituted or unsubstituted $C_{3-6}$alkenyl, substituted or unsubstituted $C_{4-6}$alkenyl, substituted or unsubstituted $C_{5-6}$alkenyl, substituted or unsubstituted $C_2$alkenyl, substituted or unsubstituted $C_3$alkenyl, substituted or unsubstituted $C_4$alkenyl, substituted or unsubstituted $C_5$alkenyl, or substituted or unsubstituted $C_6$alkenyl.

In certain embodiments, $R^1$ is substituted or unsubstituted alkynyl, e.g., substituted or unsubstituted $C_{2-6}$alkynyl, substituted or unsubstituted $C_{3-6}$alkynyl, substituted or unsubstituted $C_{4-6}$alkynyl, substituted or unsubstituted $C_{5-6}$alkynyl, substituted or unsubstituted $C_2$alkynyl, substituted or unsubstituted $C_3$alkynyl, substituted or unsubstituted $C_4$alkynyl, substituted or unsubstituted $C_5$alkynyl, or substituted or unsubstituted $C_6$alkynyl.

In certain embodiments, $R^1$ is substituted or unsubstituted carbocyclyl, e.g., substituted or unsubstituted $C_{3-6}$ cycloalkyl.

In certain embodiments, $R^1$ is substituted or unsubstituted heterocyclyl, e.g., substituted or unsubstituted 3- to 6-membered heterocyclyl, e.g., substituted or unsubstituted 3-membered heterocyclyl, substituted or unsubstituted 4-membered heterocyclyl, substituted or unsubstituted 5-membered heterocyclyl, or substituted or unsubstituted 6-membered heterocyclyl. In certain embodiments, $R^1$ is substituted or unsubstituted 5-membered heterocyclyl, e.g., pyrolidinyl. In certain embodiments, $R^1$ is substituted or unsubstituted 6-membered heterocyclyl, e.g., substituted or unsubstituted morpholinyl, substituted or unsubstituted piperidinyl, or substituted or unsubstituted piperizinyl.

In certain embodiments, $R^1$ is substituted or unsubstituted aryl, e.g., substituted or unsubstituted phenyl or substituted or unsubstituted naphthyl.

In certain embodiments, $R^1$ is substituted or unsubstituted heteroaryl. In certain embodiments, $R^1$ is substituted or unsubstituted 5-membered heteroaryl. In certain embodiments, $R^1$ is substituted or unsubstituted 5-membered heteroaryl, with 1 heteroatom. In certain embodiments, $R^1$ is substituted or unsubstituted 5-membered heteroaryl, with 2 heteroatoms. In certain embodiments, $R^1$ is substituted or unsubstituted 5-membered heteroaryl, with 3 heteroatoms. In certain embodiments, $R^1$ is substituted or unsubstituted 5-membered heteroaryl, with 4 heteroatoms. In certain embodiments, $R^1$ is heteroaryl substituted with one or more substituents selected from the group consisting of alkyl, alkenyl, alkynyl, halo, haloalkyl, haloalkenyl, haloalkylnyl, hydroxyl, alkoxy, alkoxyalkyl, amino, acyl, acylamino, oxo, cyano, aryl, heteroaryl, —SO-alkyl, —SO$_2$-alkyl, —SO-aryl, —SO$_2$-aryl, —SO-heteroaryl, —SO$_2$-heteroaryl. However, in certain embodiments, $R^1$ is an unsubstituted heteroaryl.

In certain embodiments, $R^1$ is substituted or unsubstituted heteroaryl selected from the group consisting of substituted or unsubstituted imidazolyl, pyrazolyl, 1,2,3-triazolyl, 1,2,4-triazolyl, oxadiazolyl, thiadiazolyl, tetrazolyl, quinolonyl, isoquinolonyl, dihydroquinolonyl, and dihydroisoquinolonyl. In certain embodiments, $R^1$ is imidazolyl. In certain embodiments, $R^1$ is pyrazolyl. In certain embodiments, $R^1$ is 1,2,3-triazolyl. In certain embodiments, $R^1$ is 1,2,4-triazolyl. In certain embodiments, $R^1$ is tetrazolyl.

In certain embodiments, $R^1$ is imidazolyl, pyrazolyl, 1,2,3-triazolyl, 1,2,4-triazolyl, oxadiazolyl, thiadiazolyl, or tetrazolyl; each unsubstituted or substituted with one or two substituents selected from the group consisting of —SMe, —SOMe, —SO$_2$Me, —CH$_3$, F, Cl, —CN, —CH$_2$F, —CHF$_2$, and —CF$_3$. In certain embodiments, $R^1$ is imidazol-1-yl, 1,2,3-triazol-1-yl, or 1,2,3-triazol-2-yl, each unsubstituted or substituted with one or two substituents selected from the group consisting of —SMe, —SOMe, —SO$_2$Me, —CH$_3$, F, Cl, —CN, —CH$_2$F, —CHF$_2$, and —CF$_3$.

In certain embodiments, $R^1$ is imidazolyl, pyrazolyl, 1,2,3-triazolyl, 1,2,4-triazolyl, oxadiazolyl, thiadiazolyl, or tetrazolyl; each unsubstituted or substituted with oxo.

In certain embodiments, $R^1$ is quinolinyl, isoquinolinyl, or purinyl; each unsubstituted or substituted with one or two substituents selected from the group consisting of —SMe, —SOMe, —SO$_2$Me, —CH$_3$, F, Cl, —CN, —CH$_2$F, —CHF$_2$, and —CF$_3$.

In certain embodiments, $R^1$ is quinolonyl, or isoquinolonyl; each unsubstituted or substituted with one or two substituents selected from the group consisting of —SMe, —SOMe, —SO$_2$Me, —CH$_3$, F, Cl, —CN, —CH$_2$F, —CHF$_2$, and —CF$_3$.

In certain embodiments, $R^1$ is dihydroquinolonyl or dihydroisoquinolonyl; each unsubstituted or substituted with one or two substituents selected from the group consisting of —SMe, —SOMe, —SO$_2$Me, —CH$_3$, F, Cl, —CN, —CH$_2$F, —CHF$_2$, and —CF$_3$.

In certain embodiments, $R^1$ is —OR$^{41}$, e.g., $R^1$ is —OH or —O-(heteroaryl).

In certain embodiments, $R^1$ is —SR$^{41}$, e.g., $R^1$ is —SH or —S-(heteroaryl).

In certain embodiments, $R^1$ is —OC(=O)R$^{41}$, e.g., —O—C(=O)CH$_2$—CH$_2$—CO$_2$H.

In certain embodiments, $R^1$ is —OC(=O)OR$^{41}$.
In certain embodiments, $R^1$ is —OC(=O)SR$^{41}$.
In certain embodiments, $R^1$ is —OC(=O)N(R$^{41}$)$_2$.
In certain embodiments, $R^1$ is —SC(=O)R$^{42}$.
In certain embodiments, $R^1$ is —SC(=O)OR$^{41}$.
In certain embodiments, $R^1$ is —SC(=O)SR$^{41}$.
In certain embodiments, $R^1$ is —SC(=O)N(R$^{41}$)$_2$.
In certain embodiments, $R^1$ is —OS(=O)$_2$R$^{42}$.

In certain embodiments, $R^1$ is —OS(=O)$_2$OR$^{41}$, e.g., —O—SO$_3$H.
In certain embodiments, $R^1$ is —S—S(=O)$_2$R$^{42}$.
In certain embodiments, $R^1$ is —S—S(=O)$_2$OR$^{41}$, e.g., —S—SO$_3$H.
In certain embodiments, $R^1$ is —S(=O)R$^{42}$.
In certain embodiments, $R^1$ is —SO$_2$R$^{42}$.
In certain embodiments, $R^1$ is —S(=O)$_2$OR$^{41}$, e.g., —SO$_3$H.
In certain embodiments, $R^1$ is —N(R$^{41}$)$_2$, —NHC(=O)R$^{41}$, —NHC(=O)OR$^{41}$, —NHC(=O)SR$^{41}$, —NHC(=O)N(R$^{41}$)$_2$. In certain embodiments, $R^1$ is —N(R$^{41}$)$_2$. In certain embodiments, $R^1$ is —NHC(=O)R$^{41}$. In certain embodiments, $R^1$ is —NHC(=O)OR$^{41}$. In certain embodiments, $R^1$ is —NHC(=O)SR$^{41}$. In certain embodiments, $R^1$ is —NHC(=O)N(R$^{41}$)$_2$.

In certain embodiments, $R^1$ is selected from —OH, —O—CO—CH$_2$—CH$_2$—CO$_2$H, —O—SO$_3$H, —SH, —S—SO$_3$H, heteroaryl, —O-(heteroaryl), and —S-(heteroaryl), wherein heteroaryl is imidazolyl, pyrazolyl, 1,2,3-triazolyl, 1,2,4-triazolyl, oxadiazolyl, thiadiazolyl, tetrazolyl, quinolinyl, isoquinolinyl or purinyl; and each heteroaryl is unsubstituted or substituted with one or two substituents selected from the group consisting of oxo, —CH$_3$, F, Cl, —CN, —SMe, —SOMe, —SO$_2$Me, and —CF$_3$. In certain embodiments, $R^1$ is —O-quinolinyl, —O-isoquinolinyl, —O-purinyl, —S-quinolinyl, —S-isoquinolinyl, or —S-purinyl; each unsubstituted or substituted with one or two substituents selected from the group consisting of —CH$_3$, F, Cl, —CN, —SMe, —SOMe, —SO$_2$Me, —CH$_2$F, —CHF$_2$, and —CF$_3$.

In certain embodiments, $R^1$ is —OH, —O—CH$_2$—CH$_2$—CO$_2$H, —SO$_3$H, —OSO$_3$H, —SSO$_3$H, pyrazol-1-yl, imidazol-1-yl, 1,2,4-triazol-1-yl, or 1,2,3-triazol-1-yl. In certain embodiments, $R^1$ is —OH. In certain embodiments, $R^1$ is —O—CH$_2$—CH$_2$—CO$_2$H. In certain embodiments, $R^1$ is —SO$_3$H. In certain embodiments, $R^1$ is —OSO$_3$H. In certain embodiments, $R^1$ is —SSO$_3$H. In certain embodiments, $R^1$ is pyrazol-1-yl. In certain embodiments, $R^1$ is imidazol-1-yl. In certain embodiments, $R^1$ is 1,2,4-triazol-1-yl. In certain embodiments, $R^1$ is 1,2,3-triazol-1-yl.

In certain embodiments, $R^1$ is substituted or unsubstituted alkyl, substituted or unsubstituted alkenyl, substituted or unsubstituted alkynyl, substituted or unsubstituted alkoxy, substituted or unsubstituted heterocyclyl, substituted or unsubstituted thioalkoxy (—S-alkyl), —OH, —O—CO—(CH$_2$)$_t$—CO$_2$H, —SO$_3$H, —O—SO$_3$H, —SH, —S—SO$_3$H, or substituted or unsubstituted —Y-(heteroaryl); wherein Y is a bond, —O—, —S—, C$_1$-C$_4$ alkylene, C$_2$-C$_4$ alkenylene, or C$_2$-C$_4$ alkynylene; and the subscript t is an integer between 2 and 5, inclusive.

In certain embodiments, $R^1$ is Br, —OH, —OMe, substituted or unsubstituted heterocyclyl, —O—CO—CH$_2$—CH$_2$—CO$_2$H, —SO$_3$H, —O—SO$_3$H, —S—SO$_3$H, O—P(=O)(OH)$_2$, pyrazolyl, imidazolyl, or triazolyl; each $R^2$, $R^{3'}$, $R^4$, $R^{11a}$, and $R^{11b}$ is H; and each of the dotted bonds is a single bond; then $R^3$ is not Et, —CF$_3$, ethynyl, 4-hydroxypropynyl, or (4-acyl)-phenylethynyl.

In any of the above embodiments, at least one $R^{41}$ is heteroaryl unsubstituted or substituted with one or more substituents selected from the group consisting of halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; and R$^{aa}$, R$^{bb}$, R$^{cc}$, R$^{dd}$, R$^{ee}$, and R$^{ff}$, are as described herein.

In any of the above embodiments, at least one R$^{A1}$ is heteroaryl unsubstituted or substituted with one or more substituents selected from the group consisting of alkyl, alkenyl, alkynyl, halo, haloalkyl, haloalkenyl, haloalkylnyl, hydroxyl, alkoxy, alkoxyalkyl, amino, acyl, acylamino, oxo, cyano, aryl, heteroaryl, —SO-alkyl, —SO$_2$-alkyl, —SO-aryl, —SO$_2$-aryl, —SO-heteroaryl, and —SO$_2$-heteroaryl.

In any of the above embodiments, at least one R$^{A1}$ is heteroaryl selected from the group consisting of unsubstituted pyrrolyl, imidazolyl, pyrazolyl, oxazoyl, thiazolyl, isoxazoyl, 1,2,3-triazolyl, 1,2,4-triazolyl, oxadiazolyl, thiadiazolyl, tetrazolyl, pyridinyl, pyrimidinyl, pyrazinyl, quinolinyl, isoquinolinyl, quinazolinyl, quinoxilinyl, naphthyridinyl, indolyl, indazolyl, benzimidazloyl, pyrrolopyridinyl, pyrrolopyrimidinyl, pyridopyrimidinyl, and purinyl.

In any of the above embodiments, at least one R$^{A1}$ is heteroaryl is selected from the group consisting of pyrrolyl, imidazolyl, pyrazolyl, oxazoyl, thiazolyl, isoxazoyl, 1,2,3-triazolyl, 1,2,4-triazolyl, oxadiazolyl, thiadiazolyl, tetrazolyl, pyridinyl, pyrimidinyl, pyrazinyl, quinolinyl, isoquinolinyl, quinazolinyl, quinoxilinyl, naphthyridinyl, indolyl, indazolyl, benzimidazloyl, pyrrolopyridinyl, pyrrolopyrimidinyl, pyridopyrimidinyl, and purinyl, each substituted with one or more substituents selected from the group consisting of alkyl, haloalkyl, alkenyl, alkynyl, oxo, hydoxy, halo, alkoxy, —S-alkyl, aryl, heteroaryl, —SO-alkyl, —SO$_2$-alkyl, —SO-aryl, —SO$_2$-aryl, —SO-heteroaryl, —SO$_2$-heteroaryl, amino, cyano, and acyl.

Group R$^2$

As generally defined above, R$^2$ is hydrogen, halo, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OH, —OR$^{B1}$, —OC(=O)R$^{B1}$, —NH$_2$, —N(R$^{B1}$)$_2$, or —NR$^{B1}$C(=O)R$^{B1}$, wherein each instance of R$^{B1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group when attached to an oxygen atom, a nitrogen protecting group when attached to a nitrogen atom, or two R$^{B1}$ groups are joined to form an substituted or unsubstituted heterocyclic ring.

In certain embodiments, R$^2$ is hydrogen.

In certain embodiments, R$^2$ is halo, e.g., —F, —Br, —I, or —Cl. In certain embodiments, R$^2$ is —F. In certain embodiments, R$^2$ is —Cl. In certain embodiments, R$^2$ is —Br.

In certain embodiments, R$^2$ is substituted or unsubstituted alkyl, e.g., substituted or unsubstituted C$_{1-6}$alkyl, substituted or unsubstituted C$_{1-2}$alkyl, substituted or unsubstituted C$_{2-3}$alkyl, substituted or unsubstituted C$_{3-4}$alkyl, substituted or unsubstituted C$_{4-5}$alkyl, or substituted or unsubstituted C$_{5-6}$alkyl. Exemplary R$^2$ C$_{1-6}$alkyl groups include, but are not limited to, substituted or unsubstituted methyl (C$_1$), substituted or unsubstituted ethyl (C$_2$), substituted or unsubstituted n-propyl (C$_3$), substituted or unsubstituted isopropyl (C$_3$), substituted or unsubstituted n-butyl (C$_4$), substituted or unsubstituted tert-butyl (C$_4$), substituted or unsubstituted sec-butyl (C$_4$), substituted or unsubstituted iso-butyl (C$_4$), substituted or unsubstituted n-pentyl (C$_5$), substituted or unsubstituted 3-pentanyl (C$_5$), substituted or unsubstituted amyl (C$_5$), substituted or unsubstituted neopentyl (C$_5$), substituted or unsubstituted 3-methyl-2-butanyl (C$_5$), substituted or unsubstituted tertiary amyl (C$_5$), or substituted or unsubstituted n-hexyl (C$_6$). Exemplary substituted alkyl groups include, but are not limited to, alkyl substituted with halogen groups ("haloalkyl") and alkyl substituted with alkoxy groups ("alkoxyalkyl"). Exemplary haloalkyl groups include, but are not limited to, —CF$_3$, —CH$_2$F, —CHF$_2$, difluoroethyl, 2,2,2-trifluoro-1,1-dimethyl-ethyl, —CH$_2$Cl, and —CHCl$_2$. Exemplary alkoxyalkyl groups include, but are not limited to, —CH$_2$OCH$_3$ and —CH$_2$OCH$_2$CH$_3$.

In certain embodiments, R$^2$ is substituted or unsubstituted alkenyl, e.g., substituted or unsubstituted C$_{2-6}$alkenyl, substituted or unsubstituted C$_{2-3}$alkenyl, substituted or unsubstituted C$_{3-4}$alkenyl, substituted or unsubstituted C$_{4-5}$alkenyl, or substituted or unsubstituted C$_{5-6}$alkenyl. Exemplary substituted alkenyl groups include, but are not limited to, alkenyl substituted with halogen groups ("haloalkenyl") and alkenyl substituted with alkoxy groups ("alkoxyalkenyl").

In certain embodiments, R$^2$ is substituted or unsubstituted alkynyl, e.g., substituted or unsubstituted C$_{2-6}$alkynyl, substituted or unsubstituted C$_{2-3}$alkynyl, substituted or unsubstituted C$_{3-4}$alkynyl, substituted or unsubstituted C$_{4-5}$alkynyl, or substituted or unsubstituted C$_{5-6}$alkynyl. Exemplary substituted alkynyl groups include, but are not limited to, alkynyl substituted with halogen groups ("haloalkynyl") and alkynyl substituted with alkoxy groups ("alkoxyalkynyl").

In certain embodiments, R$^2$ is substituted or unsubstituted carbocyclyl, e.g., substituted or unsubstituted C$_{3-6}$carbocyclyl, substituted or unsubstituted C$_{3-4}$carbocyclyl, substituted or unsubstituted C$_{4-5}$ carbocyclyl, or substituted or unsubstituted C$_{5-6}$ carbocyclyl.

In certain embodiments, R$^2$ is substituted or unsubstituted heterocyclyl, e.g., substituted or unsubstituted C$_{3-6}$ heterocyclyl, substituted or unsubstituted C$_{3-4}$ heterocyclyl, substituted or unsubstituted C$_{4-5}$ heterocyclyl, or substituted or unsubstituted C$_{5-6}$ heterocyclyl. For example, in certain embodiments, R$^2$ is a substituted or unsubstituted piperidinyl, substituted or unsubstituted piperazinyl, or substituted or unsubstituted morpholinyl ring. In certain embodiments, R$^2$ is a substituted or unsubstituted morpholinyl ring.

In certain embodiments, R$^2$ is substituted or unsubstituted aryl, e.g., substituted or unsubstituted phenyl.

In certain embodiments, $R^2$ is substituted or unsubstituted heteroaryl, e.g., optionally substituted 5- to 6-membered heteroaryl.

In certain embodiments, $R^2$ is —OH, —OR$^{B1}$, or —OC(=O)R$^{B1}$. In certain embodiments, R$^{B1}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. Exemplary R$^{B1}$ $C_{1-6}$alkyl groups include, but are not limited to, substituted or unsubstituted methyl ($C_1$), substituted or unsubstituted ethyl ($C_2$), substituted or unsubstituted n-propyl ($C_3$), substituted or unsubstituted isopropyl ($C_3$), substituted or unsubstituted n-butyl ($C_4$), substituted or unsubstituted tert-butyl ($C_4$), substituted or unsubstituted sec-butyl ($C_4$), substituted or unsubstituted iso-butyl ($C_4$), substituted or unsubstituted n-pentyl ($C_5$), substituted or unsubstituted 3-pentanyl ($C_5$), substituted or unsubstituted amyl ($C_5$), substituted or unsubstituted neopentyl ($C_5$), substituted or unsubstituted 3-methyl-2-butanyl ($C_5$), substituted or unsubstituted tertiary amyl ($C_5$), or substituted or unsubstituted n-hexyl ($C_6$).

In certain embodiments, $R^2$ is —NH$_2$, —N(R$^{B1}$)$_2$, or —NR$^{B1}$C(=O)R$^{B1}$. In certain embodiments, R$^{B1}$ is hydrogen or substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. Exemplary R$^{B1}$ $C_{1-6}$alkyl groups include, but are not limited to, substituted or unsubstituted methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), or n-hexyl ($C_6$).

In certain embodiments, $R^2$ is halo, substituted or unsubstituted alkyl, substituted or unsubstituted alkenyl, substituted or unsubstituted alkynyl, —OR$^{B1}$, or —OC(=O)R$^{B1}$. In certain embodiments, $R^2$ is hydrogen, alkyl, alkenyl, alkynyl, haloalkyl, haloalkenyl, haloalkynyl, alkoxyalkyl, —OH, —OR$^{B1}$, —OC(=O)R$^{B1}$, —NH$_2$, —N(R$^{B1}$)$_2$, or —NR$^{B1}$C(=O)R$^{B1}$.

In certain embodiments, $R^2$ is substituted alkyl (e.g., haloalkyl, alkoxyalkyl).

In certain embodiments, $R^2$ is —F, —Cl, methyl, ethyl, n-propyl, methoxy, ethoxy, propoxy, butoxy, ethynyl, hydroxybutynyl, methoxypropynyl, chloroethynyl, or cyclopropynyl.

In certain embodiments, $R^2$ is a non-hydrogen group in the alpha position. In certain embodiments, $R^2$ is a non-hydrogen group in the beta position.

Group $R^3$

As generally defined above, $R^3$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl.

In certain embodiments, $R^3$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. Exemplary $R^3$ $C_{1-6}$alkyl groups include, but are not limited to, substituted or unsubstituted methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), n-hexyl ($C_6$), $C_{1-6}$ alkyl substituted with 1, 2, 3, 4, 5, 6, 7, 8, 9, 10, or more fluoro groups (e.g., —CF$_3$, —CH$_2$F, —CHF$_2$, difluoroethyl, and 2,2,2-trifluoro-1,1-dimethyl-ethyl), $C_{1-6}$ alkyl substituted with 1, 2, 3, 4, 5, 6, 7, 8, 9, 10, or more chloro groups (e.g., —CH$_2$Cl, —CHCl$_2$), and $C_{1-6}$ alkyl substituted with alkoxy groups (e.g., —CH$_2$OCH$_3$ and —CH$_2$OCH$_2$CH$_3$). In certain embodiments, $R^3$ is substituted alkyl, e.g., $R^3$ is haloalkyl, alkoxyalkyl, or aminoalkyl. In certain embodiments, $R^3$ is Me, Et, n-Pr, n-Bu, i-Bu, fluoromethyl, chloromethyl, difluoromethyl, trifluoromethyl, trifluoroethyl, difluoroethyl, 2,2,2-trifluoro-1,1-dimethyl-ethyl, methoxymethyl, methoxyethyl, or ethoxymethyl. In certain embodiments, $R^{3a}$ is Me, Et, n-Pr, n-Bu, or i-Bu. In certain embodiments, $R^3$ is methoxymethyl, ethoxymethyl, propoxymethyl, methoxyethyl, or ethoxyethyl. In certain embodiments, $R^3$ is trifluoromethoxymethyl. In certain embodiments, $R^3$ is fluoromethyl, chloromethyl, difluoromethyl, trifluoromethyl, difluoroethyl, trifluoroethyl, or 2,2,2-trifluoro-1,1-dimethyl-ethyl. In certain embodiments, $R^3$ is trifluoromethyl.

In certain embodiments, $R^3$ is substituted or unsubstituted alkenyl, e.g., substituted or unsubstituted $C_{2-6}$alkenyl, substituted or unsubstituted $C_{2-3}$alkenyl, substituted or unsubstituted $C_{3-4}$alkenyl, substituted or unsubstituted $C_{4-5}$alkenyl, or substituted or unsubstituted $C_{5-6}$alkenyl. In certain embodiments, $R^3$ is ethenyl ($C_2$), propenyl ($C_3$), or butenyl ($C_4$), unsubstituted or substituted with one or more substituents selected from the group consisting of alkyl, halo, haloalkyl, alkoxyalkyl, or hydroxyl. In certain embodiments, $R^3$ is ethenyl, propenyl, or butenyl, unsubstituted or substituted with alkyl, halo, haloalkyl, alkoxyalkyl, or hydroxy. In certain embodiments, $R^3$ is ethenyl.

In certain embodiments, $R^3$ is substituted or unsubstituted alkynyl, e.g., substituted or unsubstituted $C_{2-6}$alkynyl, substituted or unsubstituted $C_{2-3}$alkynyl, substituted or unsubstituted $C_{3-4}$alkynyl, substituted or unsubstituted $C_{4-5}$alkynyl, or substituted or unsubstituted $C_{5-6}$alkynyl. Exemplary substituted or unsubstituted $R^3$ alkynyl groups include, but are not limited to, ethynyl, propynyl, or butynyl, unsubstituted or substituted with alkyl, halo, haloalkyl (e.g., CF$_3$), alkoxyalkyl, cycloalkyl (e.g., cyclopropyl or cyclobutyl), or hydroxyl. In certain embodiments, $R^3$ is selected from the group consisting of trifluoroethynyl, cyclopropylethynyl, cyclobutylethynyl, and propynyl, fluoropropynyl, and chloroethynyl. In certain embodiments, $R^3$ is ethynyl ($C_2$), propynyl ($C_3$), or butynyl ($C_4$), unsubstituted or substituted with one or more substituents selected from the group consisting of substituted or unsubstituted aryl, substituted or unsubstituted heteroaryl, substituted or unsubstituted carbocyclyl, and substituted or unsubstituted heterocyclyl. In certain embodiments, $R^3$ is ethynyl ($C_2$), propynyl ($C_3$), or butynyl ($C_4$) substituted with substituted phenyl. In certain embodiment, the phenyl substitutent is further substituted with one or more substituents selected from the group consisting of halo, alkyl, trifluoroalkyl, alkoxy, acyl, amino or amido. In certain embodiments, $R^3$ is ethynyl ($C_2$), propynyl ($C_3$), or butynyl ($C_4$) substituted with substituted or unsubstituted pyrrolyl, imidazolyl, pyrazolyl, oxazoyl, thiazolyl, isoxazoyl, 1,2,3-triazolyl, 1,2,4-triazolyl, oxadiazolyl, thiadiazolyl, or tetrazolyl.

In certain embodiments, $R^3$ is ethynyl, propynyl, or butynyl, unsubstituted or substituted with alkyl, halo, haloalkyl, alkoxyalkyl, or hydroxyl. In certain embodiments, $R^{3a}$ is ethynyl or propynyl, substituted with substituted or unsubstituted aryl. In certain embodiments, $R^3$ is ethynyl or propynyl, substituted with phenyl unsubstituted or substituted with halo, alkyl, alkoxy, haloalkyl, trihaloalkyl, or acyl. In certain embodiments, $R^3$ is ethynyl or propynyl, substituted with substituted or unsubstituted carbocyclyl. In certain embodiments, $R^3$ is ethynyl or propynyl, substituted with substituted or unsubstituted cyclopropyl, cyclobutyl, cyclopentyl, or cyclohexyl. In certain embodiments, $R^3$ is ethynyl or propynyl, substituted with substituted or unsubstituted heteroaryl. In certain embodiments, $R^3$ is ethynyl or propynyl, substituted with substituted or unsubstituted pyridinyl, or pyrimidinyl. In certain embodiments, $R^3$ is ethynyl or propynyl, substituted with substituted or unsubstituted pyrrolyl, imidazolyl, pyrazolyl, oxazoyl, thiazolyl, isoxazoyl, 1,2,3-triazolyl, 1,2,4-triazolyl, oxadiazolyl, thiadiazolyl, tetrazolyl. In certain embodiments, $R^3$ is ethynyl or propynyl, substituted with substituted or unsubstituted heterocyclyl. In certain embodiments, $R^{3a}$ is ethynyl or propynyl, substituted with substituted or unsubstituted pyrrolidinyl, piperidinyl, piperazinyl, or mopholinyl. In certain embodiments, $R^3$ is propynyl or butynyl, substituted with hydroxyl or alkoxy. In certain embodiments, $R^3$ is propynyl or butynyl, substituted with methoxy or ethoxy. In certain embodiments, $R^3$ is ethynyl or propynyl, substituted with Cl. In certain embodiments, $R^3$ is ethynyl or propynyl, substituted with trifluoromethyl.

In certain embodiments, $R^3$ is substituted or unsubstituted carbocyclyl, e.g., substituted or unsubstituted $C_{3-6}$carbocyclyl, substituted or unsubstituted $C_{3-4}$carbocyclyl, substituted or unsubstituted $C_{4-5}$ carbocyclyl, or substituted or unsubstituted $C_{5-6}$ carbocyclyl.

In certain embodiments, $R^3$ is substituted or unsubstituted heterocyclyl, e.g., substituted or unsubstituted 3-6 membered heterocyclyl, substituted or unsubstituted 3-4 membered heterocyclyl, substituted or unsubstituted 4-5 membered heterocyclyl, or substituted or unsubstituted 5-6 membered heterocyclyl.

In certain embodiments, $R^3$ is substituted or unsubstituted aryl. In certain embodiments, $R^3$ is substituted or unsubstituted phenyl.

In certain embodiments, $R^3$ is substituted or unsubstituted heteroaryl, e.g., optionally substituted 5- to 6-membered heteroaryl.

Further embodiments of $R^3$, as a substituted or unsubstituted alkyl, substituted or unsubstituted alkenyl, and substituted or unsubstituted alkynyl groups, are depicted below:

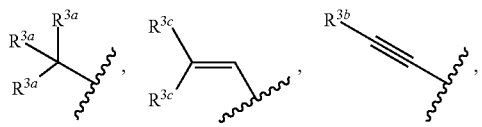

wherein each instance of $R^{3a}$ is hydrogen, halo, or —$OR^{F1}$, wherein $R^{F1}$ is substituted or unsubstituted alkyl; and each instance of $R^{3b}$ and $R^{3c}$ is independently hydrogen, halo, or substituted or unsubstituted alkyl, substituted or unsubstituted carbocyclyl, or substituted or unsubstituted heterocyclyl.

In certain embodiments, at least one $R^{3a}$ is hydrogen. In certain embodiments, at least two $R^{3c}$ is hydrogen. In certain embodiments, each $R^{3a}$ is hydrogen. In certain embodiments, at least one $R^{3a}$ is halogen (e.g., fluoro, chloro, bromo, iodo). In certain embodiments, at least two $R^{3a}$ are halogen (e.g., fluoro, chloro, bromo, iodo). In certain embodiments, each $R^{3a}$ is halogen (e.g., fluoro, to provide the group —$CF_3$). In certain embodiments, at least one $R^{3a}$ is —$OR^{F1}$ (e.g., OMe or OEt). In certain embodiments, at least two $R^{3a}$ is —$OR^{F1}$ (e.g., OMe or OEt). In certain embodiments, at least one $R^{3a}$ is hydrogen, F, —OMe, or —OEt. In certain embodiments, one of $R^{3a}$ is a non-hydrogen group (e.g., —F, —OMe, or OEt); and the rest are H, such as provided in the below formula:

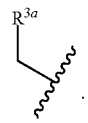

In certain embodiments, $R^{3b}$ is hydrogen. In certain embodiments, $R^{3b}$ is halogen (e.g., fluoro, chloro, bromo, iodo). In certain embodiments, $R^{3b}$ is alkyl, e.g., —$CH_3$, —$CF_3$, —$CH_2CH_2Cl$. In certain embodiments, $R^{3b}$ is substituted or unsubstituted carbocyclyl, e.g., cyclopropyl or cyclobutyl. In certain embodiments, $R^{3b}$ is hydrogen, —F, —Br, —Cl, —I, —$CH_3$, —$CF_3$, cyclopropyl, or cyclobutyl. In certain embodiments, $R^{3b}$ is substituted or unsubstituted cyclopropyl. In certain embodiments, $R^{3b}$ is hydrogen, —F, —Br, —Cl, —I, —$CH_3$, —$CF_3$, —$CH_2CH_2Cl$, cyclopropyl, or cyclobutyl. In certain embodiments, $R^{3b}$ is Me or Cl. In certain embodiments, $R^{3b}$ is substituted or unsubstituted heterocyclyl.

In certain embodiments, at least one $R^{3c}$ is hydrogen. In certain embodiments, each $R^{3c}$ is hydrogen. In certain embodiments, at least one $R^{3c}$ is halogen (e.g., fluoro, chloro, bromo, iodo). In certain embodiments, each $R^{3c}$ is halogen (e.g., fluoro, chloro, bromo, iodo). In certain embodiments, each of $R^{3c}$ is alkyl, e.g., each of $R^{2c}$ is Me. In certain embodiments, one of $R^{3c}$ is alkyl; and the other is hydrogen, e.g., one of $R^{3c}$ is Me; and the other is hydrogen. In certain embodiments, one of $R^{3c}$ is substituted or unsubstituted carbocyclyl, e.g., cyclopropyl or cyclobutyl, and the other is hydrogen. In certain embodiments, at least one $R^{3c}$ is hydrogen, —F, —Br, —Cl, —I, —$CH_3$, —$CF_3$, cyclopropyl, or cyclobutyl. In certain embodiments, each instance of $R^{3c}$ is H. In certain embodiments, each instance of $R^{3c}$ is halogen (e.g., fluoro, chloro, bromo, iodo). In certain embodiments, each instance of $R^{3c}$ is alkyl, e.g., —$CH_3$, —$CF_3$, —$CH_2CH_2Cl$. In certain embodiments, each instance of $R^{3c}$ is substituted or unsubstituted carbocyclyl, e.g., cyclopropyl or cyclobutyl. In certain embodiments, $R^{3c}$ is substituted or unsubstituted cyclopropyl. In certain embodiments, each instance of $R^{3c}$ is hydrogen, —F, —Br, —Cl, —I, —$CH_3$, —$CF_3$, —$CH_2CH_2Cl$, cyclopropyl, or cyclobutyl. In certain embodiments, $R^{3c}$ is Me or Cl. In certain embodiments, $R^{3c}$ is substituted or unsubstituted heterocyclyl.

Group $R^3$

As generally defined above, $R^{3'}$ is H, —C(=O)$R^{C1}$, —C(=O)O$R^{C1}$, —C(=O)S$R^{C1}$, —C(=O)N($R^{C1}$)$_2$, —S(=O)$_2R^{C2}$, —S(=O)$_2OR^{C1}$, —P(=O)$_2R^{C2}$, —P(=O)$_2$ $R^{C1}$, —P(=O)(O$R^{C1}$)$_2$, —P(=O)($R^{C2}$)$_2$, or —P(=O)($R^{C2}$)(O$R^{C1}$), wherein $R^{C1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group when attached to an oxygen atom, a sulfur protecting group when attached to a sulfur atom, a nitrogen protecting group when attached to a nitrogen atom, or two $R^{C1}$ groups are joined to form an substituted or unsubstituted heterocyclic ring; and $R^{C2}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl.

In certain embodiments, $R^3$ is H (hydrogen).

In certain embodiments, $R^{3'}$ is $-C(=O)R^{C1}$, $-C(=O)OR^{C1}$, $-C(=O)SR^{C1}$, $-C(=O)N(R^{C11})_2$, $-S(=O)_2R^{C1}$, $-S(=O)_2OR^{C1}$, $-P(=O)_2R^{C1}$, $-P(=O)_2OR^{C1}$, $-P(=O)(OR^{C1})_2$, $-P(=O)(R^{C1})_2$, or $-P(=O)(R^{C1})(OR^{C1})$.

In certain embodiments, at least one instance of $R^{C1}$ is hydrogen or a protecting group, i.e., an oxygen protecting group when attached to an oxygen atom, sulfur protecting group when attached to an sulfur atom, or a nitrogen protecting group when attached to a nitrogen atom. In certain embodiments, at least one instance of $R^{C1}$ is hydrogen.

In certain embodiments, at least one instance of $R^{C1}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. Exemplary $R^{C1}$ $C_{1-6}$alkyl groups include, but are not limited to, substituted or unsubstituted methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), n-hexyl ($C_6$), $C_{1-6}$ alkyl substituted with 1, 2, 3, 4, 5, 6, 7, 8, 9, 10, or more fluoro groups (e.g., $-CF_3$, $-CH_2F$, $-CHF_2$, difluoroethyl, and 2,2,2-trifluoro-1,1-dimethylethyl), $C_{1-6}$ alkyl substituted with 1, 2, 3, 4, 5, 6, 7, 8, 9, 10, or more chloro groups (e.g., $-CH_2Cl$, $-CHCl_2$), and $C_{1-6}$ alkyl substituted with alkoxy groups (e.g., $-CH_2OCH_3$ and $-CH_2OCH_2CH_3$).

In certain embodiments, at least one instance of $R^{C1}$ is substituted or unsubstituted alkenyl, e.g., substituted or unsubstituted $C_{2-6}$alkenyl, substituted or unsubstituted $C_{2-3}$alkenyl, substituted or unsubstituted $C_{3-4}$alkenyl, substituted or unsubstituted $C_{4-5}$alkenyl, or substituted or unsubstituted $C_{5-6}$alkenyl.

In certain embodiments, at least one instance of $R^{C1}$ is substituted or unsubstituted alkynyl, e.g., substituted or unsubstituted $C_{2-6}$alkynyl, substituted or unsubstituted $C_{2-3}$alkynyl, substituted or unsubstituted $C_{3-4}$alkynyl, substituted or unsubstituted $C_{4-5}$alkynyl, or substituted or unsubstituted $C_{5-6}$alkynyl.

In certain embodiments, at least one instance of $R^{C1}$ is substituted or unsubstituted carbocyclyl, e.g., substituted or unsubstituted $C_{3-6}$carbocyclyl, substituted or unsubstituted $C_{3-4}$carbocyclyl, substituted or unsubstituted $C_{4-5}$ carbocyclyl, or substituted or unsubstituted $C_{5-6}$ carbocyclyl.

In certain embodiments, at least one instance of $R^{C1}$ is substituted or unsubstituted heterocyclyl, e.g., substituted or unsubstituted 3-6 membered heterocyclyl, substituted or unsubstituted 3-4 membered heterocyclyl, substituted or unsubstituted 4-5 membered heterocyclyl, or unsubstituted 5-6 membered heterocyclyl.

In certain embodiments, at least one instance of $R^{C1}$ is substituted or unsubstituted aryl, e.g., substituted or unsubstituted phenyl.

In certain embodiments, at least one instance of $R^{C1}$ is substituted or unsubstituted heteroaryl, e.g., optionally substituted 5- to 6-membered heteroaryl.

In certain embodiments, two $R^{C1}$ groups are joined to form a substituted or unsubstituted heterocyclic ring, e.g., a substituted or unsubstituted piperidinyl, substituted or unsubstituted piperazinyl, or substituted or unsubstituted morpholinyl ring.

In certain embodiments, $R^{3'}$ is $-C(=O)R^{C1}$, $-C(=O)OR^{C1}$, $-C(=O)N(R^{C1})_2$ or $-C(=O)N(OR^{C1})(R^{C1})$, wherein $R^{C1}$ is as defined herein.

In certain embodiments, $R^{3'}$ is $-C(=O)R^{C1}$, e.g., for example, wherein $R^{C1}$ is, for example, substituted or unsubstituted methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), or n-hexyl ($C_6$). In certain embodiments, $R^{3'}$ is $-C(=O)CH_3$. In certain embodiments, $R^{3'}$ is $-C(=O)(CH_2)_mCO_2H$, wherein m is an integer between 2 and 5, inclusive. In certain embodiments, m is 2. In certain embodiments, m is 3. In certain embodiments, m is 4. In certain embodiments, m is 5. In certain embodiments, $R^{3'}$ is $-C(=O)CH_2CH_2C(=O)OH$.

In certain embodiments, $R^{3'}$ is $-C(=O)OR^{C1}$, e.g., for example, wherein $R^{C1}$ is, for example, substituted or unsubstituted methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), or n-hexyl ($C_6$).

In certain embodiments, $R^{3'}$ is $-C(=O)SR^{C1}$, e.g., for example, wherein $R^{C1}$ is, for example, substituted or unsubstituted methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), or n-hexyl ($C_6$).

In certain embodiments, $R^{3'}$ is $-C(=O)N(R^{C1})_2$, e.g., $-C(=O)NH_2$ or $-C(=O)NHR^{C1}$, wherein $R^{C1}$ is, for example, substituted or unsubstituted methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), or n-hexyl ($C_6$), or $R^{3'}$ is $-C(=O)N(R^{C1})_2$ wherein the two $R^{C1}$ groups are joined to form a substituted or unsubstituted heterocyclic ring, e.g., substituted or unsubstituted piperidinyl, substituted or unsubstituted piperazinyl, or substituted or unsubstituted morpholinyl ring.

In certain embodiments, $R^{3'}$ is $-S(=O)_2R^{C1}$ or $-S(=O)_2OR^{C1}$, wherein $R^{C1}$ is, for example, hydrogen, or substituted or unsubstituted methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), or n-hexyl ($C_6$), or substituted or unsubstituted phenyl. In certain embodiments, $R^{3'}$ is $-S(=O)_2R^{C1}$. In certain embodiments, $R^{3'}$ is $-S(=O)_2OR^{C1}$, e.g., $-SO_3H$.

In certain embodiments, $R^{3'}$ is $-P(=O)_2R^{C1}$, $-P(=O)_2OR^{C1}$, $-P(=O)(OR^{C1})_2$, $-P(=O)(R^{C1})_2$, or $-P(=O)(R^{C1})(OR^{C1})$, wherein each $R^{C1}$ is, for example, independently hydrogen, substituted or unsubstituted methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), or n-hexyl ($C_6$), or substituted or unsubstituted phenyl. In certain embodiments, $R^{3'}$ is $-P(=O)_2R^{C1}$. In certain embodiments, $R^{3'}$ is $-P(=O)_2OR^{C1}$. In certain embodiments, $R^{3'}$ is $-P(=O)(OR^{C1})_2$. In certain embodiments, $R^{3'}$ is $-P(=O)(R^{C1})_2$. In certain embodiments, $R^{3'}$ is $-P(=O)(R^{C1})(OR^{C1})$.

Groups $R^4$, $R^{6a}$, $R^{6b}$, $R^{11a}$ and $R^{11b}$

As generally defined above, $R^4$ is H, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl.

In certain embodiments, $R^4$ is H, substituted or unsubstituted alkyl, substituted or unsubstituted alkenyl, or substituted or unsubstituted alkynyl.

In certain embodiments, $R^4$ is H, —CH$_3$, or ethynyl.

In certain embodiments, $R^4$ is H.

As generally defined above, each of $R^{6a}$ and $R^{6b}$ is independently hydrogen, halo (e.g., fluoro), substituted or unsubstituted alkyl, substituted or unsubstituted alkenyl, or substituted or unsubstituted alkynyl, or $R^{6a}$ and $R^{6b}$ are joined to form an oxo (=O) group, and ----- represents a single or double bond, provided if a double bond is present in Ring B, then one of $R^{6a}$ or $R^{6b}$ is absent, and provided if a single bond is present in Ring B, then the hydrogen at C5 is in the alpha or beta position.

As generally defined above, wherein ----- independently represents a single or double bond, provided if a double bond is present in Ring B, then one of $R^{6a}$ or $R^{6b}$ is absent, and provided if a single bond is present in Ring B, then the hydrogen at C5 is in the alpha or beta position. In certain embodiments, the dashed line ----- between C5 and C6 represents a single bond, and the hydrogen at the 5-position is in the 5α-conformation. In certain embodiments, the dashed line ----- between C5 and C6 represents a single bond, and the hydrogen at the 5-position is in the 5β-conformation. In certain embodiments, the dashed line ----- between C5 and C6 represents a double bond.

In certain embodiments, wherein ----- represents a single bond, both $R^{6a}$ and $R^{6b}$ are hydrogen.

In certain embodiments, wherein ----- represents a single bond, and one of $R^{6a}$ and $R^{6b}$ is a non-hydrogen group, $R^{6a}$ is alpha (down) and $R^{6b}$ is beta (up). In certain embodiments, $R^{6b}$ is alpha (down) and $R^{6a}$ is beta (up).

In certain embodiments, wherein ----- represents a single bond, $R^{6a}$ is hydrogen, and $R^{6b}$ is halo, substituted or unsubstituted alkyl, substituted or unsubstituted alkenyl, or substituted or unsubstituted alkynyl. In certain embodiments, $R^{6a}$ is hydrogen, and $R^{6b}$ is halo (e.g., fluoro). In certain embodiments, $R^{6a}$ is hydrogen, and $R^{6b}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl, e.g., methyl, ethyl, propyl, or isopropyl. In certain embodiments, $R^{6a}$ is hydrogen, and $R^{6b}$ is substituted or unsubstituted alkenyl. In certain embodiments, $R^{6a}$ is hydrogen, and $R^{6b}$ is substituted or unsubstituted alkynyl.

In certain embodiments, wherein ----- represents a single bond, $R^{6b}$ is hydrogen, and $R^{6a}$ is halo, substituted or unsubstituted alkyl, substituted or unsubstituted alkenyl, or substituted or unsubstituted alkynyl. In certain embodiments, $R^{6b}$ is hydrogen, and $R^{6a}$ is halo (e.g., fluoro). In certain embodiments, $R^{6b}$ is hydrogen, and $R^{6a}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl, e.g., methyl, ethyl, propyl, or isopropyl. In certain embodiments, $R^{6b}$ is hydrogen, and $R^{6a}$ is substituted or unsubstituted alkenyl. In certain embodiments, $R^{6b}$ is hydrogen, and $R^{6a}$ is substituted or unsubstituted alkynyl.

Alternatively, in certain embodiments, wherein ----- represents a single bond, $R^{6a}$ and $R^{6b}$ are joined to form an oxo (=O) group.

In certain embodiments, wherein ----- represents a double bond, $R^{6a}$ is hydrogen. In certain embodiments, wherein ----- represents a double bond, $R^{6a}$ is halo, e.g., fluoro. In certain embodiments, wherein ----- represents a double bond, $R^{6a}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl, e.g., methyl, ethyl, propyl, or isopropyl. In certain embodiments, wherein ----- represents a double bond, $R^{6a}$ is substituted or unsubstituted alkenyl. In certain embodiments, wherein ----- represents a double bond, $R^{6a}$ is substituted or unsubstituted alkynyl.

As generally defined above, each of $R^{11a}$ and $R^{11b}$ is independently hydrogen, halo, substituted or unsubstituted alkyl, substituted or unsubstituted alkenyl, substituted or unsubstituted alkynyl, —OH, —OR$^{D1}$, —OC(=O)R$^{D1}$, —NH$_2$, —N(R$^{D1}$)$_2$, or —NR$^{D1}$C(=O)R$^{D1}$, wherein each instance of R$^{D1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a nitrogen protecting group when attached to a nitrogen atom, or two R$^{D1}$ groups are joined to form an substituted or unsubstituted heterocyclic ring; or $R^{11a}$ and $R^{11b}$ are joined to form an oxo (=O) group.

In certain embodiments, $R^{11a}$ is alpha (down) and $R^{11b}$ is beta (up). In certain embodiments, $R^{11b}$ is alpha (down) and $R^{11a}$ is beta (up).

In certain embodiments, at least one of $R^{11a}$ and $R^{11b}$ is hydrogen. In certain embodiments, each of $R^{11a}$ and $R^{11b}$ is H.

In certain embodiments, at least one of $R^{11a}$ and $R^{11b}$ is halo, e.g., —F, —Br, —I, or —Cl. In certain embodiments, $R^{11a}$ is halo and $R^{11b}$ is hydrogen. In certain embodiments, $R^{11b}$ is halo and $R^{11a}$ is hydrogen.

In certain embodiments, at least one of $R^{11a}$ and $R^{11b}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. Exemplary $R^{11a}$ $C_{1-6}$alkyl groups include, but are not limited to, substituted or unsubstituted methyl (C$_1$), substituted or unsubstituted ethyl (C$_2$), substituted or unsubstituted n-propyl (C$_3$), substituted or unsubstituted iso-propyl (C$_3$), substituted or unsubstituted n-butyl (C$_4$), substituted or unsubstituted tert-butyl (C$_4$), substituted or unsubstituted sec-butyl (C$_4$), substituted or unsubstituted iso-butyl (C$_4$), substituted or unsubstituted n-pentyl (C$_5$), substituted or unsubstituted 3-pentanyl (C$_5$), substituted or unsubstituted amyl (C$_5$), substituted or unsubstituted neopentyl (C$_5$), substituted or unsubstituted 3-methyl-2-butanyl (C$_5$), substituted or unsubstituted tertiary amyl (C$_5$), or substituted or unsubstituted n-hexyl (C$_6$). Exemplary substituted alkyl groups include, but are not limited to, alkyl substituted with halogen groups ("haloalkyl") and alkyl substituted with alkoxy groups ("alkoxyalkyl"). Exemplary haloalkyl groups include, but are not limited to, —CF$_3$, —CH$_2$F, —CHF$_2$, difluoroethyl, 2,2,2-trifluoro-1,1-dimethyl-ethyl, —CH$_2$Cl, and —CHCl$_2$. Exemplary alkoxyalkyl groups include, but are not limited to, —CH$_2$OCH$_3$ and —CH$_2$OCH$_2$CH$_3$. In certain embodiments, at least one of R$^{11a}$ and R$^{11b}$ is substituted alkyl (e.g., haloalkyl, alkoxyalkyl). In certain embodiments, R$^{11a}$ is alkyl and R$^{11b}$ is hydrogen. In certain embodiments, R$^{11b}$ is alkyl and R$^{11a}$ is hydrogen.

In certain embodiments, at least one of R$^{11a}$ and R$^{11b}$ is substituted or unsubstituted alkenyl, e.g., substituted or unsubstituted C$_{2-6}$alkenyl, substituted or unsubstituted C$_{2-3}$alkenyl, substituted or unsubstituted C$_{3-4}$alkenyl, substituted or unsubstituted C$_{4-5}$alkenyl, or substituted or unsubstituted C$_{5-6}$alkenyl. Exemplary substituted alkenyl groups include, but are not limited to, alkenyl substituted with halogen groups ("haloalkenyl") and alkenyl substituted with alkoxy groups ("alkoxyalkenyl"). In certain embodiments, R$^{11a}$ is alkenyl and R$^{11b}$ is hydrogen. In certain embodiments, R$^{11b}$ is alkenyl and R$^{11a}$ is hydrogen.

In certain embodiments, at least one of R$^{11a}$ and R$^{11b}$ is substituted or unsubstituted alkynyl, e.g., substituted or unsubstituted C$_{2-6}$alkynyl, substituted or unsubstituted C$_{2-3}$alkynyl, substituted or unsubstituted C$_{3-4}$alkynyl, substituted or unsubstituted C$_{4-5}$alkynyl, or substituted or unsubstituted C$_{5-6}$alkynyl. Exemplary substituted alkynyl groups include, but are not limited to, alkynyl substituted with halogen groups ("haloalkynyl") and alkynyl substituted with alkoxy groups ("alkoxyalkynyl"). In certain embodiments, R$^{11a}$ is alkynyl and R$^{11b}$ is hydrogen. In certain embodiments, R$^{11b}$ is alkynyl and R$^{11a}$ is hydrogen.

In certain embodiments, at least one of R$^{11a}$ and R$^{11b}$ is substituted or unsubstituted carbocyclyl, e.g., substituted or unsubstituted C$_{3-6}$carbocyclyl, substituted or unsubstituted C$_{3-4}$carbocyclyl, substituted or unsubstituted C$_{4-5}$ carbocyclyl, or substituted or unsubstituted C$_{5-6}$ carbocyclyl. In certain embodiments, R$^{11a}$ is carbocyclyl and R$^{11b}$ is hydrogen. In certain embodiments, R$^{11b}$ is carbocyclyl and R$^{11a}$ is hydrogen.

In certain embodiments, at least one of R$^{11a}$ and R$^{11b}$ is substituted or unsubstituted heterocyclyl, e.g., substituted or unsubstituted C$_{3-6}$ heterocyclyl, substituted or unsubstituted C$_{3-4}$ heterocyclyl, substituted or unsubstituted C$_{4-5}$ heterocyclyl, or substituted or unsubstituted C$_{5-6}$ heterocyclyl. For example, in certain embodiments, at least one of R$^{11a}$ and R$^{11b}$ is a substituted or unsubstituted piperidinyl, substituted or unsubstituted piperazinyl, or substituted or unsubstituted morpholinyl ring. In certain embodiments, at least one of R$^{11a}$ and R$^{11b}$ is a substituted or unsubstituted morpholinyl ring. In certain embodiments, R$^{11a}$ is heterocyclyl and R$^{11b}$ is hydrogen. In certain embodiments, R$^{11b}$ is heterocyclyl and R$^{11a}$ is hydrogen.

In certain embodiments, at least one of R$^{11a}$ and R$^{11b}$ is substituted or unsubstituted aryl, e.g., substituted or unsubstituted phenyl. In certain embodiments, R$^{11a}$ is aryl and R$^{11b}$ is hydrogen. In certain embodiments, R$^{11b}$ is aryl and R$^{11a}$ is hydrogen.

In certain embodiments, at least one of R$^{11a}$ and R$^{11b}$ is substituted or unsubstituted heteroaryl, e.g., optionally substituted 5- to 6-membered heteroaryl. In certain embodiments, R$^{11a}$ is heteroaryl and R$^{11b}$ is hydrogen. In certain embodiments, R$^{11b}$ is heteroaryl and R$^{11a}$ is hydrogen.

In certain embodiments, at least one of R$^{11a}$ and R$^{11b}$ is —OH, —OR$^{D1}$, or —OC(=O)R$^{D1}$. In certain embodiments, R$^{D1}$ is substituted or unsubstituted alkyl, e.g., substituted or unsubstituted C$_{1-6}$alkyl, substituted or unsubstituted C$_{1-2}$alkyl, substituted or unsubstituted C$_{2-3}$alkyl, substituted or unsubstituted C$_{3-4}$alkyl, substituted or unsubstituted C$_{4-5}$alkyl, or substituted or unsubstituted C$_{5-6}$alkyl. Exemplary R$^{D1}$ C$_{1-6}$alkyl groups include, but are not limited to, substituted or unsubstituted methyl (C$_1$), substituted or unsubstituted ethyl (C$_2$), substituted or unsubstituted n-propyl (C$_3$), substituted or unsubstituted isopropyl (C$_3$), substituted or unsubstituted n-butyl (C$_4$), substituted or unsubstituted tert-butyl (C$_4$), substituted or unsubstituted sec-butyl (C$_4$), substituted or unsubstituted iso-butyl (C$_4$), substituted or unsubstituted n-pentyl (C$_5$), substituted or unsubstituted 3-pentanyl (C$_5$), substituted or unsubstituted amyl (C$_5$), substituted or unsubstituted neopentyl (C$_5$), substituted or unsubstituted 3-methyl-2-butanyl (C$_5$), substituted or unsubstituted tertiary amyl (C$_5$), or substituted or unsubstituted n-hexyl (C$_6$). In certain embodiments, at least one of R$^{11a}$ and R$^{11b}$ is —OH. In certain embodiments, R$^{11a}$ is —OH, —OR$^{D1}$, or —OC(=O)R$^{D1}$ and R$^{11b}$ is hydrogen. In certain embodiments, R$^{11b}$ is —OH, —OR$^{D1}$, or —OC(=O)R$^{D1}$ and R$^{11a}$ is hydrogen.

In certain embodiments, at least one of R$^{11a}$ and R$^{11b}$ is —NH$_2$, —N(R$^{D1}$)$_2$, or —NR$^{D1}$C(=O)R$^{D1}$. In certain embodiments, R$^{D1}$ is hydrogen or substituted or unsubstituted alkyl, e.g., substituted or unsubstituted C$_{1-6}$alkyl, substituted or unsubstituted C$_{1-2}$alkyl, substituted or unsubstituted C$_{2-3}$alkyl, substituted or unsubstituted C$_{3-4}$alkyl, substituted or unsubstituted C$_{4-5}$alkyl, or substituted or unsubstituted C$_{5-6}$alkyl. Exemplary R$^{D1}$ C$_{1-6}$alkyl groups include, but are not limited to, substituted or unsubstituted methyl (C$_1$), substituted or unsubstituted ethyl (C$_2$), substituted or unsubstituted n-propyl (C$_3$), substituted or unsubstituted isopropyl (C$_3$), substituted or unsubstituted n-butyl (C$_4$), substituted or unsubstituted tert-butyl (C$_4$), substituted or unsubstituted sec-butyl (C$_4$), substituted or unsubstituted iso-butyl (C$_4$), substituted or unsubstituted n-pentyl (C$_5$), substituted or unsubstituted 3-pentanyl (C$_5$), substituted or unsubstituted amyl (C$_5$), substituted or unsubstituted neopentyl (C$_5$), substituted or unsubstituted 3-methyl-2-butanyl (C$_5$), substituted or unsubstituted tertiary amyl (C$_5$), or substituted or unsubstituted n-hexyl (C$_6$). In certain embodiments, at least one of R$^{11a}$ and R$^{11b}$ is —N(R$^{D1}$)$_2$, e.g., —NH$_2$, —N(CH$_3$)$_2$. In certain embodiments, R$^{11a}$ is —NH$_2$, —N(R$^{D1}$)$_2$, or —NR$^{D1}$C(=O)R$^{D1}$ and R$^{11b}$ is hydrogen. In certain embodiments, R$^{11b}$ is —NH$_2$, —N(R$^{D1}$)$_2$, or —NR$^{D1}$C(=O)R$^{D1}$ and R$^{11a}$ is hydrogen.

In certain embodiments, R$^{11a}$ and R$^{11b}$ are joined to form an oxo (=O) group.

Additional Embodiments of Formula (I) and (III)

Various combinations of the above embodiments are further contemplated herein. For example, in certain embodiments, the compound of Formula (I) is of Formula (I-a1), (I-a2), or (I-a3):

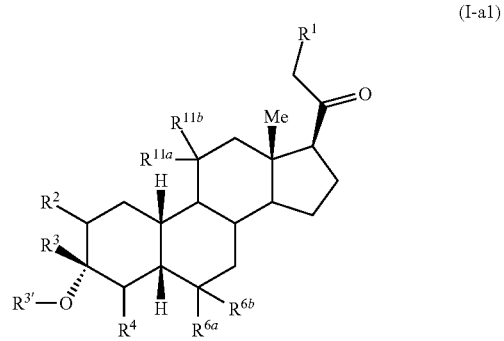

(I-a1)

-continued

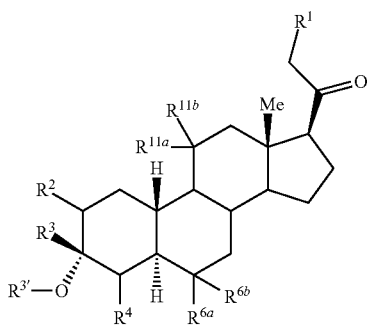
(I-a2)

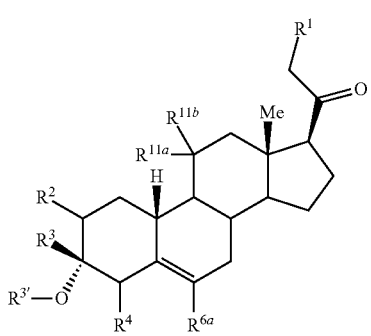
(I-a3)

or a pharmaceutically acceptable salt, solvate, hydrate, prodrug, stereoisomer, tautomer, isotopic variant, or N-oxide thereof, or a combination thereof. In certain embodiments, $R^1$ is hydrogen, halogen (e.g., bromine), —$OR^{A1}$ (e.g., —OH), —$N(R^{A1})_2$, —S—$S(=O)_2R^{A2}$, substituted or unsubstituted hetercyclyl, or substituted or unsubstituted heteroaryl. In certain embodiments, $R^1$ is hydrogen, bromine, or —OH. In certain embodiments, $R^2$ is hydrogen, substituted or unsubstituted heterocyclyl, —OH, —$OR^{B1}$, —$OC(=O)R^{B1}$, —$NH_2$, —$N(R^{B1})_2$, or —$NR^{B1}C(=O)R^{B1}$. In certain embodiments, $R^3$ is substituted or unsubstituted alkyl, substituted or unsubstituted alkenyl, or substituted or unsubstituted alkynyl. In certain embodiments, $R^{3'}$ is hydrogen. In certain embodiments, $R^4$ is hydrogen. In certain embodiments, both $R^{6a}$ and $R^{6b}$ are hydrogen. In certain embodiments, one of $R^{6a}$ and $R^{6b}$ is a non-hydrogen group. In certain embodiments, $R^{6a}$ is a non-hydrogen alpha group. In certain embodiments, $R^{6a}$ is a non-hydrogen beta group. In certain embodiments, $R^{6a}$ is halo, e.g., fluoro, or alkyl. In certain embodiments, $R^{6a}$ is halo, e.g., fluoro, or alkyl, and $R^{6b}$ is hydrogen. In certain embodiments, $R^{6a}$ and $R^{6b}$ are both halo, e.g., fluoro. In certain embodiments, $R^{6a}$ and $R^{6b}$ are both alkyl, e.g., methyl. In certain embodiments, $R^{6a}$ and $R^{6b}$ are joined to form an oxo group. In certain embodiments, both $R^{11a}$ and $R^{11b}$ are hydrogen. In certain embodiments, one of $R^{11a}$ and $R^{11b}$ is a non-hydrogen group. In certain embodiments, $R^{11a}$ and $R^{11b}$ are joined to form an oxo group.

In certain embodiments, the compound of Formula (III) is of Formula (III-a1), (III-a2), or (III-a3):

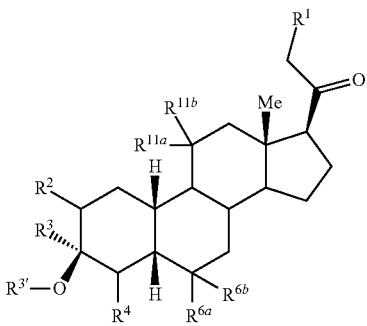
(III-a1)

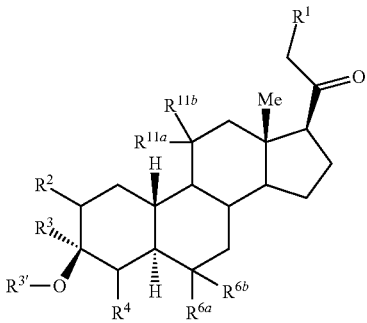
(III-a2)

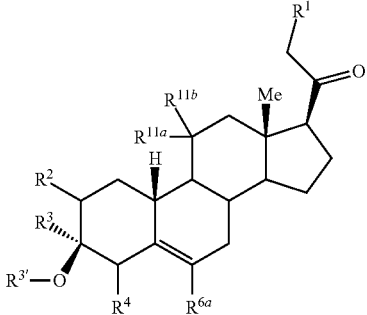
(III-a3)

or a pharmaceutically acceptable salt, solvate, hydrate, prodrug, stereoisomer, tautomer, isotopic variant, or N-oxide thereof, or a combination thereof. In certain embodiments, $R^1$ is hydrogen, halogen (e.g., bromine), —$OR^{A1}$ (e.g., —OH), —$N(R^{A1})_2$, —S—$S(=O)_2R^{A2}$, substituted or unsubstituted hetercyclyl, or substituted or unsubstituted heteroaryl. In certain embodiments, $R^1$ is hydrogen, bromine, or —OH. In certain embodiments, $R^2$ is hydrogen, substituted or unsubstituted heterocyclyl, —OH, —$OR^{B1}$, —$OC(=O)R^{B1}$, —$NH_2$, —$N(R^{B1})_2$, or —$NR^{B1}C(=O)R^{B1}$. In certain embodiments, $R^3$ is substituted or unsubstituted alkyl, substituted or unsubstituted alkenyl, or substituted or unsubstituted alkynyl. In certain embodiments, $R^{3'}$ is hydrogen. In certain embodiments, $R^4$ is hydrogen. In certain embodiments, both $R^{6a}$ and $R^{6b}$ are hydrogen. In certain embodiments, one of $R^{6a}$ and $R^{6b}$ is a non-hydrogen group. In certain embodiments, $R^{6a}$ is a non-hydrogen alpha group. In certain embodiments, $R^{6a}$ is a non-hydrogen beta group. In certain embodiments, $R^{6a}$ is halo, e.g., fluoro, or alkyl. In certain embodiments, $R^{6a}$ is halo, e.g., fluoro, or alkyl, and $R^{6b}$ is hydrogen. In certain embodiments, $R^{6a}$ and $R^{6b}$ are both halo, e.g., fluoro. In certain embodiments, $R^{6a}$ and $R^{6b}$ are both alkyl, e.g., methyl. In certain embodiments, $R^{6a}$ and $R^{6b}$ are joined to form an oxo group. In certain embodiments, both $R^{11a}$ and $R^{11b}$ are hydrogen. In certain embodiments, one of $R^{11a}$ and $R^{11b}$ is a non-hydrogen group. In certain embodiments, $R^{11a}$ and $R^{11b}$ are joined to form an oxo group.

In certain embodiments, wherein $R^2$ and $R^4$ are hydrogen, the compound of Formula (I) is of Formula (I-b1), (I-b2), or (I-b3):

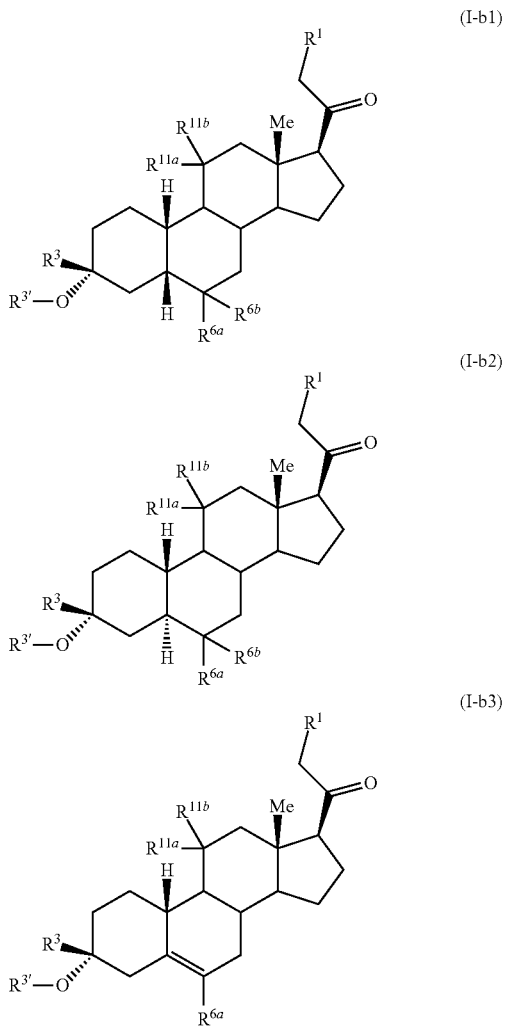

or a pharmaceutically acceptable salt, solvate, hydrate, prodrug, stereoisomer, tautomer, isotopic variant, or N-oxide thereof, or a combination thereof. In certain embodiments, $R^1$ is hydrogen, halogen (e.g., bromine), —$OR^{A1}$ (e.g., —OH), —$N(R^{A1})_2$, —S—$S(=O)_2R^{A2}$, substituted or unsubstituted hetercyclyl, or substituted or unsubstituted heteroaryl. In certain embodiments, $R^1$ is hydrogen, bromine, or —OH. In certain embodiments, $R^3$ is substituted or unsubstituted alkyl, substituted or unsubstituted alkenyl, or substituted or unsubstituted alkynyl. In certain embodiments, $R^{3'}$ is hydrogen. In certain embodiments, both $R^{6a}$ and $R^{6b}$ are hydrogen. In certain embodiments, one of $R^{6a}$ and $R^{6b}$ is a non-hydrogen group. In certain embodiments, $R^{6a}$ is a non-hydrogen alpha group. In certain embodiments, $R^{6a}$ is a non-hydrogen beta group. In certain embodiments, $R^{6a}$ is halo, e.g., fluoro, or alkyl. In certain embodiments, $R^{6a}$ is halo, e.g., fluoro, or alkyl, and $R^{6b}$ is hydrogen. In certain embodiments, $R^{6a}$ and $R^{6b}$ are both halo, e.g., fluoro. In certain embodiments, $R^{6a}$ and $R^{6b}$ are both alkyl, e.g., methyl. In certain embodiments, $R^{6a}$ and $R^{6b}$ are joined to form an oxo group. In certain embodiments, both $R^{11a}$ and $R^{11b}$ are hydrogen. In certain embodiments, one of $R^{11a}$ and $R^{11b}$ is a non-hydrogen group. In certain embodiments, $R^{11a}$ and $R^{11b}$ are joined to form an oxo group.

In certain embodiments, wherein $R^2$ and $R^4$ are hydrogen, the compound of Formula (III) is of Formula (III-b1), (III-b2), or (III-b3):

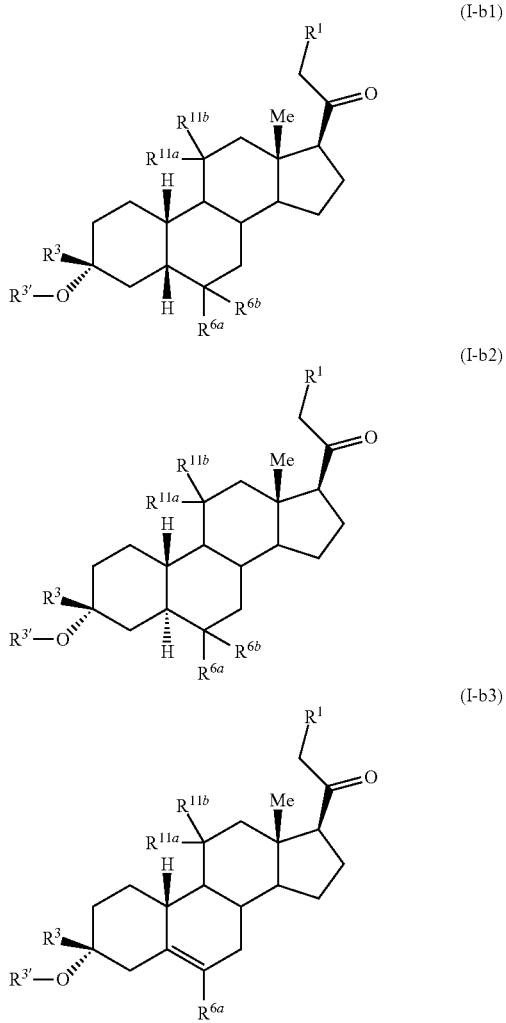

or a pharmaceutically acceptable salt, solvate, hydrate, prodrug, stereoisomer, tautomer, isotopic variant, or N-oxide thereof, or a combination thereof. In certain embodiments, $R^1$ is hydrogen, halogen (e.g., bromine), —$OR^{A1}$ (e.g., —OH), —$N(R^{A1})_2$, —S—$S(=O)_2R^{A2}$, substituted or unsubstituted hetercyclyl, or substituted or unsubstituted heteroaryl. In certain embodiments, $R^1$ is hydrogen, bromine, or —OH. In certain embodiments, $R^3$ is substituted or unsubstituted alkyl, substituted or unsubstituted alkenyl, or substituted or unsubstituted alkynyl. In certain embodiments, $R^{3'}$ is hydrogen. In certain embodiments, both $R^{6a}$ and $R^{6b}$ are hydrogen. In certain embodiments, one of $R^{6a}$ and $R^{6b}$ is a non-hydrogen group. In certain embodiments, $R^{6a}$ is a non-hydrogen alpha group. In certain embodiments, $R^{6a}$ is a non-hydrogen beta group. In certain embodiments, $R^{6a}$ is halo, e.g., fluoro, or alkyl. In certain embodiments, $R^{6a}$ is halo, e.g., fluoro, or alkyl, and $R^{6b}$ is hydrogen. In certain embodiments, $R^{6a}$ and $R^{6b}$ are both halo, e.g., fluoro. In certain embodiments, $R^{6a}$ and $R^{6b}$ are both alkyl, e.g., methyl. In certain embodiments, $R^{6a}$ and $R^{6b}$ are joined to form an oxo group. In certain embodiments, both $R^{11a}$ and $R^{11b}$ are hydrogen. In certain embodiments, one of $R^{11a}$ and $R^{11b}$ is a non-hydrogen group. In certain embodiments, $R^{11a}$ and $R^{11b}$ are joined to form an oxo group.

In certain embodiments, wherein $R^2$, $R^4$, $R^{11a}$ and $R^{11b}$ are hydrogen, the compound of Formula (I) is of Formula (I-c1), (I-c2), or (I-c3):

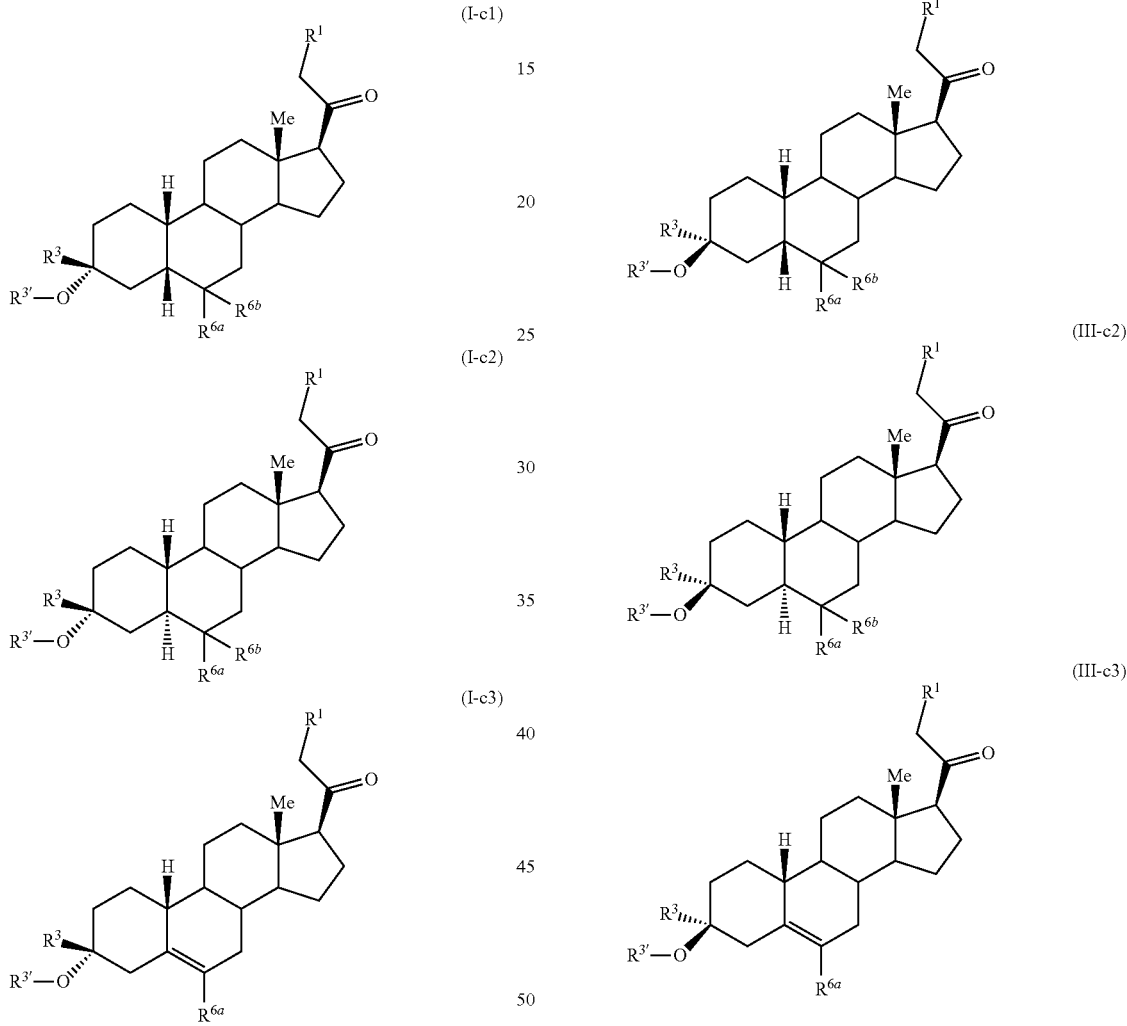

or a pharmaceutically acceptable salt, solvate, hydrate, prodrug, stereoisomer, tautomer, isotopic variant, or N-oxide thereof, or a combination thereof. In certain embodiments, $R^1$ is hydrogen, halogen (e.g., bromine), —$OR^{A1}$ (e.g., —OH), —$N(R^{A1})_2$, —S—$S(=O)_2R^{A2}$, substituted or unsubstituted hetercyclyl, or substituted or unsubstituted heteroaryl. In certain embodiments, $R^1$ is hydrogen, bromine, or —OH. In certain embodiments, $R^3$ is substituted or unsubstituted alkyl, substituted or unsubstituted alkenyl, or substituted or unsubstituted alkynyl. In certain embodiments, $R^{3'}$ is hydrogen. In certain embodiments, both $R^{6a}$ and $R^{6b}$ are hydrogen. In certain embodiments, one of $R^{6a}$ and $R^{6b}$ is a non-hydrogen group. In certain embodiments, $R^{6a}$ is a non-hydrogen alpha group. In certain embodiments, $R^{6a}$ is a non-hydrogen beta group. In certain embodiments, $R^{6a}$ is halo, e.g., fluoro, or alkyl. In certain embodiments, $R^{6a}$ is halo, e.g., fluoro, or alkyl, and $R^{6b}$ is hydrogen. In certain embodiments, $R^{6a}$ and $R^{6b}$ are both halo, e.g., fluoro. In certain embodiments, $R^{6a}$ and $R^{6b}$ are both alkyl, e.g., methyl. In certain embodiments, $R^{6a}$ and $R^{6b}$ are joined to form an oxo group.

In certain embodiments, wherein $R^2$, $R^4$, $R^{11a}$ and $R^{11b}$ are hydrogen, the compound of Formula (III) is of Formula (III-c1), (III-c2), or (III-c3):

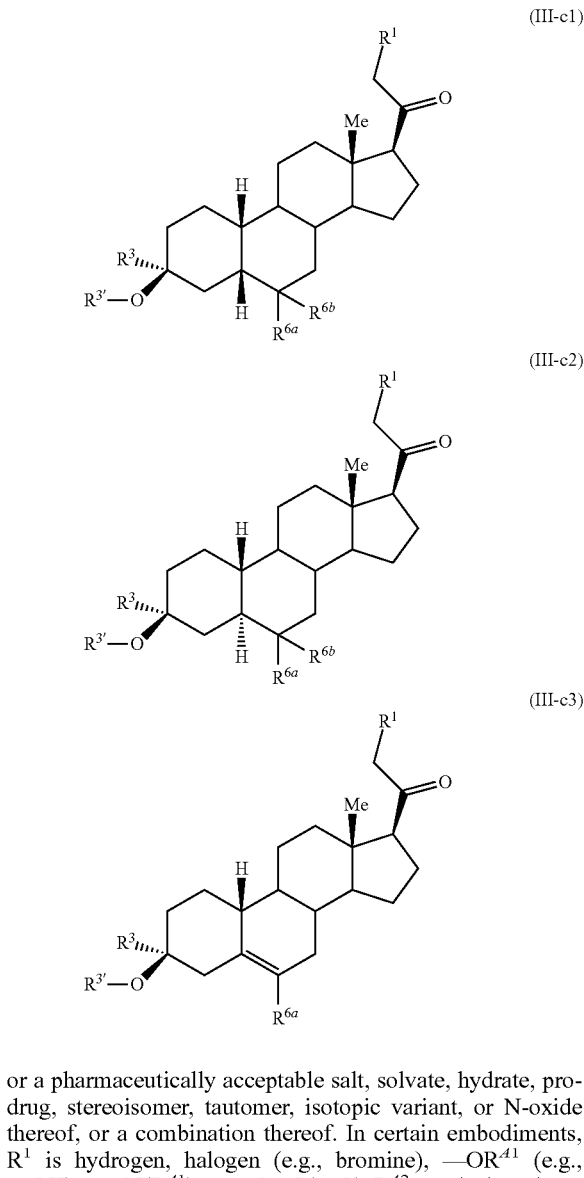

or a pharmaceutically acceptable salt, solvate, hydrate, prodrug, stereoisomer, tautomer, isotopic variant, or N-oxide thereof, or a combination thereof. In certain embodiments, $R^1$ is hydrogen, halogen (e.g., bromine), —$OR^{A1}$ (e.g., —OH), —$N(R^{A1})_2$, —S—$S(=O)_2R^{A2}$, substituted or unsubstituted hetercyclyl, or substituted or unsubstituted heteroaryl. In certain embodiments, $R^1$ is hydrogen, bromine, or —OH. In certain embodiments, $R^3$ is substituted or unsubstituted alkyl, substituted or unsubstituted alkenyl, or substituted or unsubstituted alkynyl. In certain embodiments, $R^{3'}$ is hydrogen. In certain embodiments, both $R^{6a}$ and $R^{6b}$ are hydrogen. In certain embodiments, one of $R^{6a}$ and $R^{6b}$ is a non-hydrogen group. In certain embodiments, $R^{6a}$ is a non-hydrogen alpha group. In certain embodiments, $R^{6a}$ is a non-hydrogen beta group. In certain embodiments, $R^{6a}$ is halo, e.g., fluoro, or alkyl. In certain embodiments, $R^{6a}$ is halo, e.g., fluoro, or alkyl, and $R^{6b}$ is hydrogen. In certain embodiments, $R^{6a}$ and $R^{6b}$ are both halo, e.g., fluoro. In certain embodiments, $R^{6a}$ and $R^{6b}$ are both alkyl, e.g., methyl. In certain embodiments, $R^{6a}$ and $R^{6b}$ are joined to form an oxo group.

In certain embodiments, wherein $R^2$, $R^4$, $R^{11a}$, $R^{11b}$, $R^{6a}$, $R^{6b}$ are hydrogen, the compound of Formula (I) is of Formula (I-d1), (I-d2), or (I-d3):

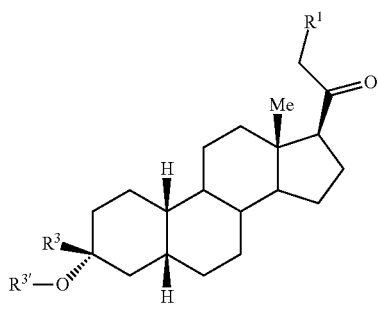

(I-d1)

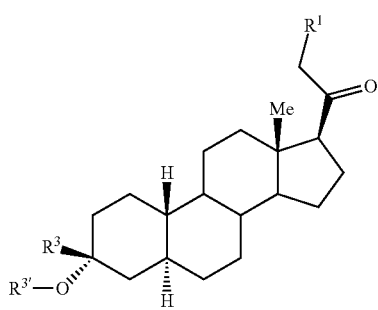

(I-d2)

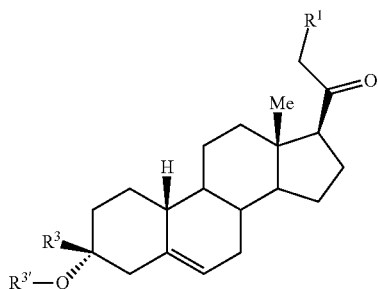

(I-d3)

or a pharmaceutically acceptable salt, solvate, hydrate, prodrug, stereoisomer, tautomer, isotopic variant, or N-oxide thereof, or a combination thereof. In certain embodiments, $R^1$ is hydrogen, halogen (e.g., bromine), —$OR^{A1}$ (e.g., —OH), —$N(R^{A1})_2$, —S—$S(=O)_2R^{A2}$, substituted or unsubstituted hetercyclyl, or substituted or unsubstituted heteroaryl. In certain embodiments, $R^1$ is hydrogen, bromine, or —OH. In certain embodiments, $R^3$ is substituted or unsubstituted alkyl, substituted or unsubstituted alkenyl, or substituted or unsubstituted alkynyl. In certain embodiments, $R^{3'}$ is hydrogen.

In certain embodiments, wherein $R^2$, $R^4$, $R^{11a}$, $R^{11b}$, $R^{6a}$, $R^{6b}$ are hydrogen, the compound of Formula (III) is of Formula (III-d1), (III-d2), or (III-d3):

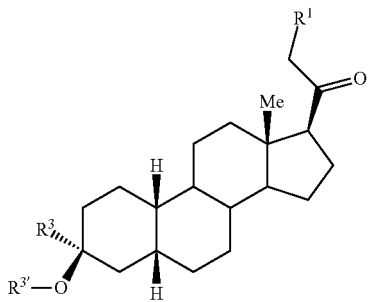

(III-d1)

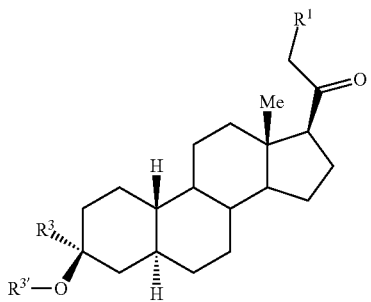

(III-d2)

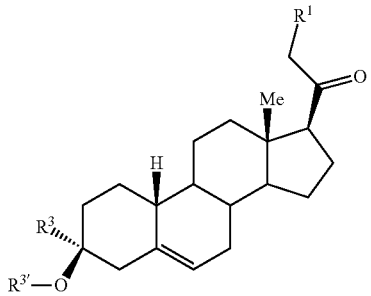

(III-d3)

or a pharmaceutically acceptable salt, solvate, hydrate, prodrug, stereoisomer, tautomer, isotopic variant, or N-oxide thereof, or a combination thereof. In certain embodiments, $R^1$ is hydrogen, halogen (e.g., bromine), —$OR^{A1}$ (e.g., —OH), —$N(R^{A1})_2$, —S—$S(=O)_2R^{A2}$, substituted or unsubstituted hetercyclyl, or substituted or unsubstituted heteroaryl. In certain embodiments, $R^1$ is hydrogen, bromine, or —OH. In certain embodiments, $R^3$ is substituted or unsubstituted alkyl, substituted or unsubstituted alkenyl, or substituted or unsubstituted alkynyl. In certain embodiments, $R^{3'}$ is hydrogen.

In certain further embodiments of Formula (I) and (III), $R^1$ is hydrogen, halogen, —$OR^{A1}$, —$SR^{A1}$, —$N(R^{A1})_2$, —$OC(=O)R^{A1}$, —$OC(=O)OR^{A1}$, —$OC(=O)SR^{A1}$, —$OC(=O)N(R^{A1})_2$, —$SC(=O)R^{A2}$, —$SC(=O)OR^{A1}$, —$SC(=O)SR^{A1}$, —$SC(=O)N(R^{A1})_2$, —$NHC(=O)R^{A1}$, —$NHC(=O)OR^{A1}$, —$NHC(=O)SR^{A1}$, —$NHC(=O)N(R^{A1})_2$, —$OS(=O)_2R^{A2}$, —$OS(=O)_2OR^{A1}$, —S—$S(=O)_2R^{A2}$, —S—$S(=O)_2OR^{A1}$, —$S(=O)R^{A2}$, —$SO_2R^{A2}$, or —$S(=O)_2OR^{A1}$; $R^2$ is hydrogen, substituted or unsubstituted heterocyclyl, —OH, —$OR^{B1}$, —$OC(=O)R^{B1}$, —$NH_2$, —$N(R^{B1})_2$, or —$NR^{B1}C(=O)R^{B1}$; $R^3$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; $R^{3'}$ is hydrogen; $R^4$ is hydrogen; each of $R^{6a}$ and $R^{6b}$ is independently hydrogen, halo, substituted or unsubstituted alkyl, substituted or unsubstituted alkenyl, or substituted or unsubstituted alkynyl, or $R^{6a}$ and $R^{6b}$ are joined to form an oxo (=O) group; and each of $R^{11A}$ and $R^{11b}$ is independently hydrogen, —OH, —$OR^{D1}$, —OC(=O)$R^{D1}$, —$NH_2$, —N($R^{D1}$)$_2$, or —$NR^{D1}$C(=O)$R^{D1}$, or $R^{11a}$ and $R^{11b}$ are joined to form an oxo (=O) group.

Additional embodiments of Formula (I) are further considered herein. For example, in certain embodiments, the compound of Formula (I) is selected from any one of the following Formula:

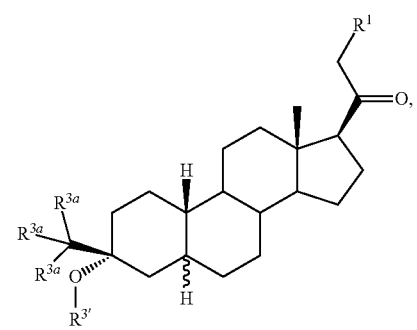
(II-a)

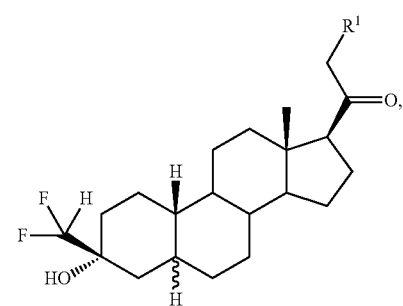
(II-a')

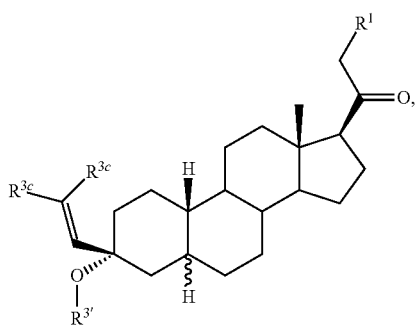
(II-b)

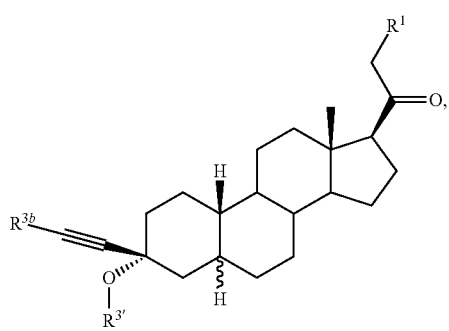
(II-c)

-continued

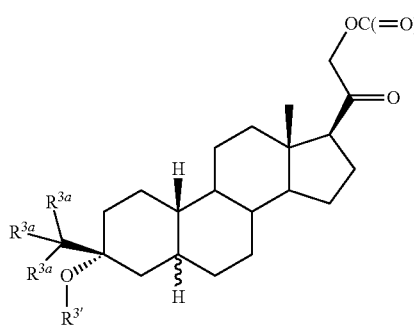
(II-e)

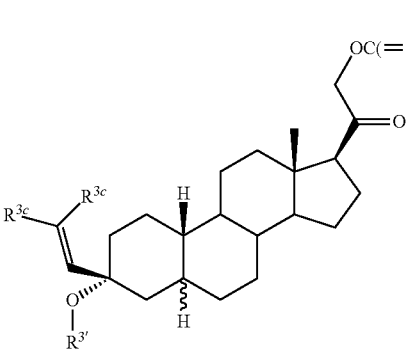
(II-f)

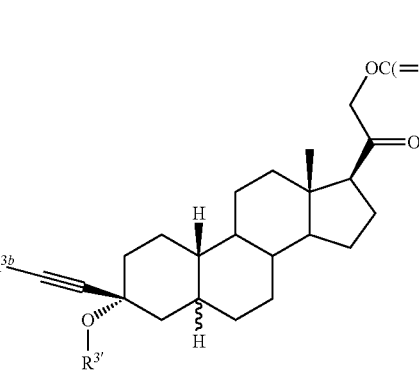
(II-g)

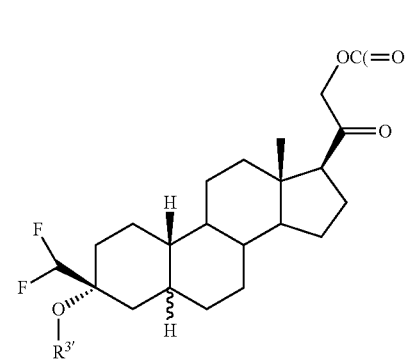
(II-h)

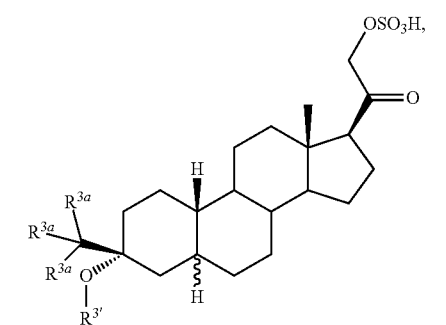 (II-j)
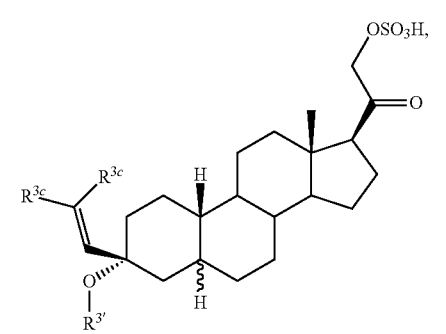 (II-k)
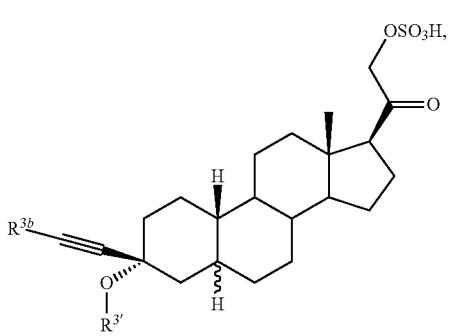 (II-l)
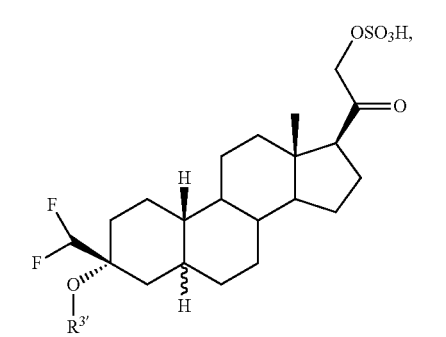 (II-m)
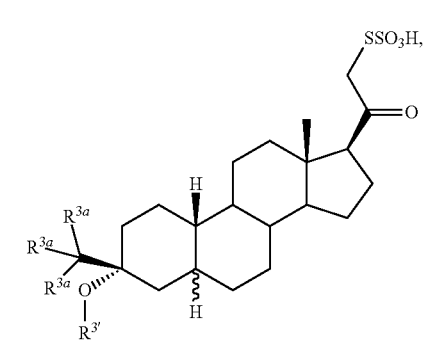 (II-n)
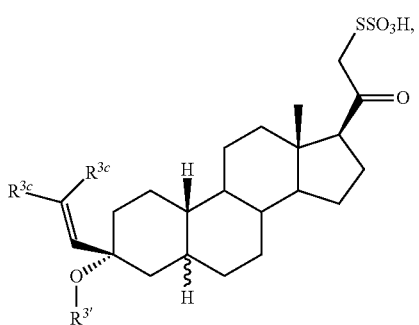 (II-o)
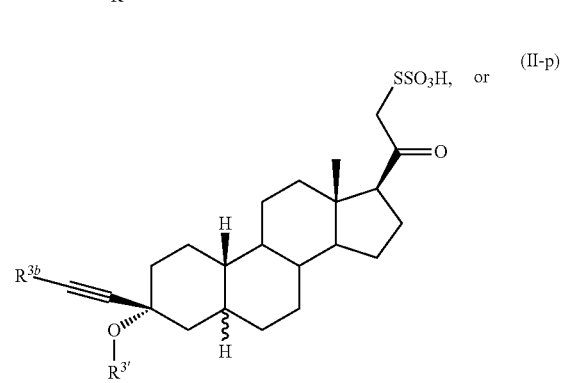 (II-p)
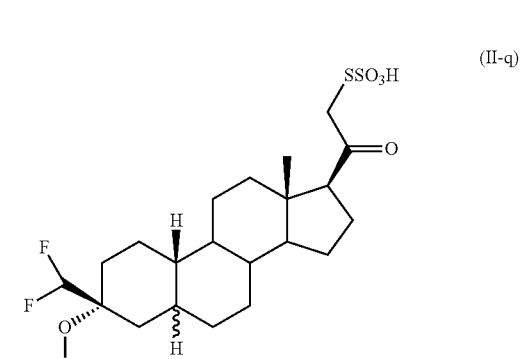 (II-q)
or a pharmaceutically acceptable salt, solvate, hydrate, prodrug, stereoisomer, tautomer, isotopic variant, or N-oxide thereof, or a combination thereof.
In certain embodiments, the compound of Formula (I) is selected from any one of the following Formula:
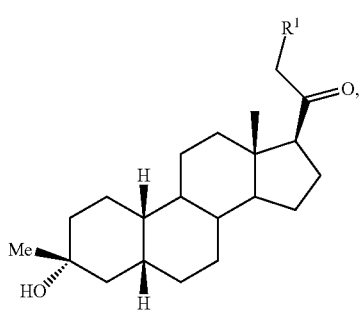 IIIa

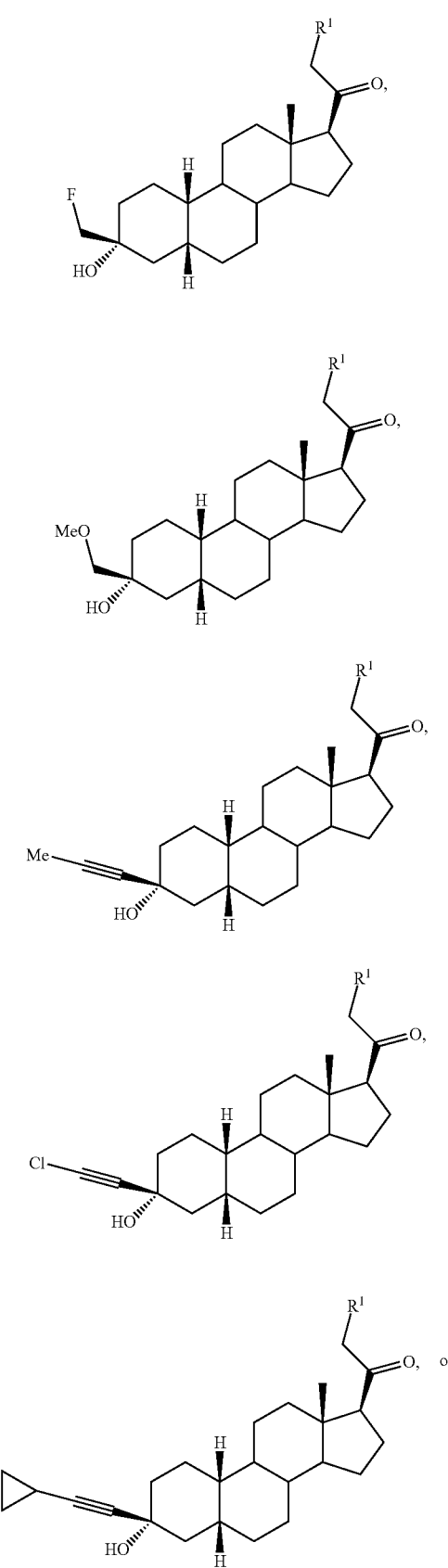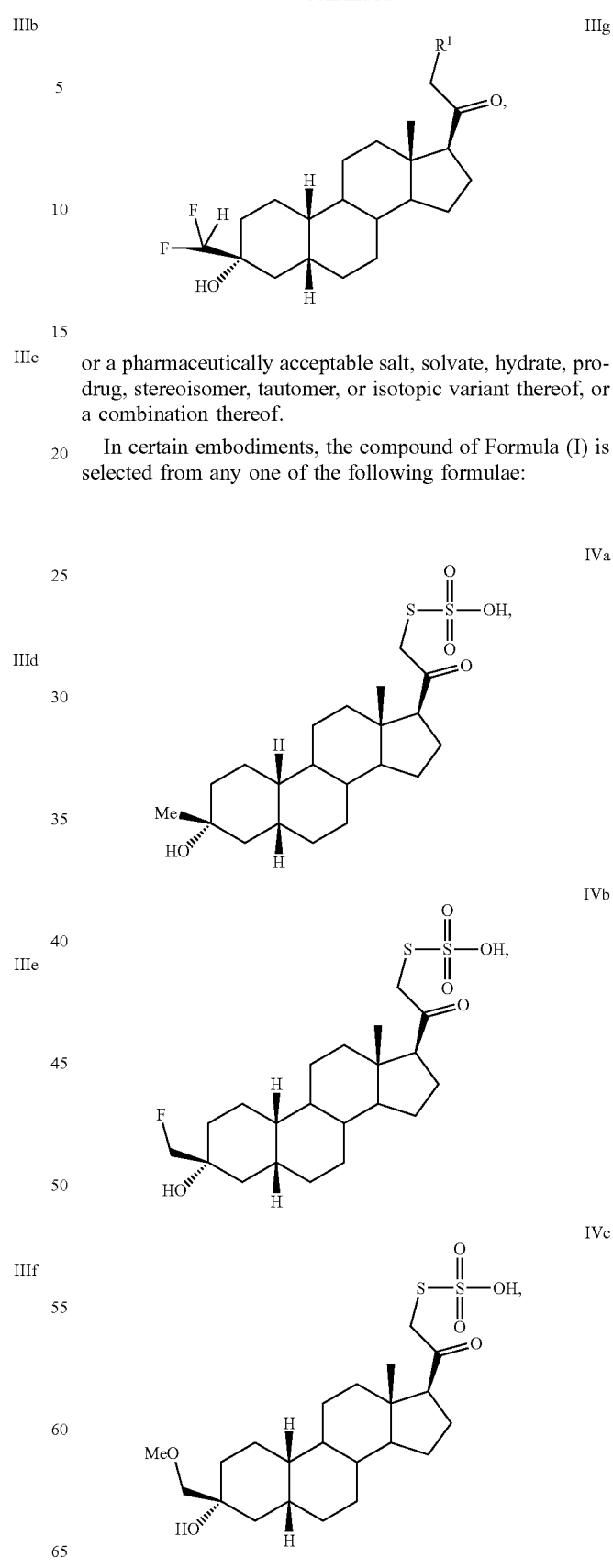
or a pharmaceutically acceptable salt, solvate, hydrate, prodrug, stereoisomer, tautomer, or isotopic variant thereof, or a combination thereof.
In certain embodiments, the compound of Formula (I) is selected from any one of the following formulae:

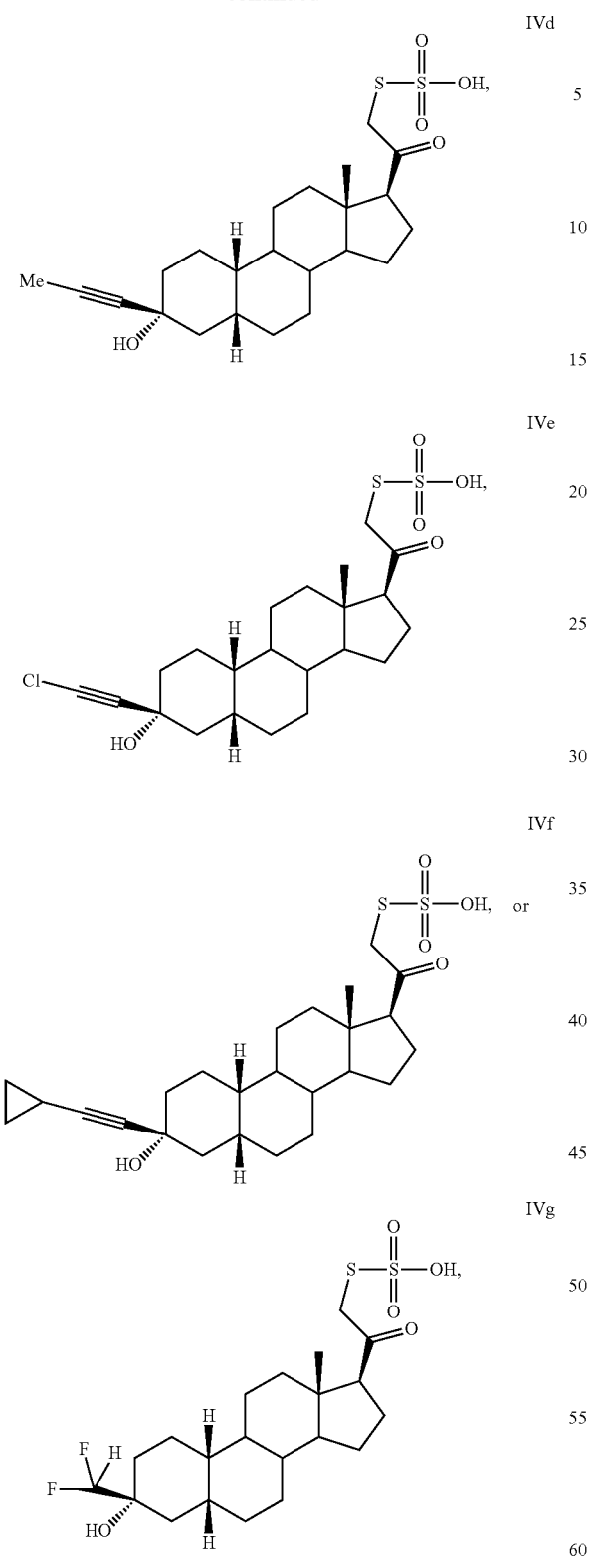
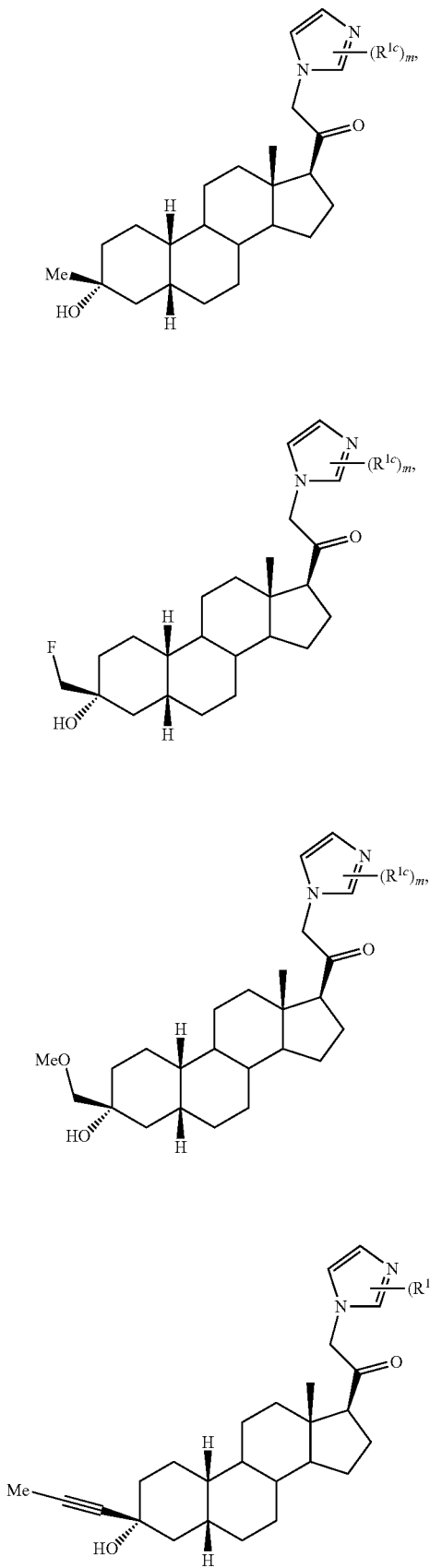
or a pharmaceutically acceptable salt, solvate, hydrate, prodrug, stereoisomer, tautomer, or isotopic variant thereof, or a combination thereof.
In certain embodiments, the compound of Formula (I) is selected from any one of the following formulae:

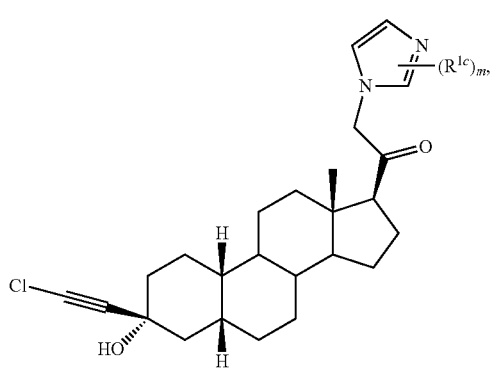
Ve

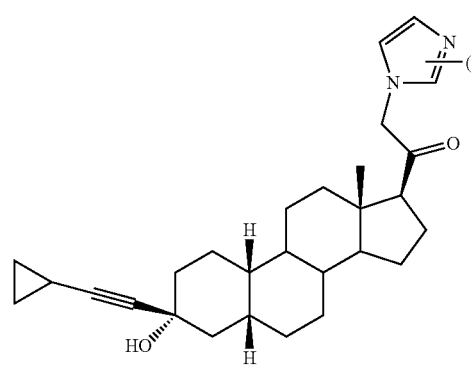
Vf or

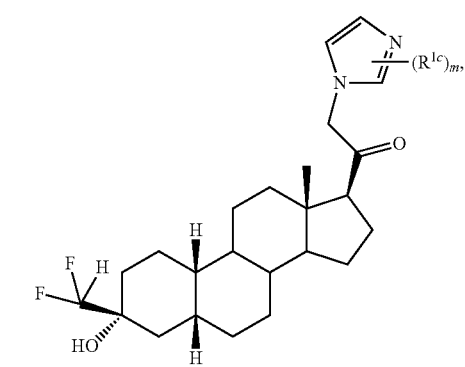
Vg

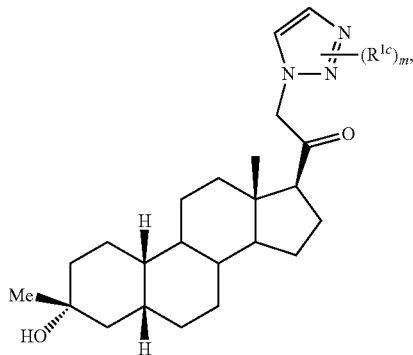
VIa

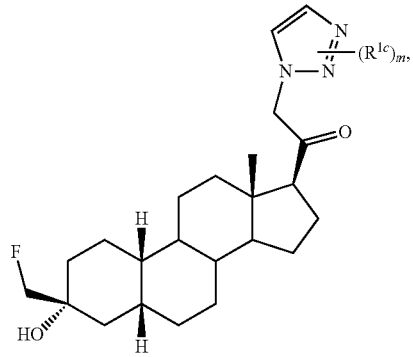
VIb

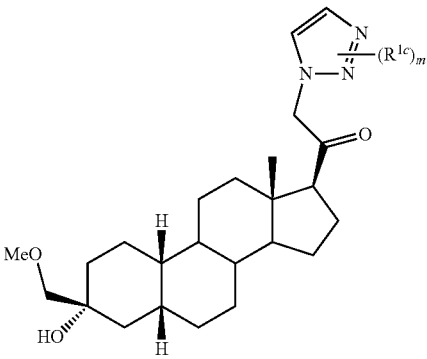
VIc

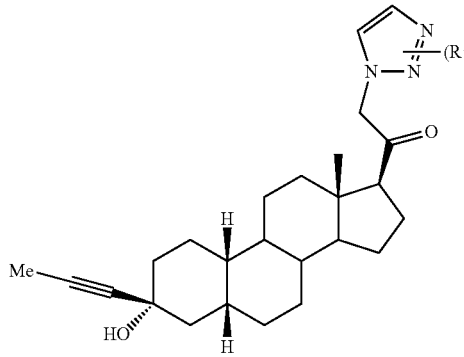
VId wherein m is 0, 1 or 2; and each $R^{1c}$ is indepependently —CH$_3$, F, Cl, —CN, —OMe, —SMe, —SOMe, —SO$_2$Me, —CH$_2$F, —CHF$_2$, or —CF$_3$; or a pharmaceutically acceptable salt, solvate, hydrate, prodrug, stereoisomer, tautomer, isotopic variant, or N-oxide thereof, or a combination thereof.

In certain embodiments, the compound of Formula (I) is selected from any one of the following formulae:

-continued

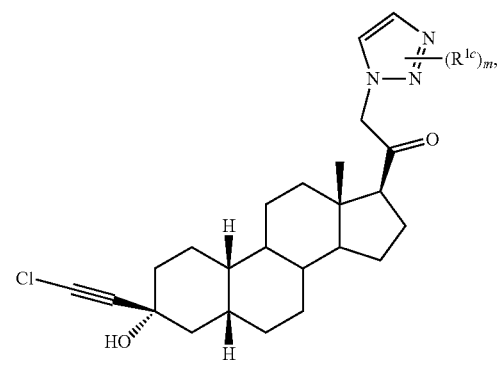
VIe

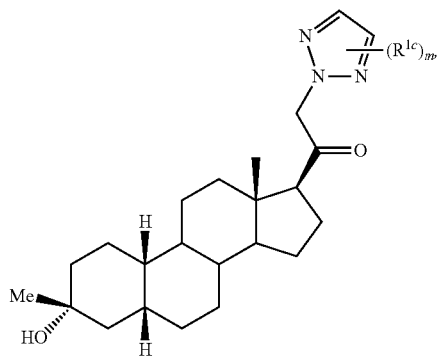
VIIa

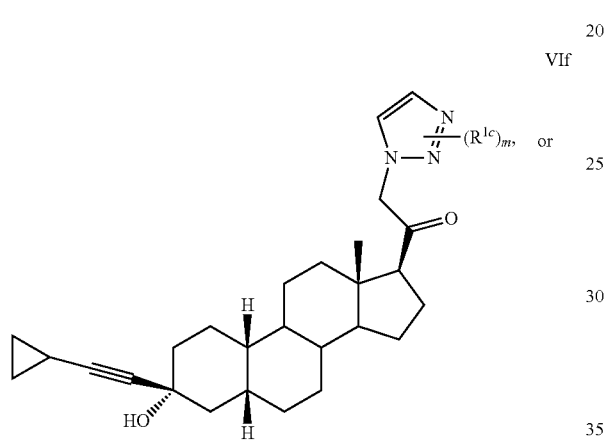
VIf or

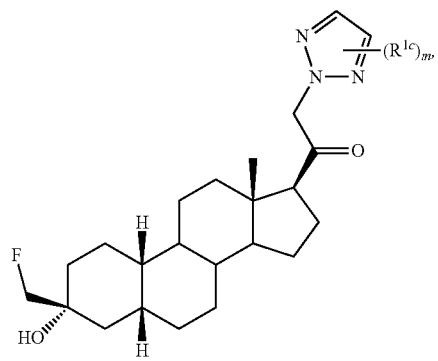
VIIb

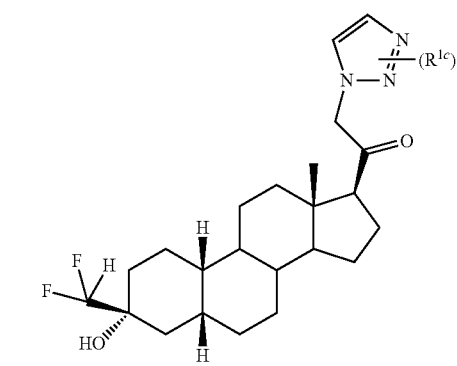
VIg

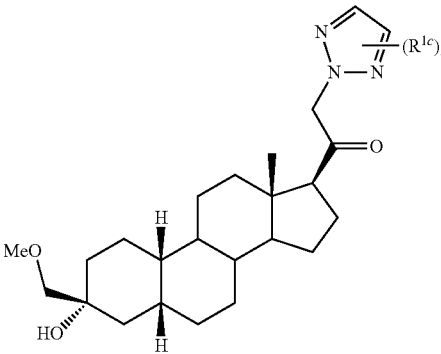
VIIc

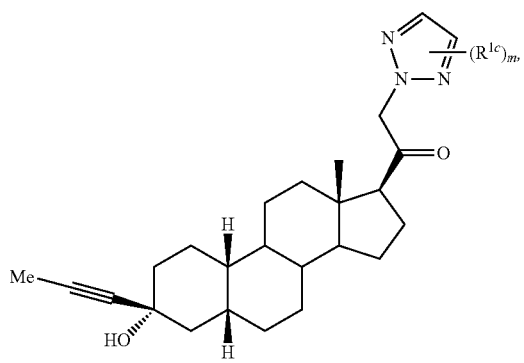
VIId wherein m is 0, 1 or 2; and each $R^{1c}$ is indepependently —$CH_3$, F, Cl, —CN, —OMe, —SMe, —SOMe, —$SO_2Me$, —$CH_2F$, —$CHF_2$, or —$CF_3$; or a pharmaceutically acceptable salt, solvate, hydrate, prodrug, stereoisomer, tautomer, isotopic variant, or N-oxide thereof, or a combination thereof.

In certain embodiments, the compound of Formula (I) is selected from any one of the following formulae:

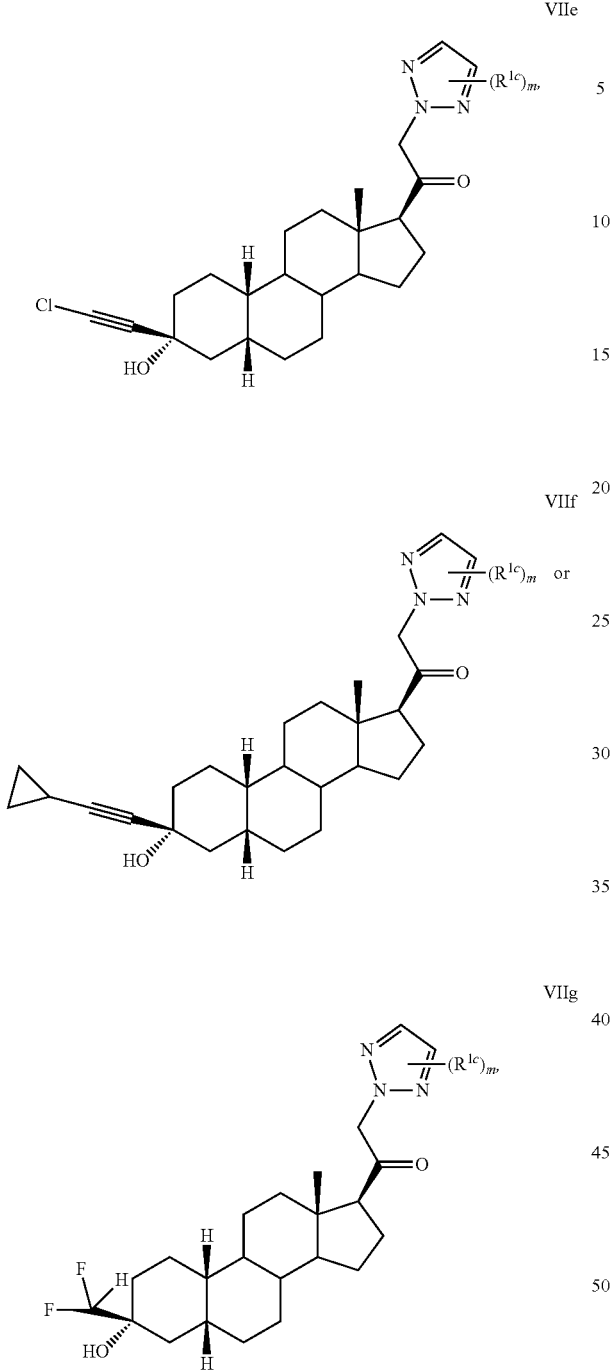
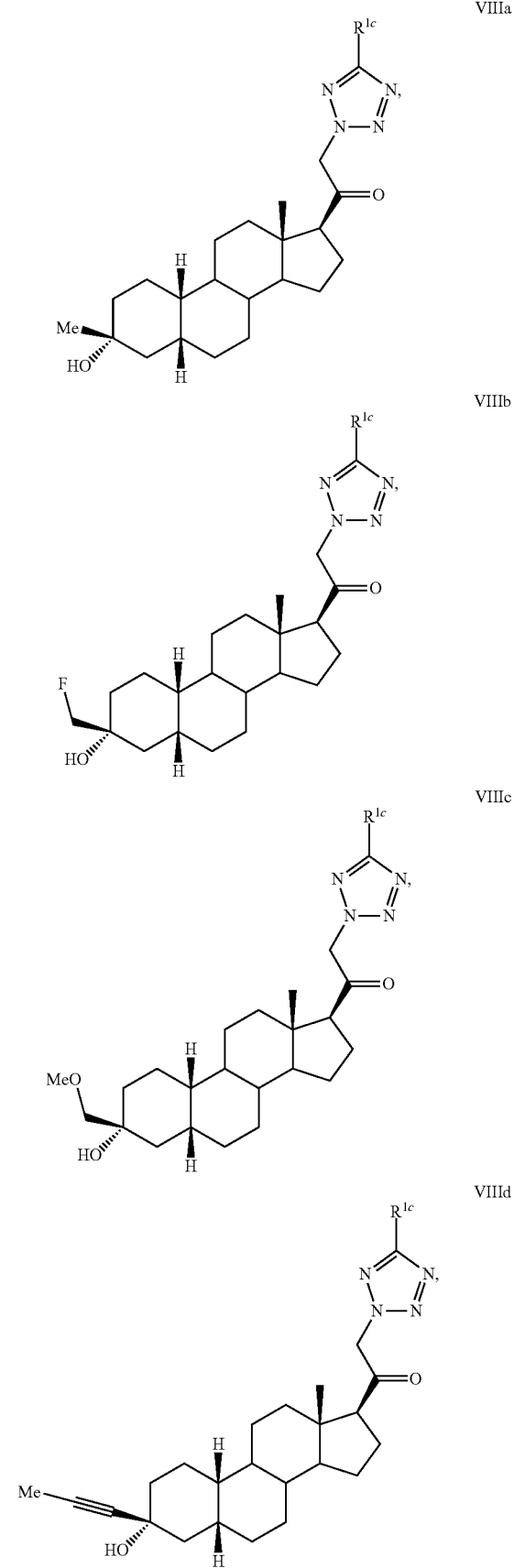

wherein m is 0, 1 or 2; and each $R^{1c}$ is indepependently —$CH_3$, Cl, F, —CN, —OMe, —SMe, —SOMe, —$SO_2Me$, —$CH_2F$, —$CHF_2$, or —$CF_3$; or a pharmaceutically acceptable salt, solvate, hydrate, prodrug, stereoisomer, tautomer, isotopic variant, or N-oxide thereof, or a combination thereof. In certain embodiments, m is 0. In certain embodiments m is 1. In certain embodiments m is 2. In certain embodiments, m is 1, and each $R^{1c}$ is —$CH_3$, Cl or —CN. In certain embodiments, m is 2, and each $R^{1c}$ is —$CH_3$, Cl or —CN.

In certain embodiments, the compound of Formula (I) is selected from any one of the following formulae:

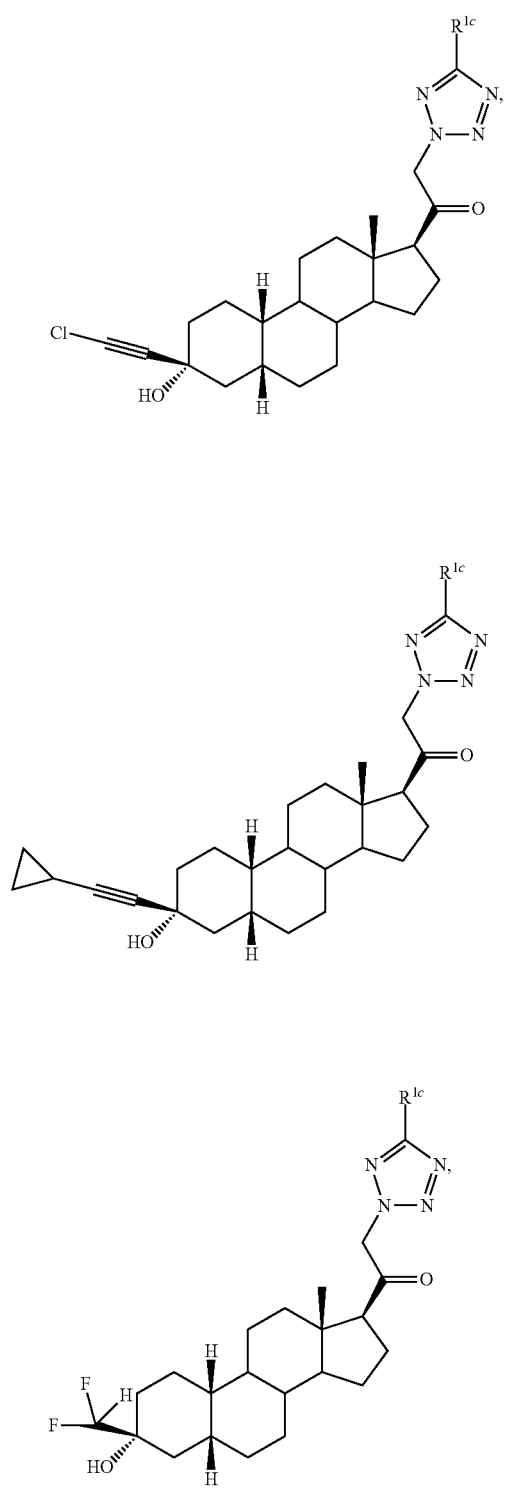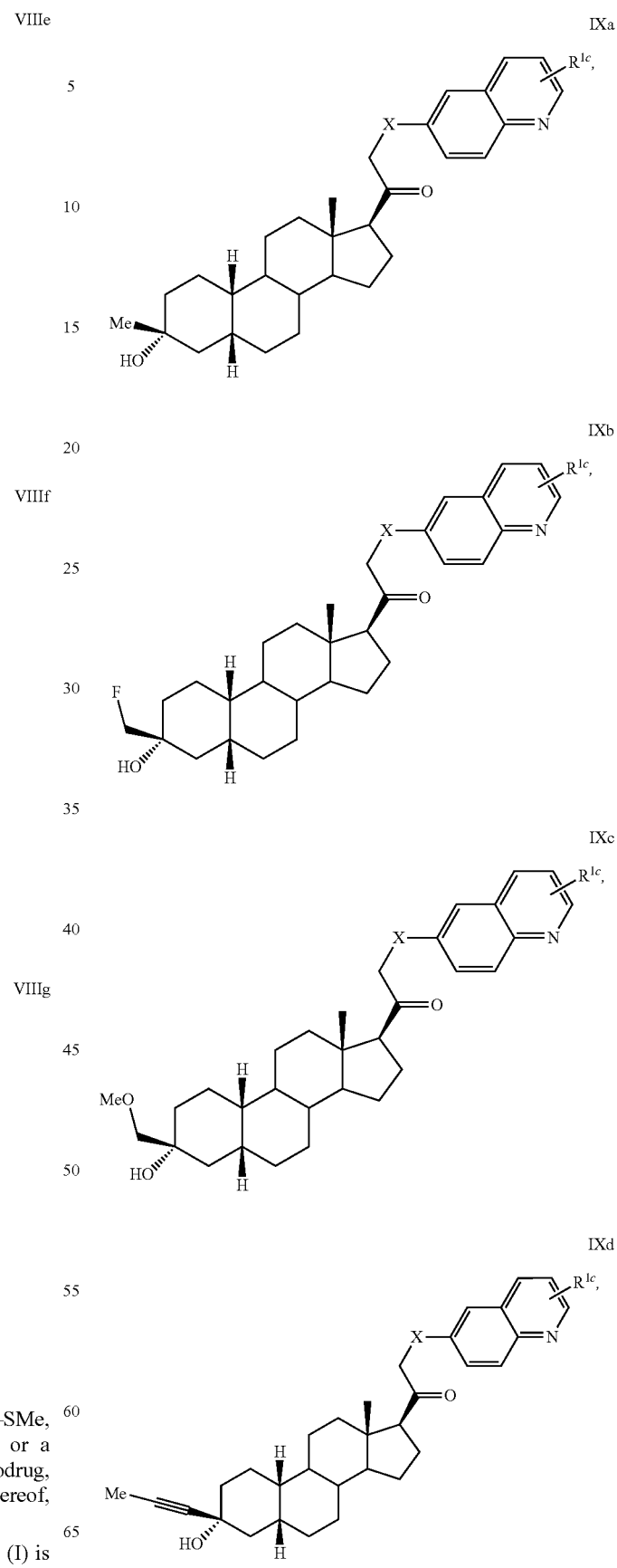
wherein $R^{1c}$ is H, —CH$_3$, Cl, F, —CN, OMe, —SMe, —SOMe, —SO$_2$Me, —CH$_2$F, —CHF$_2$, or —CF$_3$; or a pharmaceutically acceptable salt, solvate, hydrate, prodrug, stereoisomer, tautomer, isotopic variant, or N-oxide thereof, or a combination thereof.
In certain embodiments, the compound of Formula (I) is selected from any one of the following formulae:

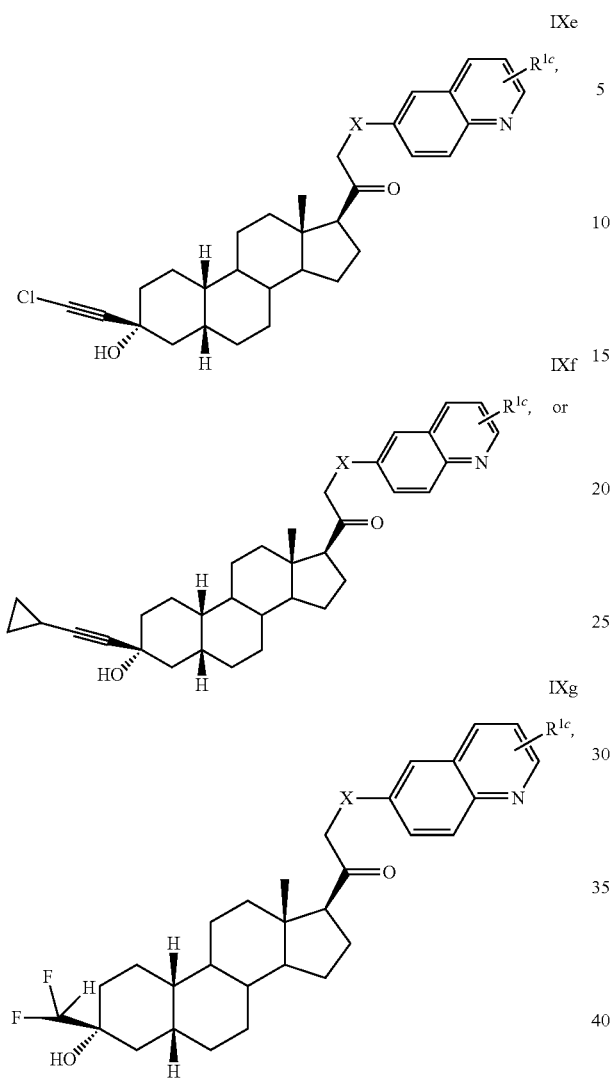

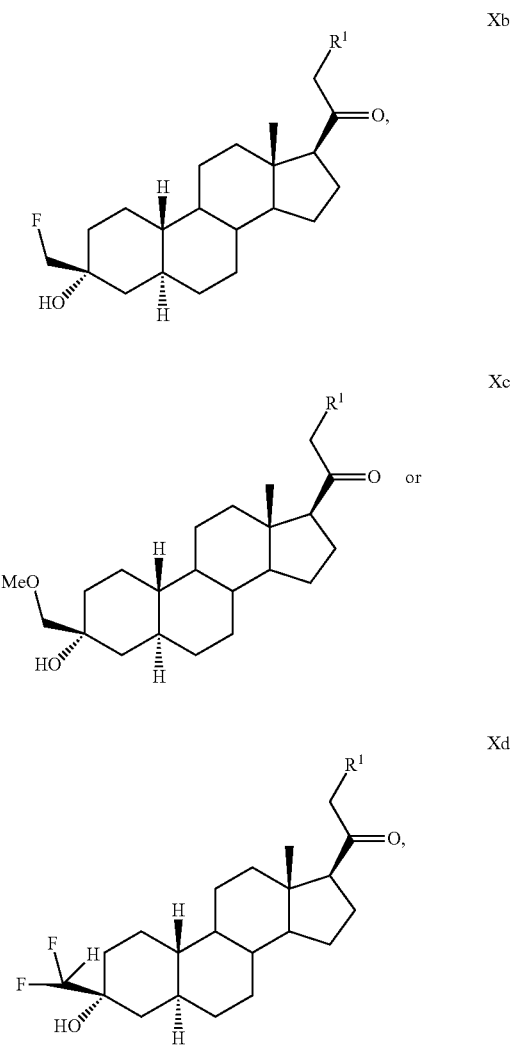

wherein X is —O— or —S—; and $R^{1c}$ is indepependently H, —CH$_3$, F, Cl, —CN, OMe, —SMe, —SOMe, —SO$_2$Me, —CH$_2$F, —CHF$_2$, or —CF$_3$; or a pharmaceutically acceptable salt, solvate, hydrate, prodrug, stereoisomer, tautomer, isotopic variant, or N-oxide thereof, or a combination thereof.

In certain embodiments, the compound of Formula (I) is selected from any one of the following formulae:

or a pharmaceutically acceptable salt, solvate, hydrate, prodrug, stereoisomer, tautomer, or isotopic variant thereof, or a combination thereof.

In certain embodiments, the compound of Formula (I) is selected from any one of the following formulae:

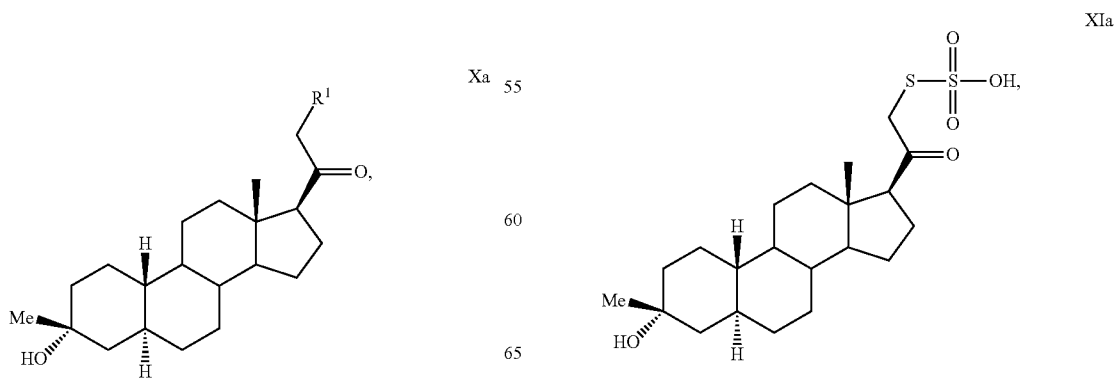

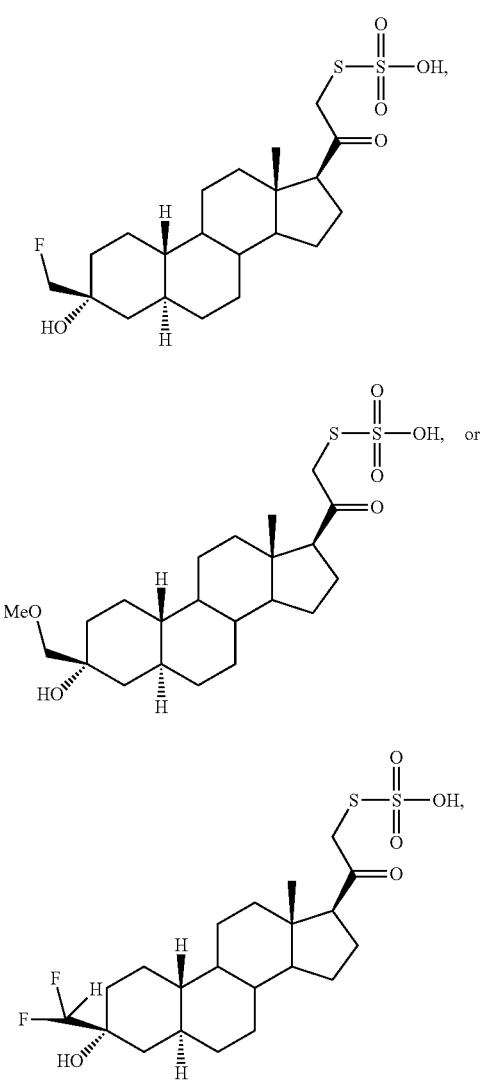

or a pharmaceutically acceptable salt, solvate, hydrate, prodrug, stereoisomer, tautomer, or isotopic variant thereof, or a combination thereof.

In certain embodiments, the compound of Formula (I) is selected from any one of the following formulae:

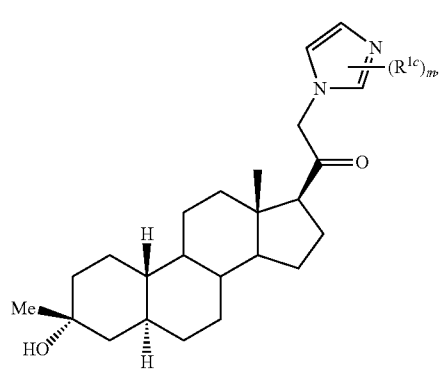

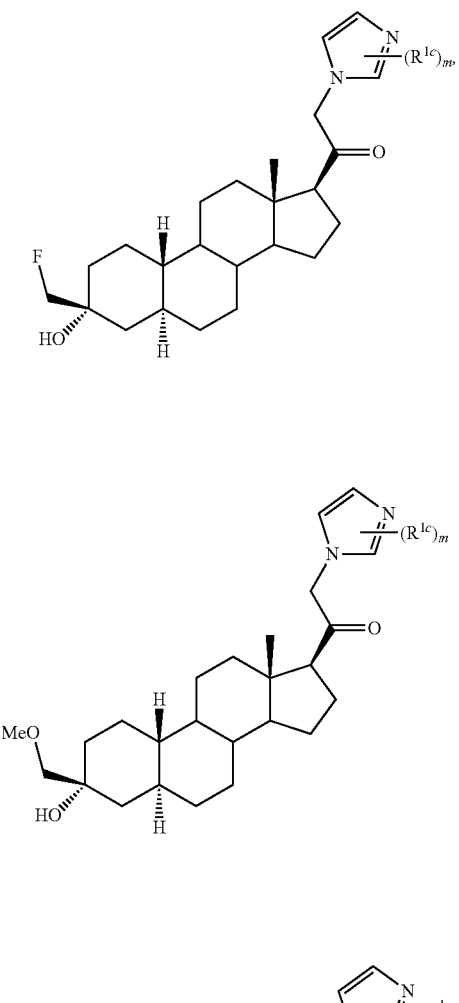

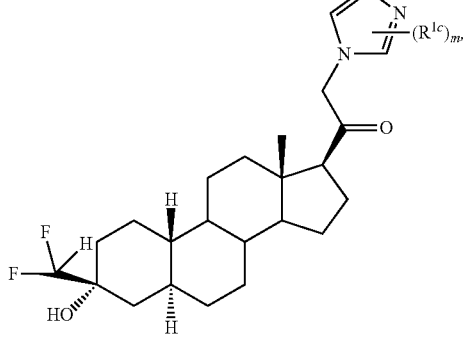

wherein m is 0, 1 or 2; and each $R^{1c}$ is indepependently —$CH_3$, F, Cl, —CN, —OMe, —SMe, —SOMe, —$SO_2$Me, —$CH_2$F, —$CHF_2$, or —$CF_3$; or a pharmaceutically acceptable salt, solvate, hydrate, prodrug, stereoisomer, tautomer, isotopic variant, or N-oxide thereof, or a combination thereof. In certain embodiments, m is 0. In certain embodiments, m is 1. In certain embodiments, m is 2. In certain embodiments, m is 2, and each $R^{1c}$ is —$CH_3$, Cl or —CN.

In certain embodiments, the compound of Formula (I) is selected from any one of the following formulae:

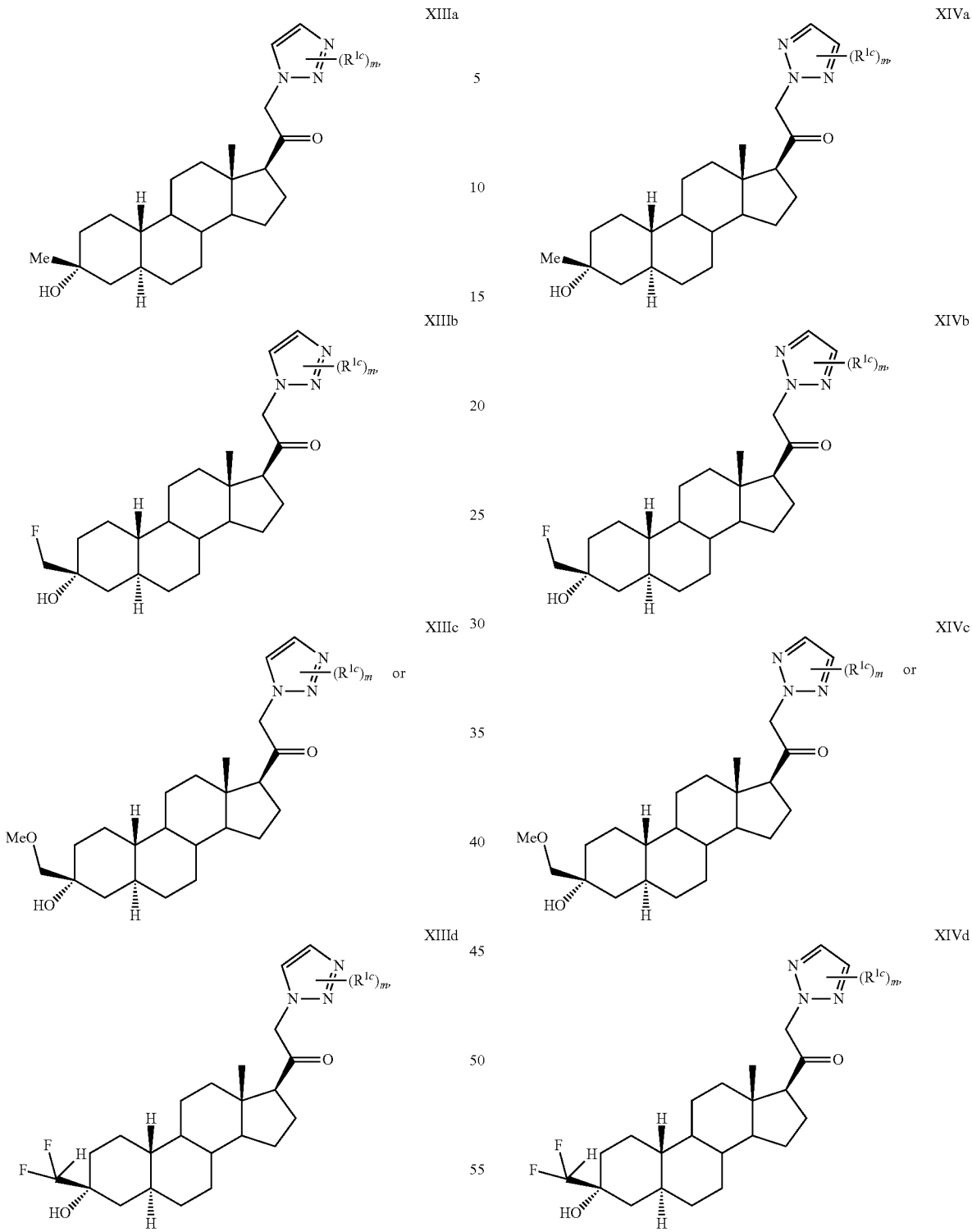

wherein m is 0, 1 or 2; and each $R^{1c}$ is indepependently —$CH_3$, F, Cl, —CN, —OMe, —SMe, —SOMe, —$SO_2Me$, —$CH_2F$, —$CHF_2$, or —$CF_3$; or a pharmaceutically acceptable salt, solvate, hydrate, prodrug, stereoisomer, tautomer, isotopic variant, or N-oxide thereof, or a combination thereof.

In certain embodiments, the compound of Formula (I) is selected from any one of the following formulae:

wherein m is 0, 1 or 2; and each $R^{1c}$ is indepependently —$CH_3$, F, Cl, —CN, —OMe, —SMe, —SOMe, —$SO_2Me$, —$CH_2F$, —$CHF_2$, or —$CF_3$; or a pharmaceutically acceptable salt, solvate, hydrate, prodrug, stereoisomer, tautomer, isotopic variant, or N-oxide thereof, or a combination thereof.

In certain embodiments, the compound of Formula (I) is selected from any one of the following formulae:

XVa
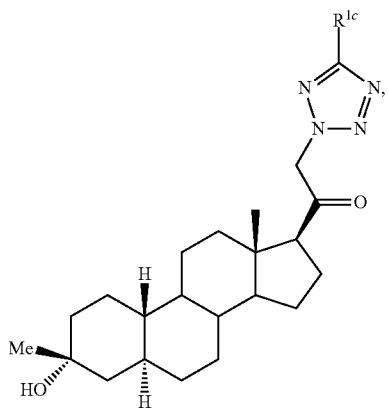
XVd
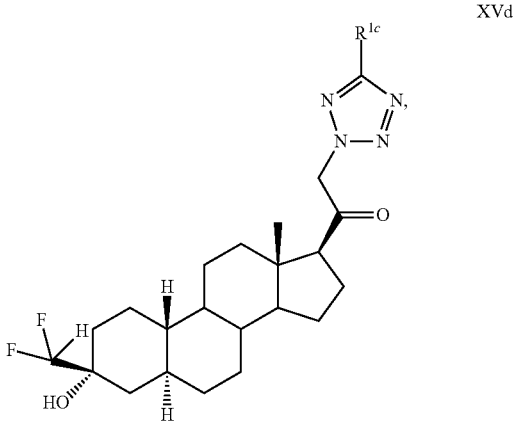
wherein $R^{1c}$ is H, —CH$_3$, Cl, —CN, —OMe, —SMe, —F, —SOMe, —SO$_2$Me, —CH$_2$F, —CHF$_2$, or —CF$_3$; or a pharmaceutically acceptable salt, solvate, hydrate, prodrug, stereoisomer, tautomer, isotopic variant, or N-oxide thereof, or a combination thereof.
In certain embodiments, the compound of Formula (I) is selected from any one of the following formulae:
XVb
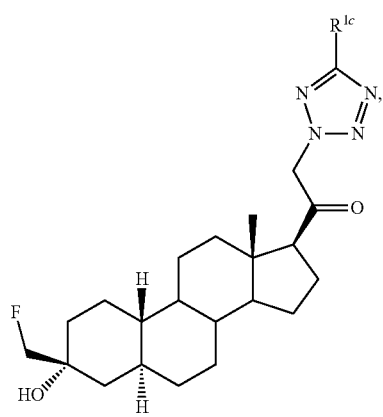
XVIa
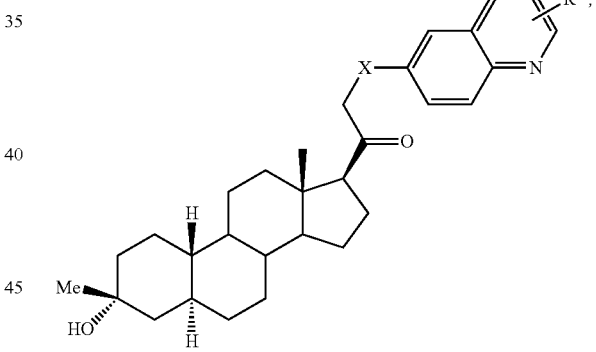
XVc
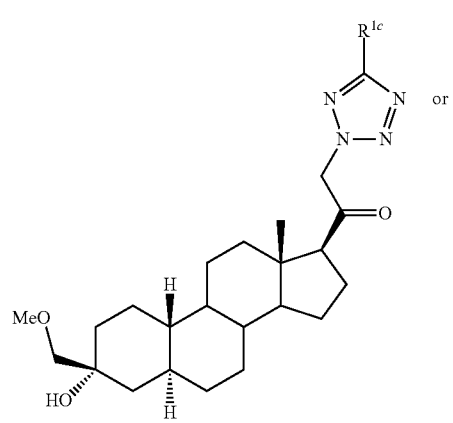
or
XVIb
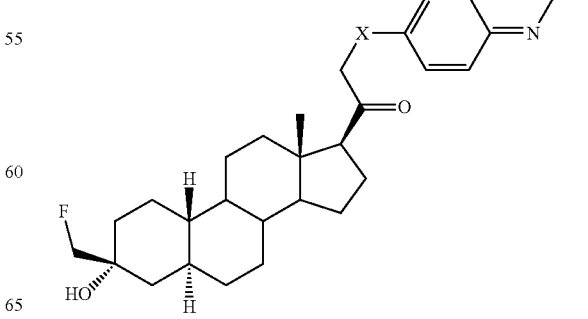

-continued

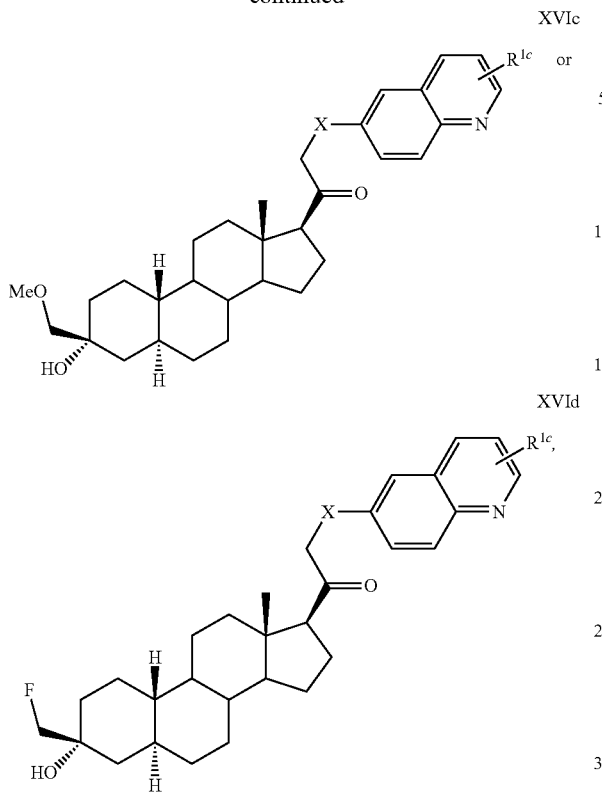

wherein X is —O— or —S—; and $R^{1c}$ is indepependently H, —CH₃, F, Cl, —CN, —OMe, —SMe, —SOMe, —SO₂Me, —CH₂F, —CHF₂, or —CF₃; or a pharmaceutically acceptable salt, solvate, hydrate, prodrug, stereoisomer, tautomer, isotopic variant, or N-oxide thereof, or a combination thereof. In certain embodiments, each $R^{1c}$ is indepependently H, —CH₃, F, Cl, —CN, —OMe, —SMe, —SOMe, —SO₂Me, —CH₂F, —CHF₂, or —CF₃. In certain embodiments, $R^{1c}$ is —CH₃, —CH₂F, —CHF₂, or —CF₃. In certain embodiments, $R^{1c}$ is F, Cl, or CN. In certain embodiments, $R^{1c}$ is OMe. In certain embodiments, $R^{1c}$ is SMe, —SOMe, or —SO₂Me. In certain embodiments, X is —O—. In certain embodiments, X is —S—.

In certain embodiments, the compound of Formula (I) is selected from any one of the following formulae:

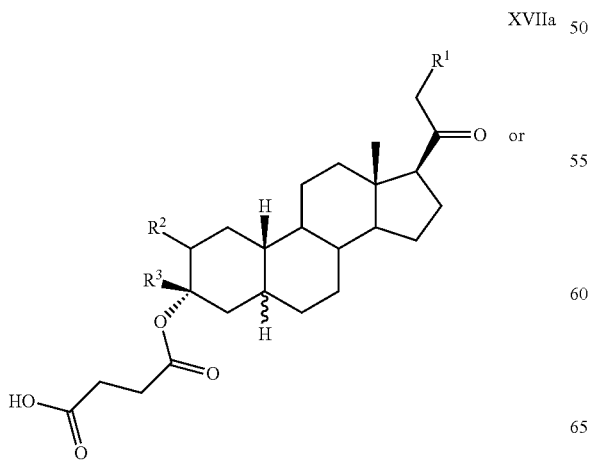

-continued

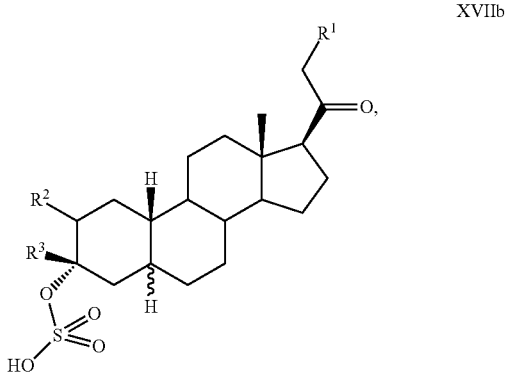

wherein $R^1$, $R^2$, and $R^3$ are as described herein; or a pharmaceutically acceptable salt, solvate, hydrate, prodrug, stereoisomer, tautomer, isotopic variant, or N-oxide thereof, or a combination thereof.

In certain embodiments, the compound of Formula (I) is selected from any one of the following compounds, or a pharmaceutically acceptable salt, solvate, prodrug, stereoisomers, tautomer, isotopic variant, N-oxide thereof, or a combination thereof:

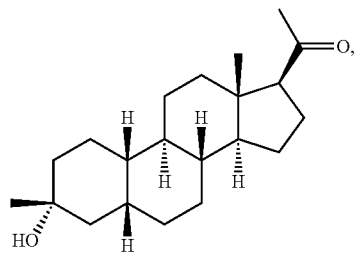

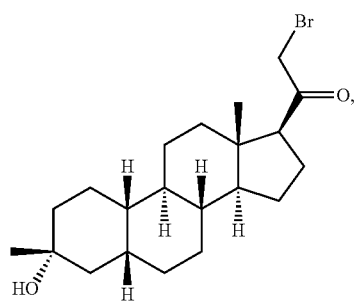

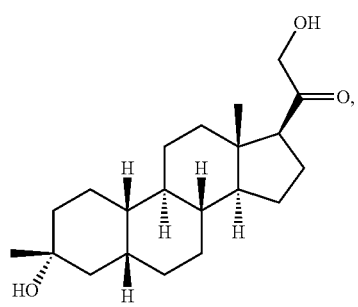

-continued
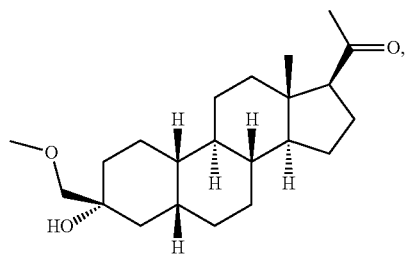
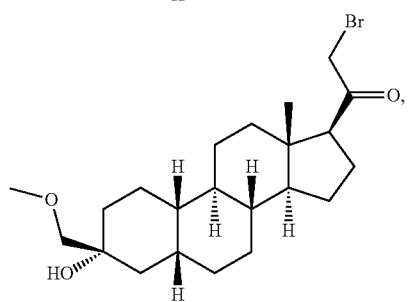
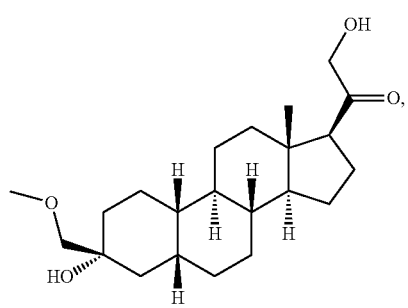
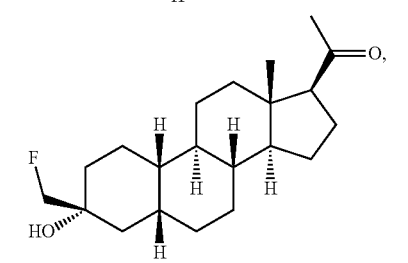
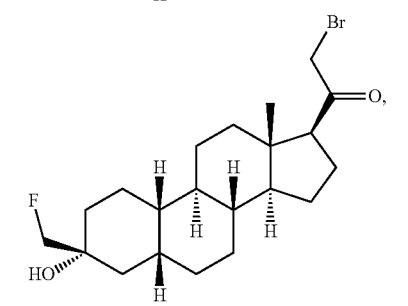
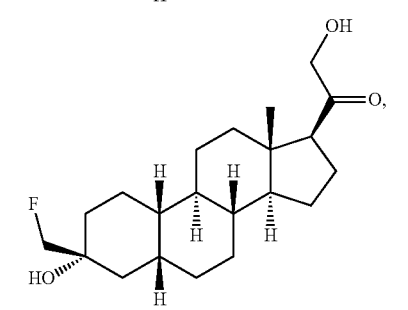
-continued
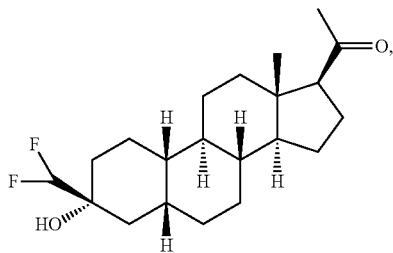
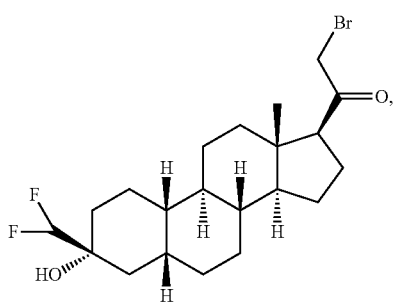
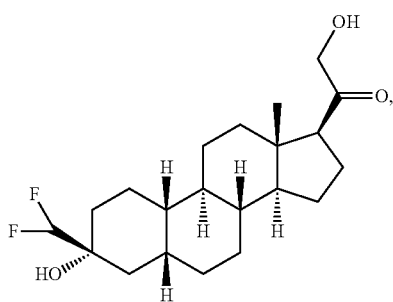
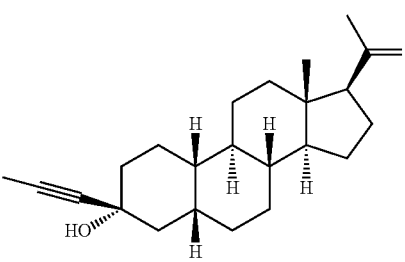
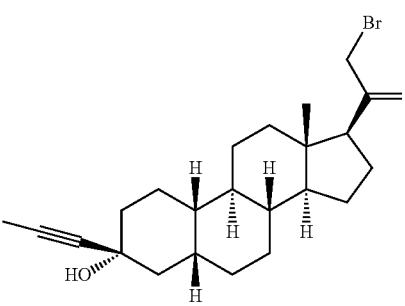
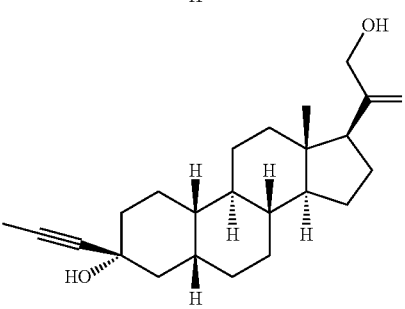

87
-continued
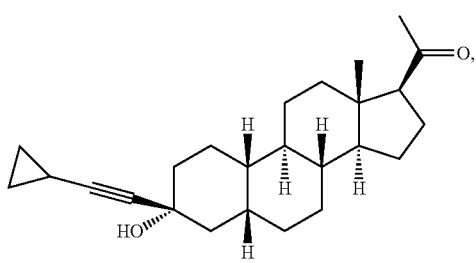
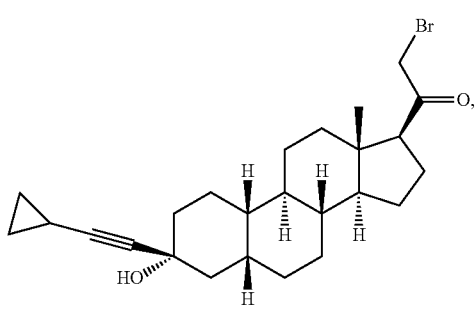
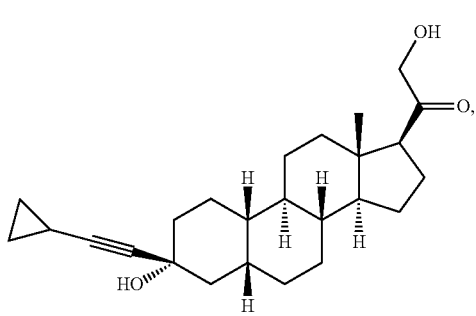
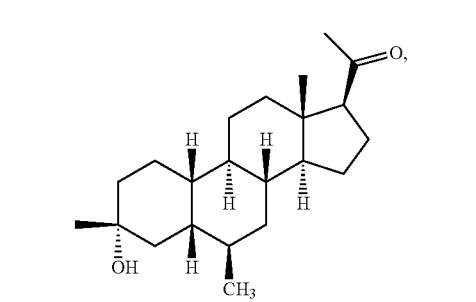
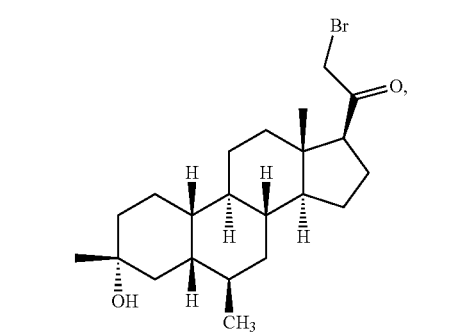
88
-continued
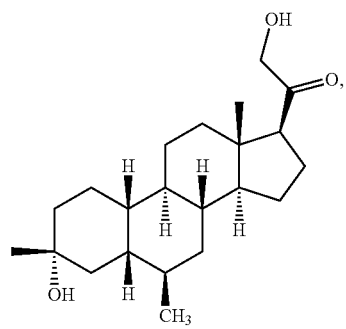
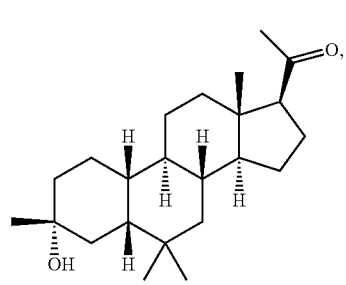
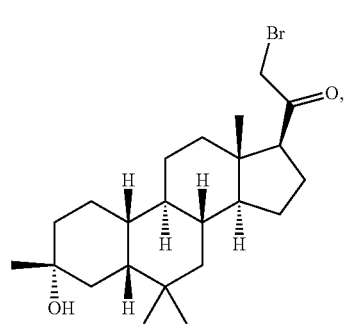
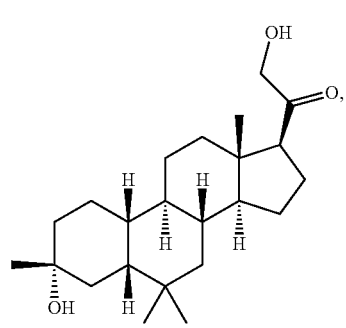
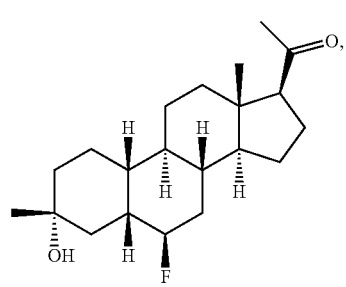

-continued
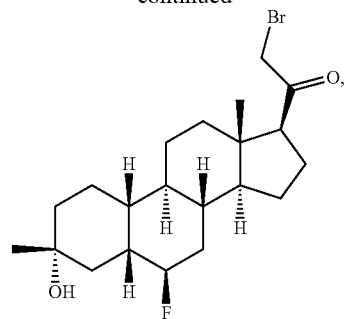
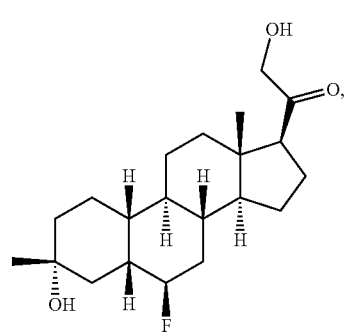
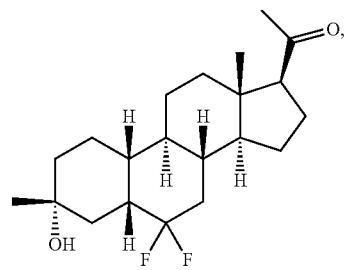
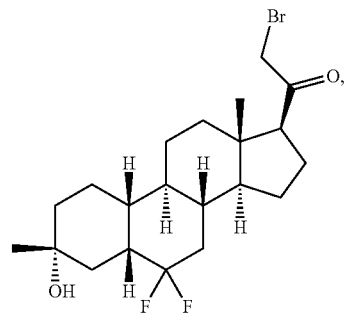
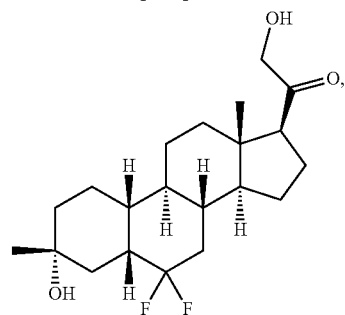
-continued
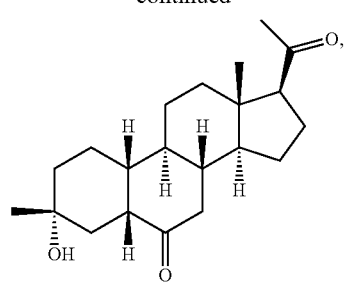
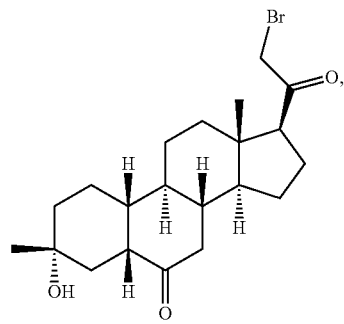
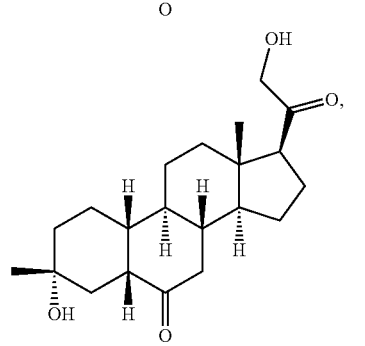
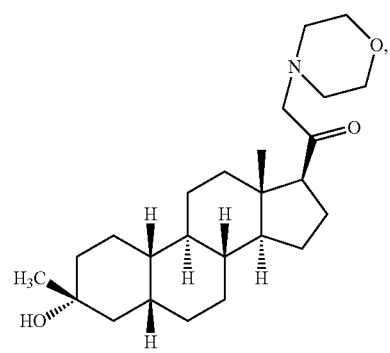
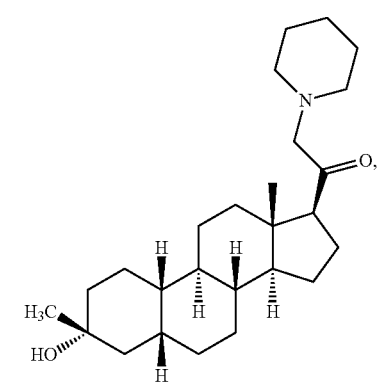

-continued
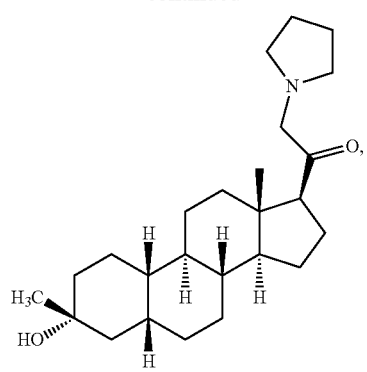
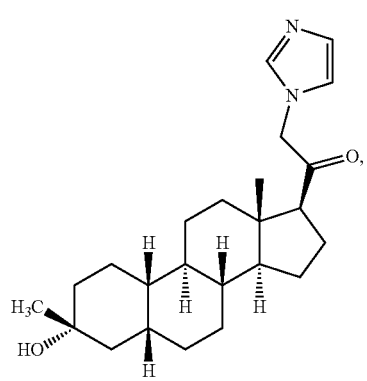
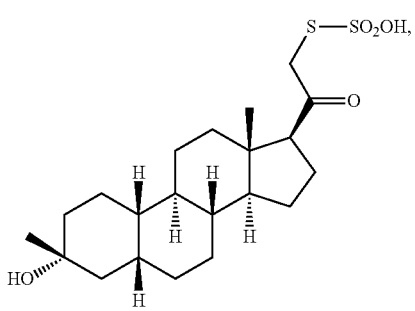
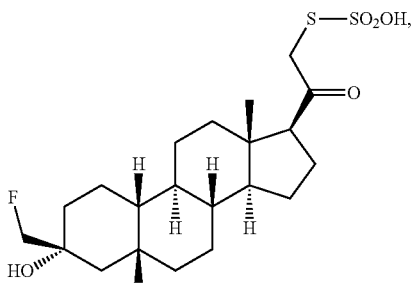
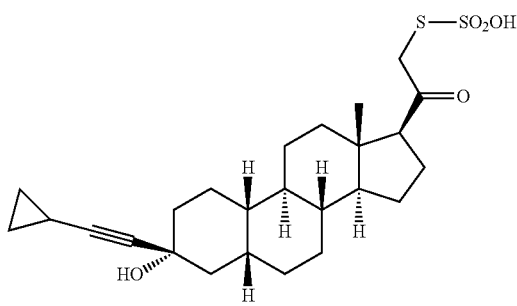
-continued
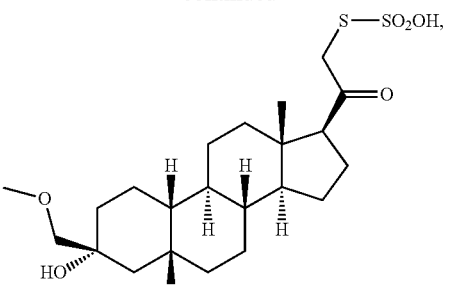
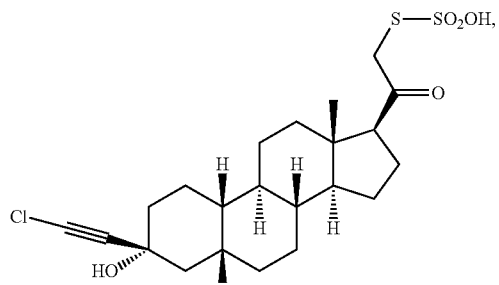
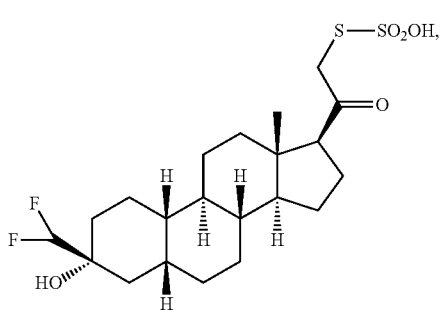
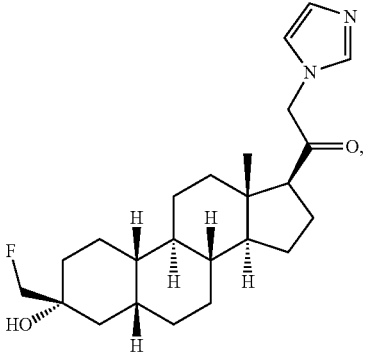
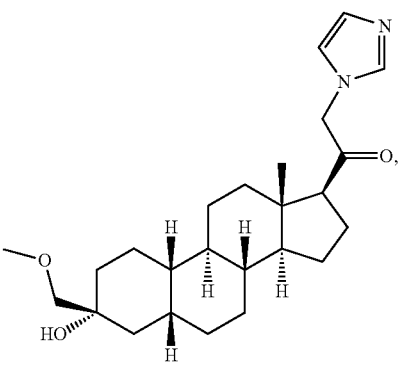

93
-continued
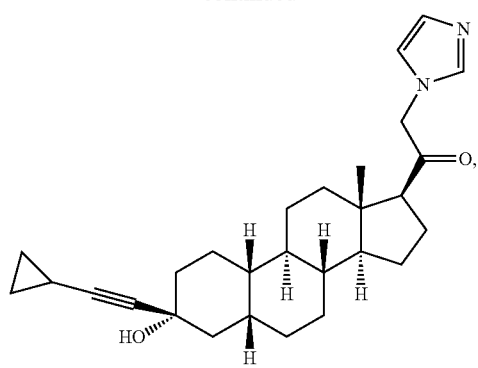
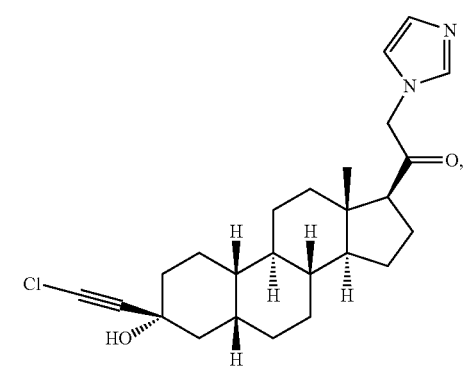
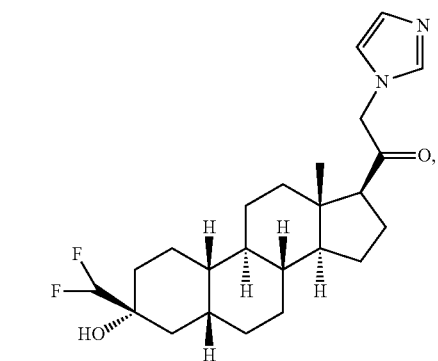
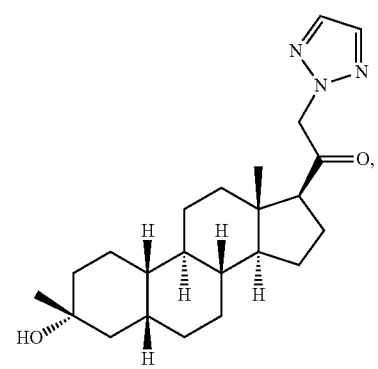
94
-continued
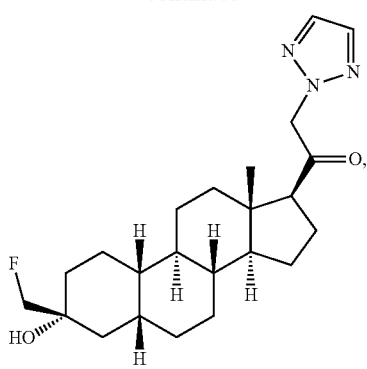
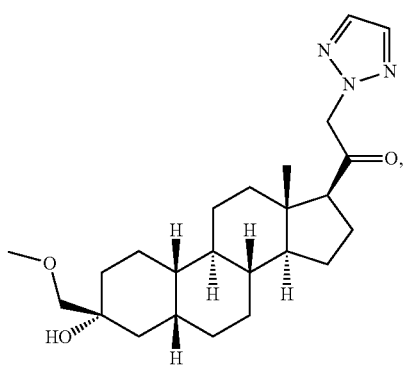
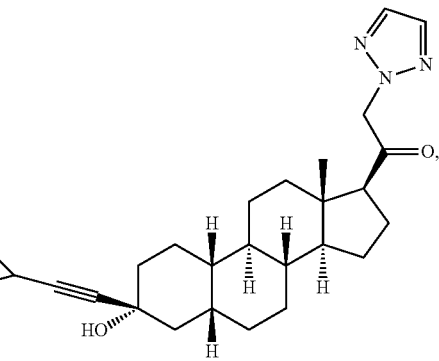
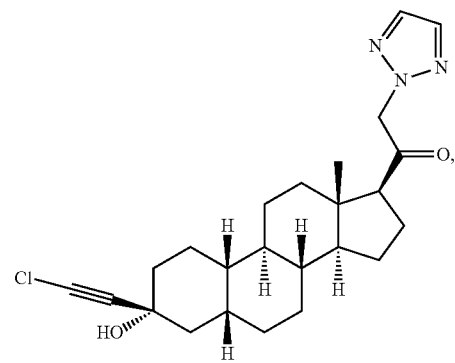

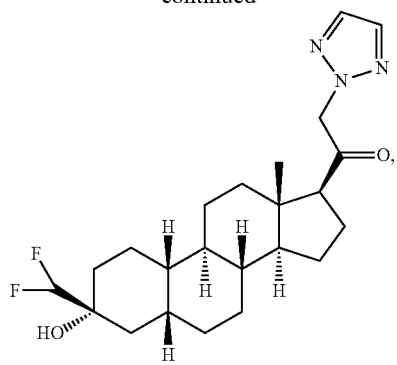
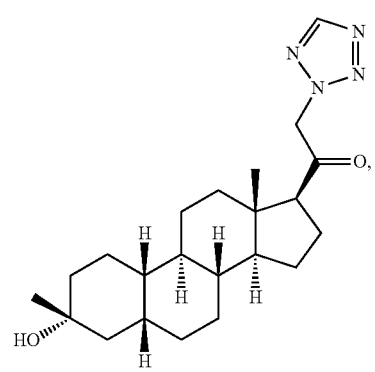
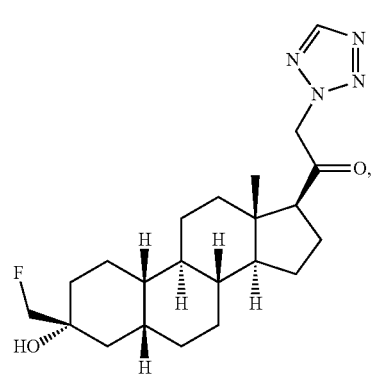
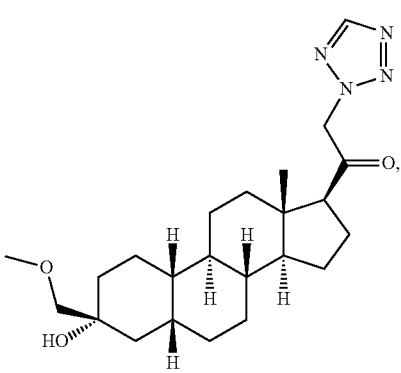
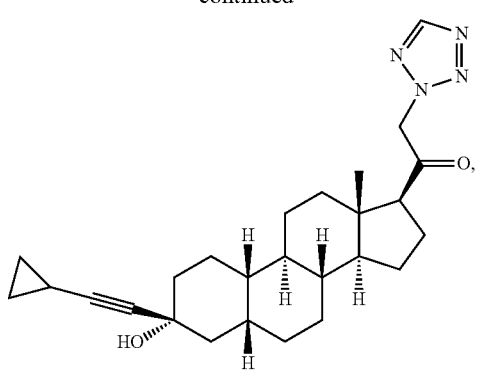
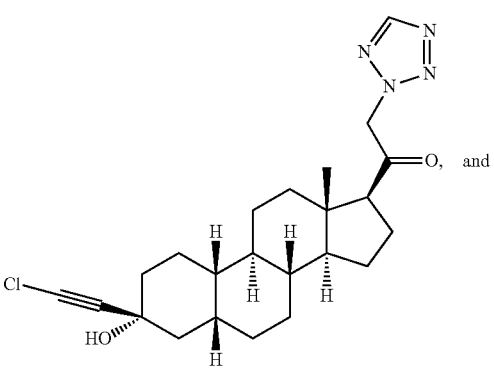
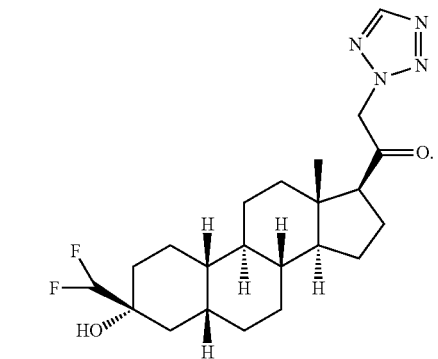
In certain embodiments, the compound of Formula (I) is selected from any one of the following compounds, or a pharmaceutically acceptable salt, solvate, prodrug, stereoisomers, tautomer, isotopic variant, N-oxide thereof, or a combination thereof:
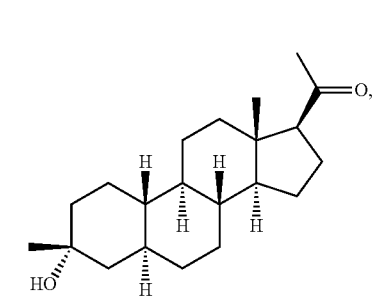

97
-continued
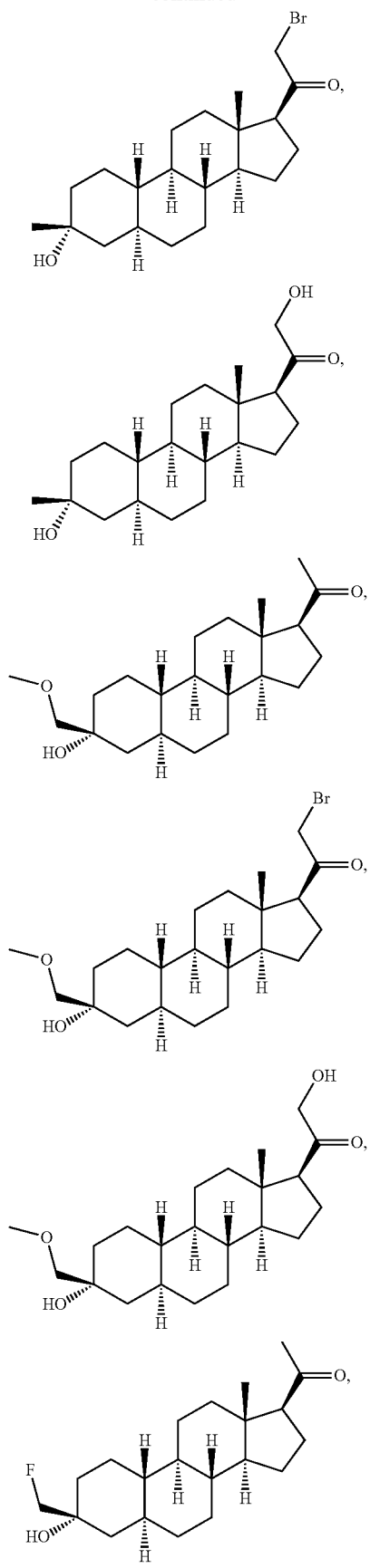
98
-continued
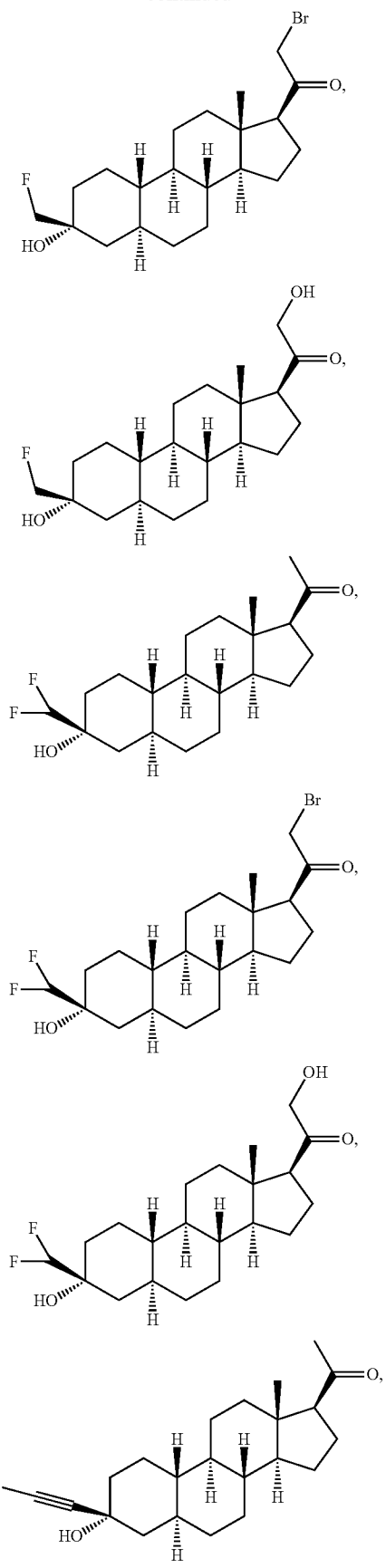

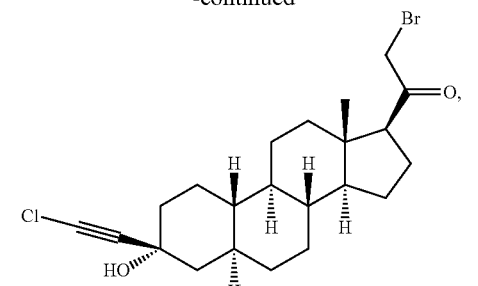
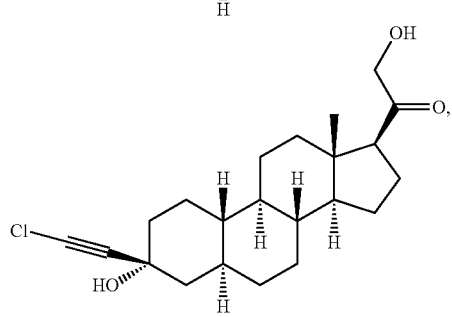
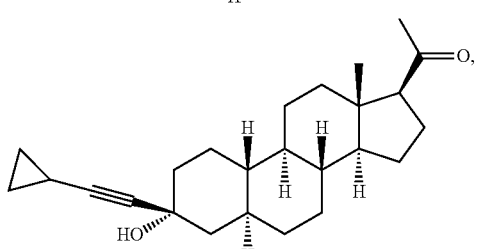
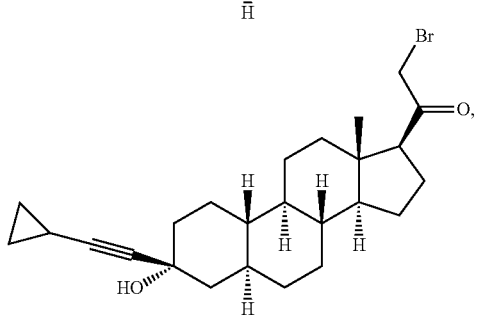
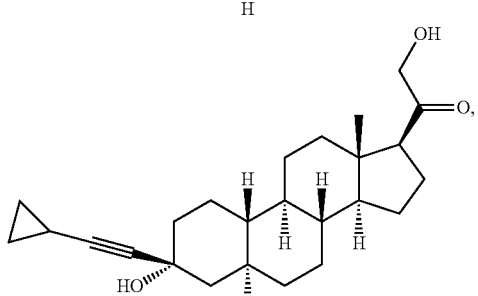
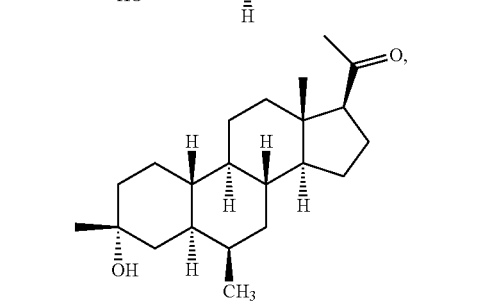
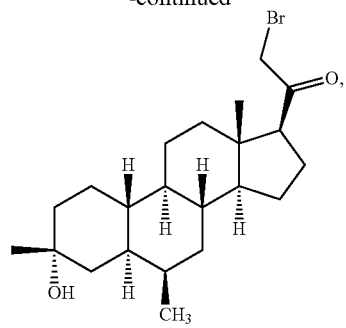
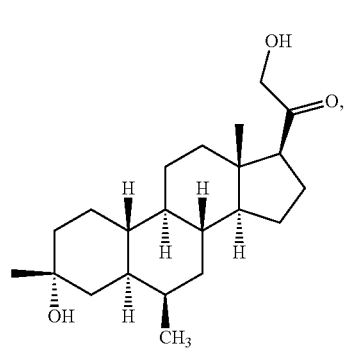
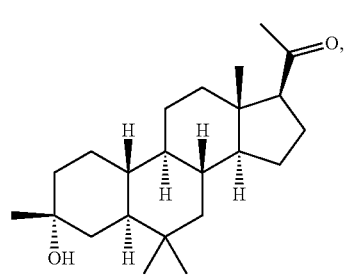
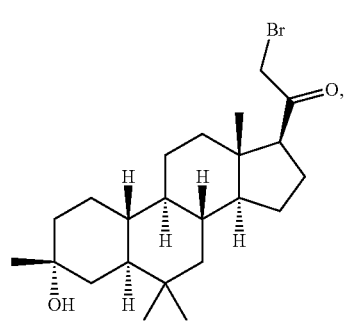
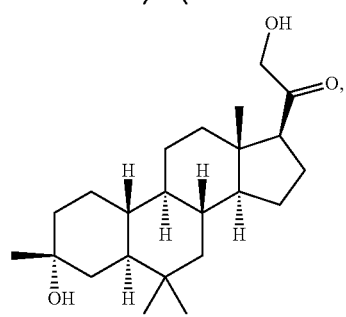

101
-continued
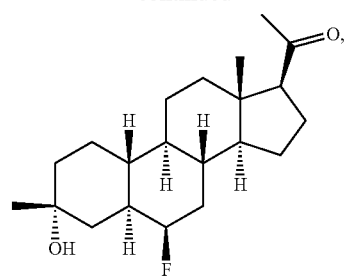
102
-continued
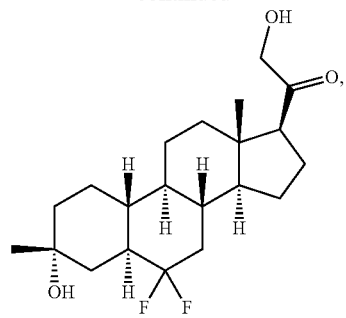
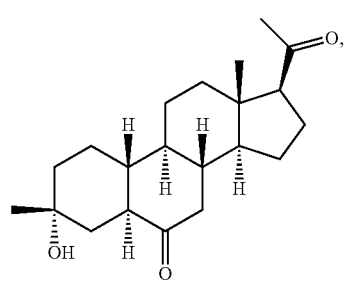
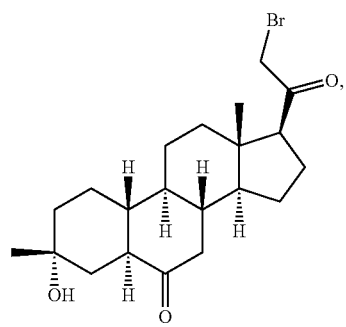
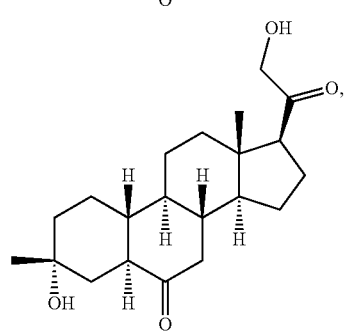
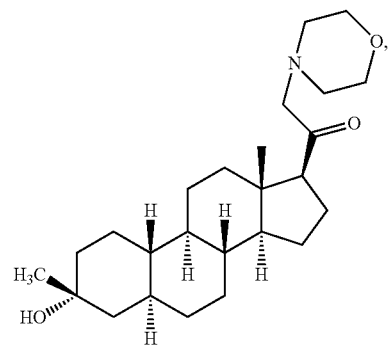

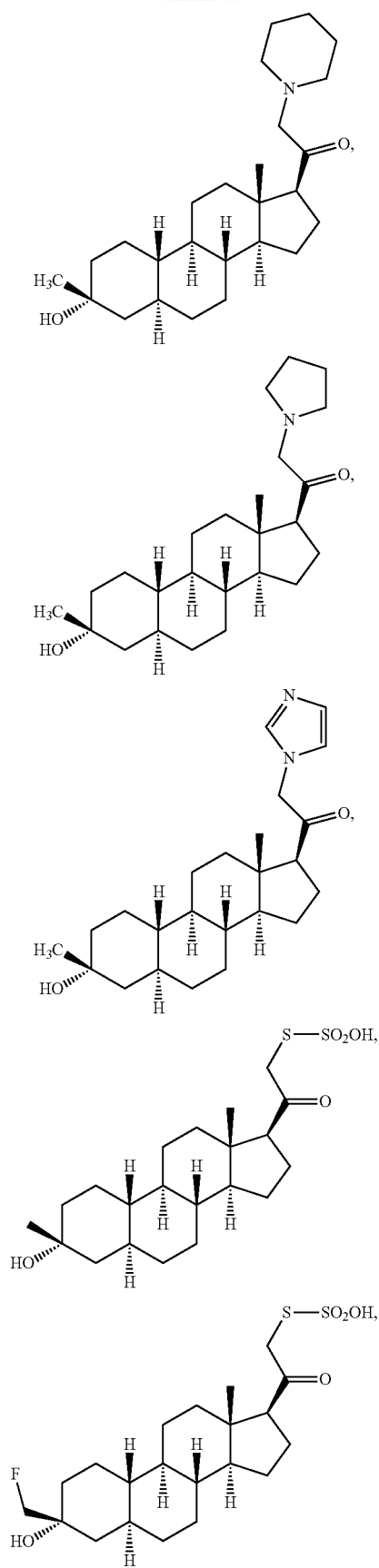
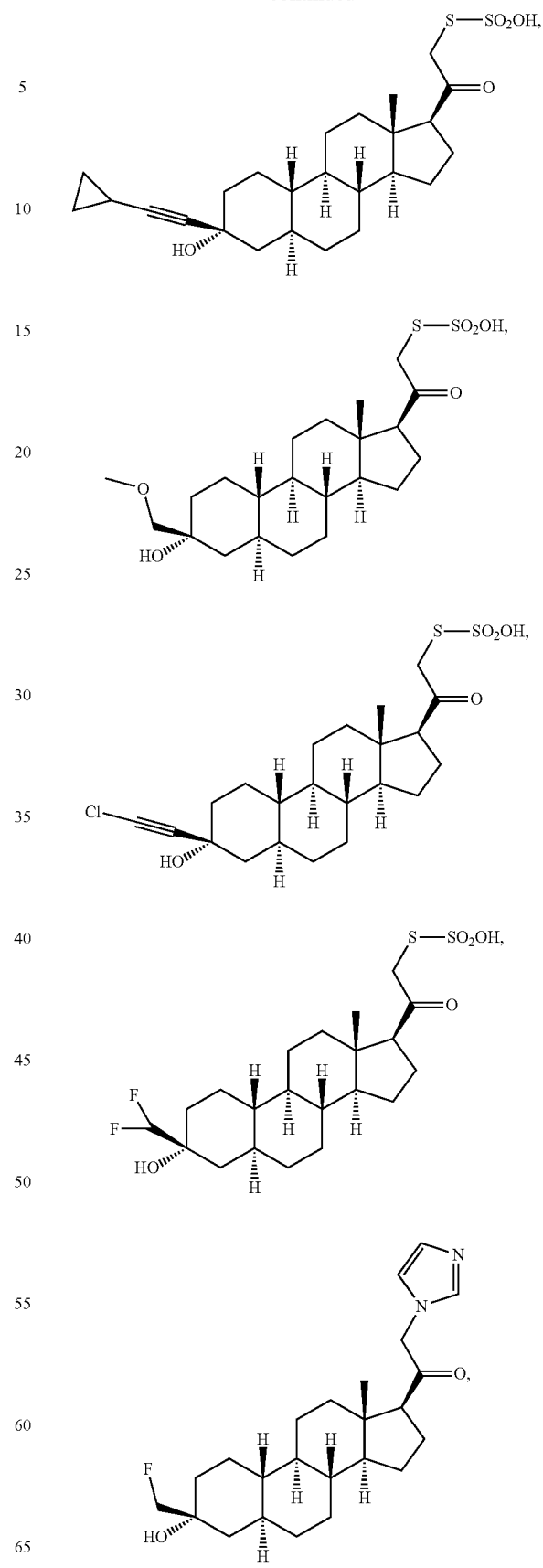

105
-continued
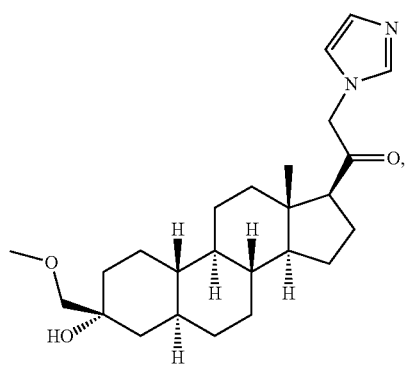
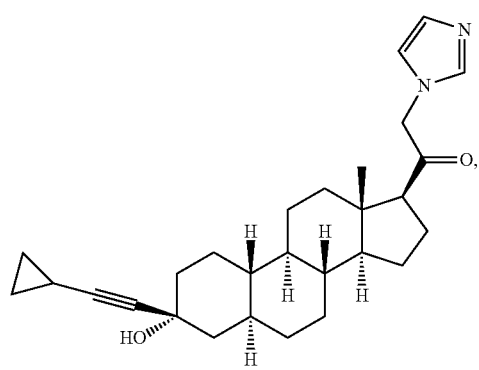
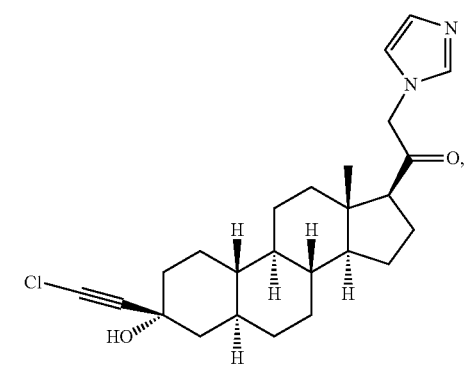
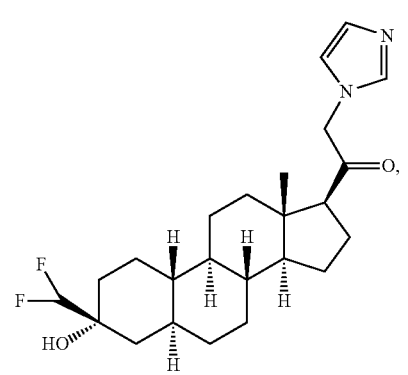
106
-continued
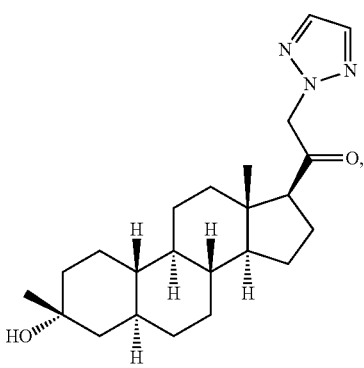
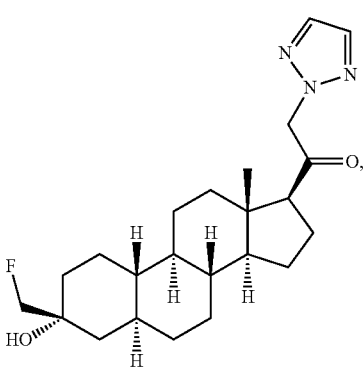
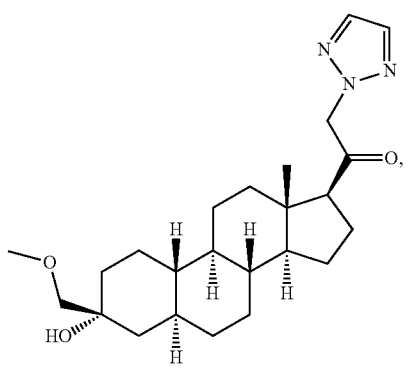
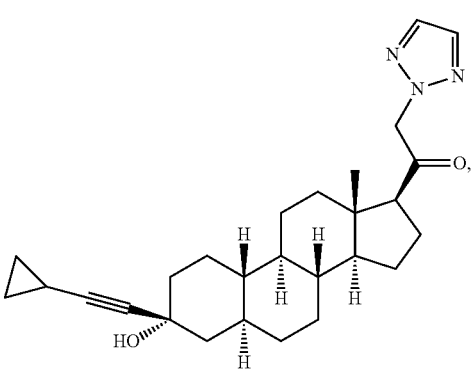

107
-continued
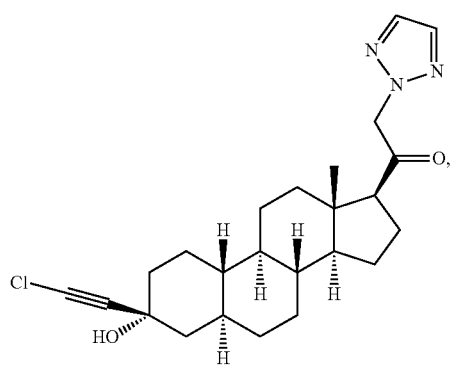
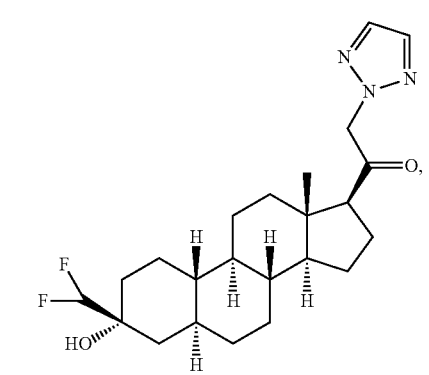
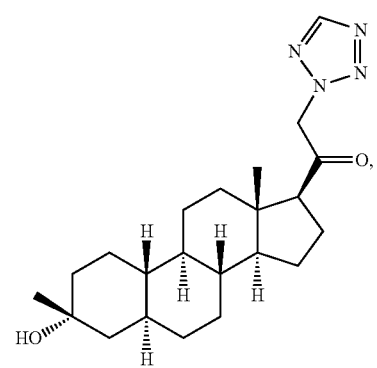
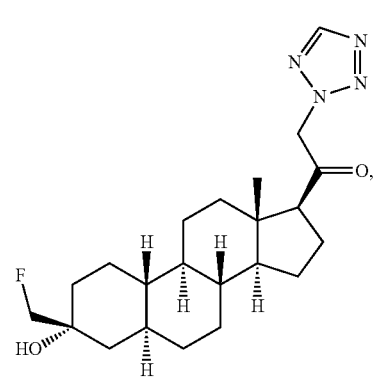
108
-continued
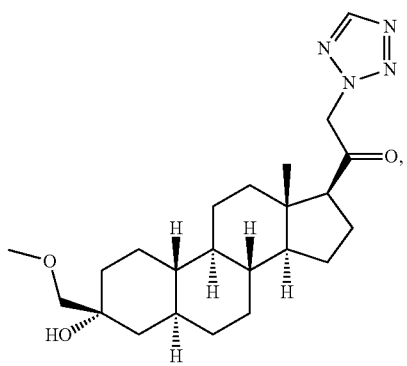
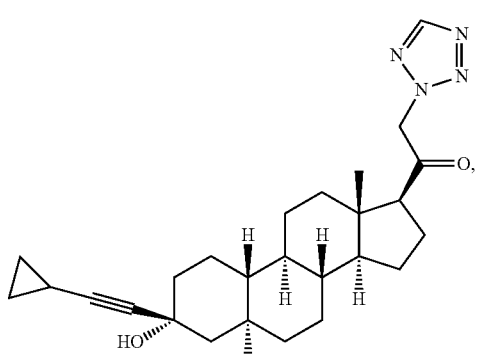
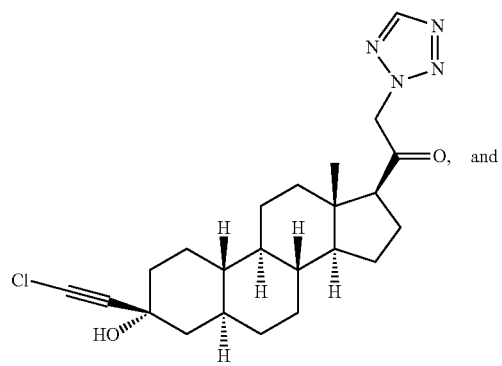, and
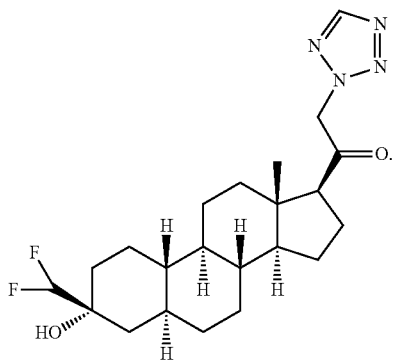
In certain embodiments, the compound of Formula (I) is selected from any one of the following compounds, or a pharmaceutically acceptable salt, solvate, prodrug, stereoisomers, tautomer, isotopic variant, N-oxide thereof, or a combination thereof:

109
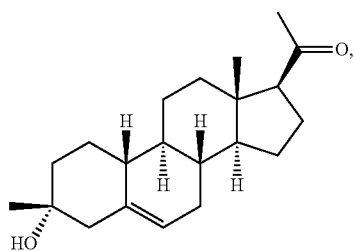
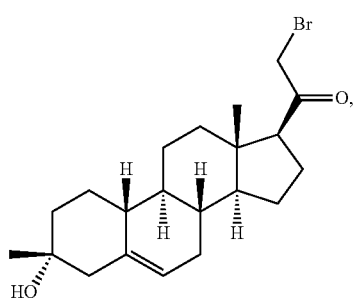
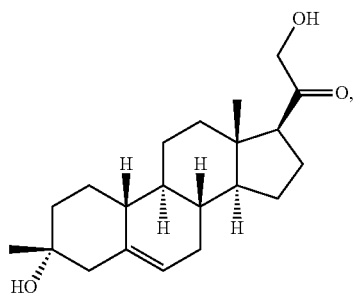
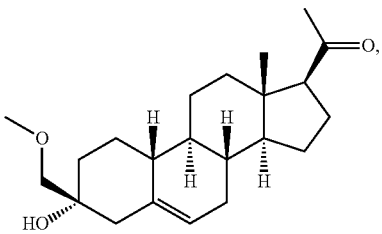
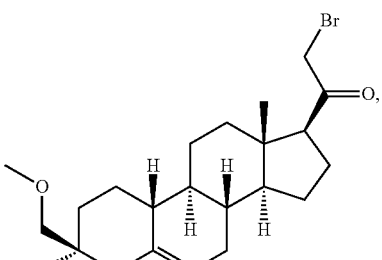
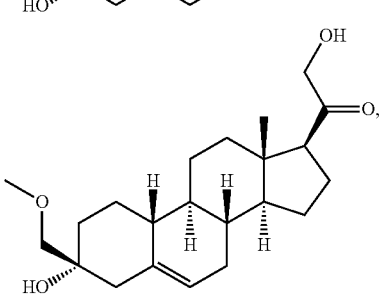
110
-continued
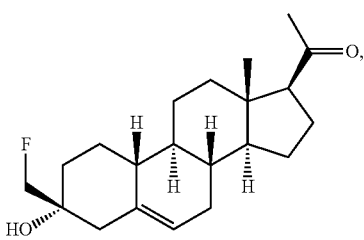
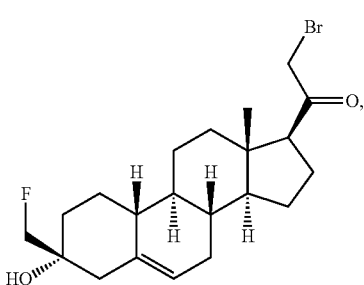
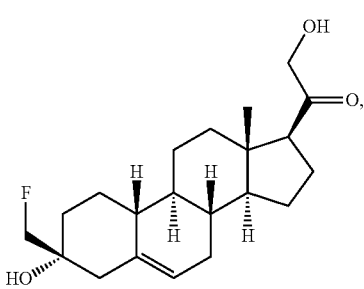
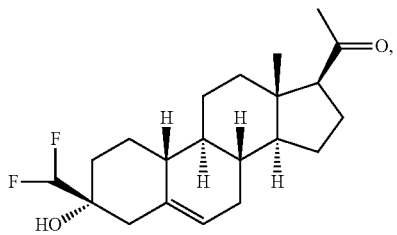
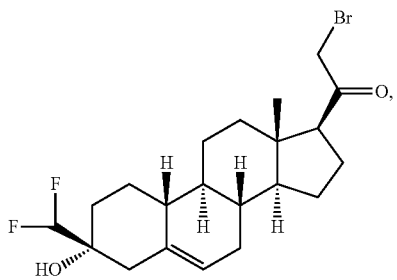
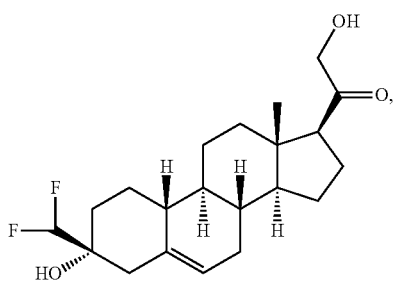

111
-continued
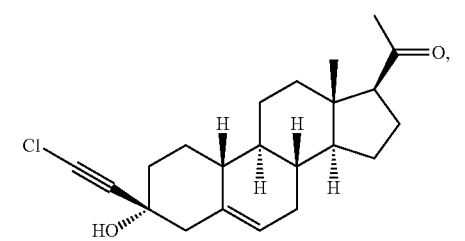
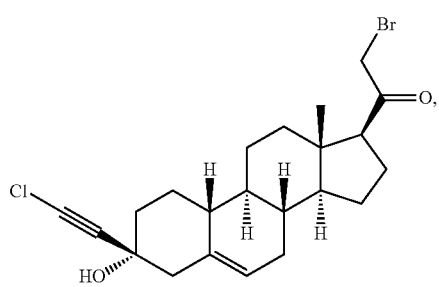
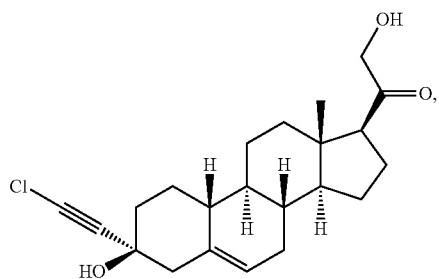
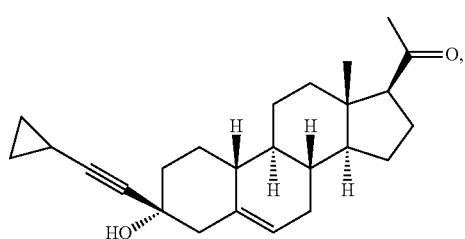
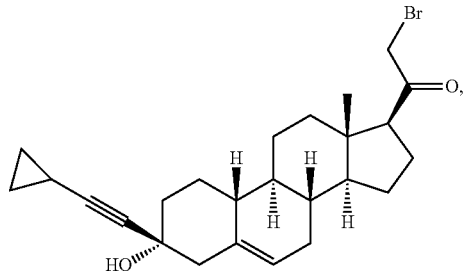
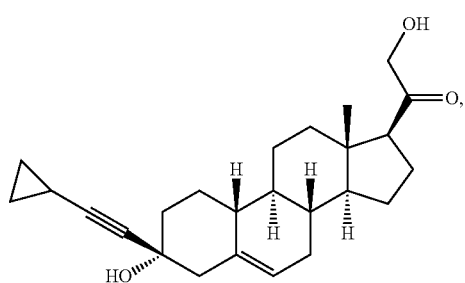
112
-continued
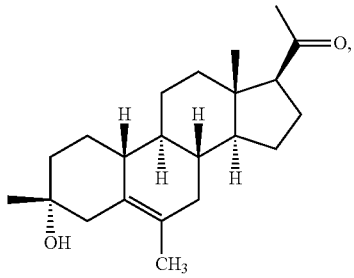
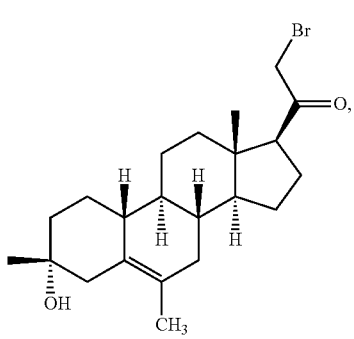
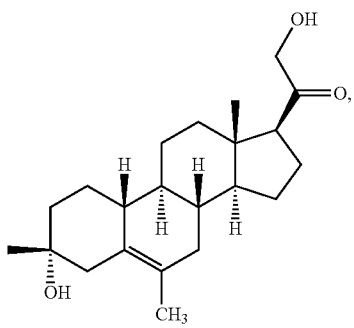
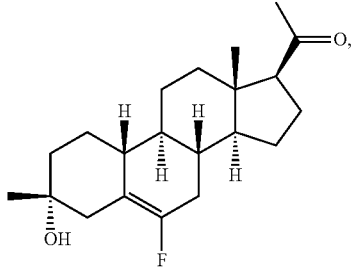
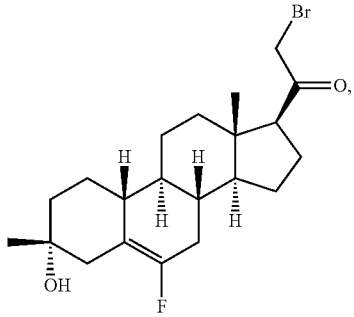

113
-continued
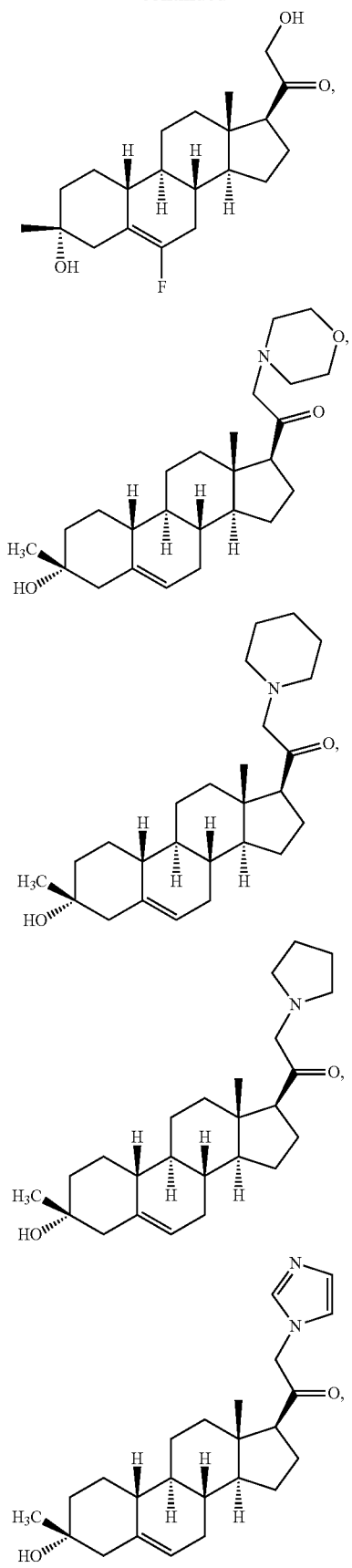
114
-continued
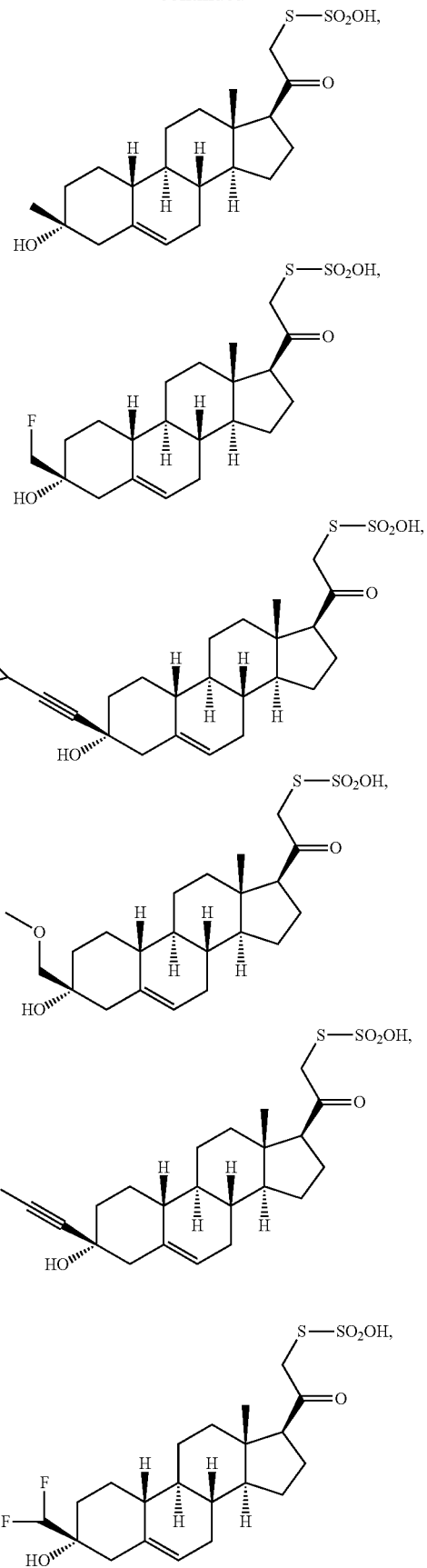

115
-continued
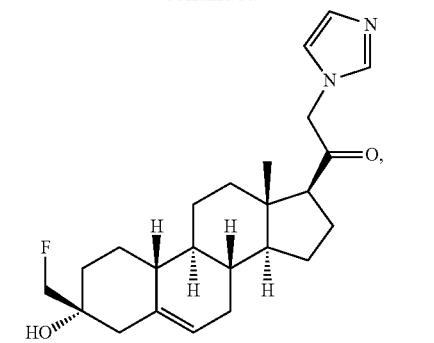
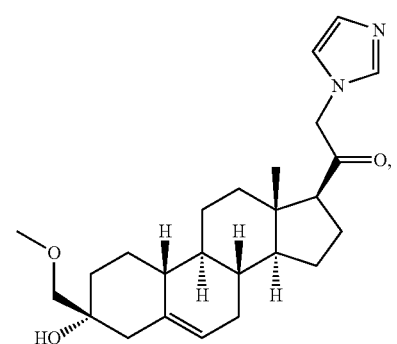
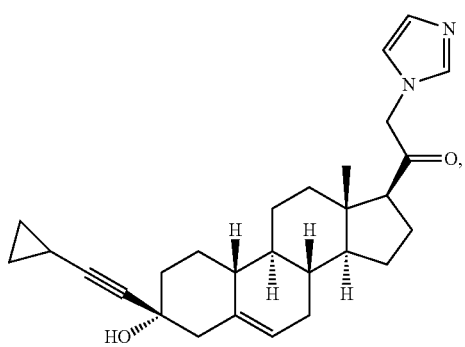
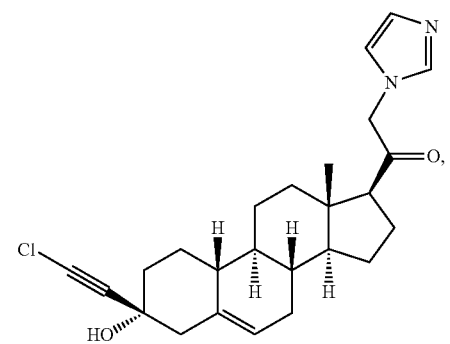
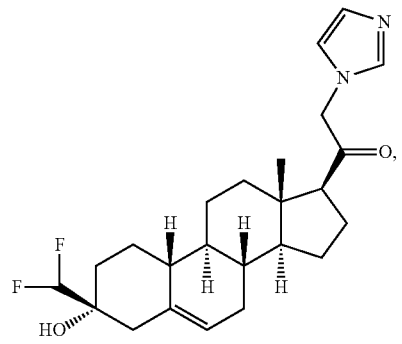
116
-continued
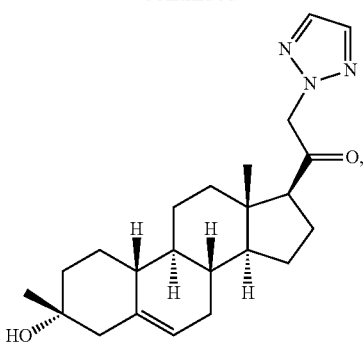
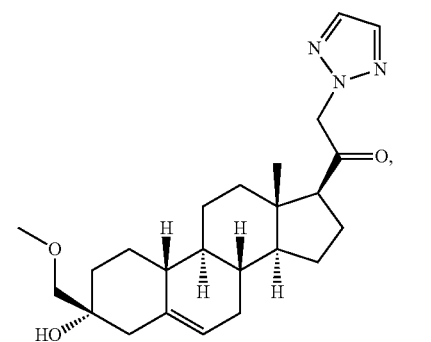
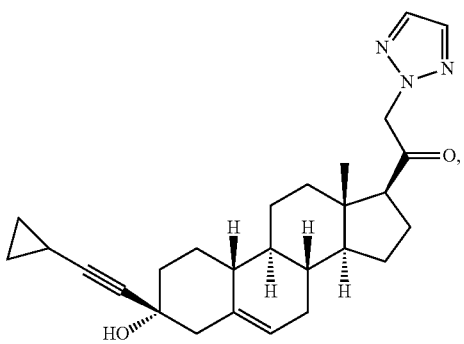
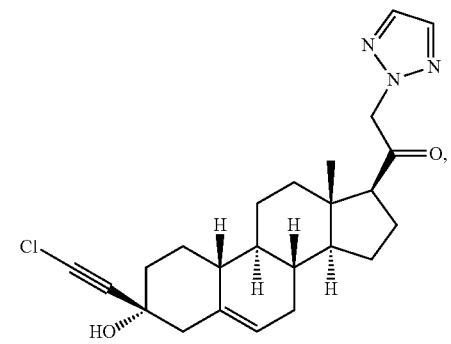

117
-continued
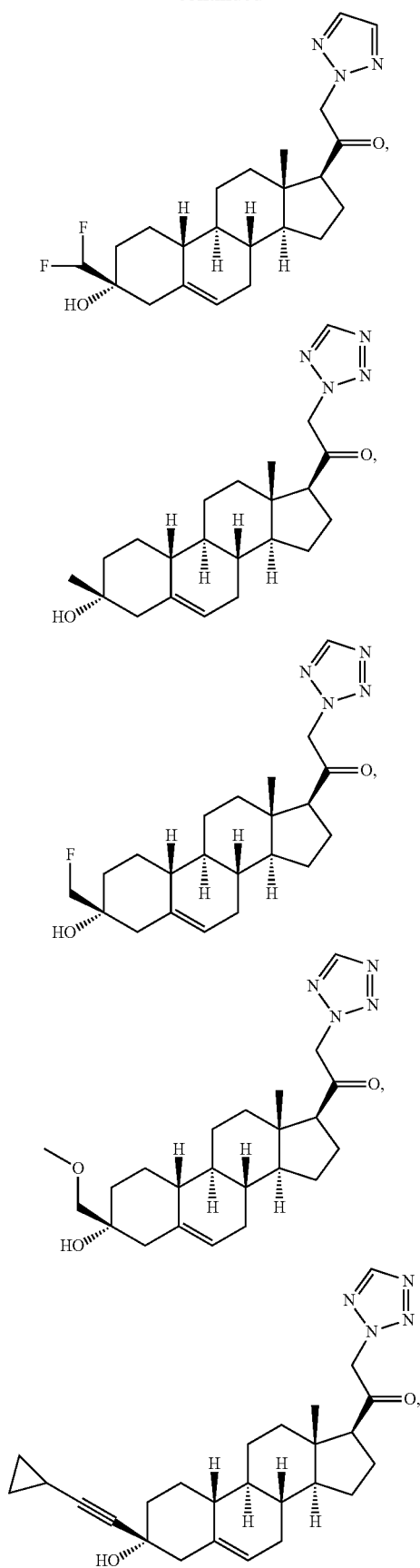
118
-continued
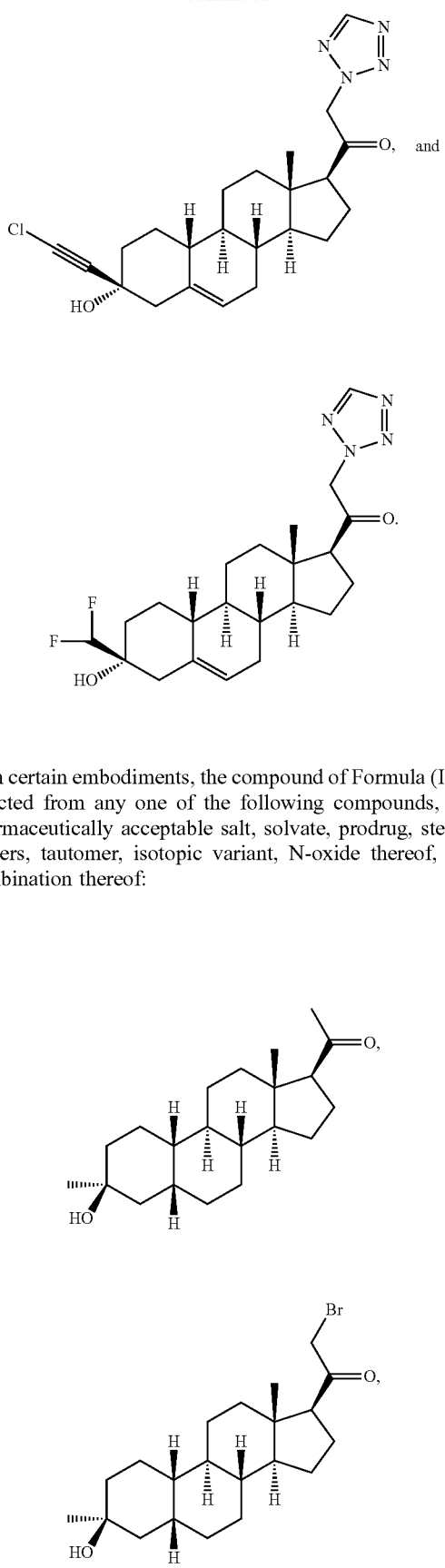
In certain embodiments, the compound of Formula (III) is selected from any one of the following compounds, or a pharmaceutically acceptable salt, solvate, prodrug, stereoisomers, tautomer, isotopic variant, N-oxide thereof, or a combination thereof:

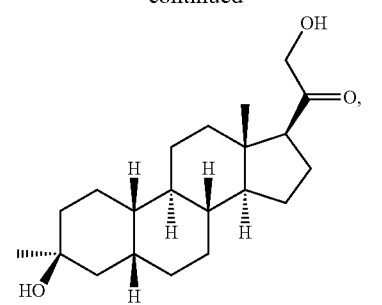
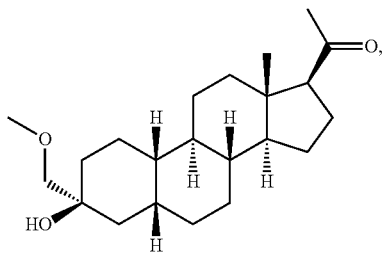
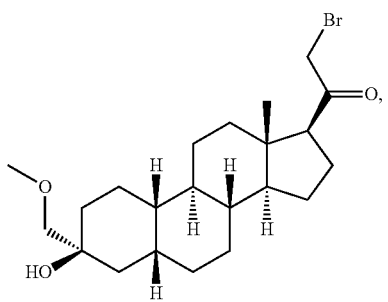
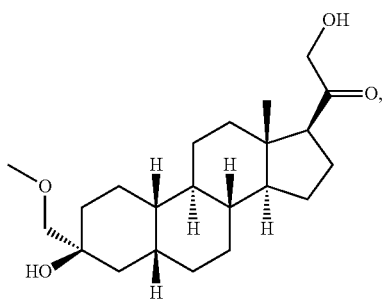
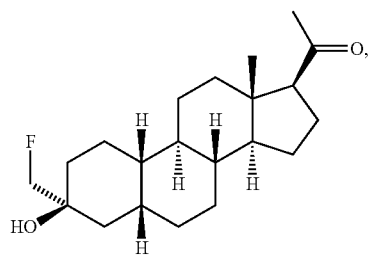
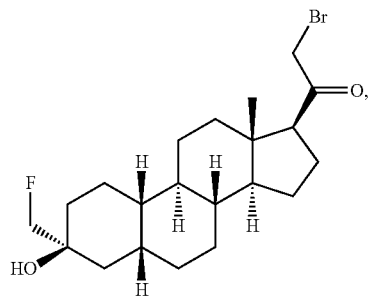
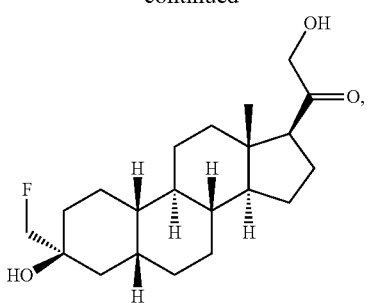
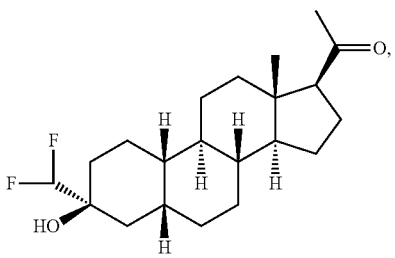
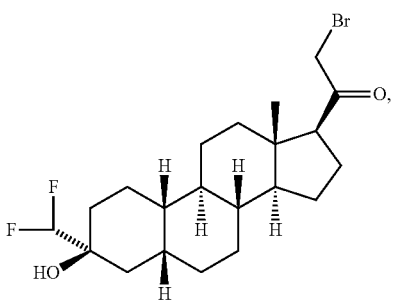
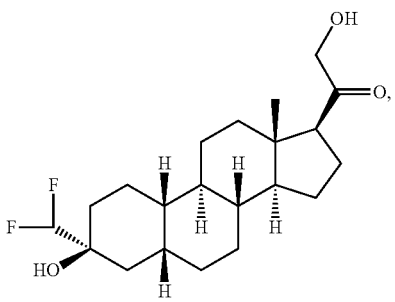
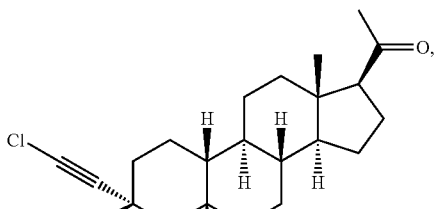
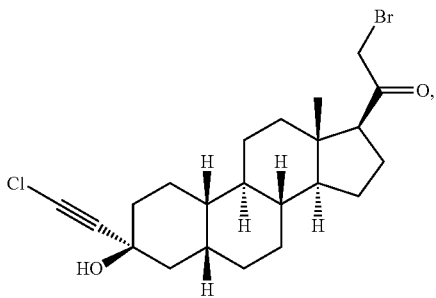

121
-continued
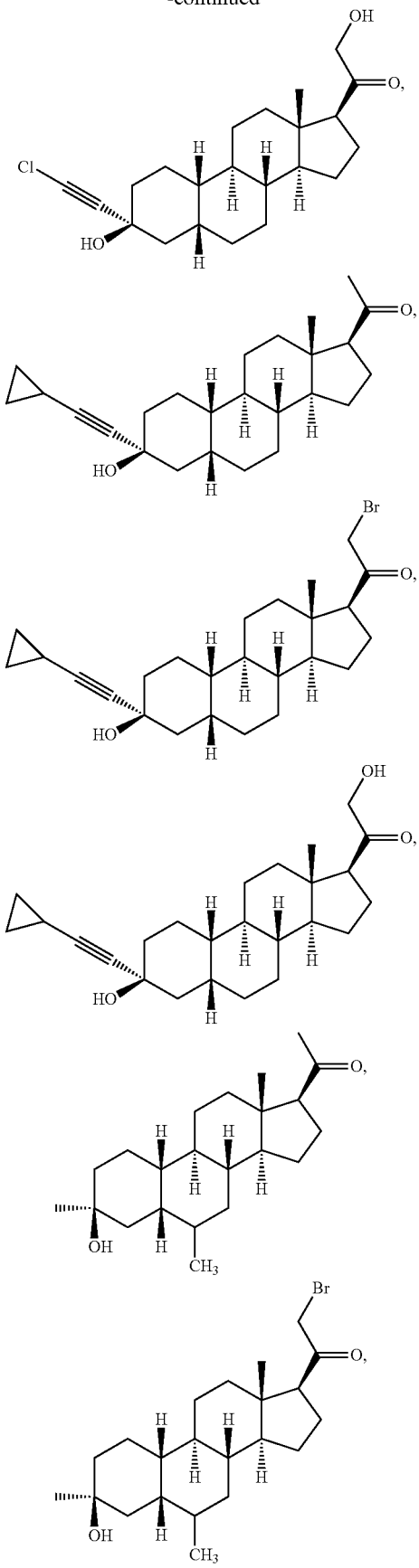
122
-continued
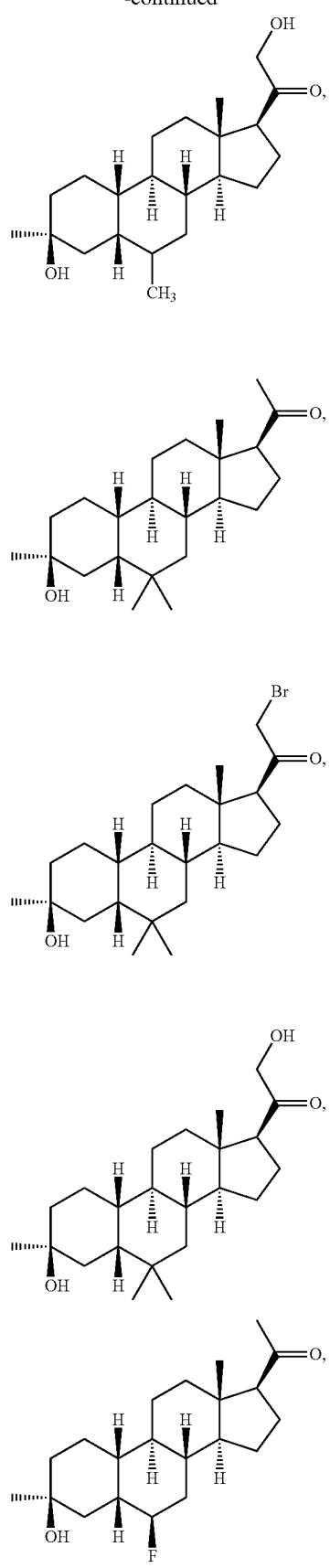

123
-continued
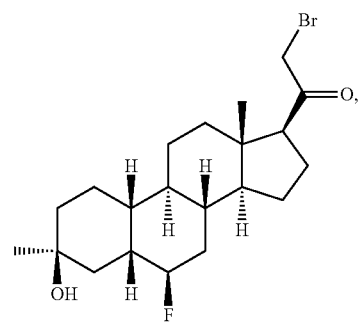
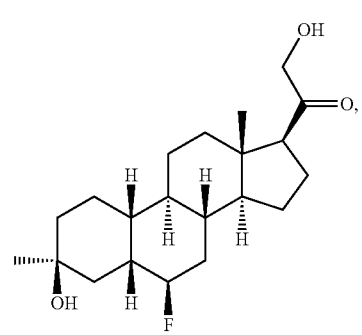
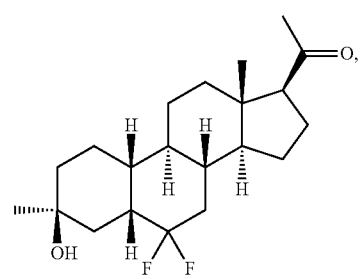
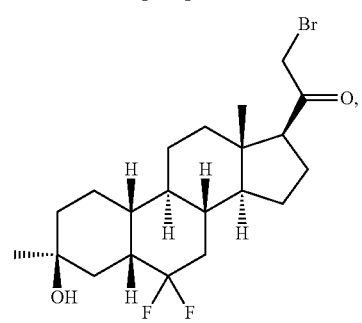
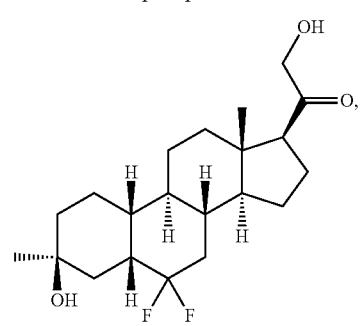
124
-continued
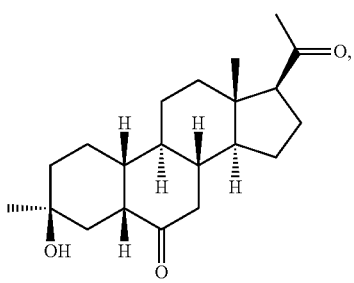
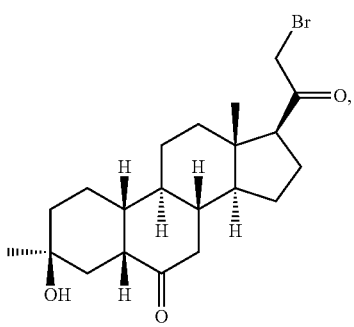
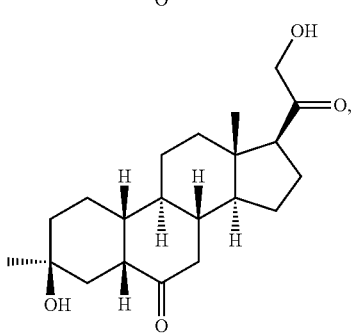
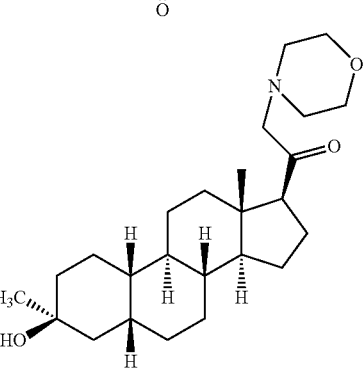
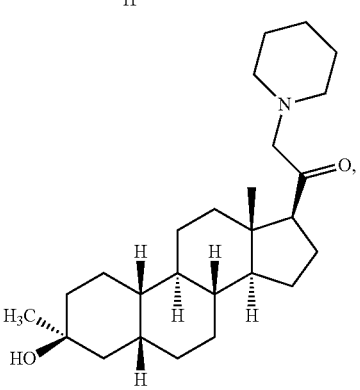

125
-continued
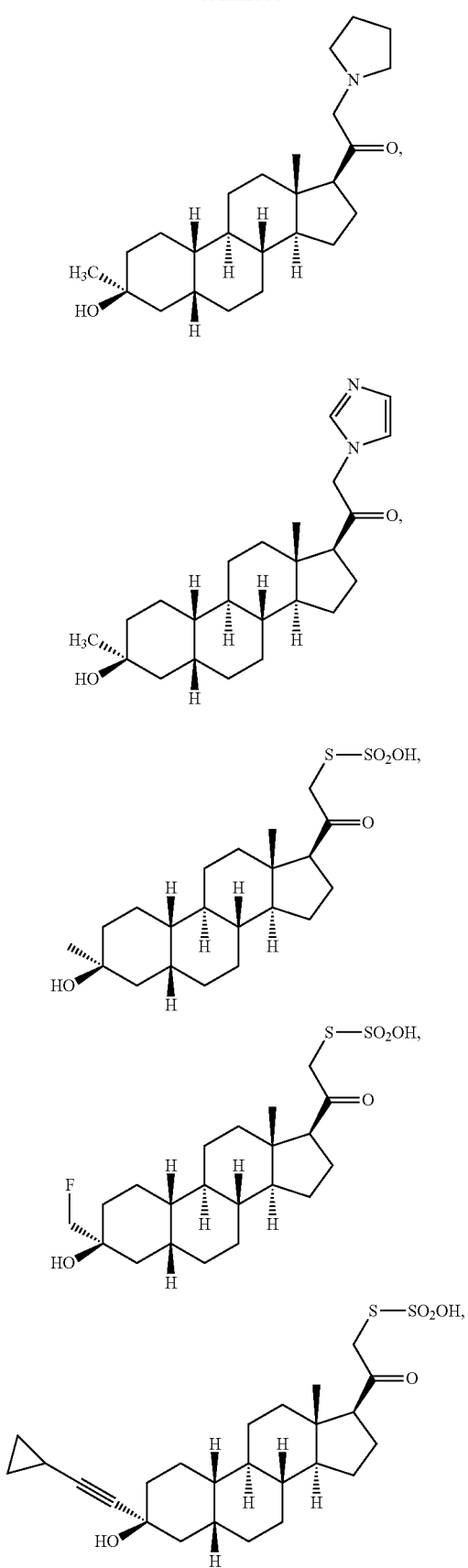
126
-continued
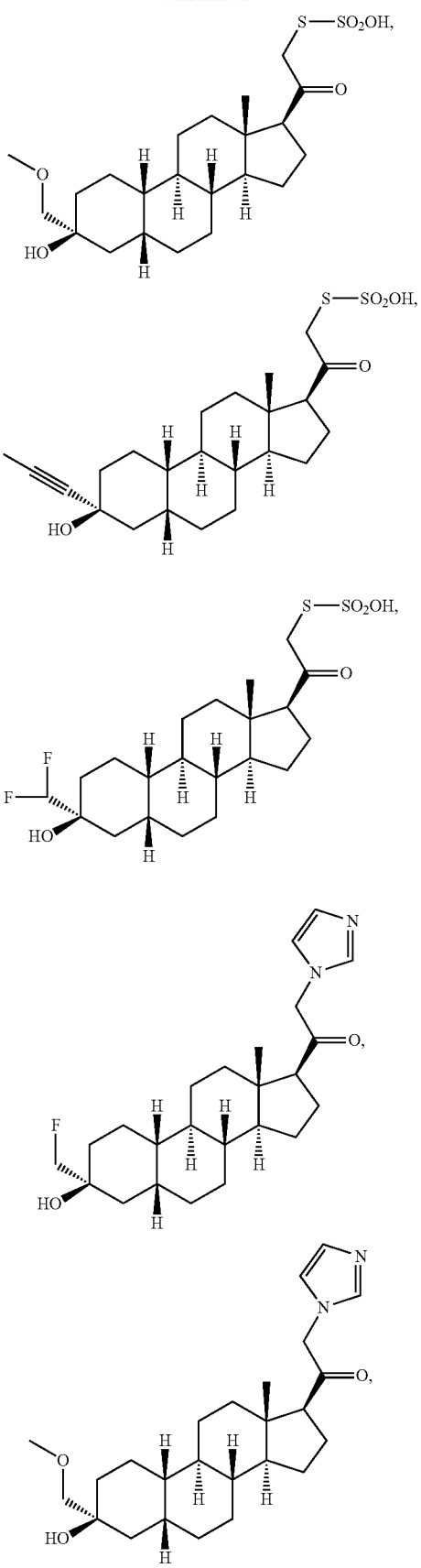

127
-continued
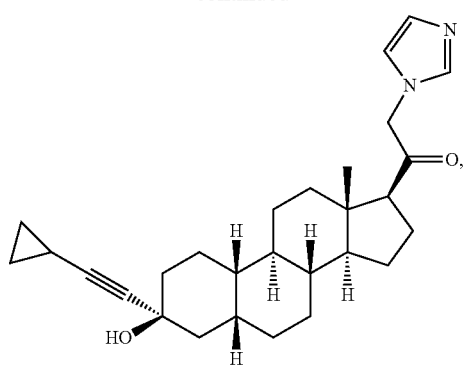
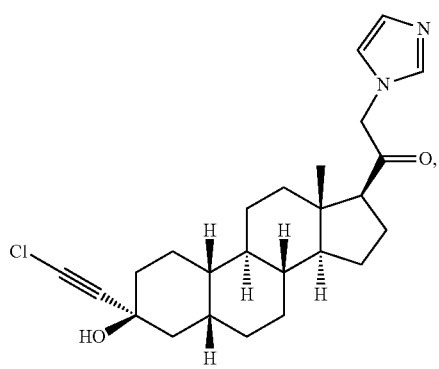
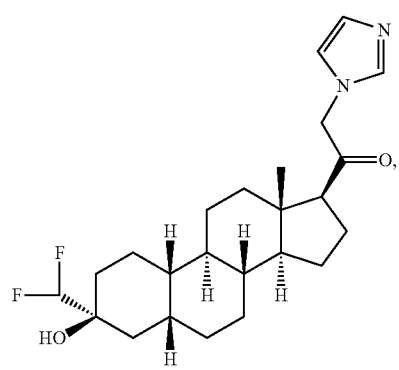
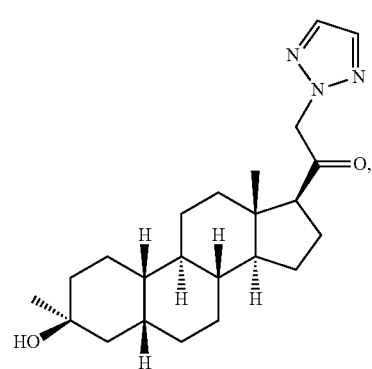
128
-continued
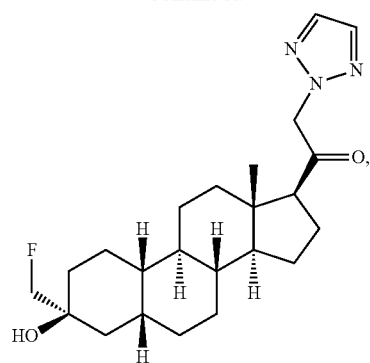
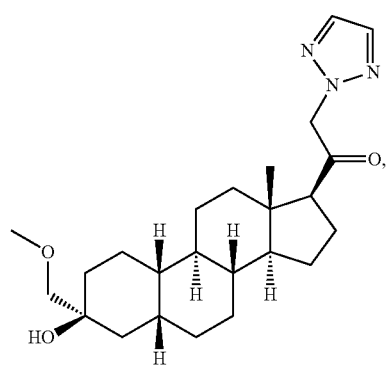
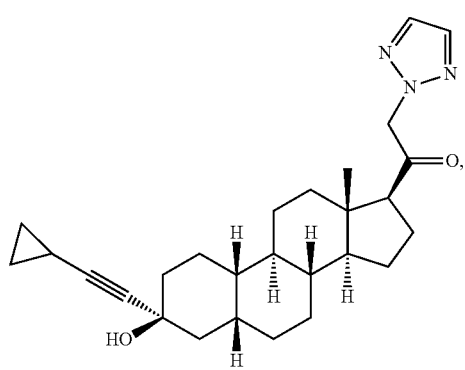
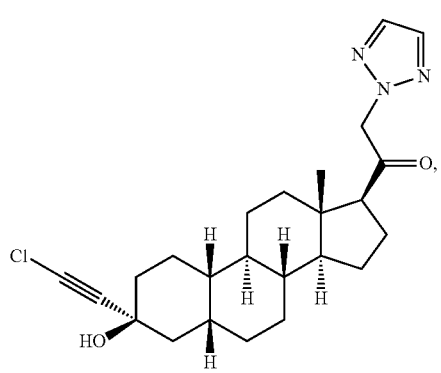

129
-continued
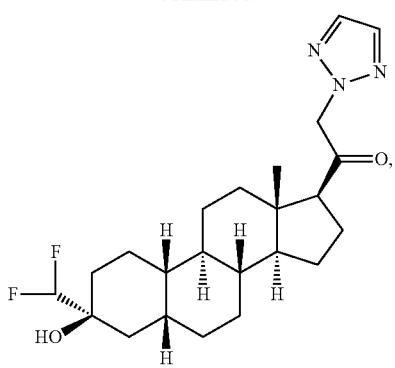
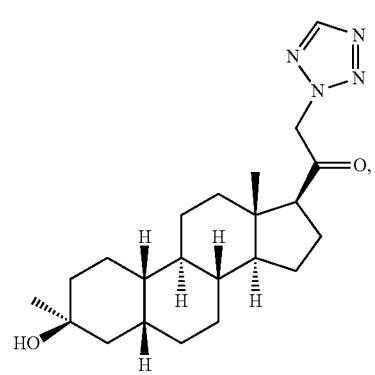
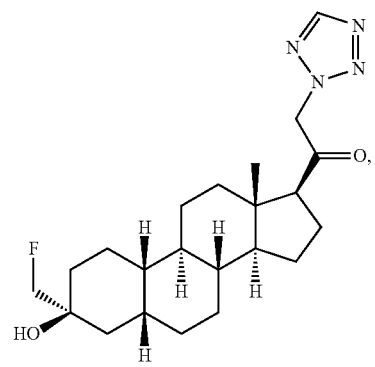
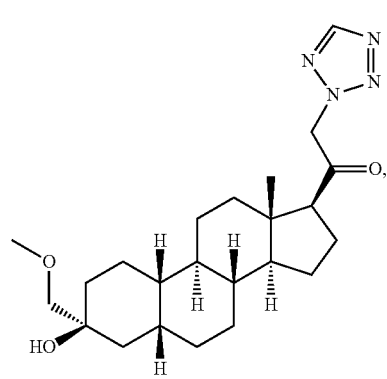
130
-continued
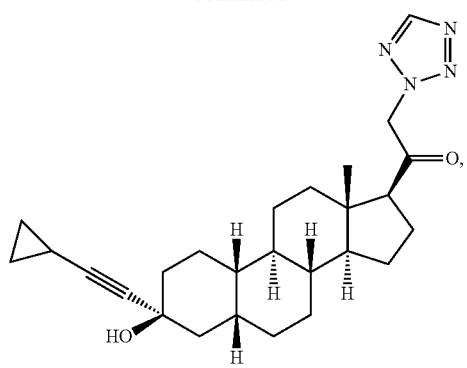
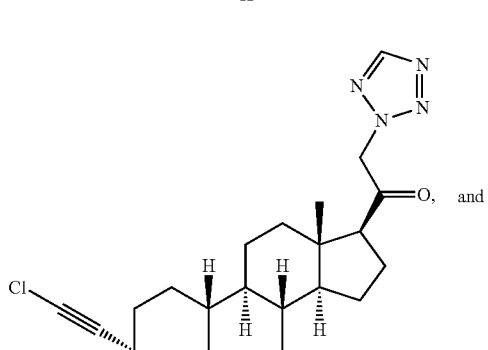
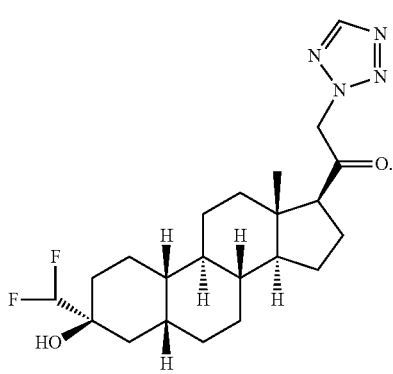
In certain embodiments, the compound of Formula (III) is selected from any one of the following compounds, or a pharmaceutically acceptable salt, solvate, prodrug, stereoisomers, tautomer, isotopic variant, N-oxide thereof, or a combination thereof:
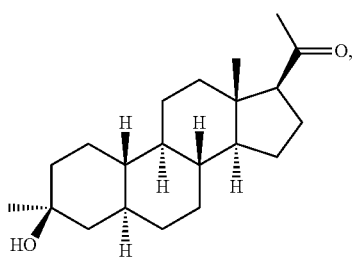

131
-continued
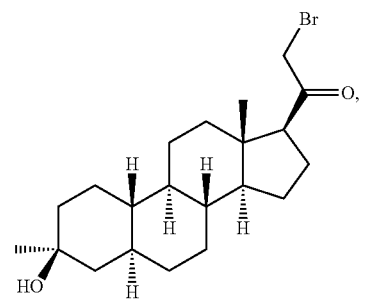
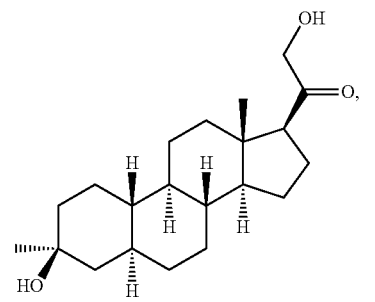
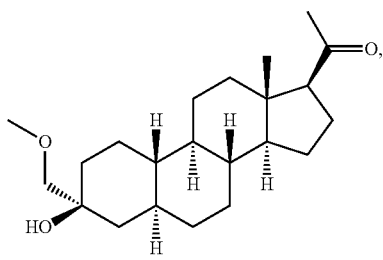
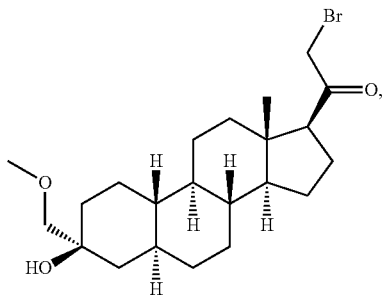
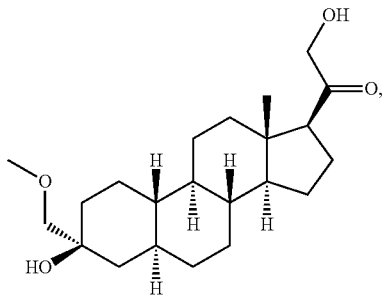
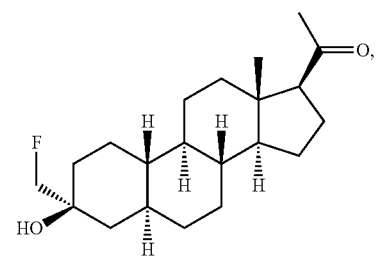
132
-continued
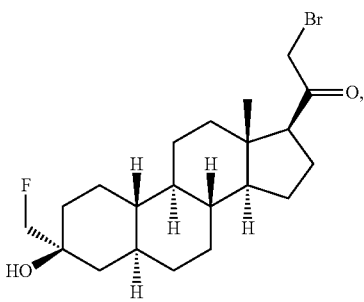
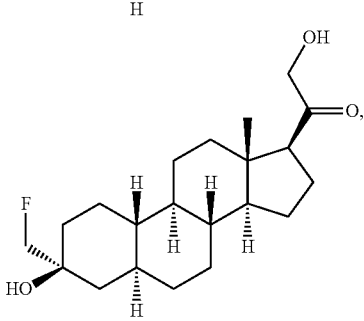
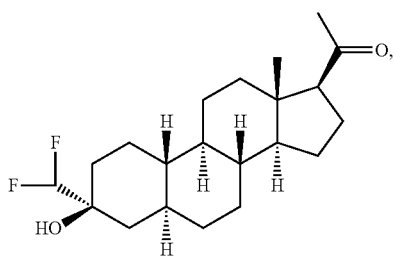
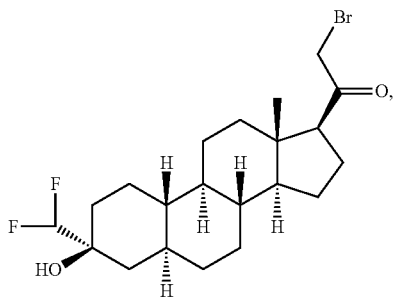
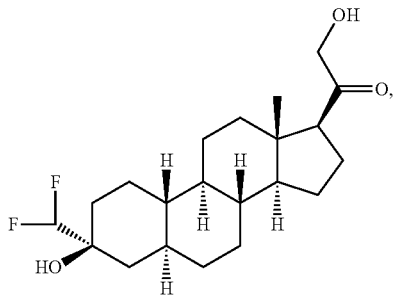
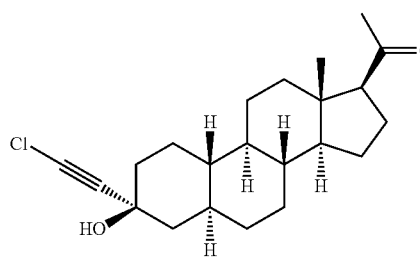

133
-continued
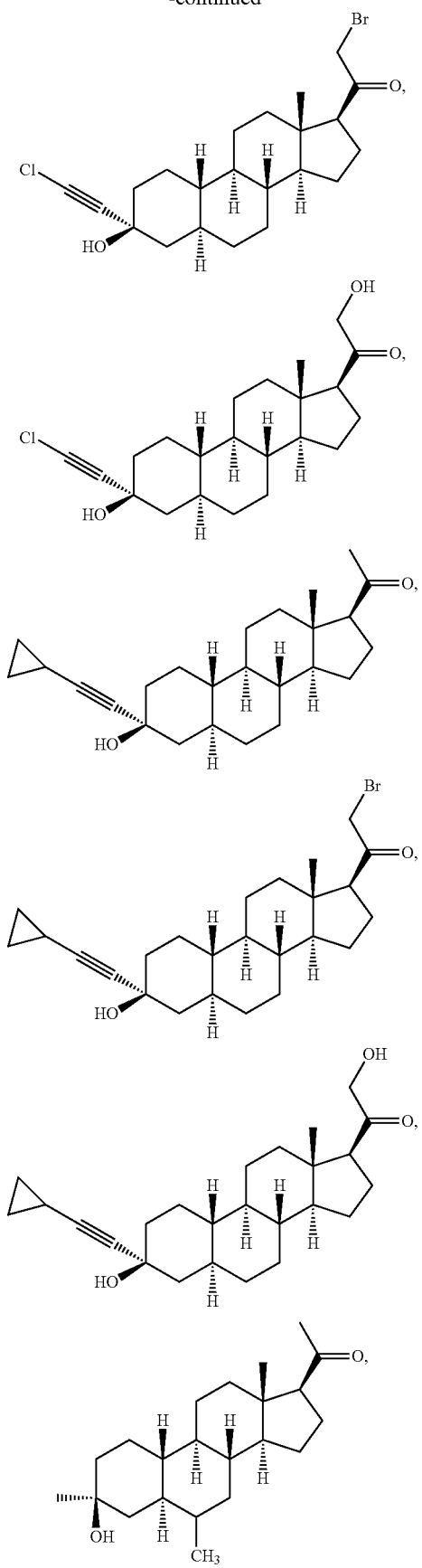
134
-continued
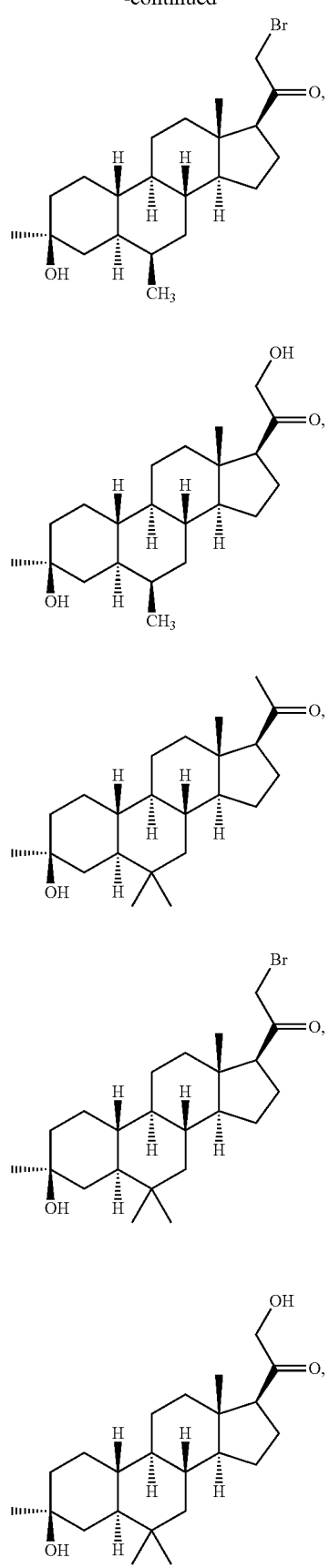

135
-continued
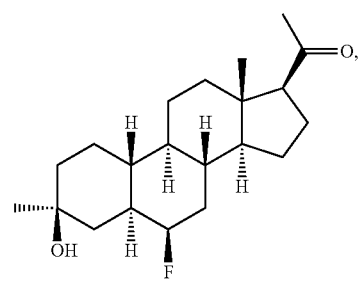
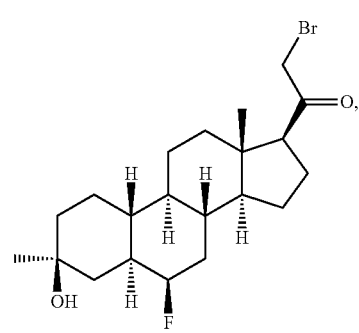
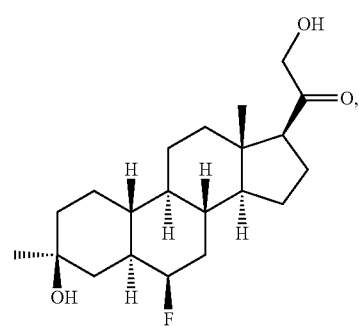
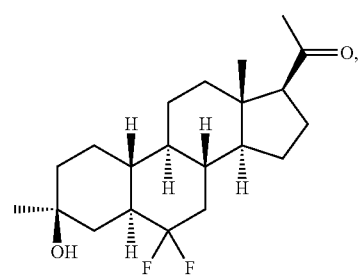
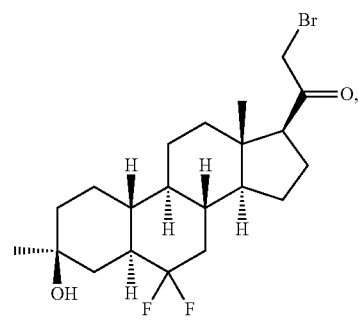
136
-continued
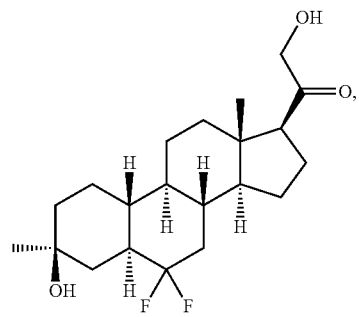
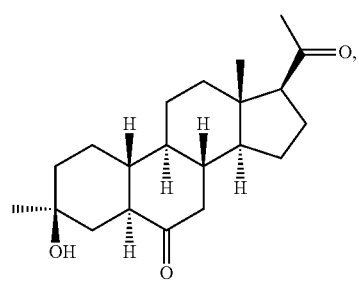
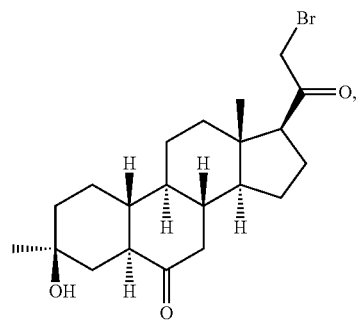
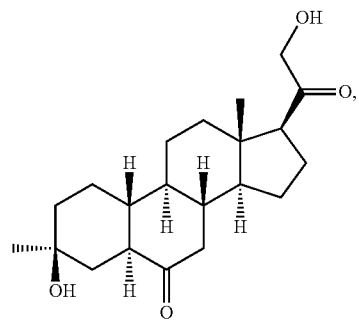
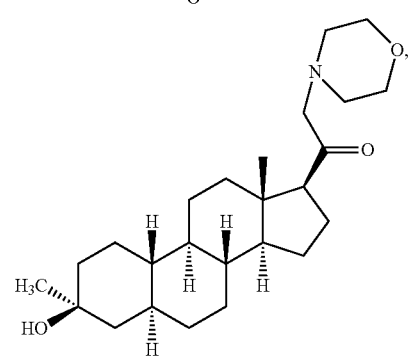

-continued
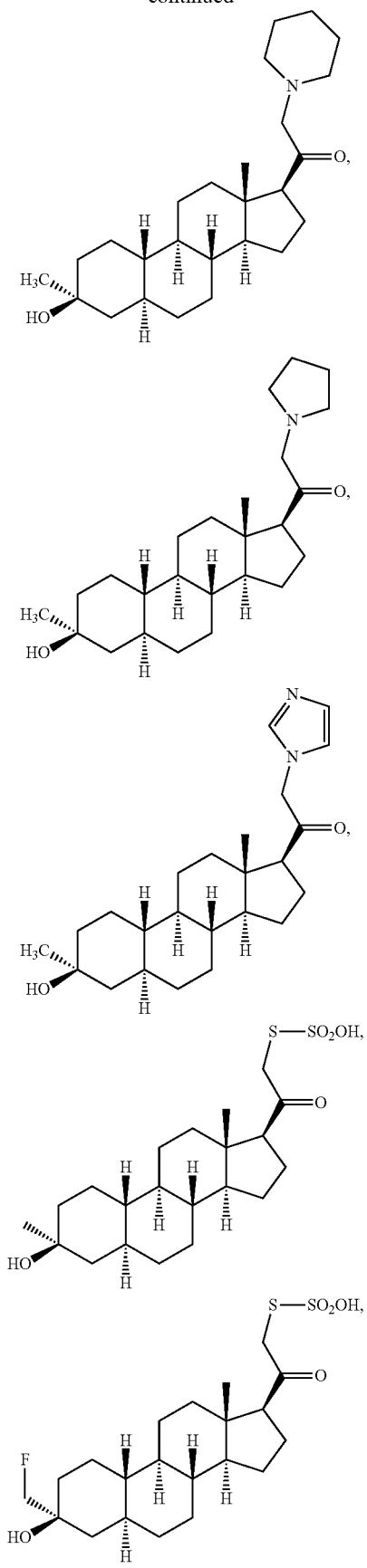
-continued
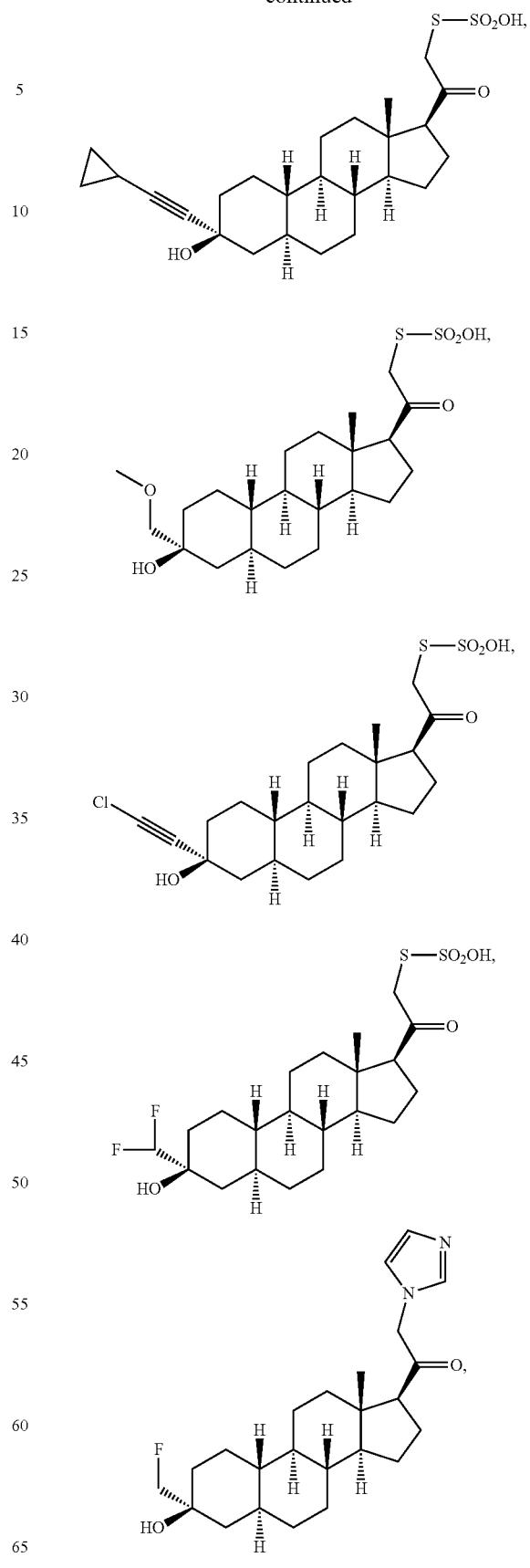

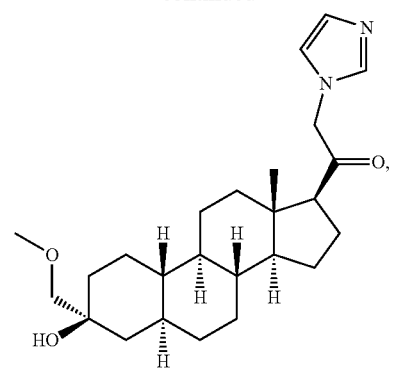
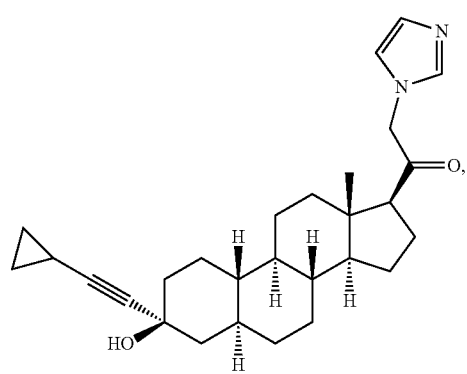
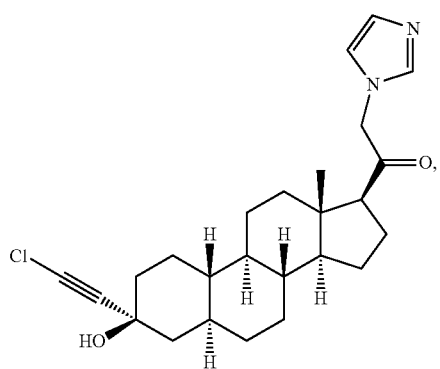
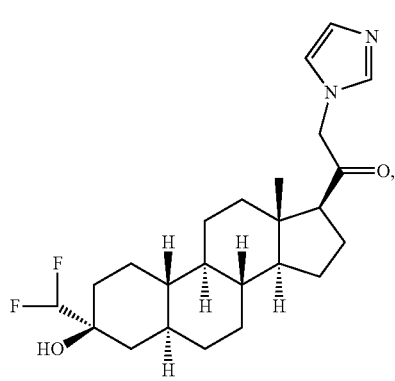
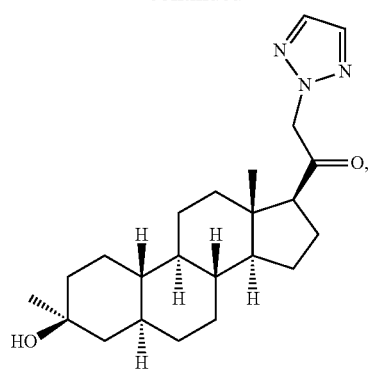
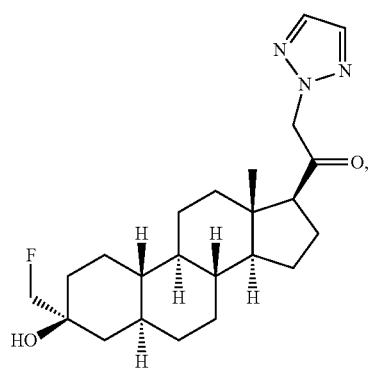
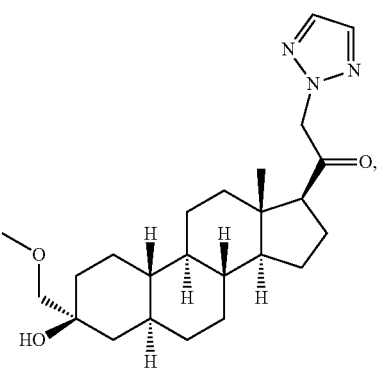
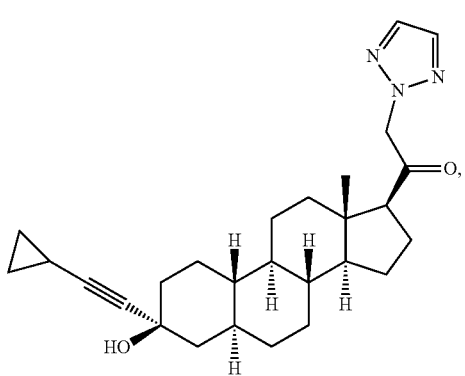

141
-continued
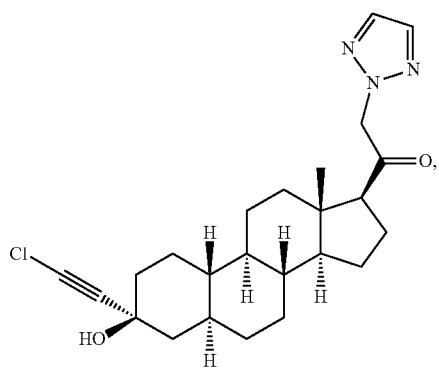
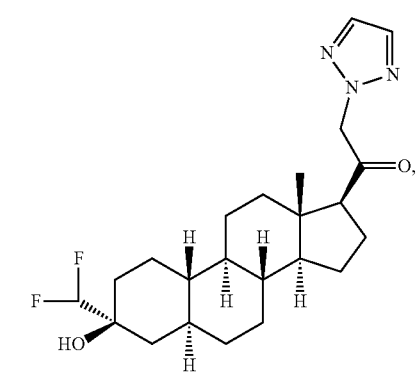
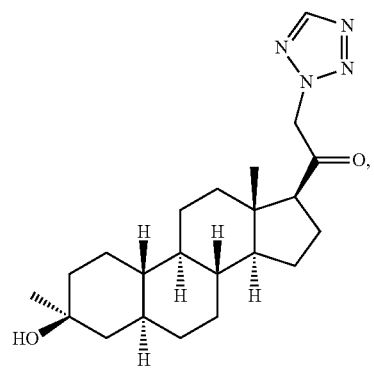
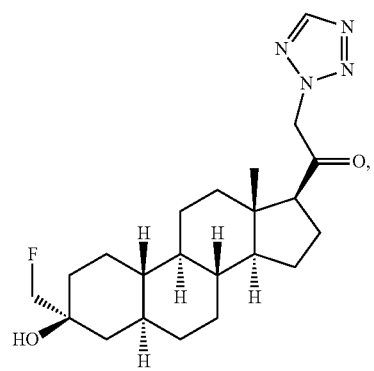
142
-continued
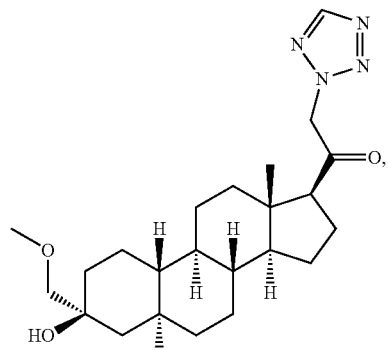
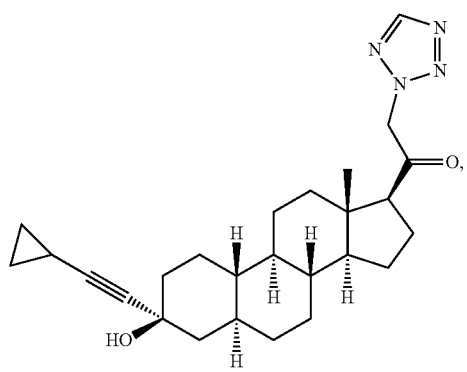
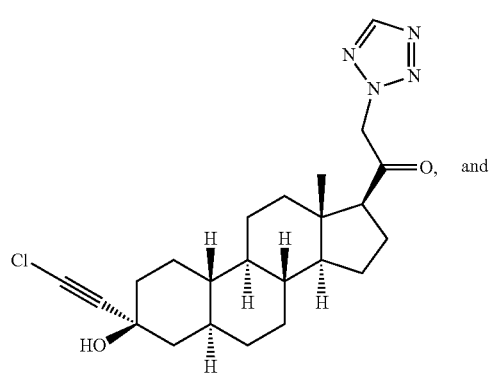 and
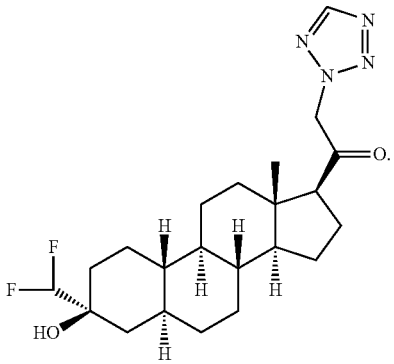
In certain embodiments, the compound of Formula (III) is selected from any one of the following compounds, or a pharmaceutically acceptable salt, solvate, prodrug, stereoisomers, tautomer, isotopic variant, N-oxide thereof, or a combination thereof:

143
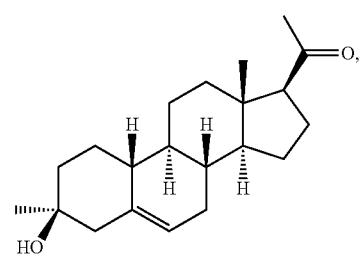
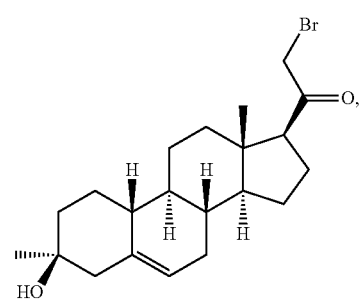
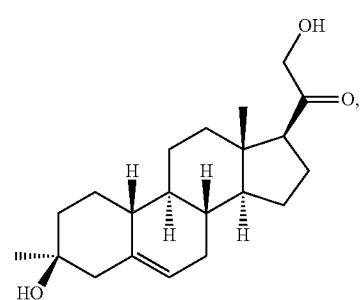
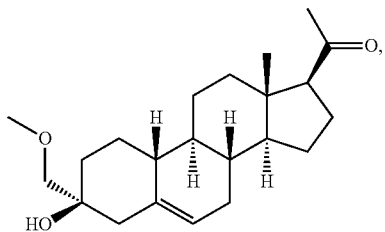
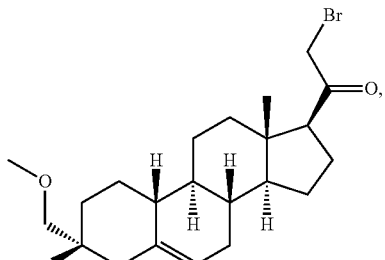
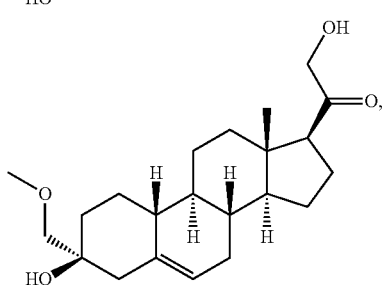
144
-continued
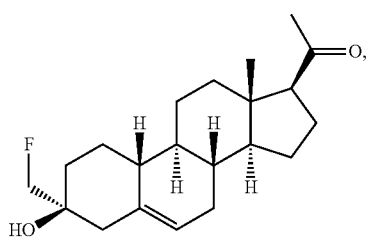
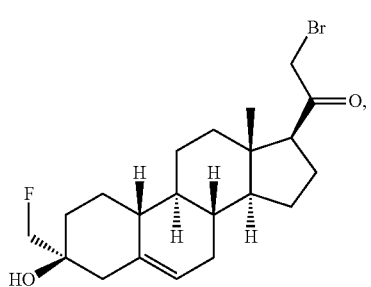
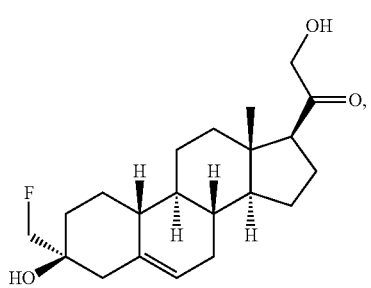
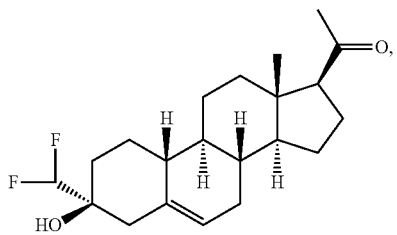
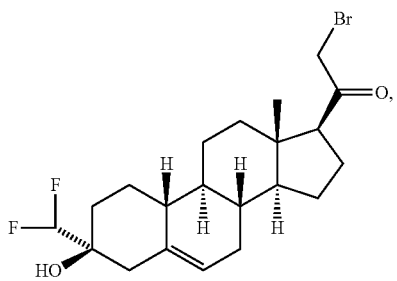
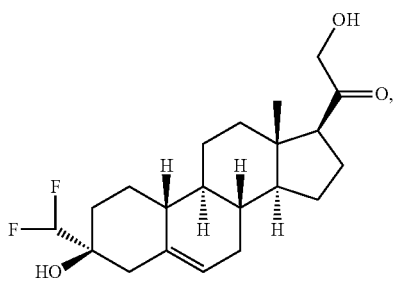

145
-continued
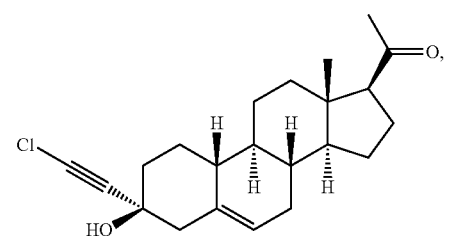
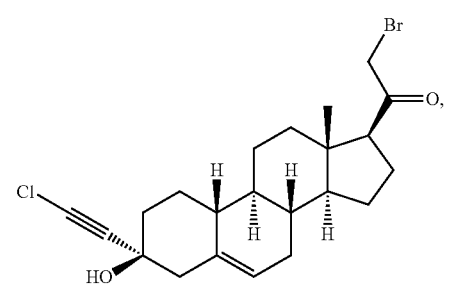
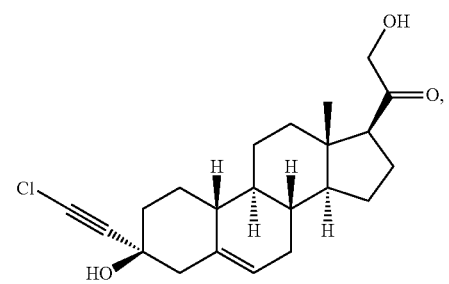
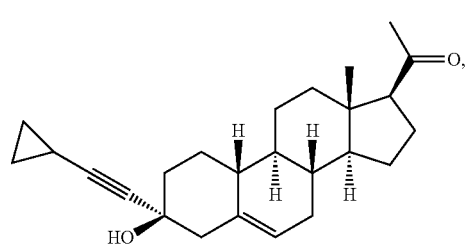
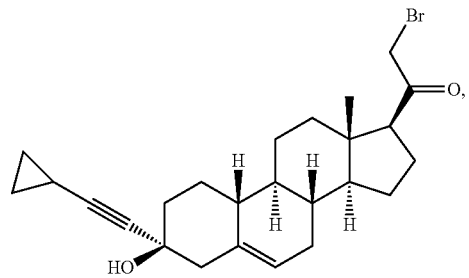
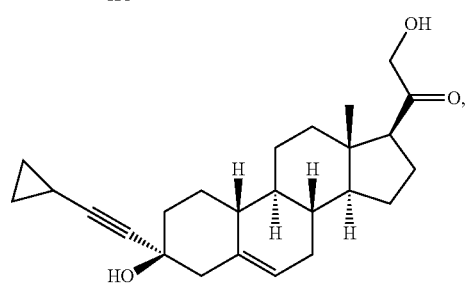
146
-continued
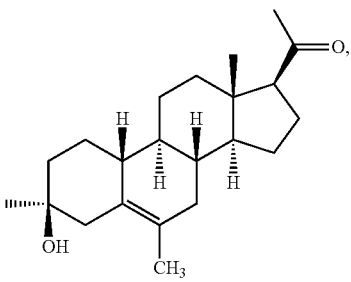
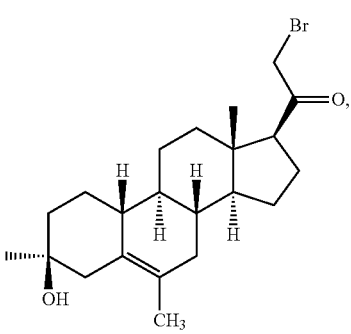
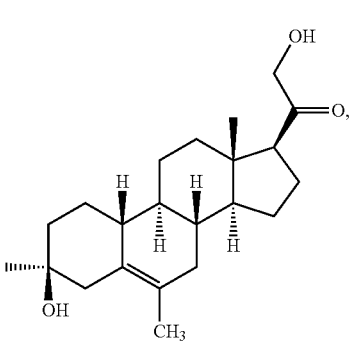
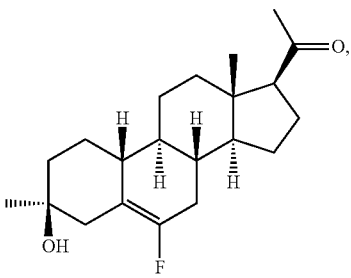
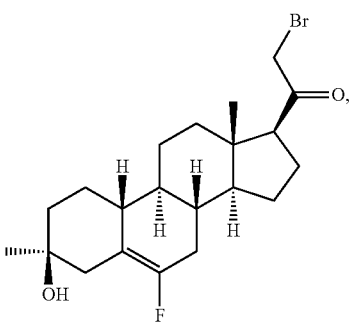

147
-continued
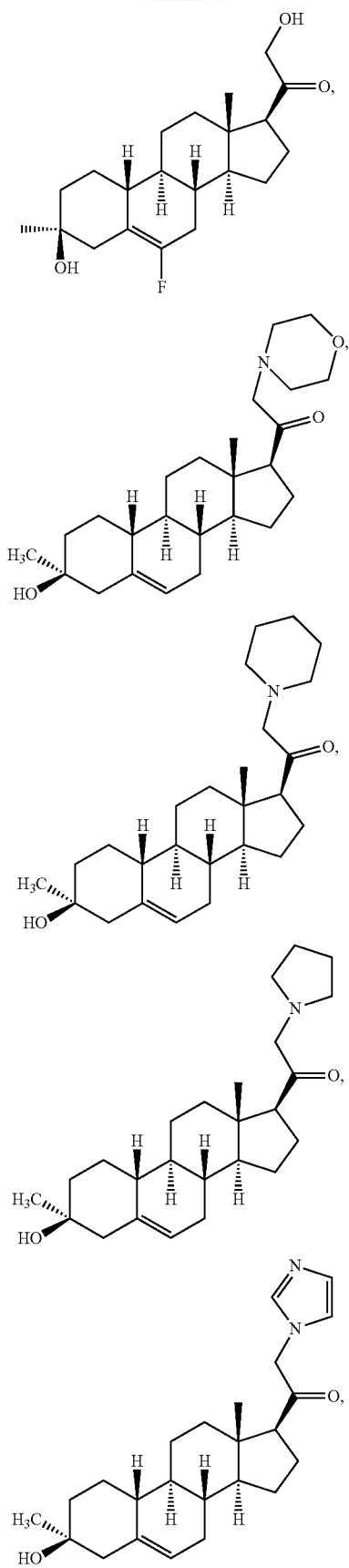
148
-continued
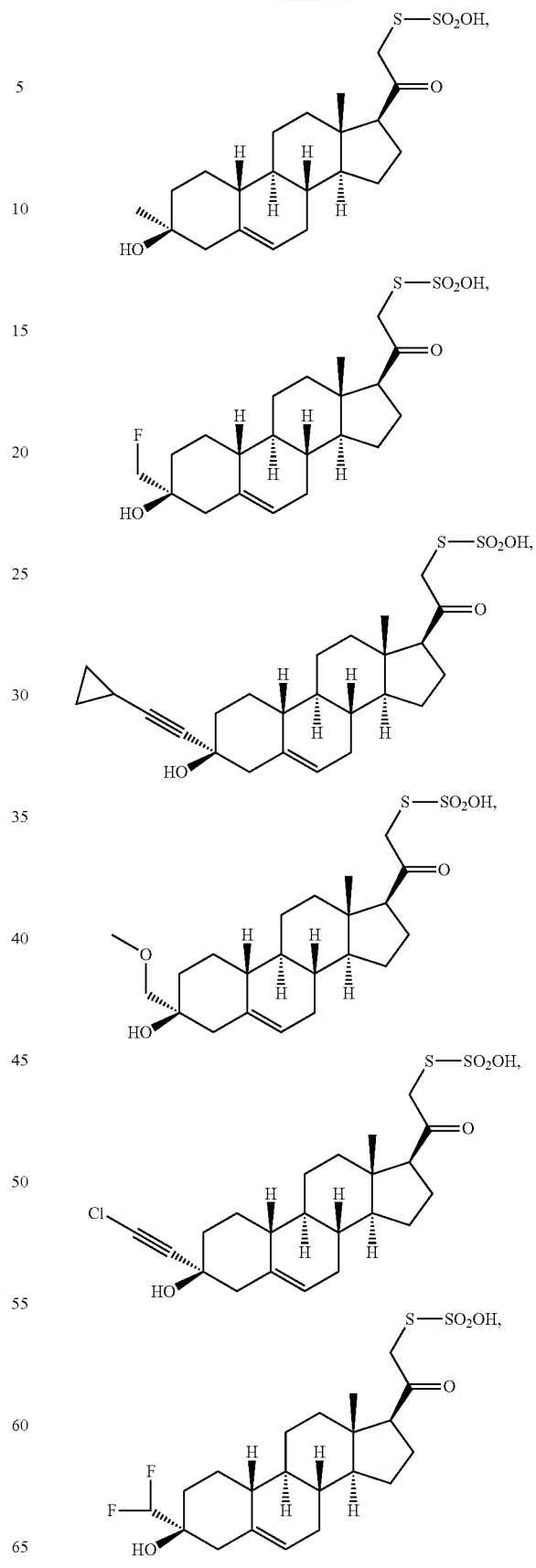

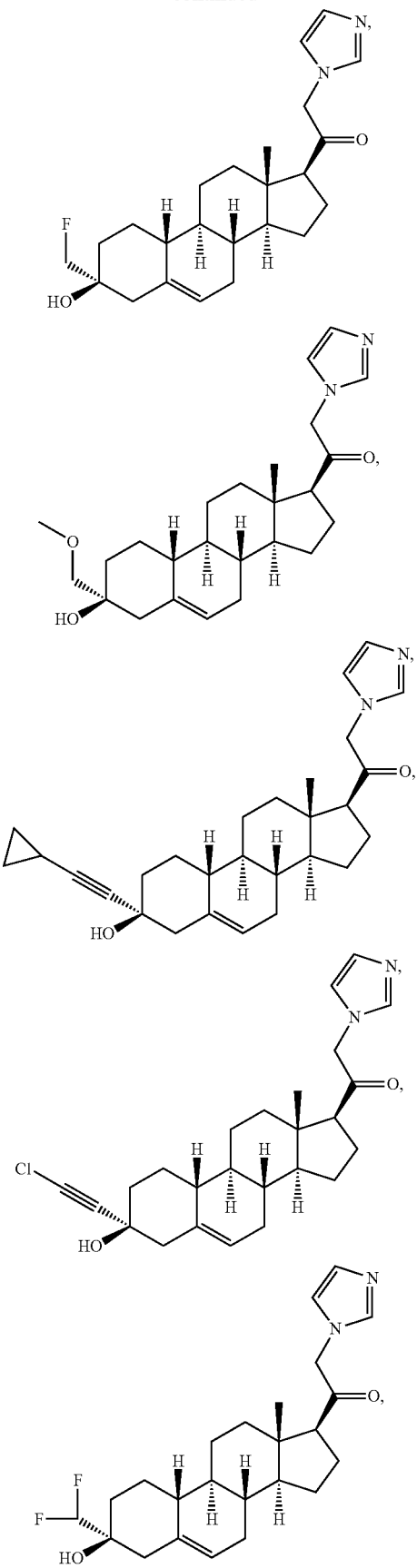
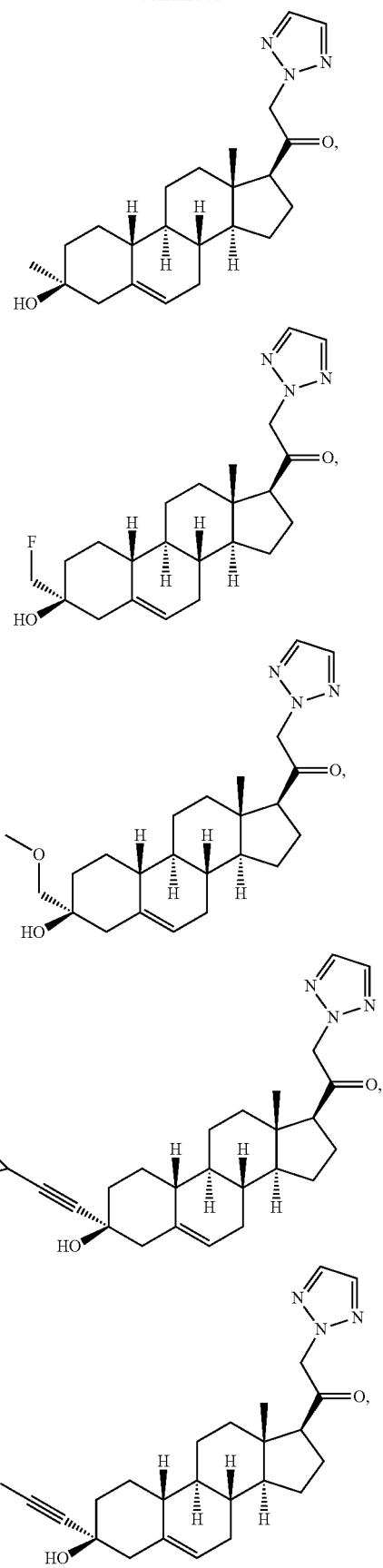

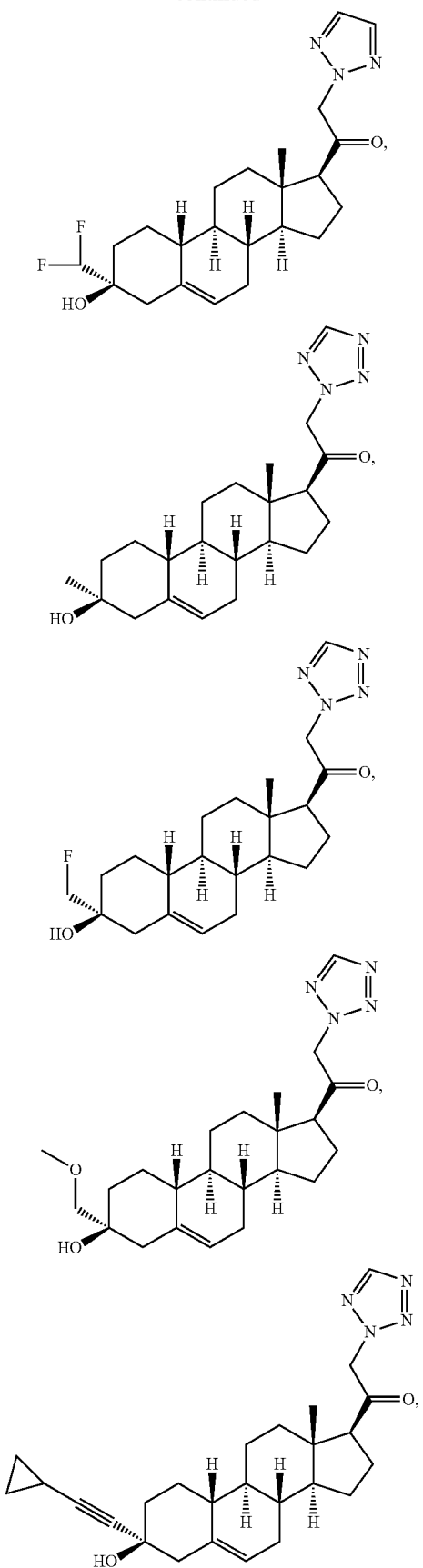

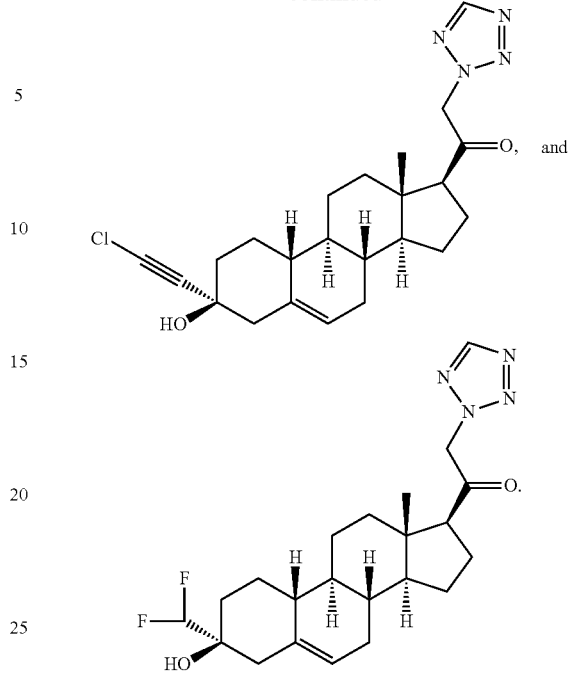

Pharmaceutical Compositions

In another aspect, the invention provides a pharmaceutical composition comprising a compound of the present invention and a pharmaceutically acceptable carrier. In certain embodiments, the pharmaceutical composition comprises an effective amount of the compound. In certain embodiments, the pharmaceutical composition comprises a therapeutically effective amount of the compound. In certain embodiments, the pharmaceutical composition comprises a prophylactically effective amount of the compound.

When employed as pharmaceuticals, the compounds provided herein are typically administered in the form of a pharmaceutical composition. Such compositions can be prepared in a manner well known in the pharmaceutical art and comprise at least one active compound.

In one embodiment, with respect to the pharmaceutical composition, the carrier is a parenteral carrier, oral carrier, or topical carrier.

The present invention also relates to a compound of the present invention or pharmaceutical composition thereof for use as a pharmaceutical or a medicament.

Generally, the compounds provided herein are administered in a therapeutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions provided herein can be administered by a variety of routes including oral, rectal, transdermal, subcutaneous, intravenous, intramuscular, and intranasal. Depending on the intended route of delivery, the compounds provided herein are preferably formulated as either injectable or oral compositions or as salves, as lotions or as patches all for transdermal administration.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The above-described components for orally administrable, injectable, or topically administrable compositions are merely representative. Other materials as well as processing techniques and the like are set forth in Part 8 of Remington's The Science and Practice of Pharmacy, 21st edition, 2005, Publisher: Lippincott Williams & Wilkins, which is incorporated herein by reference.

The compounds of this invention can also be administered in sustained release forms or from sustained release drug delivery systems. A description of representative sustained release materials can be found in Remington's Pharmaceutical Sciences.

The present invention also relates to the pharmaceutically acceptable formulations of a compound of the present invention. In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol®. See, e.g., U.S. Pat. No. 5,376,645. In certain embodiments, the formulation comprises hexapropyl-β-cyclodextrin (e.g., 10-50% in water).

The present invention also relates to the pharmaceutically acceptable acid addition salt of a compound of the present invention. The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

The following formulation examples illustrate representative pharmaceutical compositions that may be prepared in accordance with this invention. The present invention, however, is not limited to the following pharmaceutical compositions.

Exemplary Formulation 1—Tablets: A compound of the present invention may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Exemplary Formulation 2—Capsules: A compound of the present invention may be admixed as a dry powder with a starch diluent in an approximate 1:1 weight ratio. The mixture is filled into 250 mg capsules (125 mg of active compound per capsule).

Exemplary Formulation 3—Liquid: A compound of the present invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Exemplary Formulation 4—Tablets: A compound of the present invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 5—Injection: A compound of the present invention may be dissolved or suspended in a buffered sterile saline injectable aqueous medium to a concentration of approximately 5 mg/mL.

Exemplary Formulation 6—Tablets: A compound of the present invention may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 7—Tablets: A compound of the present invention may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 8—Tablets: A compound of the present invention may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 9—Tablets: A compound of the present invention may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Exemplary Formulation 10—Tablets: A compound of the present invention may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

Methods of Use and Treatment

Earlier studies (see, e.g., Gee et al., *European Journal of Pharmacology*, 136:419-423 (1987)) demonstrated that certain 3α-hydroxylated steroids are orders of magnitude more potent as modulators of the GRC than others had reported (see, e.g., Majewska et al., *Science* 232:1004-1007 (1986); Harrison et al., *J Pharmacol. Exp. Ther.* 241:346-353 (1987)). Majewska et al. and Harrison et al. taught that 3α-hydroxylated-5-reduced steroids are only capable of much lower levels of effectiveness. In vitro and in vivo experimental data have now demonstrated that the high potency of these steroids allows them to be therapeutically useful in the modulation of brain excitability via the GRC (see, e.g., Gee et al., *European Journal of Pharmacology*, 136:419-423 (1987); Wieland et al., *Psychopharmacology* 118(1):65-71 (1995)).

Various synthetic steroids have also been prepared as neuroactive steroids. See, for example, U.S. Pat. No. 5,232,917, which discloses neuroactive steroid compounds useful in treating stress, anxiety, insomnia, seizure disorders, and mood disorders, that are amenable to GRC-active agents, such as depression, in a therapeutically beneficial manner. Furthermore, it has been previously demonstrated that these steroids interact at a unique site on the GRC which is distinct from other known sites of interaction (e.g., barbiturates, benzodiazepines, and GABA) where therapeutically beneficial effects on stress, anxiety, sleep, mood disorders and seizure disorders have been previously elicited (see, e.g., Gee, K. W. and Yamamura, H. I., "Benzodiazepines and Barbiturates: Drugs for the Treatment of Anxiety, Insomnia and Seizure Disorders," in *Central Nervous System Disorders*, Horvell, ed., Marcel-Dekker, New York (1985), pp. 123-147; Lloyd, K. G. and Morselli, P. L., "Psychopharmacology of GABAergic Drugs," in *Psychopharmacology: The Third Generation of Progress*, H. Y. Meltzer, ed., Raven Press, N.Y. (1987), pp. 183-195; and Gee et al., *European Journal of Pharmacology*, 136:419-423 (1987). These compounds are desirable for their duration, potency, and oral activity (along with other forms of administration).

Accordingly, the compounds and pharmaceutical compositions provided herein find use as therapeutics for preventing and/or treating CNS conditions in mammals including humans and non-human mammals. Thus, and as stated earlier, the present invention includes within its scope, and extends to, the recited methods of treatment, as well as to the compounds for such methods, and to the use of such compounds for the preparation of medicaments useful for such methods.

In one aspect, compounds of the present invention are contemplated as therapeutic agents, e.g., for the treatment of CNS conditions in mammals, such as for the treatment of insomnia, depression, mood disorders, convulsive disorders, memory disorders, attention disorders, anxiety disorders (e.g., stress), bipolar disorder (e.g., I and/or II), schizophrenia, depression, bipolar disorder, schizoaffective disorder, mood disorders, anxiety disorders, personality disorders, psychosis, compulsive disorders, post-traumatic stress disorder (PTSD), Autism spectrum disorder (ASD), dysthymia (mild depression), social anxiety disorder, obsessive compulsive disorder (OCD), pain (e.g., a painful syndrome or disorder, e.g., acute pain, chronic pain, neuropathic pain), sleep disorders, memory disorders, dementia, Alzheimer's disease, a seizure disorder (e.g., epilepsy), traumatic brain injury, stroke, addictive disorders (e.g., addiction to opiates, cocaine, and/or alcohol), autism, Huntington's disease, Parkinson's disease, Rett syndrome, withdrawal syndromes, or tinnitus. In certain embodiments, the compounds of the present invention are useful in the treatment of depression, anxiety, mood disorders, sleep disorders, memory disorders, traumatic brain injury, stroke, epilepsy, and schizophrenia.

In another aspect, provided is a method of treating a mammal susceptible to or afflicted with a condition associated with brain excitability, which method comprises administering an effective amount of one or more of the pharmaceutical compositions described herein.

In yet another aspect, provided is the use of a compound of the present invention as a pharmaceutical, e.g., especially in the treatment or prevention of the aforementioned conditions and diseases.

In still yet another aspect, provided is a method of manufacture of a medicament for the treatment or prevention of one of the aforementioned conditions and diseases.

In still yet another aspect, the present invention provides a method for preventing, treating, ameliorating, or managing a disease or condition which comprises administering to a subject in need of such prevention, treatment, amelioration or management, a prophylactically or therapeutically effective amount of a compound of the present invention, or the pharmaceutical composition thereof.

In yet another aspect, the present invention provides a use of a compound of the present invention for the manufacture of a medicament to treat a disease or condition associated with brain excitability. In one embodiment, the disease or condition is selected from depression, anxiety, schizophrenia, sleep disorders, memory disorders, and mood disorders.

In yet another aspect, the present invention provides a method of treatment of a mammal, e.g., a human being, to treat a disease associated with brain excitability, including treating said mammal with an effective amount of a compound of the present invention or composition thereof.

In yet another aspect, the present invention provides a combination of a compound of the present invention and another pharmacologically active agent. As generally understood herein, the compounds provided herein can be administered as the sole active agent or they can be administered in combination with other agents. Administration in combination can proceed by any technique apparent to those of skill in the art including, for example, separate, sequential, concurrent, and alternating administration.

In yet another aspect, the present invention provides a use of a compound of the present invention, or composition thereof, for the manufacture of a medicament to treat a disease or condition associated with CNS in a subject. In certain embodiments, the disease or condition is selected from, sleep disorders, mood disorders, insomnia, anxiety, depression, TBI, stress, and epilepsy.

In yet another aspect, the present invention provides method of in vitro modulation of $GABA_A$ receptor-chloride ionophore complex in a subject through binding to the neurosteroid site on said complex, comprising administering to the subject an amount effective to modulate said complex of a compound of the present invention.

In yet another aspect, the present invention provides method of modulating the $GABA_A$ receptor-chloride ionophore complex in a subject through binding to the neurosteroid site on said complex, comprising administering to the subject an amount effective to modulate said complex of a compound of the present invention.

In yet another aspect, the present invention provides method of treating or preventing stress or anxiety in a subject, comprising administering to the subject in need of such treatment an effective amount of a compound of the present invention, or a composition thereof.

In yet another aspect, the present invention provides method of alleviating or preventing seizure activity in a subject, comprising administering to the subject in need of such treatment an effective amount of a compound of the present invention, or a composition thereof.

In yet another aspect, the present invention provides method of alleviating or preventing insomnia in a subject, comprising administering to the subject in need of such treatment an effective amount of a compound of the present invention, or a composition thereof.

In yet another aspect, the present invention provides method of inducing sleep and maintaining substantially the level of REM sleep that is found in normal sleep, wherein substantial rebound insomnia is not induced, comprising administering an effective amount of a compound of the present invention, or a composition thereof.

In yet another aspect, the present invention provides method of alleviating or preventing PMS or PND in a subject, comprising administering to the subject in need of such treatment an effective amount of a compound of the present invention, or a composition thereof.

In yet another aspect, the present invention provides method of treating or preventing mood disorders in a subject, comprising administering to the subject in need of such treatment an effective amount of a compound of the present invention, or a composition thereof.

In certain embodiments the mood disorder is depression.

In yet another aspect, the present invention provides a method of inducing anesthesia in a subject, comprising administering to the subject an effective amount of a compound of the present invention. In certain embodiments, the subject is a human. In certain embodiments, the compound is a pharmaceutically acceptable 3-ester or 3-diester of an acid selected from the group consisting of acetic, propionic, maleic, fumaric, ascorbic, pimelic, succinic, glutaric, bism-ethylenesalicylic, methanesulfonic, ethane-di-sulfonic, oxalic, tartaric, salicylic, citric, gluconic, itaconic, glycolic, γ-aminobenzoic, aspartic, glutamic, γ-amino-butyric, α-(2-hydroxyethylamino)-propionic, glycine and other α-amino acids, phosphoric, sulfuric, glucuronic, and 1-methyl-1,4-dihydronicotinic.

In yet another aspect, the present invention provides a method of cognition enhancement or treating memory disorder by administering to the subject a therapeutically effective amount of a compound of the present invention. In certain embodiments, the disorder is Alzheimer's disease. In certain embodiments, the disorder is Rett syndrome.

In yet another aspect, the present invention provides a method of treating attention disorders by administering to the subject a therapeutically effective amount of a compound of the present invention. In certain embodiments, the attention disorder is ADHD.

In certain embodiments, the compound is administered to the subject chronically. In certain embodiments, the compound is administered to the subject orally.

EXEMPLIFICATION

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Materials and Methods

The compounds provided herein can be prepared from readily available starting materials using the following general methods and procedures. See, e.g., Synthetic Schemes below. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, or HPLC. The following schemes are presented with details as to the preparation of representative substituted biarylamides that have been listed herein. The compounds provided herein may be prepared from known or commercially available starting materials and reagents by one skilled in the art of organic synthesis.

The enantiomerically pure compounds provided herein may be prepared according to any techniques known to those of skill in the art. For instance, they may be prepared by chiral or asymmetric synthesis from a suitable optically pure precursor or obtained from a racemate by any conventional technique, for example, by chromatographic resolution using a chiral column, TLC or by the preparation of diastereoisomers, separation thereof and regeneration of the desired enantiomer. See, e.g., *Enantiomers, Racemates and Resolutions*, by J. Jacques, A. Collet, and S. H. Wilen, (Wiley-Interscience, New York, 1981); S. H. Wilen, A. Collet, and J. Jacques, *Tetrahedron*, 2725 (1977); E. L. Eliel, *Stereochemistry of Carbon Compounds* (McGraw-Hill, NY, 1962); and S. H. Wilen *Tables of Resolving Agents and Optical Resolutions* 268 (E. L. Eliel ed., Univ. of Notre Dame Press, Notre Dame, Ind., 1972, *Stereochemistry of Organic Compounds*, Ernest L. Eliel, Samuel H. Wilen and Lewis N. Manda (1994 John Wiley & Sons, Inc.), and *Stereoselective Synthesis A Practical Approach*, Mihály Nógrádi (1995 VCH Publishers, Inc., NY, N.Y.).

In certain embodiments, an enantiomerically pure compound of Formula (I) may be obtained by reaction of the racemate with a suitable optically active acid or base. Suitable acids or bases include those described in Bighley et al., 1995, *Salt Forms of Drugs and Adsorption*, in *Encyclopedia of Pharmaceutical Technology*, vol. 13, Swarbrick & Boylan, eds., Marcel Dekker, New York; ten Hoeve & H. Wynberg, 1985, *Journal of Organic Chemistry* 50:4508-4514; Dale & Mosher, 1973, *J. Am. Chem. Soc.* 95:512; and *CRC Handbook of Optical Resolution via Diastereomeric Salt Formation*, the contents of which are hereby incorporated by reference in their entireties.

Enantiomerically pure compounds can also be recovered either from the crystallized diastereomer or from the mother liquor, depending on the solubility properties of the particular acid resolving agent employed and the particular acid enantiomer used. The identity and optical purity of the particular compound so recovered can be determined by polarimetry or other analytical methods known in the art. The diasteroisomers can then be separated, for example, by chromatography or fractional crystallization, and the desired enantiomer regenerated by treatment with an appropriate base or acid. The other enantiomer may be obtained from the racemate in a similar manner or worked up from the liquors of the first separation.

In certain embodiments, enantiomerically pure compound can be separated from racemic compound by chiral chromatography. Various chiral columns and eluents for use in the separation of the enantiomers are available and suitable conditions for the separation can be empirically determined by methods known to one of skill in the art. Exemplary chiral columns available for use in the separation of the enantiomers provided herein include, but are not limited to, CHIRALCEL® OB, CHIRALCEL® OB-H, CHIRALCEL® OD, CHIRALCEL® OD-H, CHIRALCEL® OF, CHIRALCEL® OG, CHIRALCEL® OJ, and CHIRALCEL® OK.

Synthetic Procedures

The compounds of the invention can be prepared in accordance with methods described in the art (Upasani et al., *J. Med. Chem.* 1997, 40:73-84; and Hogenkamp et al., *J. Med. Chem.* 1997, 40:61-72) and using the appropriate reagents, starting materials, and purification methods known to those skilled in the art. A few representative methods are depicted below. In any of the Schemes, depicted below, the compounds may be either 5α- or 5β-isomers.

Scheme 1. Exemplary synthesis of 3β-Methyl-3α-hydroxy-19-nor-pregnan-20-one

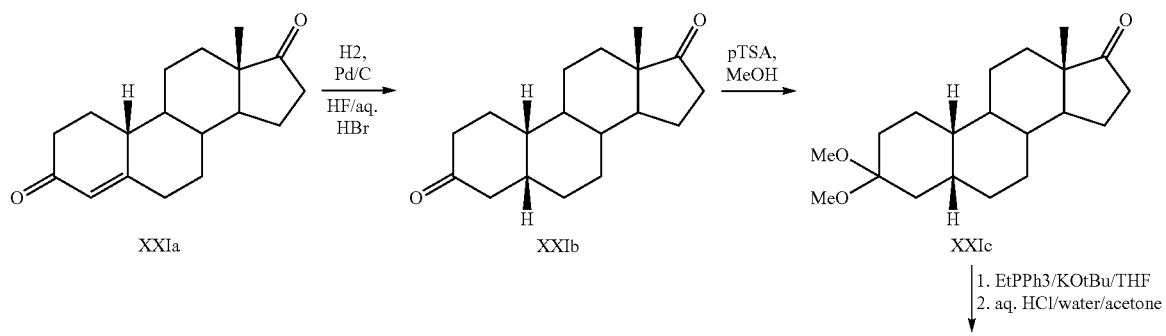

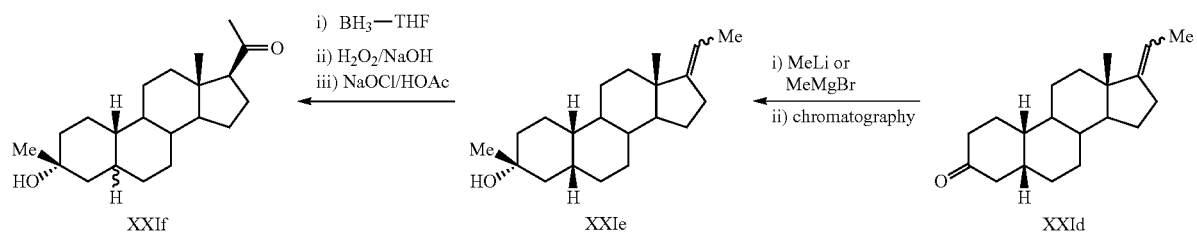
Scheme 2. Exemplary synthesis of 3β-Fluoromethyl-3α-hydroxy-19-nor-pregnan-20-one
Scheme 3. Exemplary synthesis of 3β-Difluoromethyl-3α-hydroxy-19-nor-pregnan-20-one
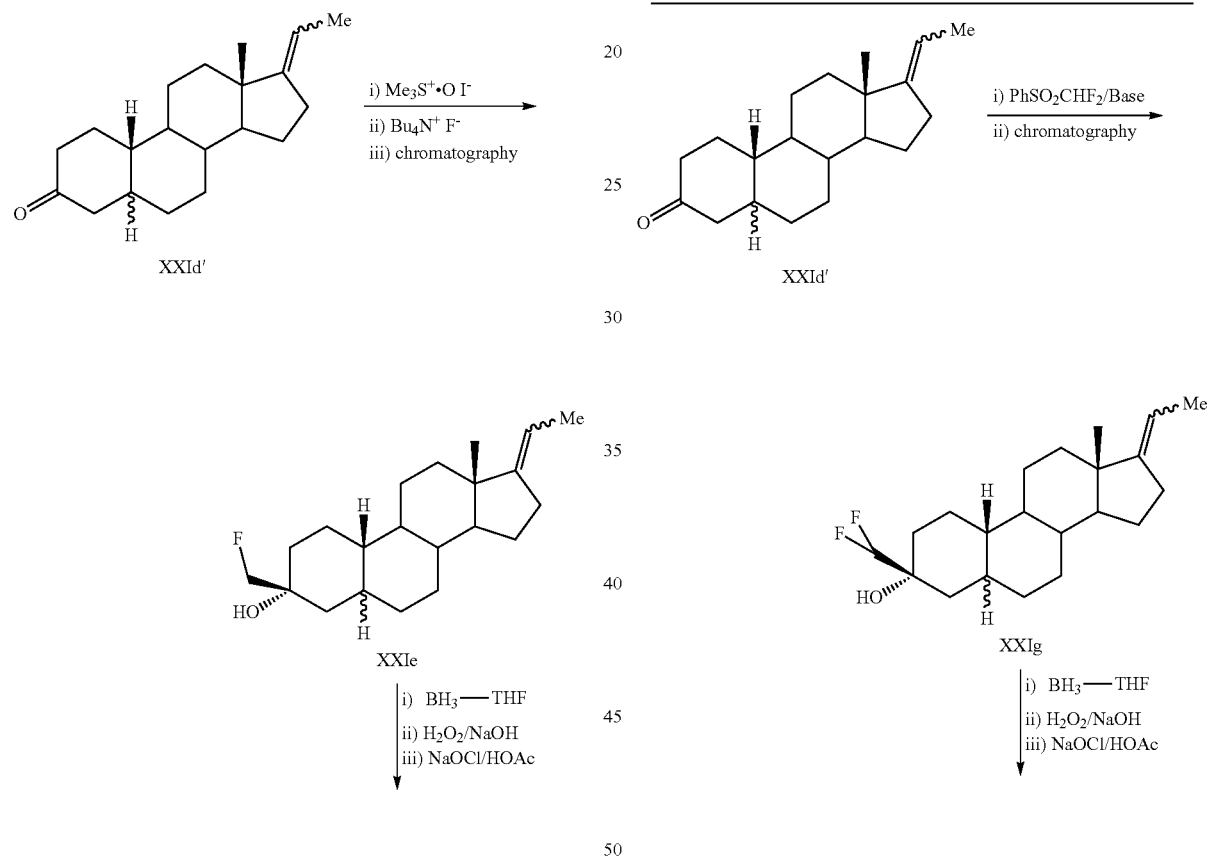
wherein Base may be K—O-t-Btu.

Scheme 4. Exemplary synthesis of 3β-Ethenyl-3α-hydroxy-19-nor-pregnan-20-one
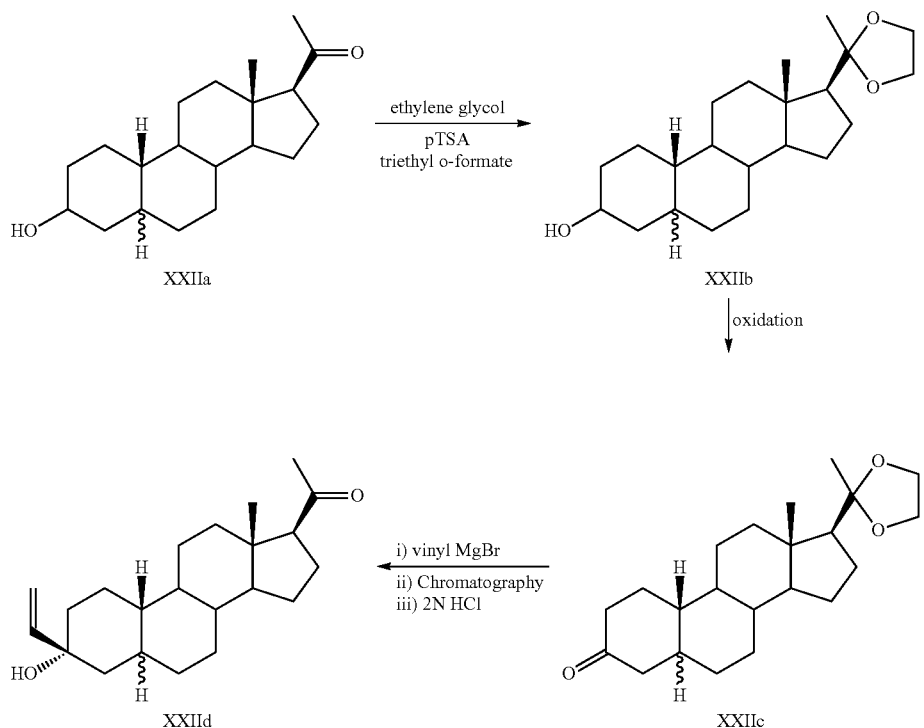
Scheme 5. Exemplary synthesis of 3β-Chloroethynyl-3α-hydroxy-19-nor-pregnan-20-one
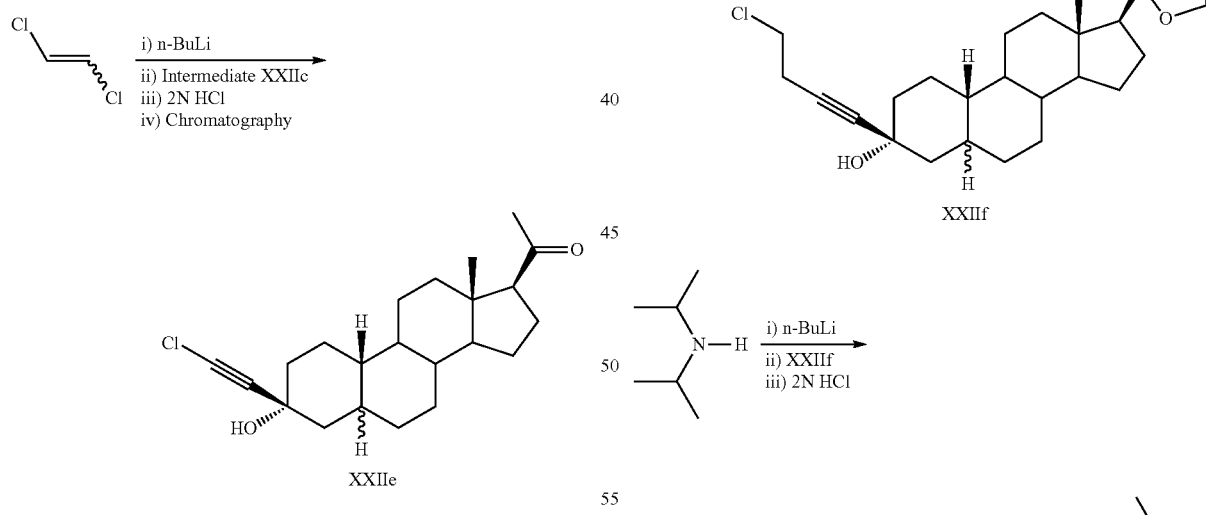
Scheme 6. Exemplary synthesis of 3β-Cyclopropylethynyl-3α-hydroxy-19-nor-pregnan-20-one

Scheme 7. Exemplary synthesis of 3β-Propyn-1-yl-3α-hydroxy-19-nor-pregnan-20-one
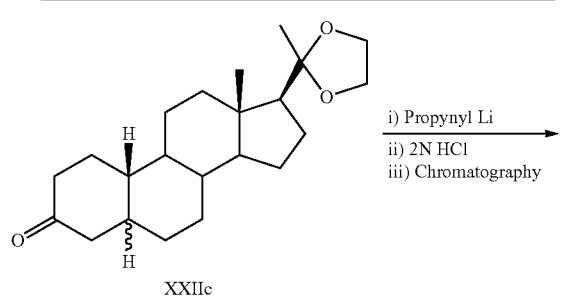
Scheme 8. Exemplary synthesis of 3β-Methoxymethyl-3α-hydroxy-19-nor-pregnan-20-one
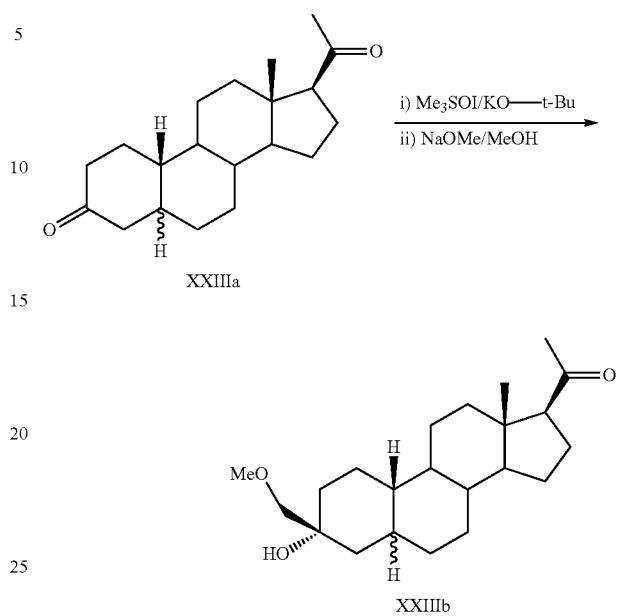
Scheme 9. Exemplary synthesis of 3β-Trifluoroethynyl-3α-hydroxy-19-nor-pregnan-20-one
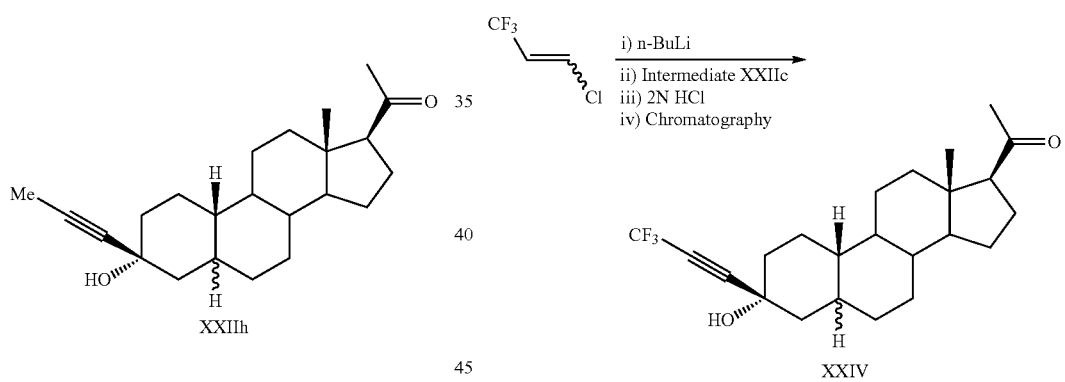
Scheme 10. Exemplary synthesis of 21-hydroxy and 21-hemisuccinate 19-norpregnanes
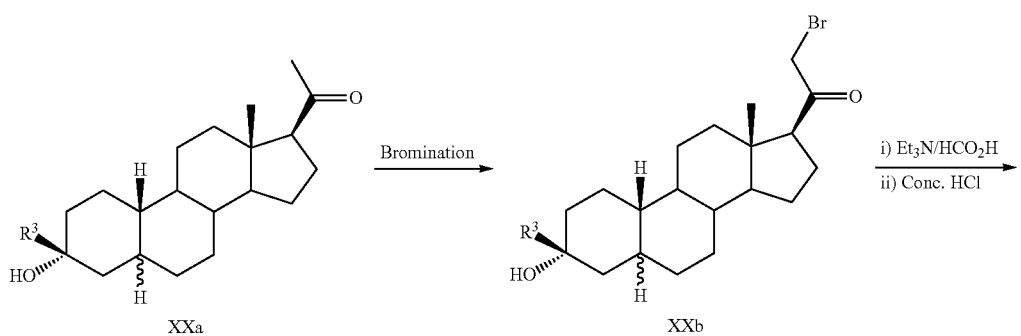

-continued
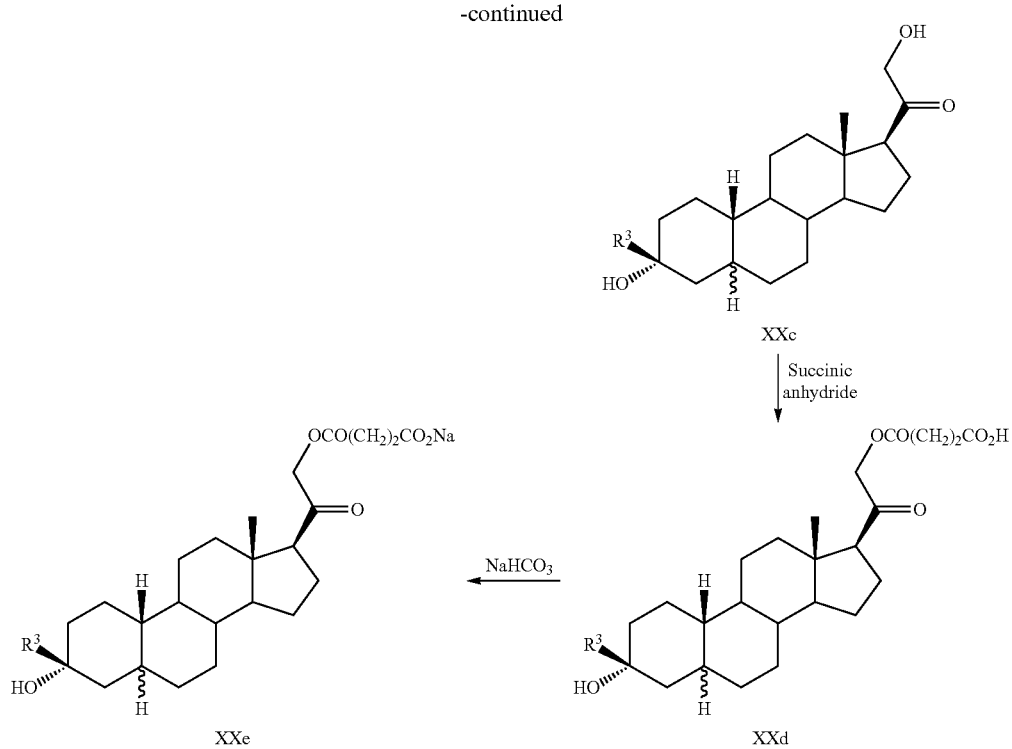
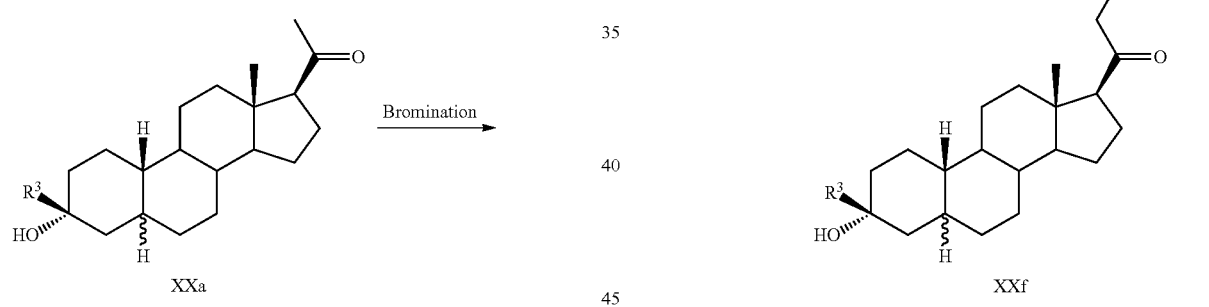
Scheme 11. Exemplary synthesis of 19-norpregnane 21-thiosulfates
-continued
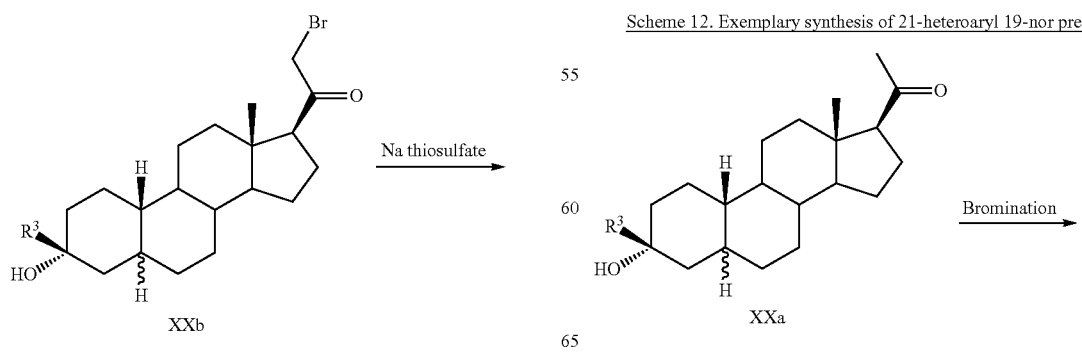
Scheme 12. Exemplary synthesis of 21-heteroaryl 19-nor pregnanes

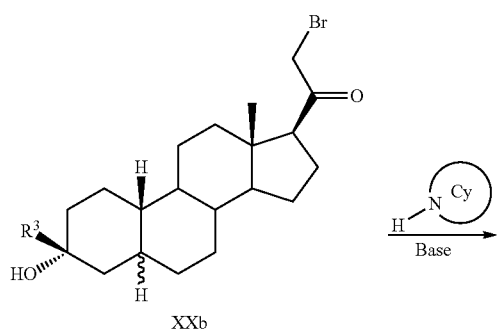
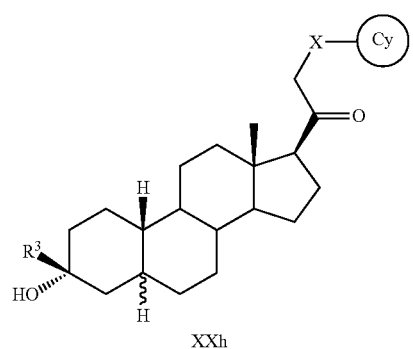
wherein Cy is heteroaryl; and X is —O— or —S—.
Example 1. Synthesis of Compounds 8a/b, 9a/b, and 10a/b
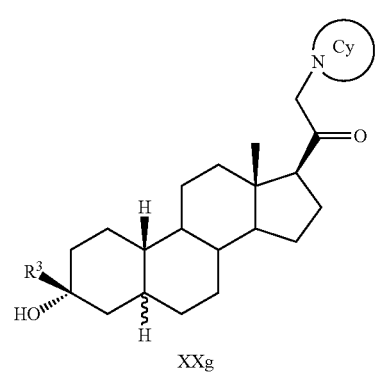
wherein Cy is N-containing heteroaryl.
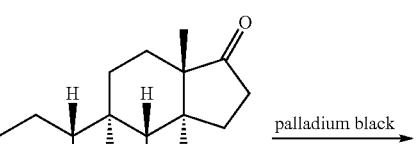
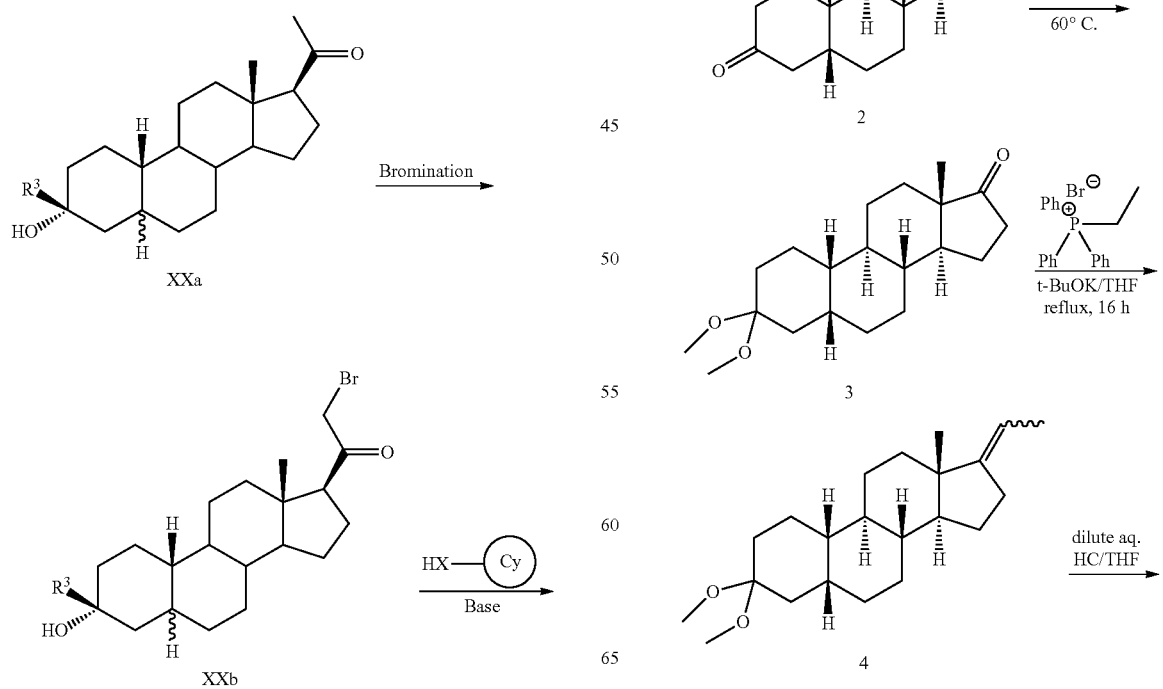

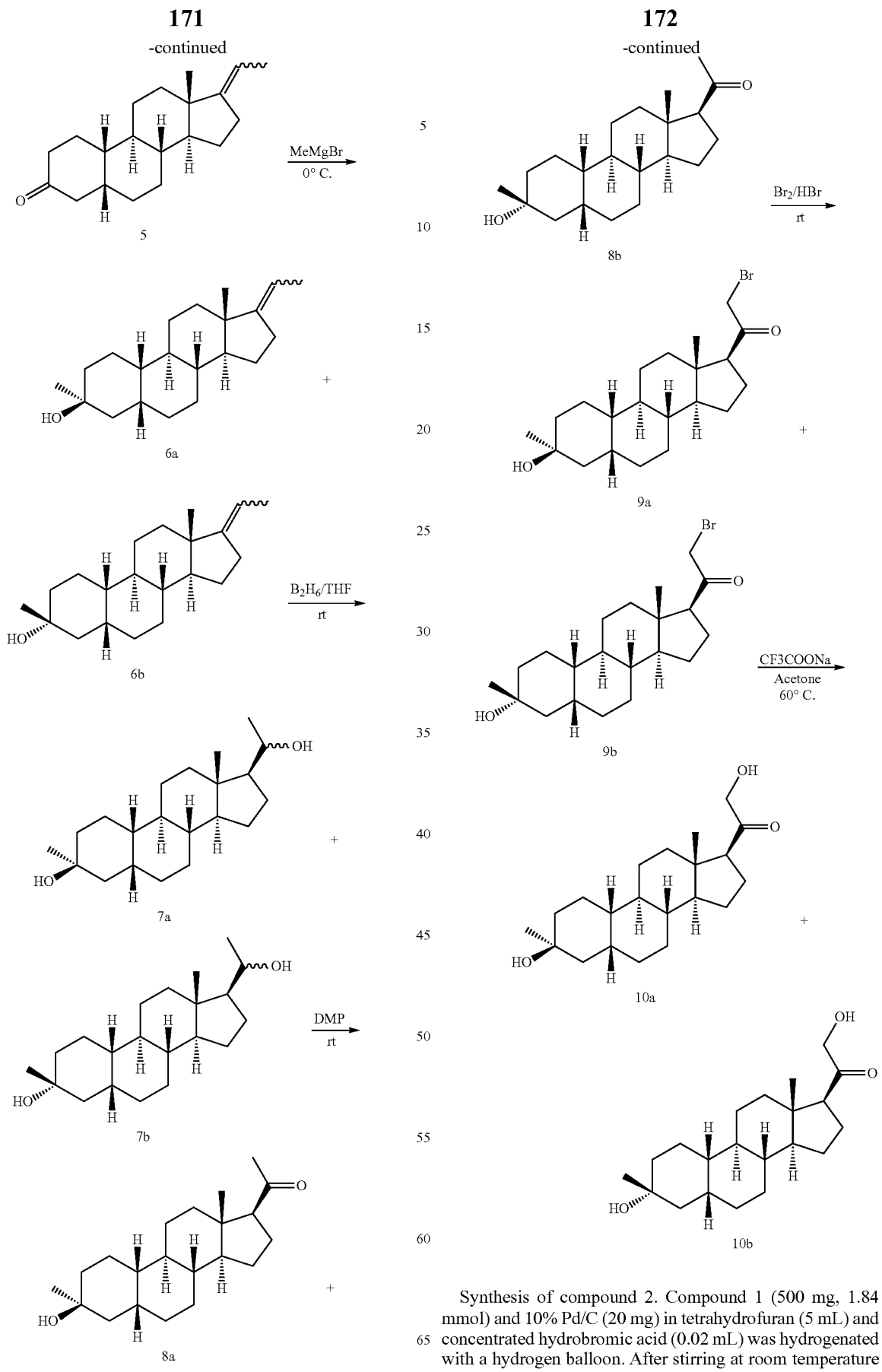
Synthesis of compound 2. Compound 1 (500 mg, 1.84 mmol) and 10% Pd/C (20 mg) in tetrahydrofuran (5 mL) and concentrated hydrobromic acid (0.02 mL) was hydrogenated with a hydrogen balloon. After stirring at room temperature for 24 h, the mixture was filtered through a pad of celite and the filtrate was concentrated in vacuo. Recrystallization from acetone to give compound 2 (367 mg, 1.34 mmol, 73%). $^1$H NMR (400 MHz, CDCl$_3$), δ (ppm), 2.61-2.54 (m, 1H), 0.98 (S, 3H).

Synthesis of compound 3. To a solution of compound 2 (274 mg, 1 mmol) in methanol (4 mL) was added iodine (0.1 mmol). After stirring at 60° C. for 12 h, TLC showed no SM and the solvent was removed in vacuo. The crude product was dissolved in dichloromethane (20 mL) and washed with saturated NaHCO$_3$ (15 mL), brine, dried over Na$_2$SO$_4$, filtered, and concentrated. The residue was purified by chromatography on basic alumina (petroleum ether/ethyl acetate=9:1) to give compound 3 (280 mg, 0.87 mmol, 87%). $^1$H NMR (400 MHz, CDCl$_3$), δ (ppm), 3.19 (S, 3H), 3.13 (S, 3H), 3.18-3.13 (m, 1H), 0.83 (S, 3H).

Synthesis of compound 4. To a suspension of t-BuOK (300 mg, 2.68 mmol) in THF (30 mL) at 0° C. was added ethyltriphenylphosphonium bromide (995 mg, 2.69 mmol) slowly. After stirring at 60° C. for 3 h, compound 3 (86 mg, 0.268 mmol) was added and the mixture was stirred at 60° C. for another 2 h. The reaction mixture was poured into saturated ammonium chloride and extracted with EtOAc (2×50 mL). The combined organic layers were washed with brine, dried over sodium sulfate, filtered and concentrate to afford the crude compound 4 (274 mg). The crude product was used in the next step without further purification.

Synthesis of compound 5. To a solution of crude compound 4 (274 mg) in THF (4 mL) was acidified to pH=3 by 1 N aqueous HCl. After stirring at room temperature for 12 h, the reaction mixture was extracted with ethyl acetate (15 mL×3). The combined organic layers were washed with brine, dried over sodium sulfate, filtered, and concentrated. The residue was purified by column chromatography (petroleum ether/ethyl acetate=10:1 to 5:1) to afford compound 5 (60 mg, 0.21 mmol, 78% for two steps). $^1$H NMR (400 MHz, CDCl3), δ (ppm), 5.13-5.08 (m, 3H), 0.73 (m, 3H).

Synthesis of compound 6a and 6b. To a solution of MeMgBr (5 mmol, 1M in THF) in THF (20 mL) at 0° C. was added a solution of compound 5 (858 mg, 3 mmol) in dry THF (5 mL) via syringe pump over 30 min. After stirring at 0° C. for 5 h, the reaction mixture was allowed to warm up and stirred at room temperature overnight. The reaction mixture was quenched with iced-cold water and extracted with ethyl acetate (15 mL×3). The combined organic layers were washed with brine, dried over sodium sulfate, filtered, and concentrated. The white residue was purified by flash column chromatography (petroleum ether/ethyl acetate=20:1 to 10:1) to give compound 6a (450 mg, 1.49 mmol, 50%; Rf=0.35, PE:EtOAc=10:1). $^1$H NMR (400 MHz, CDCl$_3$), δ (ppm), 5.14-5.08 (m, 1H), 1.26 (s, 3H), 0.87 (s, 3H) and compound 6b (150 mg, 0.50 mmol, 17%; Rf=0.30, PE:EtOAc=10:1). $^1$H NMR (400 MHz, CDCl$_3$), δ (ppm), 5.14-5.09 (m, 1H), 1.21 (s, 3H), 0.88 (s, 3H).

Synthesis of compound 7a. To a solution of compound 6a (200 mg, 0.66 mmol) in dry THF (5 mL) was added borane-tetrahydrofuran complex (2 mL of 1.0 M solution in THF). After stirring at room temperature for 1 hour, the reaction mixture was cooled in an ice bath then quenched slowly with 10% aqueous NaOH (1 mL) followed 30% aqueous solution of H$_2$O$_2$ (1.2 mL). The mixture was allowed to stir at room temperature for 1 hour then extracted with EtOAc (3×10 mL). The combined organic layers were washed with 10% aqueous Na$_2$S$_2$O$_3$ (10 mL), brine (10 mL), dried over MgSO$_4$, filtered, and concentrated to afford crude compound 7a (260 mg). The crude product was used in the next step without further purification.

Synthesis of compound 7b. To a solution of compound 6b (150 mg, 0.50 mmol) in dry THF (5 mL) was added borane-tetrahydrofuran complex (1.34 mL of 1.0 M solution in THF). After stirring at room temperature for 1 hour, the reaction mixture was cooled in an ice bath then quenched slowly with 10% aqueous NaOH (1 mL) followed 30% aqueous solution of H$_2$O$_2$ (1.2 mL). The mixture was allowed to stir at room temperature for 1 hour then extracted with EtOAc (3×10 mL). The combined organic layers were washed with 10% aqueous Na$_2$S$_2$O$_3$ (10 mL), brine (10 mL), dried over MgSO$_4$, filtered, and concentrated to afford crude compound 7b (200 mg). The crude product was used in the next step without further purification.

Synthesis of compound 8a. To a solution of crude compound 7a (260 mg) was dissolved in 10 mL of H$_2$O saturated dichloromethane (dichloromethane had been shaken with several milliliters of H$_2$O then separated from the water layer) was added Dess-Martin periodinate (449 mg, 1.06 mmol). After stirring at room temperature for 24 h, the reaction mixture was extracted with dichloromethane (3×10 mL). The combined organic layers were washed with 10% aqueous Na$_2$S$_2$O$_3$ (10 mL), brine (10 mL), dried over MgSO$_4$, filtered, and concentrated. The residue was purified by chromatography on silica gel (pertroleum ether/ethyl acetate=4:1 to 2:1) to afford title compound 8a (85 mg, 0.27 mmol, 40% for two steps) as a white solid. $^1$H NMR (400 MHz, CDCl$_3$), δ (ppm), 2.57-2.53 (m, 1H), 2.12 (S, 3H), 1.20 (S, 3H), 0.62 (S, 3H).

Synthesis of compound 8b. To a solution of crude compound 7b (200 mg) was dissolved in 10 mL of H$_2$O saturated dichloromethane (dichloromethane had been shaken with several milliliters of H$_2$O then separated from the water layer) was added Dess-Martin periodinate (400 mg, 0.94 mmol). After stirring at room temperature for 24 h, the reaction mixture was extracted with dichloromethane (3×10 mL). The combined organic layers were washed with 10% aqueous Na$_2$S$_2$O$_3$ (10 mL), brine (10 mL), dried over MgSO$_4$, filtered, and concentrated. The residue was purified by chromatography on silica gel (pertroleum ether/ethyl acetate=4:1 to 2:1) to afford title compound 8b (90 mg, 0.28 mmol, 57% for two steps) as a white solid. $^1$H NMR (400 MHz, CDCl$_3$), δ (ppm), 2.55-2.51 (m, 1H), 2.11 (S, 3H), 1.32 (S, 3H), 0.61 (S, 3H).

Synthesis of compound 9a. To a solution of compound 8a (70 mg, 0.22 mmol) in MeOH (5 mL) was added 2 drops of HBr (48%) followed by bromine (100 mg, 0.63 mmol). After stirring at room temperature for 1 h, the reaction mixture was poured into ice-water then extracted with ethyl acetate (15 mL×3). The combined organic layers were washed with brine (20 mL), dried over MgSO$_4$, filtered, and concentrated to give crude compound 9a (90 mg). The crude product was used in the next step without further purification.

Synthesis of compound 9b. To a solution of compound 8b (80 mg, 0.25 mmol) in MeOH (5 mL) was added 2 drops of HBr (48%) followed by bromine (100 mg, 0.63 mmol). After stirring at room temperature for 1 h, the reaction mixture was poured into ice-water then extracted with ethyl acetate (15 mL×3). The combined organic layers were washed with brine (20 mL), dried over MgSO$_4$, filtered, and concentrated to give crude compound 9b (95 mg). The crude product was used in the next step without further purification.

Synthesis of compound 10a. To a solution of crude compound 9a (90 mg) in acetone (10 mL) was treated with CF$_3$COOH (0.5 mL) and Et$_3$N (0.7 mL). After heating at reflux for 30 min, CF$_3$COONa salt (540 mg, 3.97 mmol) was added and the mixture was refluxed for overnight. The reaction was allowed to cool to room temperature and the solvent was removed in vacuo. The residue was extracted with ethyl acetate (10 mL×3). The combined organic layers were washed with brine (15 mL), dried over MgSO$_4$, filtered, and concentrated. The residue was purified by chromatography on silica gel (pertroleum ether/ethyl acetate=3:1) to afford compound 10a (25 mg, 0.075 mmol, 34% for two steps). $^1$H NMR (400 MHz, CDCl$_3$), δ (ppm), 4.24-4.12 (m, 2H), 2.48-2.44 (m, 1H), 1.07 (S, 3H), 0.64 (S, 3H).

Synthesis of compound 10b. To a solution of crude compound 9b (95 mg) in acetone (10 mL) was treated with CF$_3$COOH (0.5 mL) and Et$_3$N (0.7 mL). After heating at reflux for 30 min, CF$_3$COONa salt (540 mg, 3.97 mmol) was added and the mixture was refluxed for overnight. The reaction was allowed to cool to room temperature and the solvent was removed in vacuo. The residue was extracted with ethyl acetate (10 mL×3). The combined organic layers were washed with brine (15 mL), dried over MgSO$_4$, filtered, and concentrated. The residue was purified by chromatography on silica gel (pertroleumether/ethyl acetate=3:1) to afford compound 10b (34 mg, 0.10 mmol, 41% for two steps). $^1$H NMR (400 MHz, CDCl$_3$), δ (ppm), 4.25-4.12 (m, 2H), 2.48-2.44 (m, 1H), 1.32 (S, 3H), 0.64 (S, 3H).

Example 2. Synthesis of Compounds 14a/b, 15a/b, and 16a/b

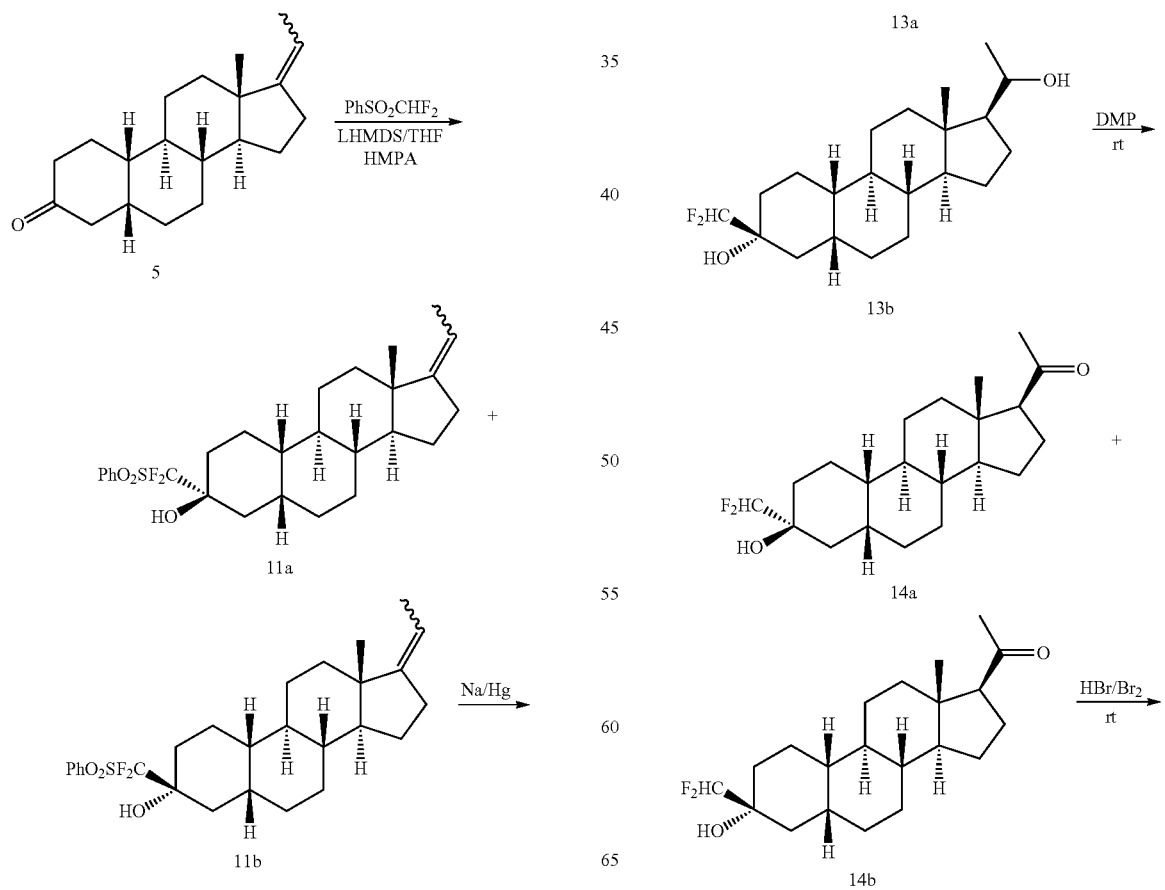

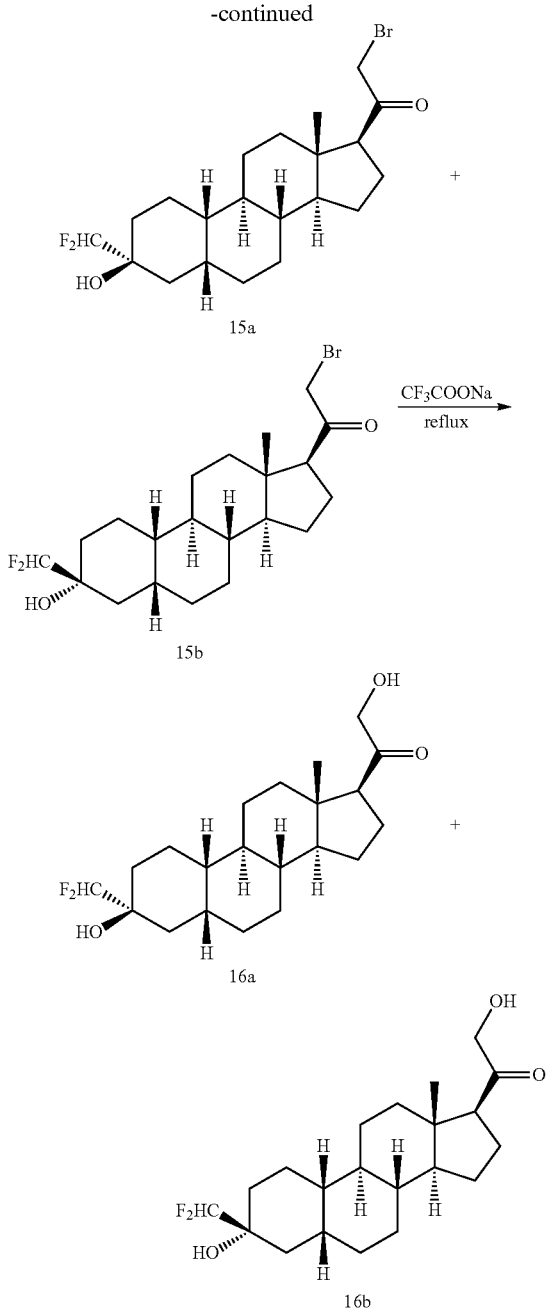

Synthesis of compound 11a and 11b. To a solution of compound 5 (800 mg, 2.79 mmol) and PhSO$_2$CF$_2$H (540 mg, 2.79 mmol) in THF (25 mL) and HMPA (0.5 mL) at −78° C. under N$_2$ was added LHMDS (4 mL, 1M in THF) dropwise. After stirring at −78° C. for 2 h, the reaction mixture was quenched with saturated aqueous NH$_4$Cl solution (10 mL) and allowed to warm to room temperature then extracted with Et$_2$O (20 mL×3). The combined organic layers were washed with brine, dried over sodium sulfate, filtered, and concentrate. The residue was purified by silica gel column chromatography (pertroleum ether/ethyl acetate=10/1) to give the mixture of compound 11a and 11b (700 mg). The mixture was further purified by chiral-HPLC to afford compound 11a (200 mg, t=4.31 min). $^1$H NMR (400 MHz, CDCl$_3$), δ (ppm), 7.99-7.97 (d, 2H, J=7.6 Hz), 7.77-7.75 (m, 1H), 7.64-7.60 (m, 2H), 5.14-5.08 (m, 1H), 0.88 (s, 3H); compound 11b (260 mg, t=5.66 min). $^1$H NMR (400 MHz, CDCl$_3$), δ (ppm), 8.00-7.98 (d, 2H, J=7.6 Hz), 7.77-7.75 (m, 1H), 7.64-7.60 (m, 2H), 5.14-5.09 (m, 1H), 0.88 (s, 3H). Chiral-HPLC separation conditions: Co-solvent: MeOH (0.1% HNEt$_2$), Column: OZ-H (4.6*250 mm 5 μm), Column Temperature: 38.9, CO$_2$ Flow Rate: 2.10, Co-Solvent Flow Rate: 0.9, Co-Solvent %: 30, PDA Start Wavelength: 214 nm, PDA Start Wavelength: 359 nm, Peak 1: 11a RT=4.31 min, Peak 2: 11b RT=5.66 min Synthesis of compound 12a. To a solution of compound 11a (100 mg, 0.209 mmol) and anhydrous Na$_2$HPO$_4$ (100 mg) in anhydrous methanol (5 mL) at −20° C. under N$_2$ was added Na/Hg amalgam (500 mg). After stirring at −20° C. to 0° C. for 1 h, the methanol solution was decanted out and the solid residue was washed with Et$_2$O (5×3 mL). The combined organic layers were washed with brine (20 mL), dried over MgSO$_4$, filtered, and concentrated. The residue was purified by silica gel chromatography (pertroleum ether/ethylacetate=10/1) to give compound 12a (30 mg, 0.089 mmol, 42%). $^1$H NMR (400 MHz, CDCl3), δ (ppm), 5.60-5.45 (t, 1H, J=60 Hz), 5.17-5.15 (m, 1H), 0.88 (m, 3H).

Synthesis of compound 12b. To a solution of compound 11b (100 mg, 0.209 mmol) and anhydrous Na$_2$HPO$_4$ (100 mg) in anhydrous methanol (5 mL) at −20° C. under N$_2$ was added Na/Hg amalgam (500 mg). After stirring at −20° C. to 0° C. for 1 h, the methanol solution was decanted out and the solid residue was washed with Et$_2$O (5×3 mL). The combined organic layers were washed with brine (20 mL), dried over MgSO$_4$, filtered, and concentrated. The residue was purified by silica gel chromatography (pertroleum ether/ethyl acetate=10/1) to give compound 12b (36 mg, 0.106 mmol, 51%). $^1$H NMR (400 MHz, CDCl$_3$), δ (ppm), 6.02-5.88 (t, 1H, J=49.2 Hz), 5.17-5.15 (m, 1H), 0.88 (s, 3H).

Synthesis of compound 13a. To a solution of compound 12a (150 mg, 0.443 mmol) in dry THF (5 mL) was added borane-tetrahydrofuran complex (1.34 mL of 1.0 M solution in THF). After stirring at room, temperature for 1 hour, the reaction mixture was cooled in an ice bath then quenched slowly with 10% aqueous NaOH (1 mL) followed 30% aqueous solution of H$_2$O$_2$ (1.2 mL). The mixture was allowed to stir at room temperature for 1 hour then extracted with EtOAc (3×10 mL). The combined organic layers were washed wiih 10% aqueous Na$_2$S$_2$O$_3$ (10 mL), brine (10 mL), dried over MgSO$_4$, filtered, and concentrated to afford crude compound 13a (200 mg). The crude product was used in the next step without further purification.

Synthesis of compound 13b. To a solution of compound 12b (150 mg, 0.443 mmol) in dry THF (5 mL) was added borane-tetrahydrofuran complex (1.34 mL of 1.0 M solution in THF). After stirring at room temperature for 1 hour, the reaction mixture was cooled in an ice bath then quenched slowly with 10% aqueous NaOH (1 mL) followed 30% aqueous solution of H$_2$O$_2$ (1.2 mL). The mixture was allowed to stir at room temperature for 1 hour then extracted with EtOAc (3×10 mL). The combined organic layers were washed with 10% aqueous Na$_2$S$_2$O$_3$ (10 mL), brine (10 mL), dried over MgSO$_4$, filtered, and concentrated to afford crude compound 13b (210 mg). The crude product was used in the next step without further purification.

Synthesis of compound 14a. To a solution of crude compound 13a (200 mg) was dissolved in 10 mL of H$_2$O saturated dichloromethane (dichloromethane had been shaken with several milliliters of H$_2$O then separated from the water layer) was added Dess-Martin periodinate (449 mg, 1.06 mmol). After stirring at room temperature for 24 h, the reaction mixture was extracted with dichloromethane (3×10 mL). The combined organic layers were washed with 10% aqueous Na$_2$S$_2$O$_3$ (10 mL), brine (10 mL), dried over MgSO$_4$, filtered, and concentrated. The residue was purified by chromatography on silica gel (pertroleum ether/ethyl acetate=5:1) to afford compound 14a (85 mg, 0.24 mmol, 54%) as a white solid. $^1$H NMR (400 MHz, CDCl$_3$), δ (ppm), 5.60-5.71 (t, 1H, J=56.8 Hz), 2.57-2.51 (m, 1H), 0.62 (S, 3H).

Synthesis of compound 14b. To a solution of crude compound 13b (210 mg) was dissolved in 10 mL of H$_2$O saturated dichloromethane (dichloromethane had been shaken with several milliliters of H$_2$O then separated from the water layer) was added Dess-Martin periodinate (380 mg, 0.896 mmol). After stirring at room temperature for 24 h, the reaction mixture was extracted with dichloromethane (3×10 mL). The combined organic layers were washed with 10% aqueous Na$_2$S$_2$O$_3$ (10 mL), brine (10 mL), dried over MgSO$_4$, filtered, and concentrated. The residue was purified by chromatography on silica gel (petroleum ether/ethyl acetate=5:1) to afford compound 14b (90 mg, 0.254 mmol, 57%) as a white solid. $^1$H NMR (400 MHz, CDCl$_3$), δ (ppm), 6.01-5.73 (t, 1H, J=56.4 Hz), 2.55-2.54 (m, 1H), 2.12 (S, 3H), 0.62 (S, 3H).

Synthesis of compound 15a. To a solution of compound 14a (70 mg, 0.197 mmol) in MeOH (5 mL) was added 2 drops of HBr (48%) followed by bromine (100 mg, 0.63 mmol). After stirring at room temperature for 1 h, the reaction mixture was poured into ice-water then extracted with ethyl acetate (15 mL×3). The combined organic layers were washed with brine (20 mL), dried over MgSO$_4$, filtered, and concentrated to give crude compound 15a (90 mg). The crude product was used in the next step without further purification.

Synthesis of compound 15b. To a solution of compound 14b (80 mg, 0.226 mmol) in MeOH (5 mL) was added 2 drops of HBr (48%) followed by bromine (100 mg, 0.63 mmol). After stirring at room temperature for 1 h, the reaction mixture was poured into ice-water then extracted with ethyl acetate (15 mL×3). The combined organic layers were washed with brine (20 mL), dried over MgSO$_4$, filtered, and concentrated to give crude compound 15b (95 mg). The crude product was used in the next step without further purification.

Synthesis of compound 16a. To a solution of crude compound 15a (90 mg) in acetone (10 mL) was treated with CF$_3$COOH (0.5 mL) and Et$_3$N (0.7 mL). After heating at reflux for 30 min, CF$_3$COONa salt (540 mg, 3.9 mmol) was added and the mixture was refluxed for overnight. The reaction was allowed to cool to room temperature and the solvent was removed in vacuo. The residue was extracted with ethyl acetate (10 mL×3). The combined organic layers were washed with brine (15 mL), dried over MgSO$_4$, filtered, and concentrated. The residue was purified by chromatography on silica gel (pertroleumether/ethyl acetate=3:1) to afford compound 16a (25 mg, 0.067 mmol, 34% for two steps). $^1$H NMR (400 MHz, CDCl$_3$), δ (ppm), 5.60-5.31 (t, 1H, J=56.8 Hz), 4.22-4.18 (m, 2H), 0.64 (S, 3H).

Synthesis of compound 16b. To a solution of crude compound 15b (95 mg) in acetone (10 mL) was treated with CF$_3$COOH (0.5 mL) and Et$_3$N (0.7 mL). After heating at reflux for 30 min, CF$_3$COONa salt (540 mg, 3.9 mmol) was added and the mixture was refluxed for overnight. The reaction was allowed to cool to room temperature and the solvent was removed in vacuo. The residue was extracted with ethyl acetate (10 mL×3). The combined organic layers were washed with brine (15 mL), dried over MgSO$_4$, filtered, and concentrated. The residue was purified by chromatography on silica gel (pertroleum:ether/ethyl acetate=3:1) to afford compound 16b (38 mg, 0.102 mmol, 46% for two steps). $^1$H NMR (400 MHz, CDCl3), δ (ppm), 6.00-5.74 (t, 1H, J=51.2 Hz), 4.42-4.18 (m, 2H), 0.64 (S, 3H).

Example 3. Synthesis of Compounds 9, 9a/b/c and 11a/b

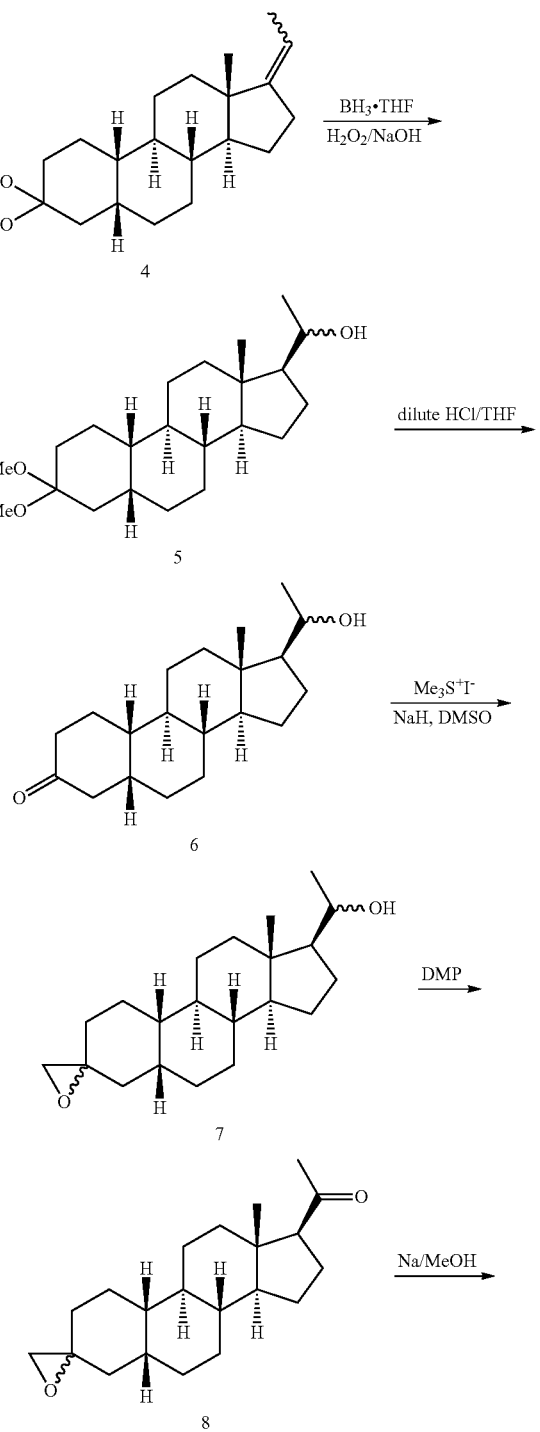

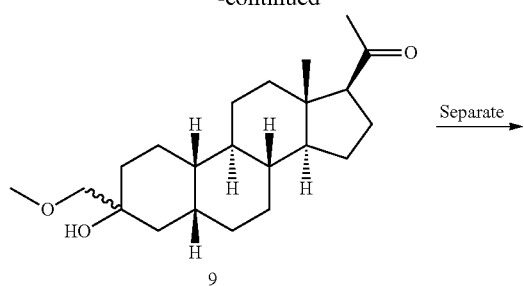

9

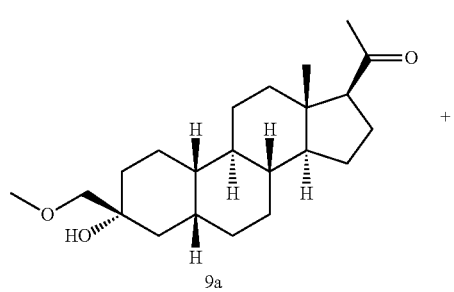

9a

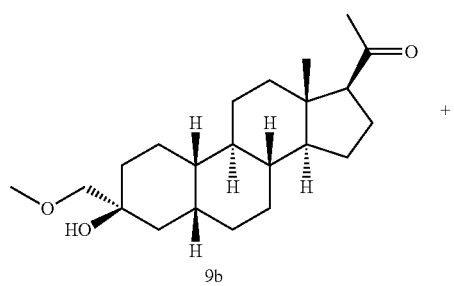

9b

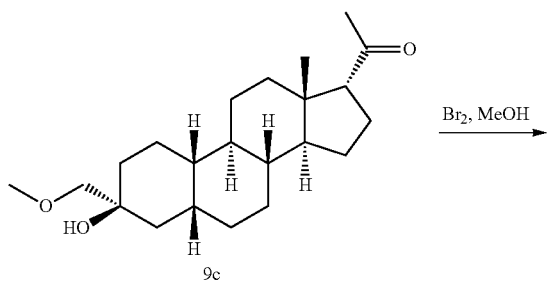

9c

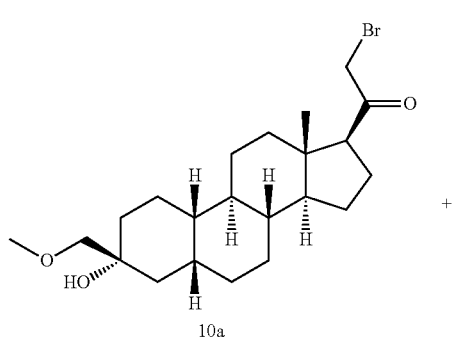

10a

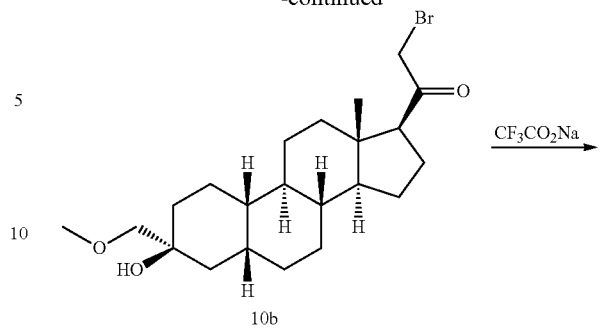

10b

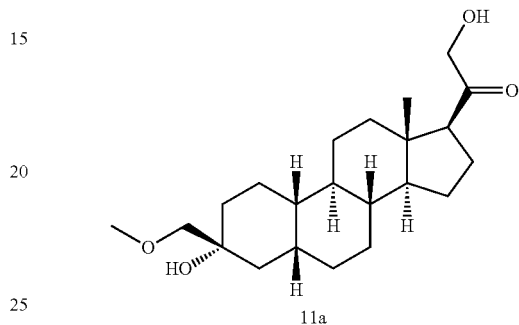

11a

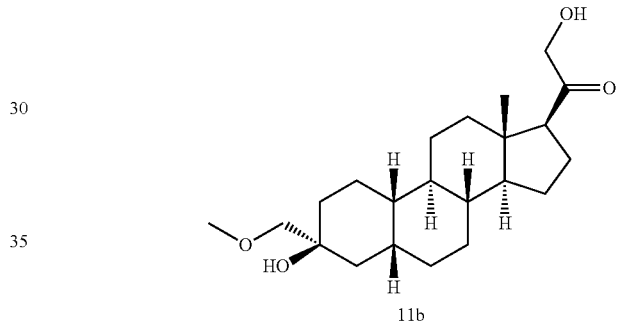

11b

Synthesis of compound 5. To a solution of 4 (5 g, 15 mmol) in dry THF (20 mL) was added borane-tetrahydrofuran complex (30 mL of 1.0 M solution in THF). After stirring at room temperature for 1 hour, the reaction mixture was cooled in an ice bath and quenched slowly with 10% aqueous NaOH (56 mL) followed by 30% aqueous solution of $H_2O_2$ (67 mL). The reaction mixture was stirred at room temperature for 1 hour then extracted with EtOAc (3×100 mL). The combined organic layers were washed with 10% aqueous $Na_2S_2O_3$ (100 mL), brine (100 mL), dried over $MgSO_4$, filtered, and concentrated to afford the crude product 5 (3.2 g, 9.0 mmol). The crude product was used in the next step without further purification.

Synthesis of compound 6. To a solution of compound 5 (3.2 g, 9 mmol) in THF (40 mL) was added hydrogen chloride (3 mL, 3 M aqueous solution). After stirring at room temperature for 12 hours, the solvent was removed under reduced pressure, and the residue was purified by silica gel chromatography (pertroleum ether/ethyl acetate=10:1 to 5:1) to give compound 6 (2.2 g, 81%) as a white solid. $^1H$ NMR (400 MHz, CDCl3), δ (ppm), 3.82-3.93 (m, 1H), 2.58-2.62 (m, 1H), 2.19-2.23 (m, 4H), 0.72 (s, 3H).

Synthesis of compound 7. To a solution of trimethylsufoxonium iodide (8.1 g, 36.9 mmol) in DMSO (100 mL) was added NaH (60%; 1.26 g, 31.5 mmol). After stirring at room temperature for 1 h, a suspension of compound 6 (2.2 g, 7.2 mmol) in DMSO (20 mL) was added dropwise. After stirring at room temperature for another 2.5 h, the reaction mixture was poured into ice-cold water and extracted with ether (100 mL×3). The combined organic layers were washed with brine (100 mL×3), dried over (MgSO$_4$), filtered, and concentrated to give compound 7 (1.6 g, 70%) as a white solid. $^1$H NMR (400 MHz, CDCl3), δ (ppm), 3.69-3.71 (m, 1H), 2.56-2.61 (m, 2H), 2.21-2.28 (m, 1H), 0.68 (s, 3H).

Synthesis of compound 8. To a solution of compound 7 (1.6 g, 5.0 mmol) in 60 mL of H$_2$O saturated dichloromethane (CH$_2$Cl$_2$ had been shaken with several milliliters of H$_2$O then separated from the water layer) was added Dess-Martin periodinane (4.2 g, 10 mmol). After stirring at room temperature for 24 h, the reaction mixture was extracted with dichloromethane (3×100 mL). The combined organic layers were washed with 10% aqueous Na$_2$S$_2$O$_3$ (100 mL), brine (100 mL), dried over MgSO$_4$, filtered, and concentrated. The residue was purified by chromatography on silica gel (pertroleum ether/ethyl acetate=20:1 to 10:1) to afford compound 8 (1.2 g, 75%) as a white solid. $^1$H NMR (400 MHz, CDCl3), δ (ppm), 2.50-2.58 (m, 2H), 2.56-2.61 (m, 2H), 2.19 (s, 3H), 0.65 (s, 3H).

Synthesis of compound 9. To a solution of compound 8 (1.2 g, 3.8 mmol) in dry methanol (250 mL) was added Na (262 mg, 11.4 mmol). After heating at reflux for 16 h, the solvent was removed in vacuo and the residue was dissolved in dichloromethane (100 mL) then washed with H$_2$O (3×50 mL) and brine (100 mL), dried over MgSO$_4$, filtered, and concentrated. The residue was purified by silica gel chromatography (pertroleum ether/ethyl acetate=10:1 to 5:1) to afford compound 9a (300 mg, 25%), 9b (100 mg, 8%) and 9c (20 mg, 2%) as a white solid. Compound 9a: $^1$H NMR (400 MHz, CDCl3), δ (ppm), 3.38-3.43 (m, 5H), 2.52-2.56 (m, 1H), 2.16 (s, 3H), 0.60 (s, 3H). Compound 9b: $^1$H NMR (400 MHz, CDCl3), δ (ppm), 3.39 (s, 3H), 3.20 (s, 2H), 2.48-2.54 (m, 1H), 2.70 (s, 3H), 0.61 (s, 3H). Compound 9c: $^1$H NMR (400 MHz, CDCl3), δ (ppm), 3.39 (s, 3H), 3.18 (s, 2H), 2.81-2.83 (d, 1H), 2.65 (s, 3H), 0.61 (s, 3H).

Synthesis of compound 10a. To a solution of compound 9a (50 mg, 0.14 mmol) in MeOH (5 mL) was added 2 drops of HBr (48%) followed by bromine (6 drops). After stirring at room temperature for 1 h, the reaction mixture was poured into ice-water then extracted with ethyl acetate (15 mL×3). The combined organic layers were washed with brine (50 mL), dried over MgSO$_4$, filtered, and concentrated to give compound 10a (46 mg, 0.11 mmol). The crude product was used in the next step without further purification.

Synthesis of compound 11a. To a solution of compound 10a (46 mg, 0.11 mmol) in acetone (10 mL) was treated with CF$_3$COOH (0.5 mL) and Et$_3$N (0.7 mL). After heating at refluxed for 30 min, CF$_3$COONa (300 mg, 2.2 mmol) was added in parts over a period of 10 hr. The reaction mixture was allowed to cool to room temperature and the solvent was removed in vacuo. The residue was extracted with ethyl acetate (10 mL×3). The combined organic layers were washed with brine (30 mL), dried over MgSO$_4$, filtered, and concentrated. The residue was purified by chromatography on silica gel (petroleum ether/ethyl acetate=10:1 to 3:1) to afford compound 11a (10 mg, 25%). Compound 11a: $^1$H NMR (400 MHz, CDCl3), δ (ppm), 4.17-4.98 (m, 2H), 3.39-3.40 (m, 5H), 2.44-2.52 (m, 1H), 2.18-2.24 (m, 1H), 0.63 (s, 3H).

Synthesis of compound 10b. To a solution of compound 9b (50 mg, 0.14 mmol) in MeOH (5 mL) was added 2 drops of HBr (48%) followed by bromine (6 drops). After stirring at room temperature for 1 h, the reaction mixture was poured into ice-water then extracted with ethyl acetate (15 mL×3). The combined organic layers were washed with brine (50 mL), dried over MgSO$_4$, filtered, and concentrated to give compound 10b (46 mg, 0.11 mmol). The crude product was used in the next step without further purification.

Synthesis of compound 11b. To a solution of compound 10b (46 mg, 0.11 mmol) in acetone (10 mL) was treated with CF$_3$COOH (0.5 mL) and Et$_3$N (0.7 mL). After heating at refluxed for 30 min, CF$_3$COONa (300 mg, 2.2 mmol) was added in parts over a period of 10 hr. The reaction mixture was allowed to cool to room temperature and the solvent was removed in vacuo. The residue was extracted with ethyl acetate (10 mL×3). The combined organic layers were washed with brine (30 mL), dried over MgSO$_4$, filtered, and concentrated. The residue was purified by chromatography on silica gel (petroleum ether/ethyl acetate=10:1 to 3:1) to afford compound 11b (10 mg, 25%). Compound 11b: $^1$H NMR (400 MHz, CDCl3), δ (ppm), 4.16-4.19 (m, 2H), 3.39 (s, 3H), 3.32 (s, 1H), 3.20 (s, 2H), 2.23-2.45 (m, 1H), 2.00-2.12 (m, 2H), 0.64 (s, 3H).

Example 3. Synthesis of 6-difluoro Analogs

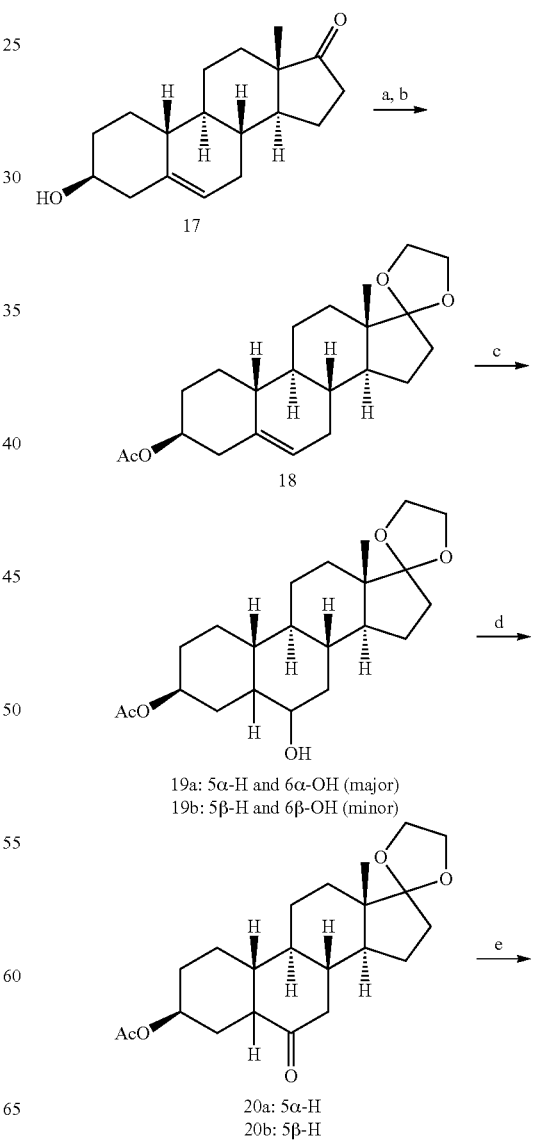

-continued

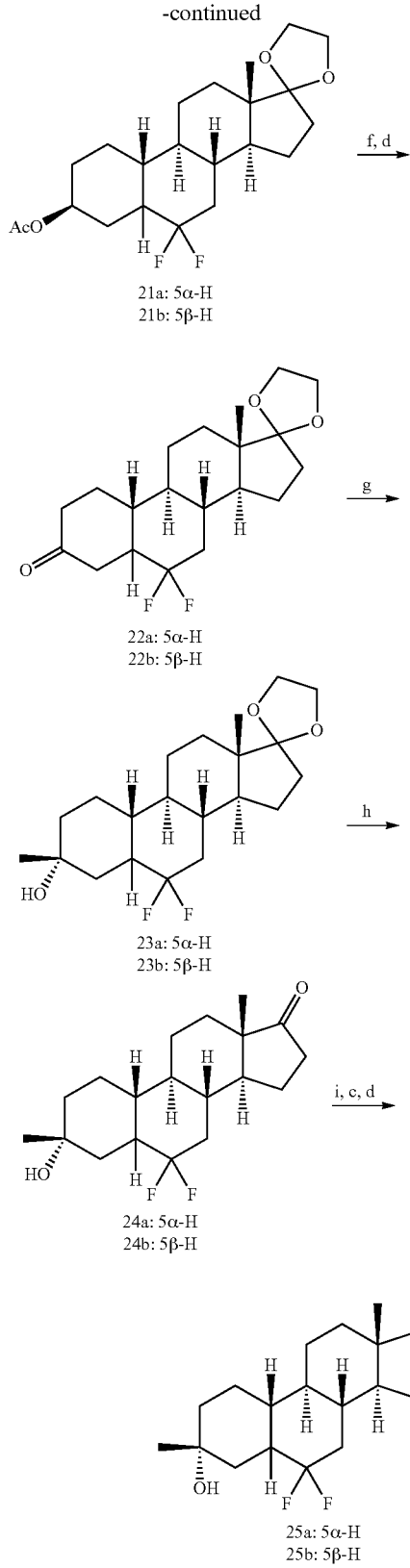

21a: 5α-H
21b: 5β-H

22a: 5α-H
22b: 5β-H

23a: 5α-H
23b: 5β-H

24a: 5α-H
24b: 5β-H

25a: 5α-H
25b: 5β-H (a) Ethane-1,2-diol, cat. TsOH, toluene, reflux overnight; (b) Ac₂O, pyridine, rt overnight; (c) BH₃, THF, NaOH/H₂O₂, 0° C. then rt; (d) Dess-Martin periodinane, CH₂Cl₂, rt overnight; (e) DAST(neat), 40° C., 4 days; (f) potassium carbonate, MeOH, rt overnight; (g) MeMgBr, THF, 0° C.; (h) 3M HCl, acetone; (i)(ethyl)-triphenylphosphonium bromide, t-BuOK, THF, 65° C.;

Example 4. Synthesis of 5,6-alkenyl-6-monofluoro Analogs

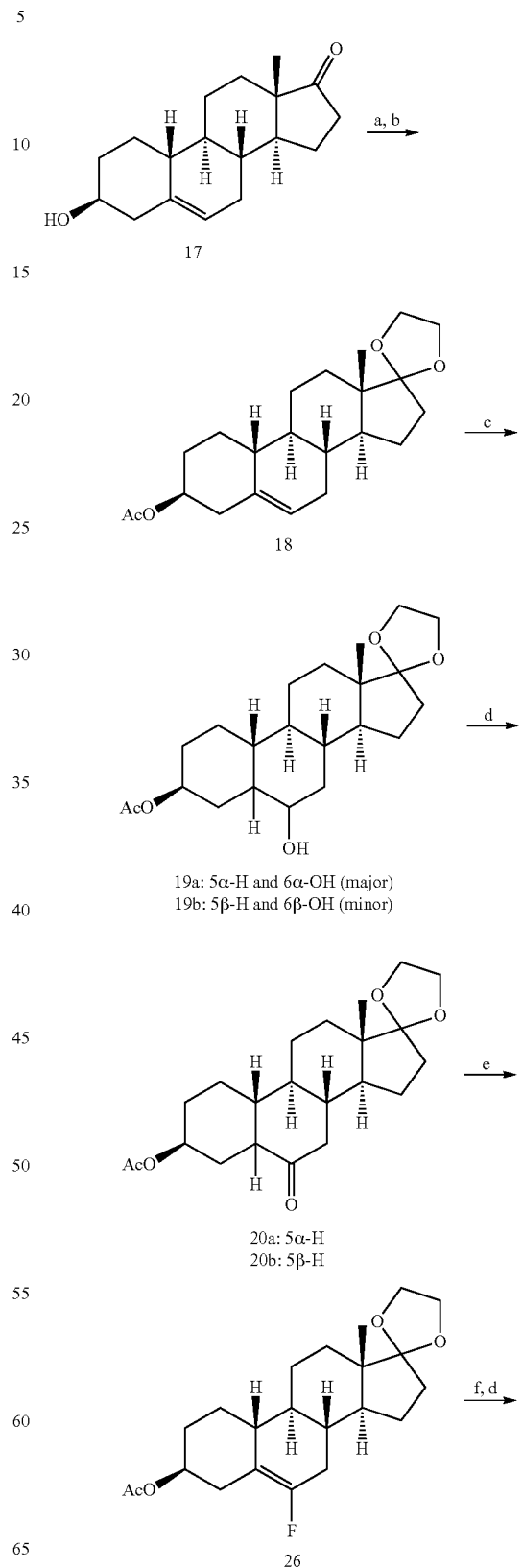

17

18

19a: 5α-H and 6α-OH (major)
19b: 5β-H and 6β-OH (minor)

20a: 5α-H
20b: 5β-H

26

187
-continued
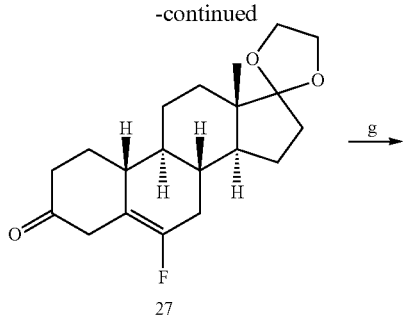
27
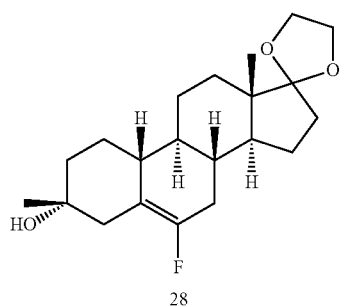
28
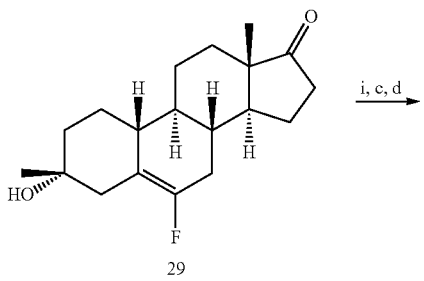
29
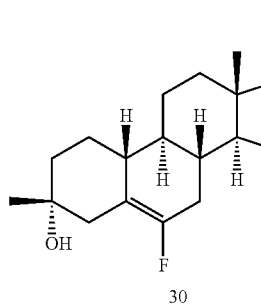
30
(a) Ethane-1,2-diol, cat.TsOH, toluene, reflux overnight; (b) Ac₂O, pyridine, rt overnight; (c) BH₃, THF, NaOH/H₂O₂, 0° C. then rt; (d) Dess-Martin periodinane, CH₂Cl₂, rt overnight; (e) DAST(neat); (f) potassium carbonate, MeOH, rt overnight; (g) MeMgBr, THF, 0° C.; (h) 3M HCl, acetone; (i) (ethyl)-triphenylphosphonium bromide, t-BuOK, THF, 65° C.
Example 5. Synthesis of 6β-Me Analogs
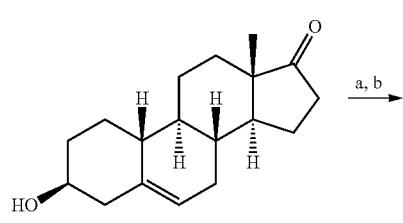
17
188
-continued
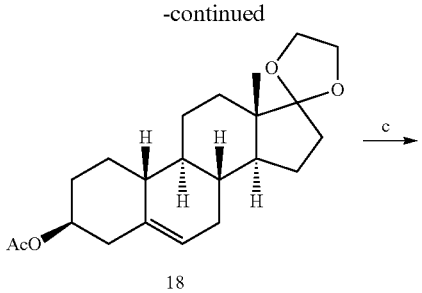
18
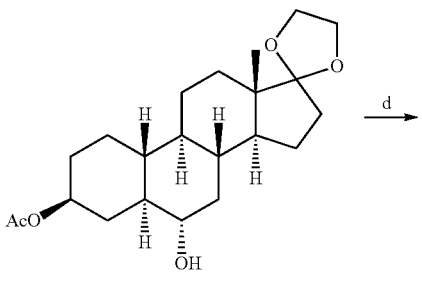
19a
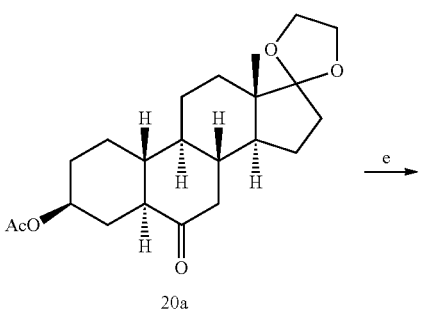
20a
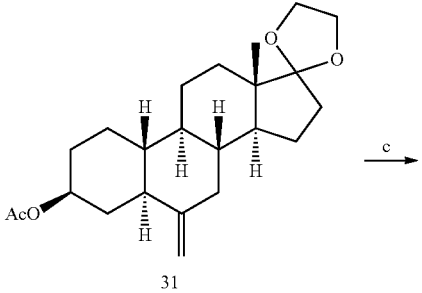
31
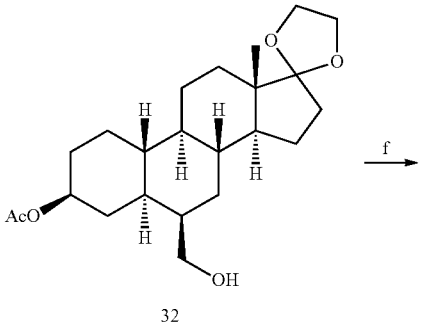
32

189
-continued

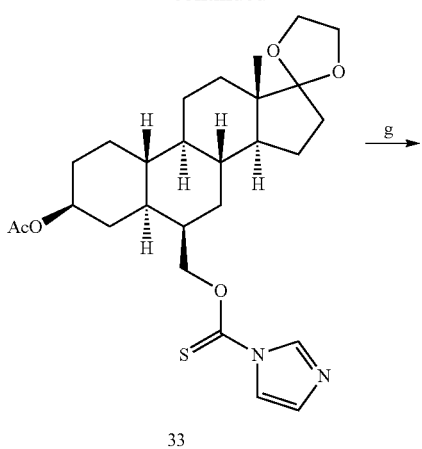

33

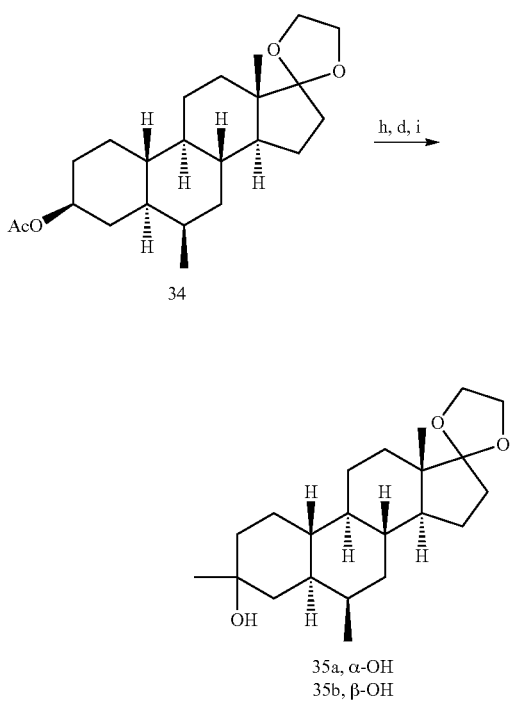

34

35a, α-OH
35b, β-OH (a) Ethane-1,2-diol, cat.TsOH, toluene, reflux overnight; (b) Ac₂O, pyridine, rt overnight; (c) BH₃, THF, NaOH/H₂O₂, 0° C. then rt; (d) Dess-Martin periodinane, CH₂Cl₂, rt overnight; (e) methyltriphenylphosphonium bromide, potassium tert-butoxide, THF, room temperature; (f) TCDI, DMAP, CH2Cl2, 40° C.; (g) Ph3SnH, AIBN, toluene, 110° C.; (h) potassium carbonate, MeOH, rt overnight; (i) MeMgBr, THF, 0° C.

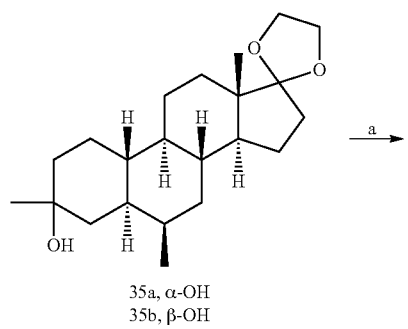

35a, α-OH
35b, β-OH

190
-continued

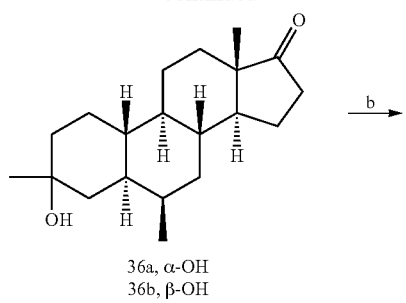

36a, α-OH
36b, β-OH

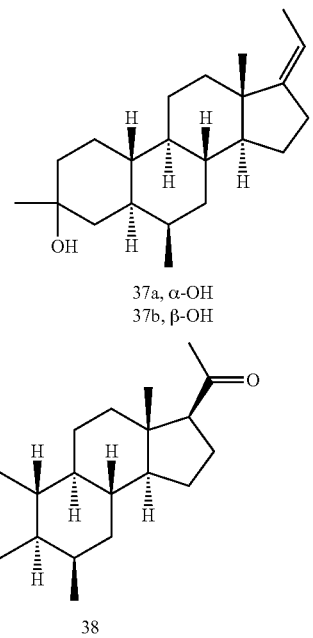

37a, α-OH
37b, β-OH

38

(a) 3M HCl, acetone; (b)(ethyl)-triphenylphosphonium bromide, t-BuOK, THF, 65° C.; (c) BH₃, THF, NaOH/H₂O₂, 0° C. then rt; (d) Dess-Martin periodinane, CH₂Cl₂, rt overnight Example 6

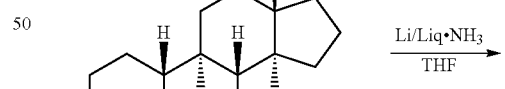

1

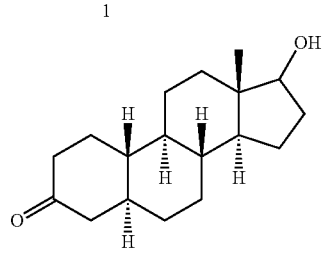

39

-continued
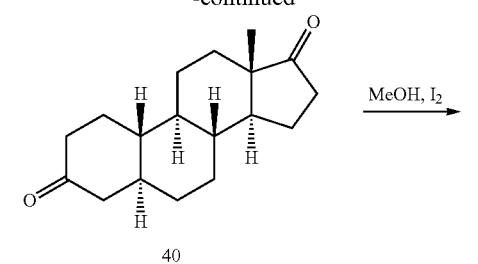
40
MeOH, I₂ →
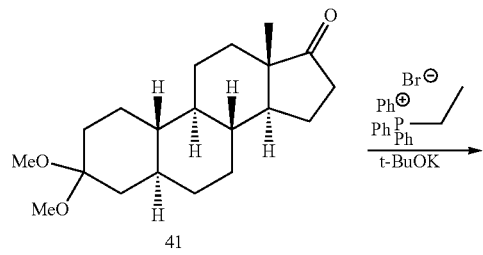
41
$\xrightarrow{\substack{Br^{\ominus} \\ Ph^{\oplus} \\ Ph\underset{Ph}{P} \\ \text{t-BuOK}}}$
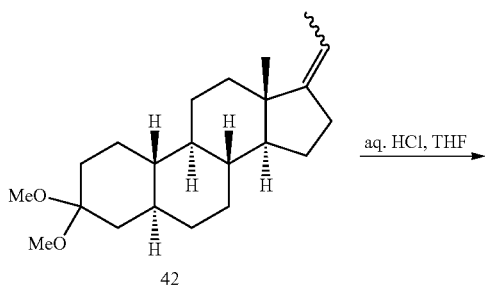
42
aq. HCl, THF →
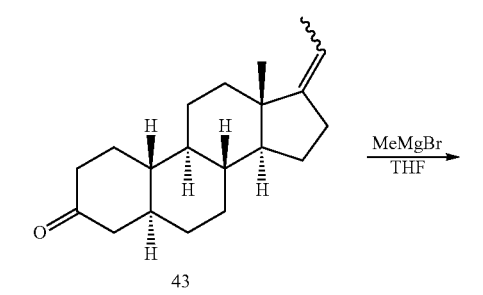
43
$\xrightarrow{\substack{MeMgBr \\ THF}}$
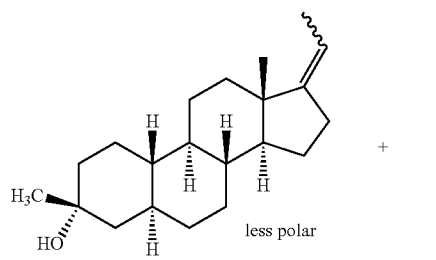
44a
3:1
less polar
+
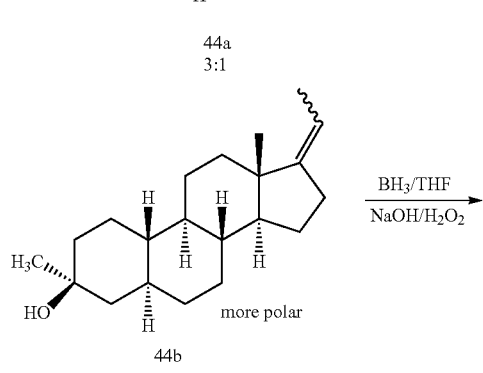
44b
more polar
$\xrightarrow{\substack{BH_3/THF \\ NaOH/H_2O_2}}$
-continued
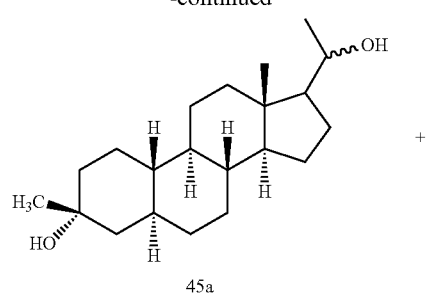
45a
+
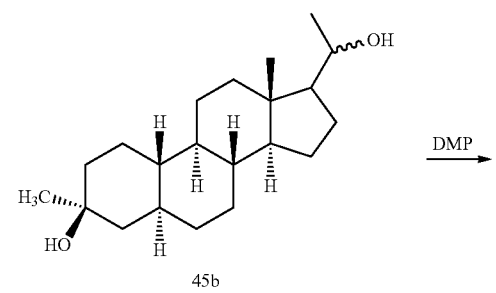
45b
$\xrightarrow{DMP}$
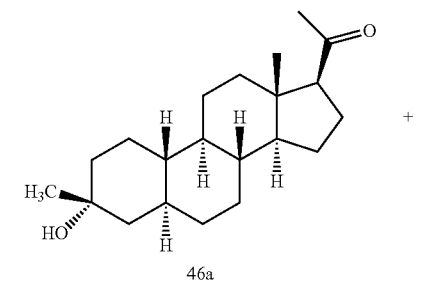
46a
+
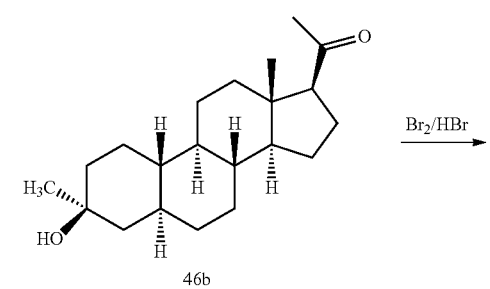
46b
$\xrightarrow{Br_2/HBr}$
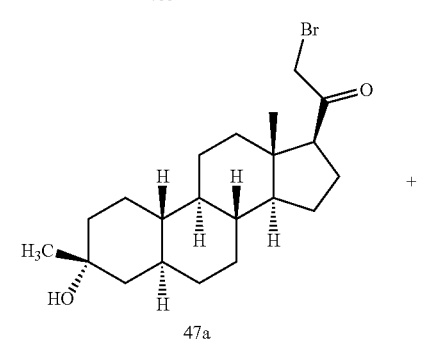
47a
+

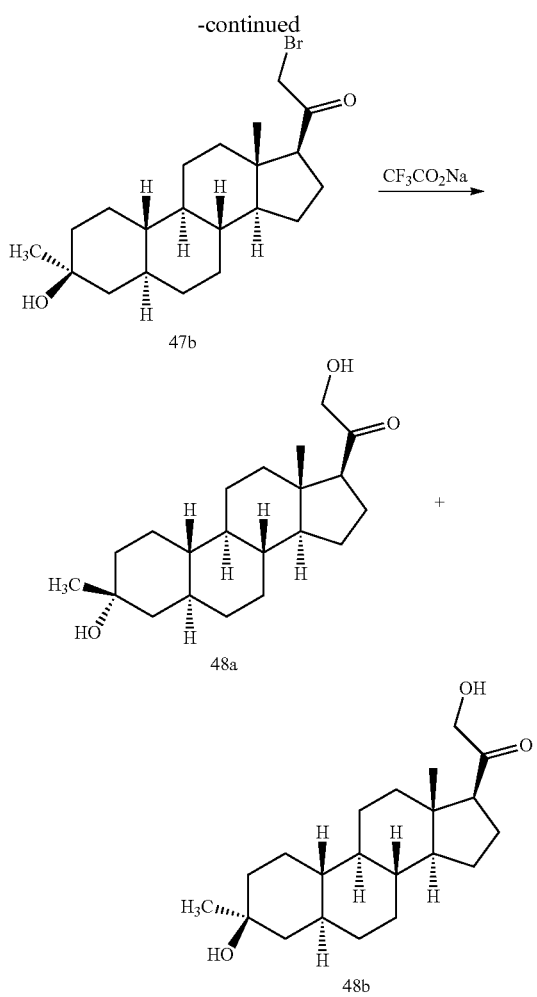

Synthesis of compounds 39 and 40. Small pieces of lithium (7.63 g, 1.1 mol) were added to 2.7 L of condensed ammonia in a three neck flask at −70° C. As soon as all lithium was dissolved, the blue solution was warmed to −50° C. A solution of 19-norandrost-4-ene-3,17-dione 1 (1, 30 g, 110 mmol) and tert-BuOH (8.14 g, 110 mmol) in 800 ml of anhydrous tetrahydrofuran was added dropwise and stirred for 90 min until the reaction mixture turned light yellow. Ammonium chloride (70 g) was added and excess ammonia was left to evaporate. The residue was extracted with 0.5N HCl (500 mL) and dichloromethane (500 mL×2). The combined organic layers were washed with saturated NaHCO$_3$ solution, dried over Na$_2$SO$_4$, filtered and concentrated to give a mixture of 39 and 40 (21 g, 70%) which was directly used in the next step without further purification. A solution of 39 and 40 (21 g, 76 mmol) in 50 mL of anhydrous dichloromethane was added to a suspension of pyridinium chlorochromate (PCC) (32.8 g, 152 mmol) in 450 mL of dichloromethane. After stirring at room temperature for 2 h, 2N NaOH solution (500 mL) was added to the dark brown reaction mixture and stirred for another 10 min. The resulting solution was extracted with dichloromethane, the combined organic layers were washed with 2N HCl, brine, dried over Na$_2$SO$_4$, filtered and concentrated. The residue was purified by chromatography on silica gel (pertroleum ether/ethyl acetate=20:1 to 10:1) to afford title compound 40 (16.8 g, 80%) as a white solid. $^1$H NMR of 39 (400 MHz, CDCl$_3$), δ (ppm), 3.65 (t, 1H, J=8 Hz, 1H), 0.77 (s, 3H). $^1$H NMR of 40 (400 MHz, CDCl$_3$), δ (ppm), 0.88 (s, 3H).

Synthesis of compound 41. To a solution of compound 40 (16.8 g, 61.3 mmol) in methanol (250 mL) was added iodine (1.54 g, 6.1 mmol). After stirring at 60° C. for 12 h, the solvent was removed in vacuo. The crude product was dissolved in dichloromethane (200 mL) and washed with saturated NaHCO$_3$ (150 mL), brine, dried over Na$_2$SO$_4$, filtered and concentrated. The residue was purified by chromatography on basic alumina (pertroleum ether/ethyl acetate=100:1) to give compound 41 (14 g, 43.8 mmol, 71%). $^1$H NMR (400 MHz, CDCl$_3$), δ (ppm), 3.18 (s, 3H), 3.12 (s, 3H), 0.85 (s, 3H).

Synthesis of compound 42. To a suspension of t-BuOK (7.36 g, 65.7 mmol) in THF (100 mL) at 0° C. was added ethyltriphenylphosphonium bromide (26 g, 70 mmol) slowly. After stirring at 60° C. for 3 h, compound 41 (7 g, 21.9 mmol) was added and the mixture was stirred at 60° C. for another 2 h. After cooling to room temperature, the reaction mixture was poured into saturated ammonium chloride and extracted with EtOAc (2×500 mL). The combined organic layers were washed with brine, dried over sodium sulfate, filtered and concentrate to afford the crude compound 42 (7.36 g, 100%). The crude product was used in the next step without further purification.

Synthesis of compound 43. A solution of crude compound 42 (7.36 g, 21.9 mmol) in THF (50 mL) was acidified to pH=3 by 1N aqueous HCl. After stirring at room temperature for 12 h, the reaction mixture was extracted with ethyl acetate (250 mL×3). The combined organic layers were washed with brine, dried over sodium sulfate, filtered and concentrated. The residue was purified by column chromatography (pertroleum ether/ethyl acetate=30:1 to 20:1) to afford compound 43 (4.8 g, 16.7 mmol, 76% for two steps). $^1$H NMR (400 MHz, CDCl$_3$), δ (ppm), 5.12-5.10 (m, 1H), 1.64-1.63 (m, 3H), 0.77 (s, 3H).

Synthesis of compound 44a and 44b. To a solution of MeMgBr (28 mmol, 1M in THF) in THF (50 mL) at 0° C. was added a solution of compound 43 (4.8 g, 16.8 mmol) in dry THF (10 mL) via syringe pump over 30 min. After stirring at 0° C. for 5 h, the reaction mixture was allowed to warm up and stirred at room temperature overnight. The reaction mixture was quenched with iced-cold water and extracted with ethyl acetate (150 mL×3). The combined organic layers were washed with brine, dried over sodium sulfate, filtered and concentrated. The white residue was purified by flash column chromatography (petroleum ether/ethyl acetate=20:1 to 10:1) to give compound 44a (2.5 g, 8.28 mmol, 49%; Rf=0.35, PE:EtOAc=10:1). $^1$H NMR (400 MHz, CDCl$_3$), δ (ppm), 5.05-5.03 (m, 1H), 1.21 (s, 3H), 0.90 (s, 3H) and compound 44b (800 mg, 2.64 mmol, 16%; Rf=0.30, PE:EtOAc=10:1). $^1$H NMR (400 MHz, CDCl$_3$), δ (ppm), 5.12-5.10 (m, 1H), 1.12 (s, 3H), 0.88 (s, 3H).

Synthesis of compound 45a. To a solution of compound 44a (2 g, 6.62 mmol) in dry THF (50 mL) was added borane-tetrahydrofuran complex (20 mL; 1.0 M solution in THF). After stirring at room temperature for 1 hour, the reaction mixture was cooled in an ice bath then quenched slowly with 10% aqueous NaOH (10 mL) followed by 30% aqueous solution of H$_2$O$_2$ (12 mL). After stirring at room temperature for one hour, the mixture was extracted with EtOAc (3×100 mL). The combined organic layers were washed with 10% aqueous Na$_2$S$_2$O$_3$ (100 mL), brine (100 mL), dried over MgSO$_4$, filtered and concentrated to afford crude compound 45a (2 g, 100%). The crude product was used in the next step without further purification.

Synthesis of compound 46a. To a solution of crude compound 45a (2 g, 6.62 mmol) in 60 mL of wet dichloromethane (dichloromethane had been shaken with several milliliters of H₂O then separated from the water layer) was added Dess-Martin periodinate (5.5 g, 13 mmol). After stirring at room temperature for 24 h, the reaction mixture was extracted with dichloromethane (3×100 mL). The combined organic layers were washed with 10% aqueous Na₂S₂O₃ (100 mL), brine (100 mL), dried over MgSO₄, filtered and concentrated. The residue was purified by chromatography on silica gel (pertroleum ether/ethyl acetate=10:1 to 5:1) to afford compound 46a (1 g, 3.14 mmol, 47% for two steps) as a white solid. ¹H NMR (400 MHz, CDCl₃), δ (ppm), 2.56-2.51 (m, 1H), 2.11 (s, 3H), 1.20 (s, 3H), 0.62 (s, 3H).

Synthesis of compound 47a. To a solution of compound 46a (600 mg, 1.89 mmol) in MeOH (20 mL) was added 5 drops of HBr (48%) followed by bromine (302 mg, 1.89 mmol). After stirring at room temperature for 1 h, the reaction mixture was poured into ice-water then extracted with ethyl acetate (100 mL×3). The combined organic layers were washed with brine (200 mL), dried over MgSO₄, filtered and concentrated to give crude compound 47a (600 mg). The crude product was used in the next step without further purification.

Synthesis of compound 48a. A solution of compound 47a (600 mg, 1.5 mmol) in acetone 10 mL was treated with CF₃COOH (6.8 mL) and Et₃N (9.5 mL). After refluxed for 30 min, CF₃COONa salt (4.49 g, 33 mmol) was added in parts over a period of 10 hr. The reaction mixture was allowed to cool to room temperature and the solvent was removed in vaccuo. The residue was extracted with ethyl acetate, dried over MgSO₄, filtered and concentrated. The mixture was purified by chromatography on silica gel (pertroleum ether/ethyl acetate=10:1 to 3:1) to afford 48a (300 mg, yield: 50% for two steps). ¹H NMR (400 MHz, CDCl₃), δ (ppm), 4.23-4.13 (m, 2H), 2.48-2.44 (m, 1H), 2.24-2.17 (m, 1H), 1.20 (s, 3H), 0.64 (s, 3H).

Synthesis of compound 45b. To a solution of compound 44b (500 mg, 1.66 mmol) in dry THF (13 mL) was added borane-tetrahydrofuran complex (5 mL; 1.0 M solution in THF). After stirring at room temperature for 1 hour, the reaction mixture was cooled in an ice bath then quenched slowly with 10% aqueous NaOH (2.5 mL) followed 30% aqueous solution of H₂O₂ (3 mL). The mixture was allowed to warm to room temperature and stirred for 1 hour then extracted with EtOAc (3×25 mL). The combined organic layers were washed with 10% aqueous Na₂S₂O₃ (25 mL), brine (25 mL), dried over MgSO₄, filtered and concentrated to afford crude compound 45b (500 mg). The crude product was used in the next step without further purification.

Synthesis of compound 46b. To a solution of crude compound 45b (500 mg, 1.66 mmol) in 15 mL wet dichloromethane (dichloromethane had been shaken with several milliliters of H₂O then separated from the water layer) was added Dess-Martin periodinate (1.38 g, 3.3 mmol). After stirring at room temperature for 24 h, the reaction mixture was extracted with dichloromethane (3×25 mL). The combined organic layers were washed with 10% aqueous Na₂S₂O₃ (25 mL), brine (25 mL), dried over MgSO₄, filtered and concentrated. The residue was purified by chromatography on silica gel (pertroleum ether/ethyl acetate=10:1 to 5:1) to afford title compound 46b (250 mg, 0.79 mmol, 47% for two steps) as a white solid. ¹H NMR (400 MHz, CDCl₃), δ (ppm), 2.54-2.50 (m, 1H), 2.11 (s, 3H), 1.23 (s, 3H), 0.62 (s, 3H).

Synthesis of compound 47b. To a solution of compound 46b (250 mg, 0.79 mmol) in MeOH (5 mL) was added 2 drops of HBr (48%) followed by bromine (126 mg, 0.79 mmol). After stirring at room temperature for 1 h, the reaction mixture was poured into ice-water then extracted with ethyl acetate (10 mL×3). The combined organic layers were washed with brine (20 mL), dried over MgSO₄, filtered and concentrated to give crude compound 47b (250 mg). The crude product was used in the next step without further purification.

Synthesis of compound 48b. A solution of compound 47b (60 mg, 0.15 mmol) in acetone (10 mL) was treated with CF₃COOH (0.7 mL) and Et₃N (0.9 mL). After refluxed for 30 min, CF₃COONa salt (449 mg, 3.3 mmol) was added in parts over a period of 10 hr. The reaction mixture was allowed to cool to room temperature and the solvent was removed in vaccuo. The residue was extracted with ethyl acetate, dried over MgSO₄, filtered and concentrated. The residue was purified by chromatography on silica gel (pertroleum ether/ethyl acetate=10:1 to 3:1) to afford 48b (20 mg, yield: 33% for two steps). ¹H NMR (400 MHz, CDCl₃), δ (ppm), 4.24-4.12 (m, 2H), 2.48-2.43 (m, 1H), 2.24-2.16 (m, 1H), 1.23 (s, 3H), 0.64 (s, 3H).

Example 7

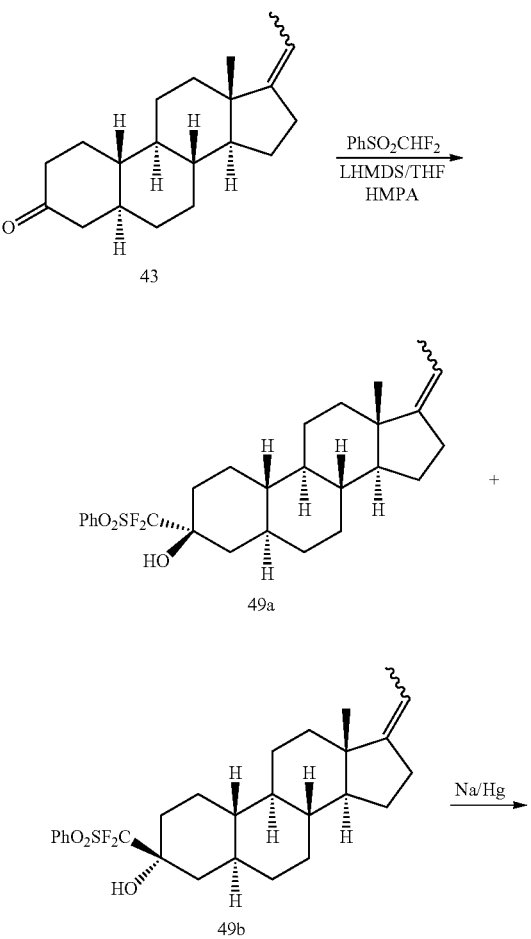

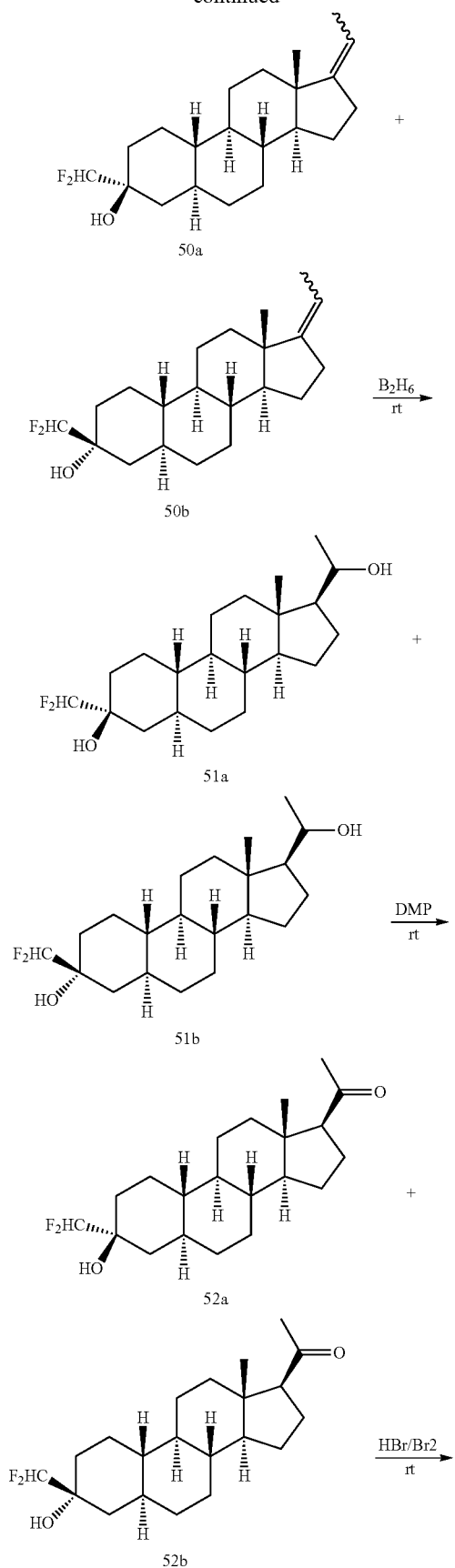
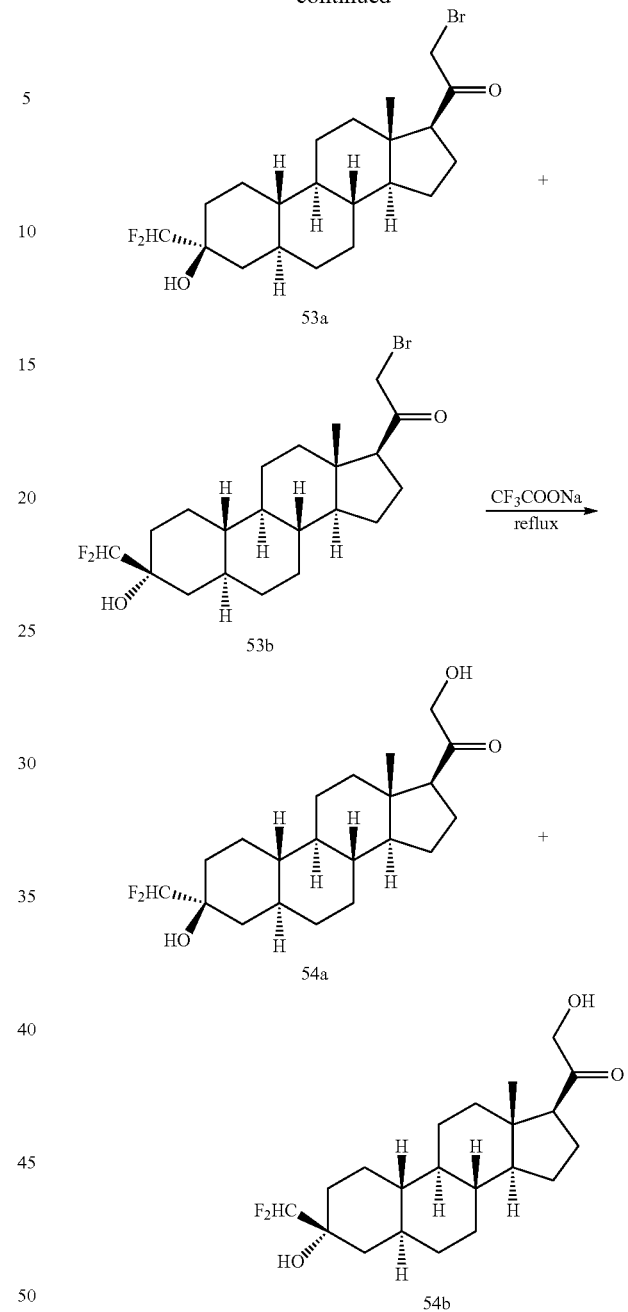

Synthesis of compound 49a and 49b. To a solution of compound 43 (800 mg, 2.79 mmol) and PhSO$_2$CF$_2$H (540 mg, 2.79 mmol) in THF (25 mL) and HMPA (0.5 mL) at −78° C. under N$_2$ was added LHMDS (4 mL, 1M in THF) dropwise. After stirring at −78° C. for 2 h, the reaction mixture was quenched with saturated aqueous NH$_4$Cl solution (10 mL) and allowed to warm to room temperature then extracted with Et$_2$O (20 mL×3). The combined organic layers were washed with brine, dried over sodium sulfate, filtered and concentrate. The residue was purified by silica gel column chromatography (pertroleum ether/ethyl acetate=10/1) to give the mixture of compound 49a and 49b (650 mg). The mixture was further purified by chiral-HPLC to afford compound 49a (250 mg, t=3.29 min) and 49b (230 mg, t=3.89 min). Chiral-HPLC conditions: Elutant=MeOH (0.1% DEA); Column=AS-H (4.6*250 mm, 5 um).

Synthesis of compound 50a. To a solution of compound 49a (250 mg, 0.524 mmol) and anhydrous $Na_2HPO_4$ (150 mg) in anhydrous methanol (5 mL) at −20° C. under $N_2$ was added Na/Hg amalgam (800 mg). After stirring at −20° C. to 0° C. for 1 h, the methanol solution was decanted out and the solid residue was washed with $Et_2O$ (5×3 mL). The combined organic phase was removed under vacuum, and 20 ml brine was added, followed by extracting with $Et_2O$. The combined ether phase was dried with $MgSO_4$, filtered and concentrated. The crude product was purified by silica gel chromatography (PE/EA=10/1) to give compound 49a (130 mg, 73%). $^1$H NMR (400 MHz, $CDCl_3$), δ (ppm), 5.60-5.30 (t, 1H, J=63.6 Hz), 5.14-5.09 (m, 1H), 0.88 (m, 3H).

Synthesis of compound 50b. To a solution of compound 49b (230 mg, 0.489 mmol) and anhydrous $Na_2HPO_4$ (150 mg) in anhydrous methanol (5 mL) at −20° C. under $N_2$ was added Na/Hg amalgam (700 mg). After stirring at −20° C. to 0° C. for 1 h, the methanol solution was decanted out and the solid residue was washed with $Et_2O$ (5×3 mL). The combined organic phase was removed under vacuum, and 20 ml brine was added, followed by extracting with $Et_2O$. The combined ether phase was dried with $MgSO_4$, filtered and concentrated. The crude product was purified by silica gel chromatography (PE/EA=10/1) to give compound 50b (120 mg, 73%). $^1$H NMR (400 MHz, $CD_3COCD_3$), δ (ppm), 6.02-5.88 (t, 1H, J=59.6 Hz), 5.13-5.08 (m, 1H), 0.92 (s, 3H).

Synthesis of compound 51a. To a solution of compound 50a (130 mg, 0.384 mmol) in dry THF (5 mL) was added borane-tetrahydrofuran complex (1.3 mL; 1.0 M solution in THF). After stirring at room temperature for 1 hour, the reaction mixture was cooled in an ice bath then quenched slowly with 10% aqueous NaOH (1 mL) followed by 30% aqueous solution of $H_2O_2$ (1.2 mL). The mixture was allowed to stir at room temperature for 1 hour then extracted with EtOAc (3×10 mL). The combined organic layers were washed with 10% aqueous $Na_2S_2O_3$ (10 mL), brine (10 mL), dried over $MgSO_4$, filtered and concentrated to afford compound 51a (200 mg, crude). The crude product was used in the next step without further purification.

Synthesis of compound 51b. To a solution of compound 50b (120 mg, 0.355 mmol) in dry THF (5 mL) was added borane-tetrahydrofuran complex (1.20 mL; 1.0 M solution in THF). After stirring at room temperature for 1 hour, the reaction mixture was cooled in an ice bath then quenched slowly with 10% aqueous NaOH (1 mL) followed by 30% aqueous solution of $H_2O_2$ (1.2 mL). The mixture was allowed to stir at room temperature for 1 hour then extracted with EtOAc (3×10 mL). The combined organic layers were washed with 10% aqueous $Na_2S_2O_3$ (10 mL), brine (10 mL), dried over $MgSO_4$, filtered and concentrated to afford compound 51b (180 mg, crude). The crude product was used in the next step without further purification.

Synthesis of compound 52a. To a solution of compound 51a (200 mg, crude) in 10 mL of wet dichloromethane (dichloromethane had been shaken with several milliliters of $H_2O$ then separated from the water layer) was added Dess-Martin periodinate (400 mg, 0.94 mmol). After stirring at room temperature for 24 h, the reaction mixture was extracted with dichloromethane (3×10 mL). The combined organic layers were washed with 10% aqueous $Na_2S_2O_3$ (10 mL), brine (10 mL), dried over $MgSO_4$, filtered and concentrated. The residue was purified by chromatography on silica gel (pertroleum ether/ethyl acetate=1:5) to afford compound 52a (75 mg, 55.1% for two steps) as a white solid. $^1$H NMR (400 MHz, CDCl3), δ (ppm), 5.58-5.32 (t, 1H, J=52.0 Hz), 2.53-2.51 (m, 1H), 2.14 (s, 3H), 0.62 (s, 3H).

Synthesis of compound 52b. To a solution of compound 51b (180 mg, crude) in 10 mL of wet dichloromethane (dichloromethane had been shaken with several milliliters of $H_2O$ then separated from the water layer) was added Dess-Martin periodinate (380 mg, 0.896 mmol). After stirring at room temperature for 24 h, the reaction mixture was extracted with dichloromethane (3×10 mL). The combined organic layers were washed with 10% aqueous $Na_2S_2O_3$ (10 mL), brine (10 mL), dried over $MgSO_4$, filtered and concentrated. The residue was purified by chromatography on silica gel (pertroleum ether/ethyl acetate=1:5) to afford compound 52b (70 mg, 55.7% for two steps) as a white solid. $^1$H NMR (400 MHz, CDCl3), δ (ppm), 5.90-5.61 (t, 1H, J=60 Hz), 2.48-2.43 (m, 1H), 2.10 (s, 3H), 0.55 (s, 3H).

Synthesis of compound 53a. To a solution of compound 52a (40 mg, 0.113 mmol) in MeOH (5 mL) was added 2 drops of HBr (48%) followed by bromine (100 mg, 0.62 mmol). After stirring at room temperature for 1 h, the reaction mixture was poured into ice-water then extracted with ethyl acetate (15 mL×3). The combined organic layers were washed with brine (20 mL), dried over $MgSO_4$, filtered and concentrated to give compound 53a (84 mg, crude). The crude product was used in the next step without further purification.

Synthesis of compound 53b. To a solution of compound 52b (50 mg, 0.14 mmol) in MeOH (5 mL) was added 2 drops of HBr (48%) followed by bromine (100 mg, 0.62 mmol). After stirring at room temperature for 1 h, the reaction mixture was poured into ice-water then extracted with ethyl acetate (15 mL×3). The combined organic layers were washed with brine (20 mL), dried over $MgSO_4$, filtered and concentrated to give compound 53b (72 mg, crude). The crude product was used in the next step without further purification.

Synthesis of compound 54a. To a solution of compound 53a (84 mg, crude) in acetone (6 mL) was treated with $CF_3COOH$ (0.3 mL) and $Et_3N$ (0.5 mL). After heating at reflux for 30 min, $CF_3COONa$ salt (432 mg, 3.12 mmol) was added and the mixture was refluxed for overnight. The reaction was allowed to cool to room temperature and the solvent was removed in vacuo. The residue was extracted with ethyl acetate (10 mL×3). The combined organic layers were washed with brine (15 mL), dried over $MgSO_4$, filtered and concentrated. The residue was purified by chromatography on silica gel (pertroleum ether/ethyl acetate=3:1) to afford compound 54a (15 mg, 36% for two steps). $^1$H NMR (500 MHz, CDCl3), δ (ppm), 5.56-5.33 (t, 1H, J=56.5 Hz), 4.22-4.13 (m, 2H), 3.25-3.23 (m, 1H), 0.64 (s, 3H).

Synthesis of compound 54b. To a solution of compound 53b (72 mg, crude) in acetone (5 mL) was treated with $CF_3COOH$ (0.3 mL) and $Et_3N$ (0.45 mL). After heating at reflux for 30 min, $CF_3COONa$ salt (270 mg, 1.95 mmol) was added and the mixture was refluxed for overnight. The reaction was allowed to cool to room temperature and the solvent was removed in vacuo. The residue was extracted with ethyl acetate (10 mL×3). The combined organic layers were washed with brine (10 mL), dried over $MgSO_4$, filtered and concentrated. The residue was purified by chromatography on silica gel (pertroleum ether/ethyl acetate=3:1) to afford compound 54b (10 mg, 19.2% for two steps). $^1$H NMR (400 MHz, CDCl3), δ (ppm), 5.96-5.68 (t, 1H, J=56 Hz), 4.24-4.10 (m, 2H), 3.2 (s, 1H), 0.64 (s, 3H).

Example 8
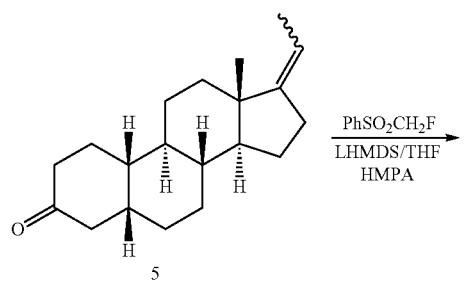
5
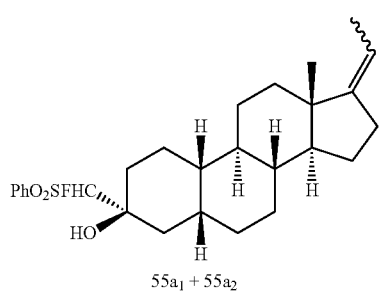
$55a_1 + 55a_2$
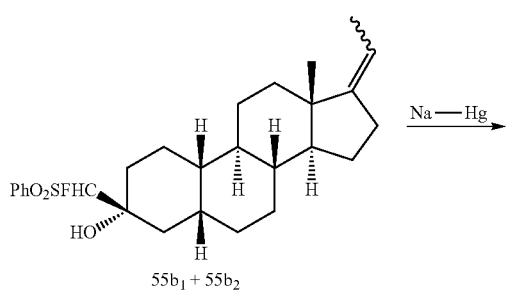
$55b_1 + 55b_2$
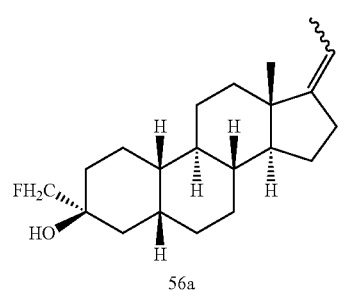
56a
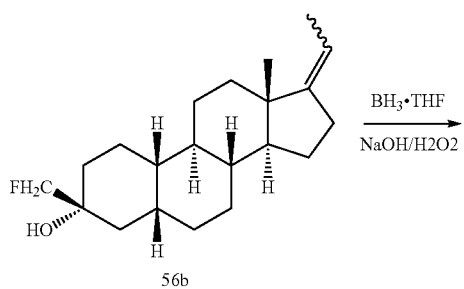
56b
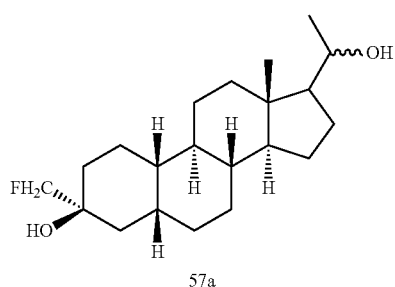
57a
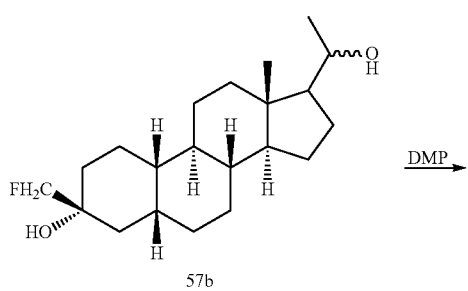
57b
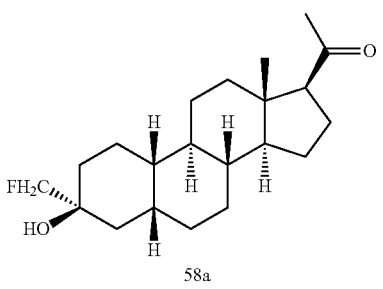
58a
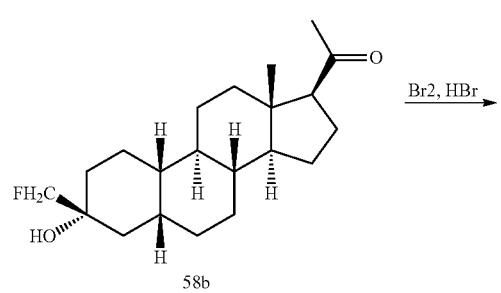
58b
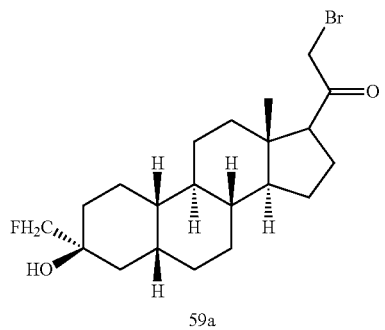
59a

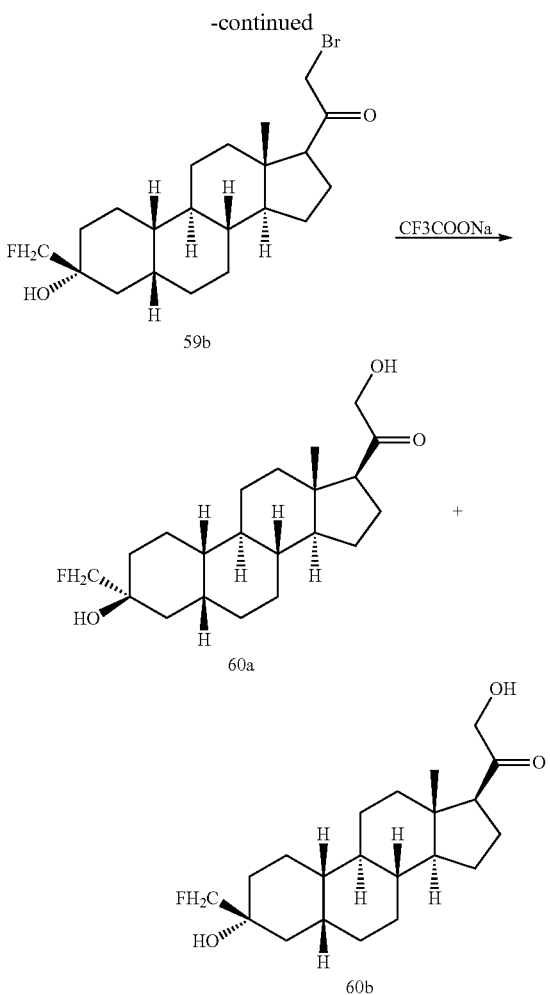

Synthesis of compound 55a and 55b. To a solution of compound 5 (1.2 g, 4.2 mmol) and PhSO$_2$CF$_2$H (730 mg, 4.2 mmol) in THF (25 mL) and HMPA (0.5 mL) at −78° C. under N$_2$ was added LHMDS (5.5 mL, 1M in THF) dropwise. After stirring at −78° C. for 2 h, the reaction mixture was quenched with saturated aqueous NH$_4$Cl solution (10 mL). The mixture was allowed to warm to room temperature and extracted with Et$_2$O (20 mL×3). The combined organic layers were washed with brine, dried over sodium sulfate, filtered and concentrated. The residue was purified by silica gel column chromatography (pertroleum ether/ethyl acetate=10/1) to give the mixture of compound 55a and 55b (1.4 g). The mixture was further purified by chiral-HPLC to afford compound 55a1 (220 mg, t=3.62 min). $^1$H NMR (500 MHz, CDCl3), δ (ppm), 7.99-7.97 (d, 2H, J=7.6 Hz), 7.76-7.72 (m, 1H), 7.62-7.60 (m, 2H), 5.17-5.13 (m, 1H), 4.88-4.78 (d, 1H, J=46 Hz), 0.88 (s, 3H); 55a2 (200 mg, t=3.94 min) $^1$H NMR (500 MHz, CDCl3), δ (ppm), 7.97-7.95 (d, 2H, J=7.6 Hz), 7.77-7.76 (m, 1H), 7.66-7.62 (m, 2H), 5.11-5.10 (m, 1H), 4.88-4.78 (d, 1H, J=46 Hz), 0.88 (s, 3H); 55b1 (235 mg, t=4.95 min). $^1$H NMR (500 MHz, CDCl3), δ (ppm), 7.98-7.96 (d, 2H, J=7.5 Hz), 7.72-7.76 (m, 1H), 7.62-7.59 (m, 2H), 5.37-5.27 (d, 1H, J=46 Hz), 5.07-5.05 (m, 1H), 0.88 (s, 3H); 55b2 (220 mg, t=6.92 min). $^1$H NMR (500 MHz, CDCl3), δ (ppm), 7.98-7.96 (d, 2H, J=7.5 Hz), 7.76-7.72 (m, 1H), 7.62-7.59 (m, 2H), 5.37-5.27 (d, 1H, J=46 Hz), 5.07-4.98 (m, 1H), 0.88 (s, 3H). Chiral-HPLC conditions: Elutant=MeOH (0.1% DEA); Column=IC (4.6*250 mm, 5 um).

Synthesis of compound 56a. To a solution of compound 55a1 (200 mg, 0.434 mmol) and anhydrous Na$_2$HPO$_4$ (100 mg) in anhydrous methanol (15 mL) at −20° C. under N$_2$ was added Na/Hg amalgam (400 mg). After stirring at −20° C. to 0° C. for 1 h, the methanol solution was decanted out and the solid residue was washed with Et$_2$O (5×3 mL). The combined organic phase was removed under vacuum, and 20 mL brine was added, followed by extracting with Et$_2$O. The combined ether phase was dried with MgSO$_4$, filtered and concentrated. The crude product was purified by silica gel chromatography (PE/EA=10/1) to give compound 56a (90 mg, 65%). $^1$H NMR (500 MHz, CDCl3), δ (ppm), 5.12-5.11 (m, 1H), 4.2-4.15 (d, 2H, J=48 Hz), 0.62 (s, 3H).

Synthesis of compound 56b. To a solution of compound 55b2 (200 mg, 0.434 mmol) and anhydrous Na$_2$HPO$_4$ (100 mg) in anhydrous methanol (5 mL) at −20° C. under N$_2$ was added Na/Hg amalgam (500 mg). After stirring at −20° C. to 0° C. for 1 h, the methanol solution was decanted out and the solid residue was washed with Et$_2$O (5×3 mL). The combined organic phase was removed under vacuum, and 20 mL brine was added, followed by extracting with Et$_2$O. The combined ether phase was dried with MgSO$_4$, filtered and concentrated. The crude product was purified by silica gel chromatography (PE/EA=10/1) to give compound 56b (95 mg, 68%). $^1$H NMR (500 MHz, CDCl3), δ (ppm), 5.14-4.10 (m, 1H), 4.50-4.35 (m, 2H), 0.79 (s, 3H).

Synthesis of compound 57a. To a solution of compound 56a (90 mg, 0.281 mmol) in dry THF (5 mL) was added borane-tetrahydrofuran complex (1 mL; 1.0 M solution in THF). After stirring at room temperature for 1 hour, the reaction mixture was cooled in an ice bath then quenched slowly with 10% aqueous NaOH (1 mL) followed by 30% aqueous solution of H$_2$O$_2$ (1.2 mL). The mixture was allowed to stir at room temperature for 1 hour then extracted with EtOAc (3×10 mL). The combined organic layers were washed with 10% aqueous Na$_2$S$_2$O$_3$ (10 mL), brine (10 mL), dried over MgSO$_4$, filtered and concentrated to afford compound 57a (130 mg, crude). The crude product was used in the next step without further purification.

Synthesis of compound 57b. To a solution of compound 56b (95 mg, 0.297 mmol) in dry THF (5 mL) was added borane-tetrahydrofuran complex (1.1 mL; 1.0 M solution in THF). After stirring at room temperature for 1 hour, the reaction mixture was cooled in an ice bath then quenched slowly with 10% aqueous NaOH (1 mL) followed by 30% aqueous solution of H$_2$O$_2$ (1.2 mL). The mixture was allowed to stir at room temperature for 1 hour then extracted with EtOAc (3×10 mL). The combined organic layers were washed with 10% aqueous Na$_2$S$_2$O$_3$ (10 mL), brine (10 mL), dried over MgSO$_4$, filtered and concentrated to afford compound 57b (135 mg crude). The crude product was used in the next step without further purification.

Synthesis of compound 58a. To a solution of compound 57a (130 mg crude) in 10 mL of wet dichloromethane (dichloromethane had been shaken with several milliliters of H$_2$O then separated from the water layer) was added Dess-Martin periodinate (300 mg, 707 mmol). After stirring at room temperature for 24 h, the reaction mixture was extracted with dichloromethane (3×10 mL). The combined organic layers were washed with 10% aqueous Na$_2$S$_2$O$_3$ (10 mL), brine (10 mL), dried over MgSO$_4$, filtered and concentrated. The residue was purified by chromatography on silica gel (pertroleum ether/ethyl acetate=1:5) to afford compound 58a (60 mg, 64% for two steps) as a white solid. $^1$H NMR (500 MHz, CDCl3), δ (ppm), 4.23-4.11 (d, 2H, J=60 Hz), 2.55-2.51 (m, 1H), 2.09 (s, 3H), 0.62 (s, 3H).

Synthesis of compound 58b. To a solution of compound 57b (135 mg crude) in 10 mL of wet dichloromethane (dichloromethane had been shaken with several milliliters of H₂O then separated from the water layer) was added Dess-Martin periodinate (380 mg, 0.896 mmol). After stirring at room temperature for 24 h, the reaction mixture was extracted with dichloromethane (3×10 mL). The combined organic layers were washed with 10% aqueous Na₂S₂O₃ (10 mL), brine (10 mL), dried over MgSO₄, filtered and concentrated. The residue was purified by chromatography on silica gel (pertroleum ether/ethyl acetate=1:5) to afford compound 58b (68 mg, 69%) as a white solid. $^1$H NMR (500 MHz, CDCl3), δ (ppm), 4.50-4.34 (m, 2H), 2.56-2.52 (m, 1H), 2.15 (s, 3H), 0.61 (s, 3H).

Synthesis of compound 59a. To a solution of compound 58a (40 mg, 0.119 mmol) in MeOH (5 mL) was added 2 drops of HBr (48%) followed by bromine (100 mg, 0.62 mmol). After stirring at room temperature for 1 h, the reaction mixture was poured into ice-water then extracted with ethyl acetate (15 mL×3). The combined organic layers were washed with brine (20 mL), dried over MgSO₄, filtered and concentrated to give compound 59a (60 mg crude). The crude product was used in the next step without further purification.

Synthesis of compound 60a. To a solution of compound 59a (60 mg crude) in acetone (5 mL) was treated with CF₃COOH (0.1 mL) and Et₃N (0.17 mL). After heating at reflux for 30 min, CF₃COONa salt (180 mg, 1.3 mmol) was added and the mixture was refluxed for overnight. The reaction was allowed to cool to room temperature and the solvent was removed in vacuo. The residue was extracted with ethyl acetate (10 mL×3). The combined organic layers were washed with brine (15 mL), dried over MgSO₄, filtered and concentrated. The residue was purified by chromatography on silica gel (pertroleum ether/ethyl acetate=3:1) to afford compound 60a (15 mg, 36% for two steps). $^1$H NMR (500 MHz, CDCl3), δ (ppm), 4.21-4.11 (m, 4H), 3.39-3.36 (m, 1H), 2.84 (s, 1H), 0.65 (s, 3H).

Example 9

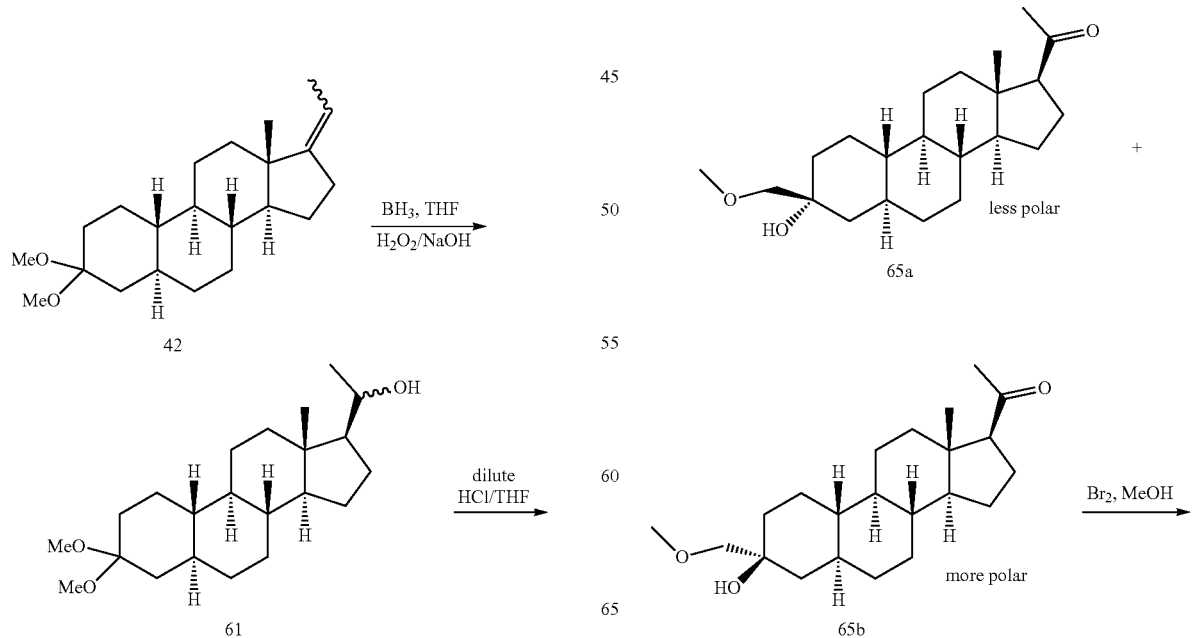

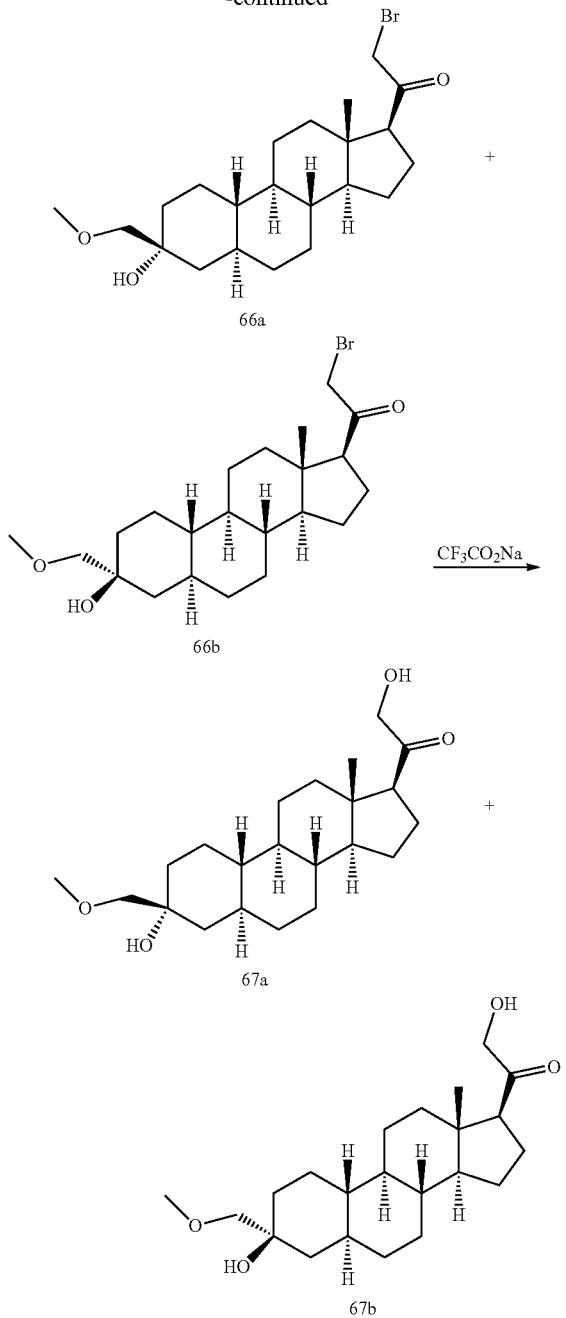

Synthesis of compound 61. To a solution of compound 42 (5 g, 15 mmol) in dry THF (20 mL) was added borane-tetrahydrofuran complex (30 mL; 1.0 M solution in THF). After stirring at room temperature for 1 hour, the reaction mixture was cooled in an ice bath then quenched slowly with 10% aqueous NaOH (56 mL) followed by 30% aqueous solution of $H_2O_2$ (67 mL). After stirring at room temperature for one hour, the mixture was extracted with EtOAc (3×100 mL). The combined organic layers were washed with 10% aqueous $Na_2S_2O_3$ (100 mL), brine (100 mL), dried over $MgSO_4$, filtered and concentrated to afford crude compound 61 (5 g). The crude product was used in the next step without further purification.

Synthesis of compound 62. A solution of crude compound 61 (3.2 g, 9 mmol) in THF (50 mL) was acidified to pH=3 by 1N aqueous HCl. After stirring at room temperature for 12 h, the reaction mixture was extracted with ethyl acetate (150 mL×3). The combined organic layers were washed with brine, dried over sodium sulfate, filtered and concentrated. The residue was purified by column chromatography (pertroleum ether/ethyl acetate=30:1 to 20:1) to afford compound 62 (2.2 g, 7 mmol, 81% for two steps), m/z (ES+ APCI)$^+$: [M+H]$^+$ 305.

Synthesis of compound 63. To a stirred solution of trimethylsulfonium iodide (8.1 g, 36.9 mmol) in 100 mL of DMSO was added NaH (60%; 1.26 g, 31.5 mmol). After stirring at room temperature for 1 h, a suspension of compound 62 (2.2 g, 7.2 mmol) in DMSO (20 mL) was added dropwise. The mixture was stirred for another 2.5 h, then poured into ice-cold water and extracted with ether (100 mL×3). The combined ether layers were then washed with brine (100 mL×3), dried over $MgSO_4$, filtered, and concentrated to give the crude product 63 (2.2 g). The crude product was used in the next step without further purification.

Synthesis of compound 64. To a solution of crude compound 63 (1.6 g, 5 mmol) in 60 mL of wet dichloromethane (dichloromethane had been shaken with several milliliters of $H_2O$ then separated from the water layer) was added Dess-Martin periodinate (4.2 g, 10 mmol). After stirring at room temperature for 24 h, the reaction mixture was extracted with dichloromethane (3×100 mL). The combined organic layers were washed with 10% aqueous $Na_2S_2O_3$ (100 mL), brine (100 mL), dried over $MgSO_4$, filtered and concentrated. The residue was purified by chromatography on silica gel (pertroleum ether/ethyl acetate=20:1 to 10:1) to afford compound 64 (1.2 g, 3.8 mmol, 75% for two steps) as a white solid. $^1$H NMR (400 MHz, CDCl$_3$), δ (ppm), 2.63-2.58 (m, 3H), 2.11 (s, 3H), 0.63 (s, 3H).

Synthesis of compound 65. To a solution of compound 64 (1.2 g, 3.8 mmol) in dry methanol (250 mL) was added Na (262 mg, 11.4 mmol). After reflux for 16 h, the solvent was evaporated and the residue was dissolved in dichloromethane. The mixture was washed with $H_2O$ (3×50 mL), brine (100 mL), dried over $MgSO_4$, filtered, and concentrated. The crude product was purified by silica gel chromatography (pertroleum ether/ethyl acetate=10:1 to 5:1) to give compound 65a (300 mg, 25%) and compound 65b (100 mg, 8%) as a white solid. 65a, 1H NMR (400 MHz, CDCl$_3$), δ (ppm), 3.38 (s, 3H), 3.18 (s, 2H), 2.56-2.51 (m, 1H), 2.11 (s, 3H), 0.61 (s, 3H). 65b, 1H NMR (400 MHz, CDCl$_3$), δ (ppm), 3.40 (s, 3H), 3.37 (s, 2H), 2.54-2.50 (m, 1H), 2.11 (s, 3H), 0.62 (s, 3H).

Synthesis of compound 66a. To a solution of compound 65a (50 mg, 0.14 mmol) in MeOH (10 mL) was added 2 drops of HBr (48%) followed by bromine (23 mg, 0.14 mmol). After stirring at room temperature for 1 h, the reaction mixture was poured into ice-water then extracted with ethyl acetate (10 mL×3). The combined organic layers were washed with brine (20 mL), dried over $MgSO_4$, filtered and concentrated to give crude compound 66a (46 mg, 92%). The crude product was used in the next step without further purification.

Synthesis of compound 67a. A solution of compound 66a (46 mg, 0.11 mmol) in acetone 10 mL was treated with CF$_3$COOH (0.5 mL) and Et$_3$N (0.7 mL). After refluxed for 30 min, CF$_3$COONa salt (300 mg, 2.2 mmol) was added in parts over a period of 10 hr. The reaction mixture was allowed to cool to room temperature and the solvent was removed in vaccuo. The residue was extracted with ethyl acetate, dried over $MgSO_4$, filtered and concentrated. The mixture was purified by chromatography on silica gel (pertroleum ether/ethyl acetate=10:1 to 3:1) to afford 67a (10 mg, yield: 25% for two steps). 67a, 1H NMR (400 MHz, CDCl₃), δ (ppm), 4.20-4.16 (m, 2H), 3.39 (s, 3H), 3.25 (m, 1H), 3.18 (s, 2H), 2.48-2.45 (m, 1H), 2.23-2.17 (m, 1H), 0.64 (s, 3H).

Example 10

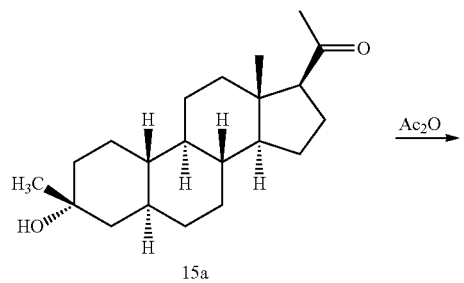
15a

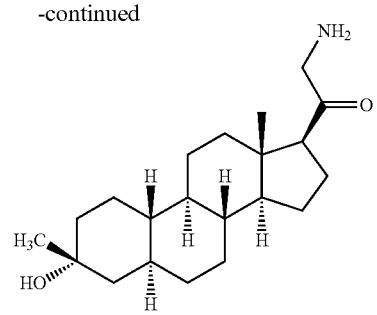

Synthesis of Compound 71

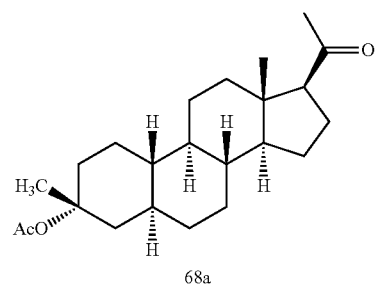
68a

Synthesis of compound 68a. To a solution of compound 15a (200 mg, 0.63 mmol) in acetic anhydride (10 mL) was added pyridine (50 mg, 0.63 mmol). The reaction mixture was stirred at 80° C. for 10 hour. The reaction mixture was poured into ice-cold water and extracted with ethyl acetate (20 mL×3). The combined ether layers were then washed with brine (10 mL×3), dried over MgSO₄, filtered and concentrated to give crude product 68a (160 mg, 80%). The crude product was used in the next step without further purification. ¹HNMR (400 MHz, CDCl₃), δ (ppm), 2.55-2.50 (t, J=9.2 Hz, 1H), 2.38-2.34 (m, 1H), 2.11 (s, 3H), 2.00 (s, 3H), 1.45 (s, 3H), 0.62 (s, 3H).

Example 11

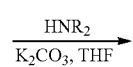
47a

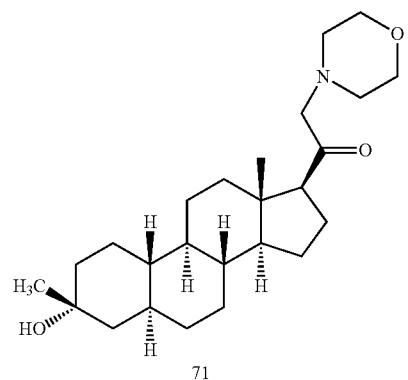
71

To a suspension of K₂CO₃ (25 mg, 0.18 mmol) in THF (5 mL) was added morpholine (16 mg, 0.18 mmol) and compound 16a (36 mg, 0.09 mmol). After stirring at room temperature for 15 h, the reaction mixture was poured in to 5 mL H₂O and extracted with EtOAc (2×10 mL). The combined organic layers were washed with brine, dried over sodium sulfate, filtered and concentrate. The reaction mixture was purified with by reverse-phase prep-HPLC to afford the title compound as a white solid (12 mg, 33%). 1HNMR (500 MHz, CDCl₃), δ (ppm), 3.77-3.75 (m, 4H), 3.19-3.18 (m, 2H), 2.59-2.50 (m, 5H), 2.19-2.12 (m, 1H), 1.20 (s, 3H), 0.63 (s, 3H).

Synthesis of Compound 72

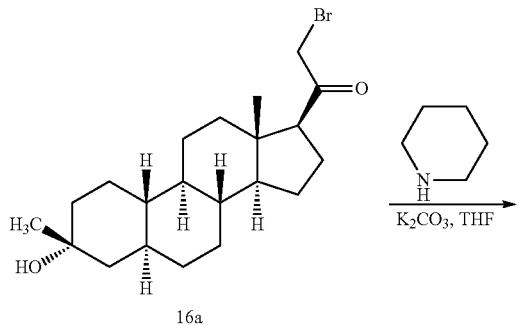

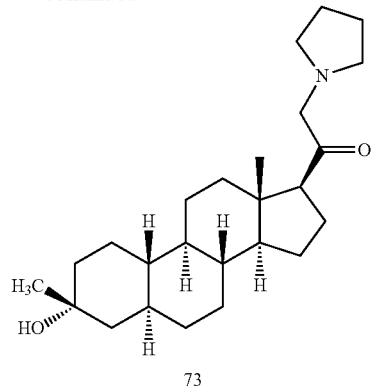

To a suspension of $K_2CO_3$ (25 mg, 0.18 mmol) in THF (5 mL) was added pyrrolidine (13 mg, 0.18 mmol) and compound 16a (36 mg, 0.09 mmol). After stirring at room temperature for 15 h, the reaction mixture was poured in to 5 mL $H_2O$ and extracted with EtOAc (2×10 mL). The combined organic layers were washed with brine, dried over sodium sulfate, filtered and concentrate. The reaction mixture was purified with by reverse-phase prep-HPLC to afford the title compound as a white solid (15 mg, 42%). 1HNMR (400 MHz, $CDCl_3$), δ (ppm), 3.43-3.31 (m, 2H), 2.61-2.53 (m, 5H), 2.21-2.13 (m, 1H), 1.20 (s, 3H), 0.63 (s, 3H).

Synthesis of Compound 74

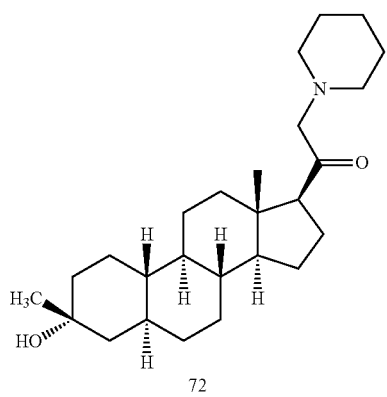

To a suspension of $K_2CO_3$ (25 mg, 0.18 mmol) in THF (5 mL) was added piperidine (16 mg, 0.18 mmol) and compound 16a (36 mg, 0.09 mmol). After stirring at room temperature for 15 h, the reaction mixture was poured in to 5 mL $H_2O$ and extracted with EtOAc (2×10 mL). The combined organic layers were washed with brine, dried over sodium sulfate, filtered and concentrate. The reaction mixture was purified with by reverse-phase prep-HPLC to afford the title compound as a white solid (12 mg, 33%). 1HNMR (500 MHz, $CDCl_3$), δ (ppm), 3.12-3.04 (m, 2H), 2.57-2.53 (t, J=9 Hz, 1H), 2.59-2.50 (m, 5H), 2.19-2.12 (m, 1H), 1.20 (s, 3H), 0.63 (s, 3H).

Synthesis of Compound 73

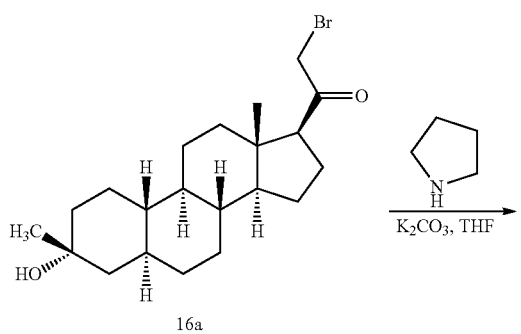

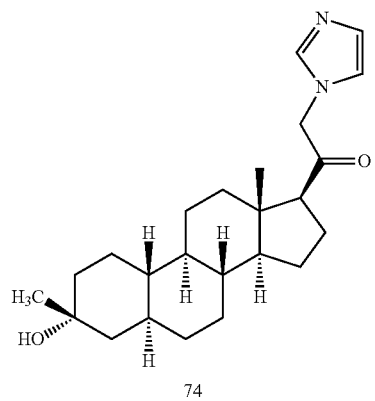

To a suspension of $K_2CO_3$ (14 mg, 0.10 mmol) in THF (5 mL) was added 1H-imidazole (7 mg, 0.10 mmol) and compound 16a (20 mg, 0.05 mmol). After stirring at room temperature for 15 h, the reaction mixture was poured in to 5 mL $H_2O$ and extracted with EtOAc (2×10 mL). The combined organic layers were washed with brine, dried over sodium sulfate, filtered and concentrate. The reaction mixture was purified with by reverse-phase prep-HPLC to afford the title compound as a white solid (7 mg, 35%). 1HNMR (500 MHz, CDCl$_3$), δ (ppm), 7.49 (s, 1H), 7.12 (s, 1H), 6.86 (s, 1H), 4.75-4.66 (m, 2H), 2.60-2.56 (t, J=8.5 Hz, 1H), 2.21-2.13 (m, 1H), 1.21 (s, 3H), 0.68 (s, 3H).

Example 12

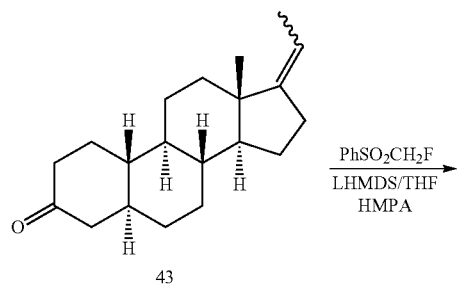

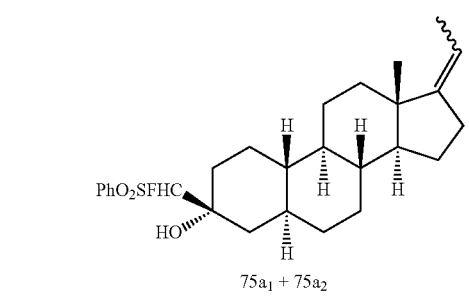

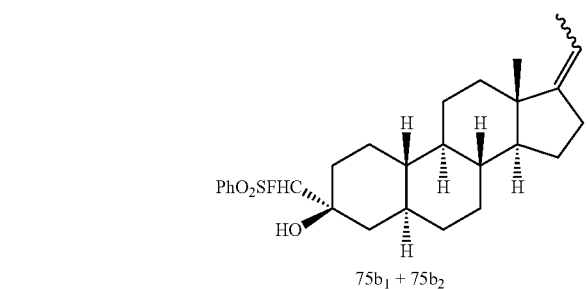

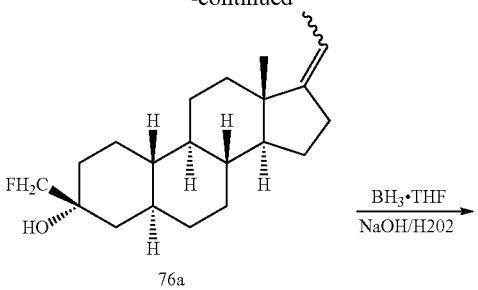

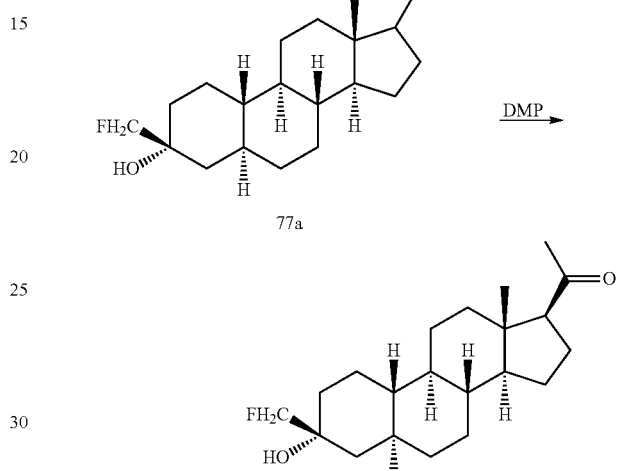

Synthesis of compound 75a and 75b. To a solution of compound 43 (1.3 g, 4.5 mmol) and PhSO$_2$CH$_2$F (790 mg, 4.5 mmol) in THF (25 mL) and HMPA (0.5 mL) at −78° C. under N$_2$ was added LHMDS (5.5 mL, 1M in THF) dropwise. After stirring at −78° C. for 2 h, the reaction mixture was quenched with saturated aqueous NH$_4$Cl solution (10 mL) and allowed to warm to room temperature then extracted with Et$_2$O (20 mL×3). The combined organic layers were washed with brine, dried over sodium sulfate, filtered and concentrate. The residue was purified by silica gel column chromatography (pertroleum ether/ethyl acetate=10/1) to give the mixture of compound 75a and 75b (1.53 g). The mixture was further purified by chiral-HPLC to afford compound 75a1 (220 mg, t=3.41 min). $^1$H NMR (500 MHz, CDCl3), δ (ppm), 7.99-7.97 (m, 2H), 7.75-7.74 (m, 1H), 7.62-7.55 (m, 2H), 5.13-5.09 (m, 1H), 4.86-4.78 (d, 1H, J=42 Hz), 0.88 (s, 3H); 75a2 (200 mg, t=3.66 min); $^1$H NMR (500 MHz, CDCl3), δ (ppm), 7.96-7.95 (m, 1H), 7.71-7.69 (m, 1H), 7.62-7.58 (m, 2H), 5.13-5.09 (m, 1H), 4.87-4.77 (d, 1H, J=46.5 Hz), 0.88 (s, 3H); 75b1 (235 mg, t=4.9 min). $^1$H NMR (500 MHz, CDCl3), δ (ppm), 7.99-7.97 (m, 1H), 7.72-7.70 (m, 1H), 7.62-7.59 (m, 2H), 5.29-5.20 (d, 1H, J=43 Hz), 4.88-4.78 (m, 1H), 0.88 (s, 3H); 75b2 (220 mg, t=5.2 min). $^1$H NMR (500 MHz, CDCl3), δ (ppm), 7.99-7.97 (m, 2H), 7.72 (m, 1H), 7.62-7.59 (m, 2H), 5.30-5.20 (d, 1H, J=46.5 Hz), 5.09-5.08 (m, 1H), 0.88 (s, 3H). Chiral HPLC conditions: Elutant=MeOH (0.1% DEA); Column=IC (4.6*250 mm, 5 um).

Synthesis of compound 76a. To a solution of compound 75a1 (200 mg, 0.434 mmol) and anhydrous Na$_2$HPO$_4$ (100 mg) in anhydrous methanol (15 mL) at −20° C. under N$_2$ was added Na/Hg amalgam (400 mg). After stirring at −20°

C. to 0° C. for 1 h, the methanol solution was decanted out and the solid residue was washed with $Et_2O$ (5×3 mL). The solvent of combined organic phase was removed under vacuum, and 20 ml brine was added, followed by extracting with Et2O. The combined ether phase was dried with MgSO4, and the ether was removed to give the crude product, which was further purified by silica gel chromatography (PE/EA=10/1) to give compound 76a (99 mg, 69%). $^1$H NMR (500 MHz, CDCl3), δ (ppm), 5.12-5.10 (m, 1H,), 4.21-24.11 (d, 2H, J=47.5 Hz), 0.88 (s, 3H).

Synthesis of compound 77a. To a solution of compound 76a (95 mg, 0.296 mmol) in dry THF (5 mL) was added borane-tetrahydrofuran complex (1 mL of 1.0 M solution in THF). After stirring at room temperature for 1 hour, the reaction mixture was cooled in an ice bath then quenched slowly with 10% aqueous NaOH (1 mL) followed by 30% aqueous solution of $H_2O_2$ (1.2 mL). The mixture was allowed to stir at room temperature for 1 hour then extracted with EtOAc (3×10 mL). The combined organic layers were washed with 10% aqueous $Na_2S_2O_3$ (10 mL), brine (10 mL), dried over $MgSO_4$, filtered and concentrated to afford compound 77a (120 mg crude). The crude product was used in the next step without further purification.

Synthesis of compound 78a. To a solution of compound 77a (120 mg crude) was dissolved in 10 mL of wet dichloromethane (dichloromethane had been shaken with several milliliters of $H_2O$ then separated from the water layer) was added Dess-Martin periodinate (300 mg, 707 mmol). After stirring at room temperature for 24 h, the reaction mixture was extracted with dichloromethane (3×10 mL). The combined organic layers were washed with 10% aqueous $Na_2S_2O_3$ (10 mL), brine (10 mL), dried over $MgSO_4$, filtered and concentrated. The residue was purified by chromatography on silica gel (pertroleum ether/ethyl acetate=1:5) to afford compound 78a (70 mg, 70% for two steps) as a white solid. $^1$H NMR (500 MHz, CDCl3), δ (ppm), 4.21-4.11 (d, 2H, J=48 Hz), 2.19 (s, 3H), 0.62 (s, 3H).

Assay Methods

Compounds provided herein can be evaluated using various in vitro and in vivo assays; examples of which are described below.

Steroid Inhibition of TBPS Binding

TBPS binding assays using rat brain cortical membranes in the presence of 5 μM GABA has been described (Gee et al, *J. Pharmacol. Exp. Ther.* 1987, 241, 346-353; Hawkinson et al, *Mol. Pharmacol.* 1994, 46, 977-985).

Briefly, cortices are rapidly removed following decapitation of carbon dioxide-anesthetized Sprague-Dawley rats (200-250 g). The cortices are homogenized in 10 volumes of ice-cold 0.32 M sucrose using a glass/teflon homogenizer and centrifuged at 1500×g for 10 min at 4° C. The resultant supernatants are centrifuged at 10,000×g for 20 min at 4° C. to obtain the P2 pellets. The P2 pellets are resuspended in 200 mM NaCl/50 mM Na—K phosphate pH 7.4 buffer and centrifuged at 10,000×g for 10 min at 4° C. This ishing procedure is repeated twice and the pellets are resuspended in 10 volumes of buffer. Aliquots (100 μL) of the membrane suspensions are incubated with 2 nM [$^{35}$S]-TBPS and 5 μL aliquots of test drug dissolved in dimethyl sulfoxide (DMSO) (final 0.5%) in the presence of 5 μM GABA. The incubation is brought to a final volume of 1.0 mL with buffer. Nonspecific binding is determined in the presence of 2 μM unlabeled TBPS and ranged from 15 to 25%. Following a 90 min incubation at room temp, the assays are terminated by filtration through glass fiber filters (Schleicher and Schuell No. 32) using a cell harvester (Brandel) and rinsed three times with ice-cold buffer. Filter bound radioactivity is measured by liquid scintillation spectrometry. Non-linear curve fitting of the overall data for each drug averaged for each concentration is done using Prism (GraphPad). The data are fit to a partial instead of a full inhibition model if the sum of squares is significantly lower by F-test. Similarly, the data are fit to a two component instead of a one component inhibition model if the sum of squares is significantly lower by F-test. The concentration of test compound producing 50% inhibition ($IC_{50}$) of specific binding and the maximal extent of inhibition ($I_{max}$) are determined for the individual experiments with the same model used for the overall data and then the means±SEM.s of the individual experiments are calculated.

Various compounds are or can be screened to determine their potential as modulators of [$^{35}$S]-TBPS binding in vitro. These assays are or can be performed in accordance with the above discussed procedures.

In Vivo Pharmacology

Male NSA mice weighing between 15-20 g are obtained from Harlan Sprague-Dawley (San Diego, Calif.). Upon arrival they are housed in standard polycarbonate cages (4 per cage) containing a sterilized bedding material in a room of constant temp (23.0°±2.5° C.) with a 12 h (07.00-19.00 light) light/dark cycle. Food (Teklad LM 485) and water are freely available. Mice are acclimated a minimum of 4 days prior to experimentation.

Pentylenetetrazol-Induced Seizures

Seizures are induced by administration of 85 mg/kg, s.c pentylenetetrazol (30 min observation period). The dose used is previously determined to be the $CD_{97}$. A clonic seizure is defined as forelimb clonus of ≥3 sec duration. Data are treated quantally.

Maximal Electroshock-Induced Seizures

Seizures are induced by application of current (50 mA, 60 pulses/sec, 0.8 msec pulse width, 1 sec duration, D.C.) using a Ugo Basile ECT device (Model 7801). Mice are restrained by gripping the loose skin on their dorsal surface and saline-coated corneal electrodes are held lightly against the two cornea. Current is applied and mice are observed for a period of up to 30 sec for the occurrence of a tonic hindlimb extensor response. A tonic seizure is defined as a hindlimb extension in excess of 90 degrees from the plane of the body. Results are treated in a quantal manner.

Hanging Wire

The hanging-wire test used a custom-built apparatus that consisted of a metal wire (2 mm diameter) suspended horizontally above a padded surface (25 cm). Mice are held by the base of the tail, their forepaws placed in contact with the wire, and then released. Animals are required to bring both hindpaws in contact with the wire within 5 sec in order to be scored as a pass. Results are treated quantally.

Drug Metabolism and Pharmacokinetics: HERG Assay.

HEK 293 cells which stably express the HERG potassium channel are used for electrophysiological studies. The methodology for stable transfection of this channel in HEK cells can be found elsewhere (Zhou et al., *Biophys. J.* 74:30-41, 1998). Before the day of experimentation, the cells are harvested from culture flasks and plated onto glass coverslips in a standard Minimum Essential Medium (MEM) medium with 10% Fetal Calf Serum (FCS). The plated cells are stored in an incubator at 37° C. maintained in an atmosphere of 95% $O_2$/5% $CO_2$. Cells are studied between 15-28 hrs after harvest.

HERG currents are studied using standard patch clamp techniques in the whole-cell mode. During the experiment the cells are superfused with a standard external solution of the following composition (mM); NaCl, 130; KCl, 4; $CaCl_2$, 2; MgCl$_2$, 1; Glucose, 10; HEPES, 5; pH 7.4 with NaOH. Whole-cell recordings are made using a patch clamp amplifier and patch pipettes which have a resistance of 1-3 MOhm when filled with the standard internal solution of the following composition (mM); KCl, 130; MgATP, 5; MgCl$_2$, 1.0; HEPES, 10; EGTA 5, pH 7.2 with KOH. Only those cells with access resistances below 15 MOhm and seal resistances>1 GOhm are accepted for further experimentation. Series resistance compensation was applied up to a maximum of 80%. No leak subtraction is done. However, acceptable access resistance depended on the size of the recorded currents and the level of series resistance compensation that can safely be used. Following the achievement of whole cell configuration and sufficient time for cell dialysis with pipette solution (>5 min), a standard voltage protocol is applied to the cell to evoke membrane currents. The voltage protocol is as follows. The membrane is depolarized from a holding potential of −80 mV to +40 mV for 1000 ms. This was followed by a descending voltage ramp (rate 0.5 mV msec-1) back to the holding potential. The voltage protocol is applied to a cell continuously throughout the experiment every 4 seconds (0.25 Hz). The amplitude of the peak current elicited around −40 mV during the ramp is measured. Once stable evoked current responses are obtained in the external solution, vehicle (0.5% DMSO in the standard external solution) is applied for 10-20 min by a peristalic pump. Provided there were minimal changes in the amplitude of the evoked current response in the vehicle control condition, the test compound of either 0.3, 1, 3, or 10 mM is applied for a 10 min period. The 10 min period included the time which supplying solution was passing through the tube from solution reservoir to the recording chamber via the pump. Exposing time of cells to the compound solution was more than 5 min after the drug concentration in the chamber well reached the attempting concentration. There is a subsequent wash period of a 10-20 min to assess reversibility. Finally, the cells is exposed to high dose of dofetilide (5 mM), a specific IKr blocker, to evaluate the insensitive endogenous current.

All experiments are performed at room temperature (23±1° C.). Evoked membrane currents were recorded on-line on a computer, filtered at 500-1 KHz (Bessel −3 dB) and sampled at 1-2 KHz using the patch clamp amplifier and a specific data analyzing software. Peak current amplitude, which occurred at around −40 mV, is measured off line on the computer.

The arithmetic mean of the ten values of amplitude is calculated under vehicle control conditions and in the presence of drug. Percent decrease of IN in each experiment was obtained by the normalized current value using the following the formula: IN=(1−ID/IC)×100, where ID is the mean current value in the presence of drug and IC is the mean current value under control conditions. Separate experiments are performed for each drug concentration or time-matched control, and arithmetic mean in each experiment is defined as the result of the study.

Patch Clamp Electrophysiology of Recombinant $\alpha_1\beta_2\gamma_2$ GABA$_A$ Receptors Cellular electrophysiology is used to measure in vitro potency and efficacy of our GABA$_A$ receptor modulators in Ltk cells. Each compound is tested for its ability to affect GABA mediated currents at a submaximal agonist dose (GABA EC10=0.5 µM) in a whole cell patch clamp technique using a EPC-10, HEKA Electronics Amplifier and PatchMaster software. These experiments measure potency, efficacy (Emax), direct gating properties and acute desensitization. Test article is added at 0.1, 1.0 and 10 uM.

Drug Metabolism and Pharmacokinetics: Half-Life in Human Liver Microsomes (HLM)

Test compounds (1 µM) are incubated with 3.3 mM MgCl$_2$ and 0.78 mg/mL HLM (HL101) in 100 mM potassium phosphate buffer (pH 7.4) at 37° C. on the 96-deep well plate. The reaction mixture is split into two groups, a non-P450 and a P450 group. NADPH is only added to the reaction mixture of the P450 group. An aliquot of samples of P450 group is collected at 0, 10, 30, and 60 min time point, where 0 min time point indicated the time when NADPH was added into the reaction mixture of P450 group. An aliquot of samples of non-P450 group is collected at −10 and 65 min time point. Collected aliquots are extracted with acetonitrile solution containing an internal standard. The precipitated protein is spun down in centrifuge (2000 rpm, 15 min). The compound concentration in supernatant is measured by LC/MS/MS system. The half-life value is obtained by plotting the natural logarithm of the peak area ratio of compounds/internal standard versus time. The slope of the line of best fit through the points yields the rate of metabolism (k). This is converted to a half-life value using the equation: Half-life=ln 2/k.

TABLE 1

| | Patchclamp electrophysiology potentiation and TBPS binding data | | | |
|---|---|---|---|---|
| Structure | % potentiation at 100 nM | % potentiation at 1000 nM | % potentiation at 10000 nM | TBPS binding IC50 (nM) |
| 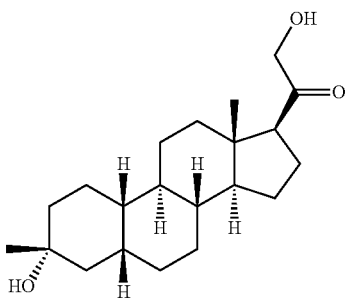 | | 101 | 163 | 86 |

TABLE 1-continued

Patchclamp electrophysiology potentiation and TBPS binding data

| Structure | % potentiation at 100 nM | % potentiation at 1000 nM | % potentiation at 10000 nM | TBPS binding IC50 (nM) |
|---|---|---|---|---|
| | | | | 33 |
| | | | | 170 |
| | | | | 41 |
| 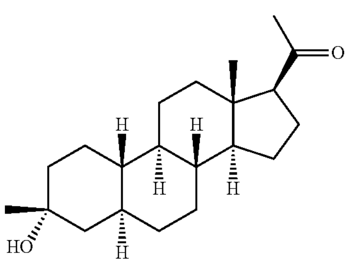 | 80 | 157 | 270 | 93 |
| | | 130 | 227 | 220 |

TABLE 1-continued

| | Patchclamp electrophysiology potentiation and TBPS binding data | | | |
|---|---|---|---|---|
| Structure | % potentiation at 100 nM | % potentiation at 1000 nM | % potentiation at 10000 nM | TBPS binding IC50 (nM) |
| 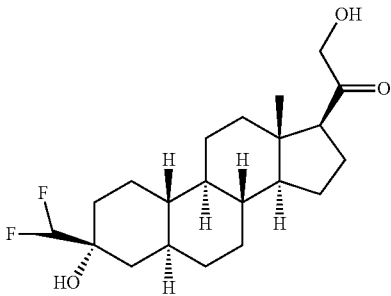 | | 0 | 100 | >10000 |
| 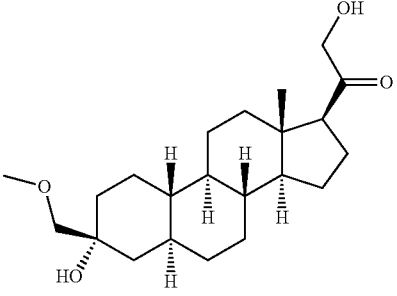 | | | | 94 |
| 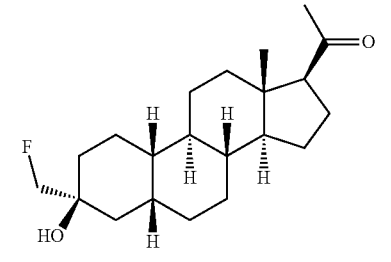 | | | | 100 |

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A process for preparing a compound of Formula 10b:
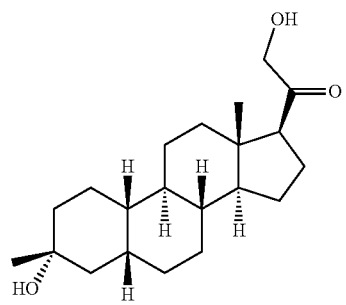
the process comprising treating a compound of Formula 9b:
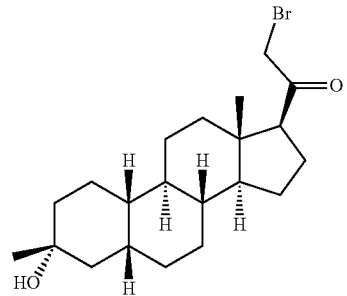
with a) trifluoroacetic acid and triethylamine, and b) sodium trifluoroacetate, in refluxing acetone.
* * * * *